(12) United States Patent
Oggenfuss et al.

(10) Patent No.: US 11,357,401 B2
(45) Date of Patent: Jun. 14, 2022

(54) MINIATURIZED MOBILE, LOW COST OPTICAL COHERENCE TOMOGRAPHY SYSTEM FOR HOME BASED OPHTHALMIC APPLICATIONS

(71) Applicant: ACUCELA INC., Seattle, WA (US)

(72) Inventors: Christian Oggenfuss, Lyss (CH); Karim Haroud, Villeneuve (CH); Lukas Scheibler, Telluride, CO (US); Matthias Pfister, Liebefeld-Bern (CH); Urban Schnell, Munchenbuchsee (CH); Stefan Troller, Sissach (CH); Ryo Kubota, Seattle, WA (US); Philip M. Buscemi, Mount Pleasant, SC (US)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 17/247,630

(22) Filed: Dec. 18, 2020

(65) Prior Publication Data

US 2021/0127969 A1  May 6, 2021

Related U.S. Application Data

(63) Continuation of application No. PCT/US2019/038270, filed on Jun. 20, 2019.
(Continued)

(51) Int. Cl.
*A61B 3/10* (2006.01)
*A61B 3/00* (2006.01)
*A61B 3/13* (2006.01)

(52) U.S. Cl.
CPC .......... *A61B 3/102* (2013.01); *A61B 3/0008* (2013.01); *A61B 3/1005* (2013.01); *A61B 3/132* (2013.01);
(Continued)

(58) Field of Classification Search
CPC ..... A61B 3/102; A61B 3/0008; A61B 3/1005; A61B 3/132; A61B 2560/0431;
(Continued)

(56) References Cited

U.S. PATENT DOCUMENTS

| | | | |
|---|---|---|---|
| 5,255,274 | A | 10/1993 | Wysocki |
| 5,396,325 | A | 3/1995 | Carome |

(Continued)

FOREIGN PATENT DOCUMENTS

| | | |
|---|---|---|
| CN | 105188540 | 12/2015 |
| CN | 105263415 | 1/2016 |
| CN | 105792728 | 7/2016 |
| DE | 102016121246 | 5/2018 |
| EP | 2725508 | 4/2014 |
| EP | 2759254 | 7/2014 |

(Continued)

OTHER PUBLICATIONS

International Search Report and Written Opinion for International Application No. PCT/US2017/067603 (dated Mar. 5, 2018).
(Continued)

*Primary Examiner* — Mohammed A Hasan
(74) *Attorney, Agent, or Firm* — Fisherbroyles LLP; John Shimmick

(57) ABSTRACT

Improved optical coherence tomography systems and methods to measure thickness of the retina are presented. The systems may be compact, handheld, provide in-home monitoring, allow the patient to measure himself or herself, and be robust enough to be dropped while still measuring the retina reliably.

25 Claims, 116 Drawing Sheets

Related U.S. Application Data

(60) Provisional application No. 62/687,686, filed on Jun. 20, 2018.

(52) U.S. Cl.
CPC ............... *A61B 2560/0431* (2013.01); *A61B 2562/0214* (2013.01); *A61B 2562/0257* (2013.01); *A61B 2562/223* (2013.01)

(58) Field of Classification Search
CPC .... A61B 2562/0214; A61B 2562/0257; A61B 2562/223; A61B 3/1225; G01B 9/02007; G01B 9/02091
USPC .......................................................... 351/221
See application file for complete search history.

(56) References Cited

U.S. PATENT DOCUMENTS

| | | |
|---|---|---|
| 6,053,613 A | 4/2000 | Wei |
| 6,325,512 B1 | 12/2001 | Wei |
| 6,362,919 B1 | 3/2002 | Flanders |
| 6,409,395 B1 | 6/2002 | Wang |
| 6,419,360 B1 | 7/2002 | Hauger |
| 6,445,944 B1 | 9/2002 | Ostrovsky |
| 6,552,796 B2 | 4/2003 | Magnin |
| 6,726,325 B2 | 4/2004 | Xie |
| 6,736,508 B2 | 5/2004 | Xie |
| 6,769,769 B2 | 8/2004 | Podoleanu |
| 6,778,307 B2 | 8/2004 | Clark |
| 7,113,818 B2 | 9/2006 | Podoleanu |
| 7,126,693 B2 | 10/2006 | Everett |
| 7,140,730 B2 | 11/2006 | Wei |
| 7,301,644 B2 | 11/2007 | Knighton |
| 7,324,569 B2 | 1/2008 | Flanders |
| 7,347,548 B2 | 3/2008 | Huang |
| 7,375,818 B2 | 5/2008 | Kawahara |
| 7,391,520 B2 | 6/2008 | Zhou |
| 7,452,077 B2 | 11/2008 | Meyer |
| 7,482,589 B2 | 1/2009 | Flanders |
| 7,542,145 B2 | 6/2009 | Toida |
| 7,594,730 B2 | 9/2009 | Podoleanu |
| 7,602,500 B2 | 10/2009 | Izatt |
| 7,633,623 B2 | 12/2009 | Hatori |
| 7,633,627 B2 | 12/2009 | Choma |
| 7,701,585 B2 | 4/2010 | Hatori |
| 7,761,139 B2 | 7/2010 | Tearney |
| 7,783,337 B2 | 8/2010 | Feldman |
| 7,864,335 B2 | 1/2011 | Terakawa |
| 7,872,759 B2 | 1/2011 | Tearney |
| 7,929,148 B2 | 4/2011 | Kemp |
| 7,954,947 B2 | 6/2011 | Sugita |
| 7,971,999 B2 | 7/2011 | Zinser |
| 7,980,694 B2 | 7/2011 | Keating |
| 7,980,696 B1 | 7/2011 | Taki |
| 7,997,728 B2 | 8/2011 | Huang |
| 7,997,729 B2 | 8/2011 | McLean |
| 8,025,403 B2 | 9/2011 | Maloca |
| 8,049,900 B2 | 11/2011 | Kemp |
| 8,055,107 B2 | 11/2011 | Masuda |
| 8,079,711 B2 | 12/2011 | Stetson |
| 8,123,354 B2 | 2/2012 | Olivier |
| 8,139,226 B2 | 3/2012 | Johnson |
| 8,192,024 B2 | 6/2012 | Yumikake |
| 8,205,991 B2 | 6/2012 | Wei |
| 8,220,924 B2 | 7/2012 | Hanebuchi |
| 8,251,510 B2 | 8/2012 | Kobayashi |
| 8,251,511 B2 | 8/2012 | Stetson |
| 8,282,211 B2 | 10/2012 | Campbell |
| 8,289,522 B2 | 10/2012 | Tearney |
| 8,348,427 B2 | 1/2013 | Buckland |
| 8,348,429 B2 | 1/2013 | Walsh |
| 8,351,665 B2 | 1/2013 | Tearney |
| 8,403,481 B2 | 3/2013 | Izatt |
| 8,405,834 B2 | 3/2013 | Srinivasan |
| 8,421,855 B2 | 4/2013 | Buckland |
| 8,425,037 B2 | 4/2013 | Uhlhorn |
| 8,442,284 B2 | 5/2013 | Rogers |
| 8,446,593 B1 | 5/2013 | Ellerbee |
| 8,457,440 B1 | 6/2013 | Johnson |
| 8,467,051 B2 | 6/2013 | Flanders |
| 8,474,978 B2 | 7/2013 | Huang |
| 8,500,279 B2 | 8/2013 | Everett |
| 8,526,006 B2 | 9/2013 | Nebosis |
| 8,529,062 B2 | 9/2013 | Buckland |
| 8,594,757 B2 | 11/2013 | Boppart |
| 8,608,314 B2 | 12/2013 | Yoon |
| 8,630,697 B2 | 1/2014 | Meyer |
| 8,665,450 B2 | 3/2014 | Johnson |
| 8,711,366 B2 | 4/2014 | Everett |
| 8,721,078 B2 | 5/2014 | Torii |
| 8,724,870 B2 | 5/2014 | Sekine |
| 8,757,803 B2 | 6/2014 | Everett |
| 8,781,287 B2 | 7/2014 | Flanders |
| 8,794,763 B2 | 8/2014 | Stetson |
| 8,801,184 B2 | 8/2014 | Hacker |
| 8,820,931 B2 | 9/2014 | Walsh |
| 8,836,953 B2 | 9/2014 | Johnson |
| 8,870,376 B2 | 10/2014 | Hogan |
| 8,894,207 B2 | 11/2014 | Hee |
| 8,913,248 B2 | 12/2014 | Sharma |
| 8,922,782 B2 | 12/2014 | Flanders |
| 8,926,097 B2 | 1/2015 | Sakagawa |
| 8,939,582 B1 | 1/2015 | Spaide |
| 8,947,648 B2 | 2/2015 | Swanson |
| 8,953,167 B2 | 2/2015 | Johnson |
| 8,971,360 B2 | 3/2015 | Lewandowski |
| 8,992,018 B2 | 3/2015 | Makihira |
| 8,994,753 B2 | 3/2015 | Nakano |
| 8,998,412 B2 | 4/2015 | Makihira |
| 9,016,862 B2 | 4/2015 | Carnevale |
| 9,025,160 B2 | 5/2015 | Moore |
| 9,025,847 B2 | 5/2015 | Kitamura |
| 9,033,504 B2 | 5/2015 | Everett |
| 9,033,510 B2 | 5/2015 | Narasimha-Iyer |
| 9,044,164 B2 | 6/2015 | Hacker |
| 9,055,891 B2 | 6/2015 | Suehira |
| 9,060,689 B2 | 6/2015 | Tearney |
| 9,084,562 B2 | 7/2015 | Kakuma |
| 9,095,281 B2 | 8/2015 | Sharma |
| 9,119,562 B2 | 9/2015 | Naba |
| 9,138,141 B2 | 9/2015 | Makihira |
| 9,144,378 B2 | 9/2015 | Suehira |
| 9,149,182 B2 | 10/2015 | Walsh |
| 9,161,690 B2 | 10/2015 | Tomatsu |
| 9,163,929 B2 | 10/2015 | Lim |
| 9,163,930 B2 | 10/2015 | Buckland |
| 9,167,964 B2 | 10/2015 | Everett |
| 9,171,367 B2 | 10/2015 | Iwase |
| 9,176,319 B2 | 11/2015 | Bouma |
| 9,178,330 B2 | 11/2015 | Oh |
| 9,192,294 B2 | 11/2015 | Sharma |
| 9,200,888 B2 | 12/2015 | Jaillon |
| 9,217,707 B2 | 12/2015 | Bajraszewski |
| 9,226,653 B2 | 1/2016 | Torii |
| 9,226,660 B2 | 1/2016 | De Boer |
| 9,241,626 B2 | 1/2016 | Narasimha-Iyer |
| 9,243,885 B2 | 1/2016 | Johnson |
| 9,259,151 B2 | 2/2016 | Murase |
| 9,267,783 B1 | 2/2016 | Sharma |
| 9,273,950 B2 | 3/2016 | Yazdanfar |
| 9,291,446 B2 | 3/2016 | Schneider |
| 9,310,182 B2 | 4/2016 | Goldberg |
| 9,339,186 B2 | 5/2016 | Somani |
| 9,354,038 B2 | 5/2016 | Yasuno |
| 9,373,933 B2 | 6/2016 | Njegovec |
| 9,375,158 B2 | 6/2016 | Vakoc |
| 9,377,293 B2 | 6/2016 | Hauger |
| 9,380,935 B2 | 7/2016 | Iwase |
| 9,408,532 B2 | 8/2016 | Makihira |
| 9,427,147 B2 | 8/2016 | Lujan |
| 9,427,150 B2 | 8/2016 | Muto |
| 9,433,353 B2 | 9/2016 | Hanebuchi |
| 9,468,374 B2 | 10/2016 | Makihira |

(56) References Cited

U.S. PATENT DOCUMENTS

| | | | |
|---|---|---|---|
| 9,492,077 B2 | 11/2016 | Ebersbach |
| 9,492,079 B2 | 11/2016 | Walsh |
| 9,526,412 B2 | 12/2016 | Yang |
| 9,526,415 B2 | 12/2016 | Fukuma |
| 9,526,425 B2 | 12/2016 | Feldman |
| 9,532,713 B2 | 1/2017 | Levecq |
| 9,545,199 B2 | 1/2017 | Wang |
| 9,584,098 B2 | 2/2017 | Yamanari |
| 9,612,105 B2 | 4/2017 | Kemp |
| 9,615,736 B2 | 4/2017 | Yamashita |
| 9,633,424 B2 | 4/2017 | Nebosis |
| 9,649,024 B2 | 5/2017 | Hacker |
| 9,649,025 B2 | 5/2017 | Jeglorz |
| 9,671,620 B2 | 6/2017 | Gupta |
| 9,696,132 B2 | 7/2017 | Jayaraman |
| 9,702,686 B2 | 7/2017 | Hattersley |
| 9,778,018 B2 | 10/2017 | Schmoll |
| 9,778,020 B2 | 10/2017 | Tumlinson |
| 9,784,559 B2 | 10/2017 | Huber |
| 9,812,846 B2 | 11/2017 | Yun |
| 9,869,542 B2 | 1/2018 | Goldberg |
| 9,897,538 B2 | 2/2018 | Tearney |
| 9,915,520 B2 | 3/2018 | Cable |
| 9,939,659 B2 | 4/2018 | Gupta |
| 9,948,061 B2 | 4/2018 | Njegovec |
| 9,977,184 B1 | 5/2018 | Wong |
| 9,978,159 B2 | 5/2018 | Kraus |
| 9,993,153 B2 | 6/2018 | Chong |
| 10,045,692 B2 | 8/2018 | Tumlinson |
| 10,049,470 B2 | 8/2018 | Pintal |
| 10,098,537 B2 | 10/2018 | Iwase |
| 10,114,232 B2 | 10/2018 | Gupta |
| 10,327,631 B2 | 6/2019 | Huang |
| 10,413,175 B2 | 9/2019 | Yun |
| 10,478,058 B2 | 11/2019 | Cheng |
| 10,568,501 B2 | 2/2020 | Boss |
| 10,595,723 B2 | 3/2020 | Meznaric |
| 10,610,096 B2 | 4/2020 | Scheibler |
| 10,952,607 B2 | 3/2021 | Scheibler |
| 10,959,613 B1 | 3/2021 | Kubota |
| 2005/0018133 A1 | 1/2005 | Huang |
| 2006/0131488 A1 | 6/2006 | Thingbo |
| 2006/0152106 A1 | 7/2006 | Jun |
| 2006/0244339 A1 | 11/2006 | Mazz |
| 2007/0076217 A1 | 4/2007 | Baker |
| 2007/0183643 A1 | 8/2007 | Jayaraman |
| 2007/0230856 A1 | 10/2007 | Yamazaki |
| 2008/0100612 A1 | 5/2008 | Dastmalchi |
| 2008/0117427 A1 | 5/2008 | Teramura |
| 2008/0181263 A1 | 7/2008 | Bouma |
| 2008/0296480 A1 | 12/2008 | Haber |
| 2009/0123044 A1 | 5/2009 | Huang |
| 2009/0141237 A1* | 6/2009 | Izatt ............... G01B 9/02091 |
| | | | 351/211 |
| 2010/0110376 A1 | 5/2010 | Everett |
| 2010/0110377 A1 | 5/2010 | Maloca |
| 2011/0043757 A1 | 2/2011 | Everett |
| 2011/0164633 A1 | 7/2011 | Moench |
| 2011/0299034 A1 | 12/2011 | Walsh |
| 2012/0033227 A1 | 2/2012 | Bower |
| 2012/0092616 A1 | 4/2012 | Peyman |
| 2012/0300216 A1 | 11/2012 | Johnson |
| 2012/0327365 A1 | 12/2012 | Makihira |
| 2013/0010259 A1 | 1/2013 | Carnevale |
| 2013/0010302 A1 | 1/2013 | Sharma |
| 2013/0016360 A1 | 1/2013 | Ensher |
| 2013/0103014 A1 | 4/2013 | Gooding |
| 2013/0158392 A1 | 6/2013 | Papac |
| 2013/0235343 A1 | 9/2013 | Hee |
| 2013/0250241 A1 | 9/2013 | Everett |
| 2014/0028997 A1 | 1/2014 | Cable |
| 2014/0112562 A1 | 4/2014 | Yamakawa |
| 2014/0121508 A1 | 5/2014 | Latimer |
| 2014/0125987 A1 | 5/2014 | Flanders |
| 2014/0180075 A1 | 6/2014 | Kulkarni |
| 2014/0218745 A1 | 8/2014 | Hattersley |
| 2014/0241605 A1 | 8/2014 | Izatt |
| 2014/0268050 A1 | 9/2014 | Jayaraman |
| 2014/0268169 A1 | 9/2014 | Jayaraman |
| 2014/0269796 A1 | 9/2014 | Geske |
| 2014/0285812 A1 | 9/2014 | Levitz |
| 2014/0307078 A1 | 10/2014 | Charles |
| 2014/0307753 A1 | 10/2014 | Minneman |
| 2014/0340689 A1 | 11/2014 | Namati |
| 2014/0347632 A1 | 11/2014 | Mordaunt |
| 2015/0010031 A1 | 1/2015 | Makino |
| 2015/0018674 A1* | 1/2015 | Scott ............... A61B 3/107 |
| | | | 600/427 |
| 2015/0055089 A1 | 2/2015 | Aono |
| 2015/0062532 A1 | 3/2015 | Sharma |
| 2015/0085253 A1 | 3/2015 | Walsh |
| 2015/0109579 A1 | 4/2015 | Orlowski |
| 2015/0110376 A1 | 4/2015 | Gessner |
| 2015/0216412 A1 | 8/2015 | Hillmann |
| 2015/0327761 A1 | 11/2015 | Narasimha-Iyer |
| 2015/0327762 A1 | 11/2015 | Isogai |
| 2016/0000368 A1 | 1/2016 | Wang |
| 2016/0007857 A1 | 1/2016 | Wang |
| 2016/0025478 A1 | 1/2016 | Johnson |
| 2016/0040977 A1 | 2/2016 | An |
| 2016/0040978 A1 | 2/2016 | Boppart |
| 2016/0081545 A1 | 3/2016 | Hauger |
| 2016/0082129 A1 | 3/2016 | Peters |
| 2016/0106310 A1 | 4/2016 | Moriguchi |
| 2016/0106312 A1 | 4/2016 | Moriguchi |
| 2016/0106314 A1 | 4/2016 | Everett |
| 2016/0166143 A1 | 6/2016 | Goto |
| 2016/0206190 A1 | 7/2016 | Reisman |
| 2016/0242638 A1 | 8/2016 | Durbin |
| 2016/0252340 A1 | 9/2016 | Hollenbeck |
| 2016/0270656 A1* | 9/2016 | Samec ............... A61B 3/063 |
| 2016/0321828 A1 | 11/2016 | Tachikawa |
| 2016/0338589 A1 | 11/2016 | Carrasco-Zevallos |
| 2016/0367129 A1 | 12/2016 | Coelho |
| 2016/0367132 A1 | 12/2016 | Yun |
| 2017/0007182 A1 | 1/2017 | Samec |
| 2017/0020387 A1 | 1/2017 | Fingler |
| 2017/0049318 A1 | 2/2017 | Walsh |
| 2017/0055829 A1 | 3/2017 | Tan |
| 2017/0065169 A1 | 3/2017 | Fukasawa |
| 2017/0074640 A1 | 3/2017 | Cable |
| 2017/0102223 A1 | 4/2017 | Izatt |
| 2017/0105618 A1 | 4/2017 | Schmoll |
| 2017/0140560 A1 | 5/2017 | Kraus |
| 2017/0205223 A1 | 7/2017 | Cable |
| 2017/0227350 A1 | 8/2017 | Sarunic |
| 2017/0231489 A1 | 8/2017 | Fujimori |
| 2017/0241763 A1 | 8/2017 | Wang |
| 2017/0268987 A1 | 9/2017 | Swanson |
| 2017/0276471 A1 | 9/2017 | Jiang |
| 2017/0280993 A1 | 10/2017 | Fukuhara |
| 2017/0311795 A1 | 11/2017 | Sumiya |
| 2017/0356740 A1 | 12/2017 | Ansari |
| 2018/0012359 A1 | 1/2018 | Prentasic |
| 2018/0031363 A1 | 2/2018 | Johnson |
| 2018/0051978 A1 | 2/2018 | Flanders |
| 2018/0055358 A1 | 3/2018 | Nakajima |
| 2018/0084994 A1 | 3/2018 | Su |
| 2018/0125354 A1 | 5/2018 | Pulaski |
| 2018/0135962 A1 | 5/2018 | Murata |
| 2018/0156598 A1 | 6/2018 | Cable |
| 2018/0157924 A1 | 6/2018 | Hogan |
| 2018/0168445 A1 | 6/2018 | Horn |
| 2018/0206716 A1 | 7/2018 | Chong |
| 2018/0289256 A1 | 10/2018 | Murata |
| 2019/0365220 A1 | 12/2019 | Frisken |
| 2019/0380574 A1 | 12/2019 | Chen |
| 2020/0093363 A1 | 3/2020 | Saika |
| 2020/0196858 A1 | 6/2020 | Scheibler |

(56) References Cited

U.S. PATENT DOCUMENTS

2020/0342595 A1    10/2020    Jia
2020/0372632 A1    11/2020    Chauhan

FOREIGN PATENT DOCUMENTS

| | | |
|---|---|---|
| EP | 2892413 | 7/2015 |
| JP | 201172716 | 4/2011 |
| JP | 201483266 | 5/2014 |
| JP | 2016514828 | 5/2016 |
| WO | 9320743 | 10/1993 |
| WO | 2009120544 | 10/2009 |
| WO | 2015082001 | 6/2015 |
| WO | 2015116981 | 8/2015 |
| WO | 2015120055 | 8/2015 |
| WO | 2016040534 | 3/2016 |
| WO | 2016073840 | 5/2016 |
| WO | 2016115387 | 7/2016 |
| WO | 2016125474 | 8/2016 |
| WO | 2016127140 | 8/2016 |
| WO | 2016148569 | 9/2016 |
| WO | 2016178298 | 11/2016 |
| WO | 2016179431 | 11/2016 |
| WO | 2016196463 | 12/2016 |
| WO | 2016203245 | 12/2016 |
| WO | 2017002379 | 1/2017 |
| WO | 2017025583 | 2/2017 |
| WO | 2017046225 | 3/2017 |
| WO | 2017048832 | 3/2017 |
| WO | 2017165793 | 9/2017 |
| WO | 2017176301 | 10/2017 |
| WO | 2017206929 | 12/2017 |
| WO | 2017216242 | 12/2017 |
| WO | 2018086173 | 5/2018 |
| WO | 2018089682 | 5/2018 |
| WO | 2018105549 | 6/2018 |
| WO | 2018116128 | 6/2018 |
| WO | 2018119077 | 6/2018 |
| WO | 2019210079 | 10/2019 |
| WO | 2019246412 | 12/2019 |
| WO | 2020036182 | 2/2020 |
| WO | 2021134087 | 7/2021 |

OTHER PUBLICATIONS

International Search Report and Written Opinion for International Application No. PCT/US2019/030682, 33 pages (dated Nov. 1, 2019).

Moon, S., et al., "VCSEL-based swept source for low-cost optical coherence tomography", Biomedical Optics Express, 8(2):1110-1121 (Feb. 1, 2017).

ORR. Notal Vision—Home-Based Optical Coherence Tomograph (OCT). Slide deck (11 pgs.) (Nov. 9, 2017).

Bengio, Yoshua, et al., "Curriculum Learning," 8 pages, retrieved from http://machinelearning.org/archive/icml2009/papers/119.pdf on Jun. 14, 2021.

Huang, Huimin, et al., "UNET 3+: A Full-Scale Connected UNET for Medical Image Segmentation," 5 pages, retrieved from https://arxiv.org/ftp/arxiv/papers/2004/2004.08790.pdf on Jun. 14, 2021.

Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).

Khan, Zuhaib, et al., "High-brightness and high-speed vertical-cavity surface-emitting laser arrays," Optica, 7(4):267-275 (Apr. 2020).

Kim, Sanghoon, et al., "Design and implementation of a low-cost, portable OCT system," Biomedical Optics Express, 9(3):1232-1243 (Mar. 2018).

Mishra, Z., et al., "Automated Retinal Layer Segmentation Using Graph-based Algorithm Incorporating Deep-learning-derived Information," Sci Rep. 10(1):9541 (2020).

Zara, J.M., et al., "Electrostatic micromachine scanning mirror for optical coherence tomography," Optics Letters, 28(8):628-630 (Apr. 15, 2003).

Girish et al. Segmentation of Intra-Retinal Cysts From Optical Coherence Tomography Images Using a Fully Convolutional Neural Network Model. IEEE Journal of Biomedical and Health Informatics, vol. 23, No. 1, Jan. 2019, pp. 296-304 (Year: 2019).

Haglund, Erik, et al., "Multi-wavelength VCSEL arrays using high-contrast gratings," Proc. of SPIE vol. 10113, 7 pages (2017).

Huang, et al., "Optical coherence tomograph," Science, 254(5035):1178-1181 (Nov. 22, 1991).

WO 2020/036182 A1 machine translation from Japanese to English (132 pages).

Bertera, J.H., et al., "Stabilized Retinal Mapping of Known Retinal Loci," Proceedings of the Annual Northeast Bioengineering Conference, IEEE, vol. Conf. 14, No. 1988, XP000010509 (Mar. 10, 1988).

Pierro, L., et al., "Macular Thickness Interoperator and Intraoperator Reproducibility in Healthy Eyes Using 7 Optical Coherence Tomography Instruments," American Journal of Ophthalmology, 150(2): 199-204, XP027174249 (Aug. 1, 2010).

* cited by examiner

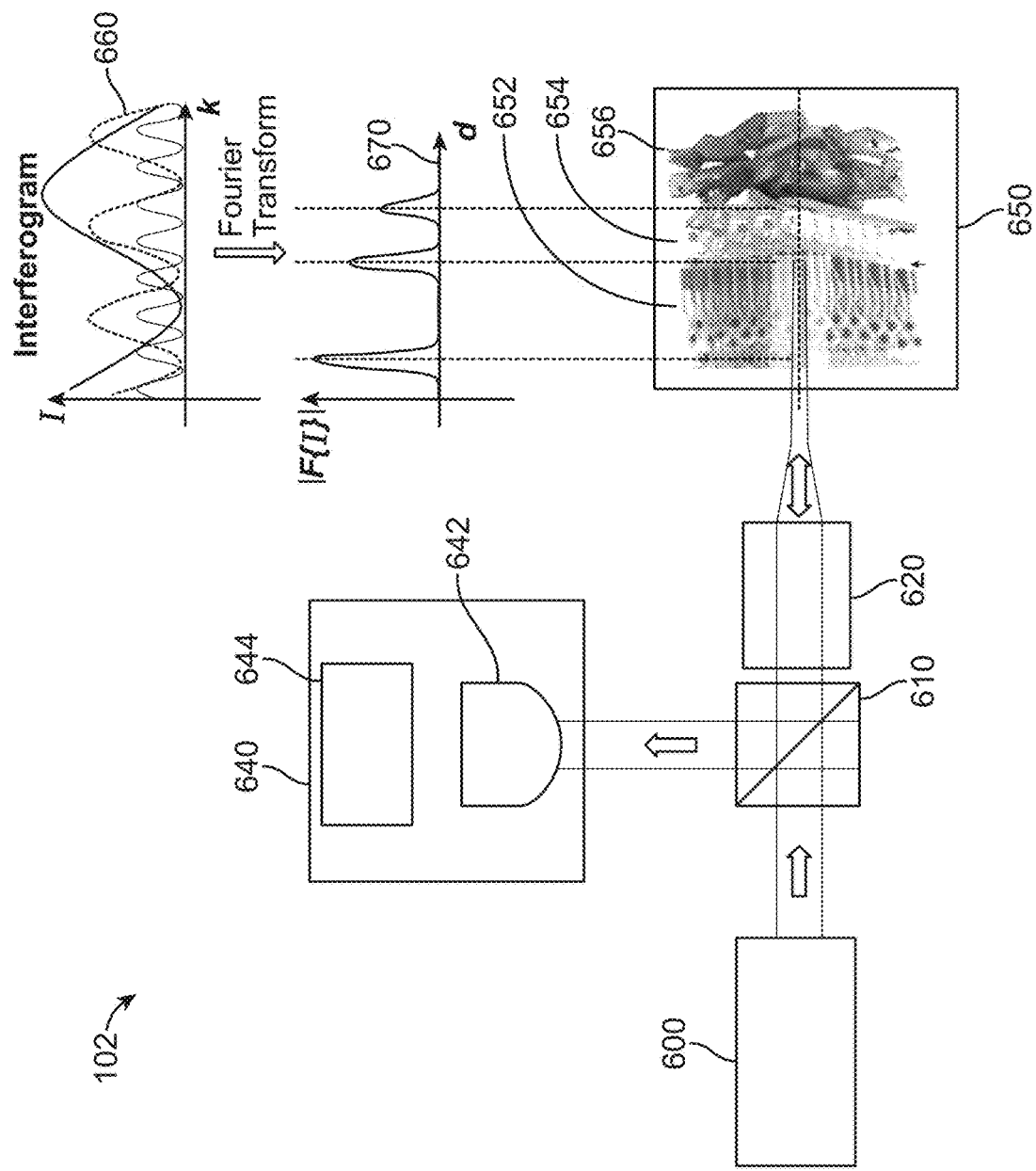

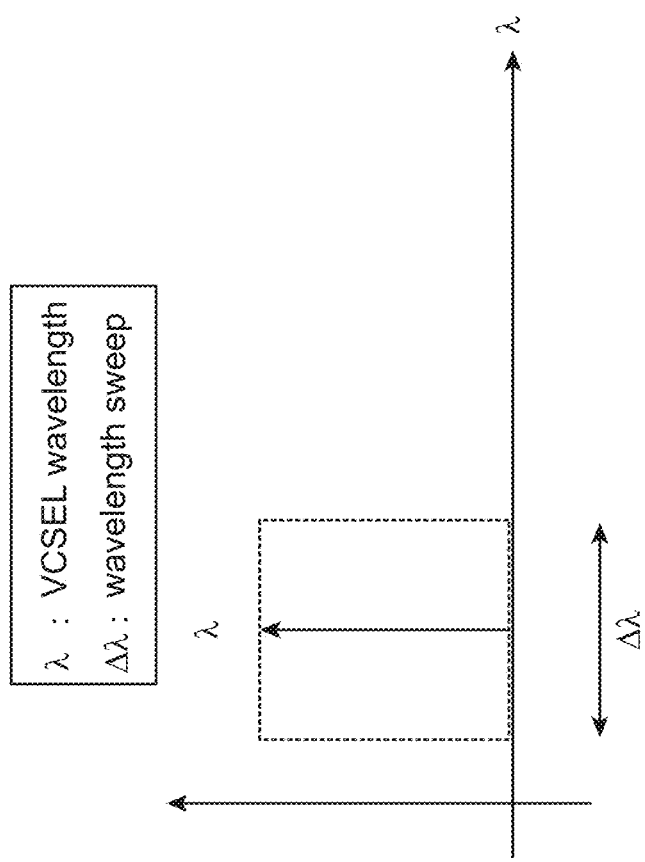

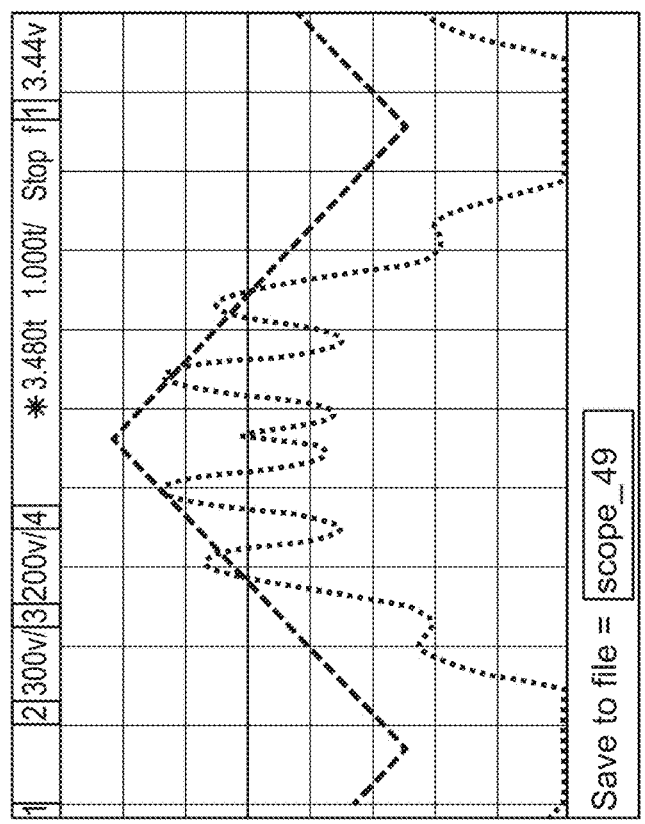
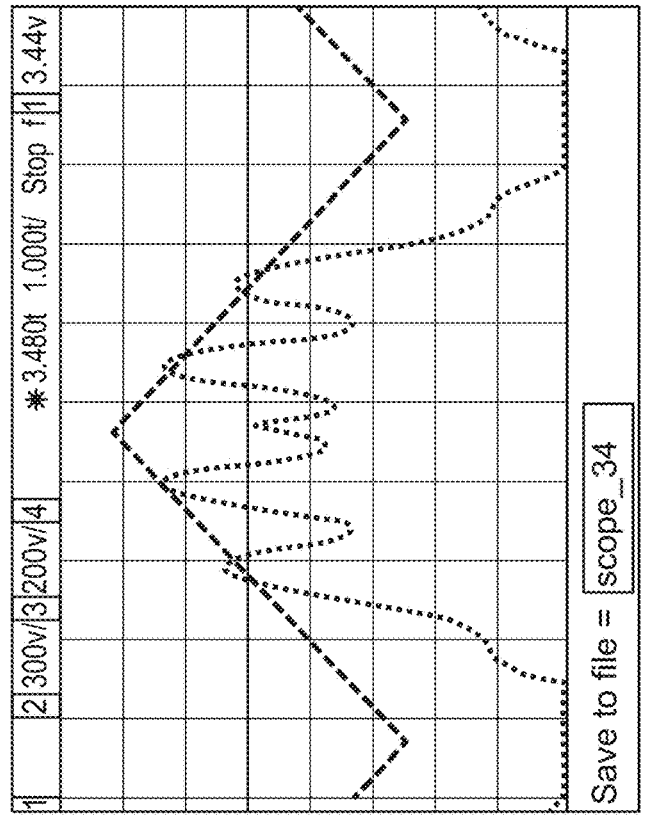
FIG. 16

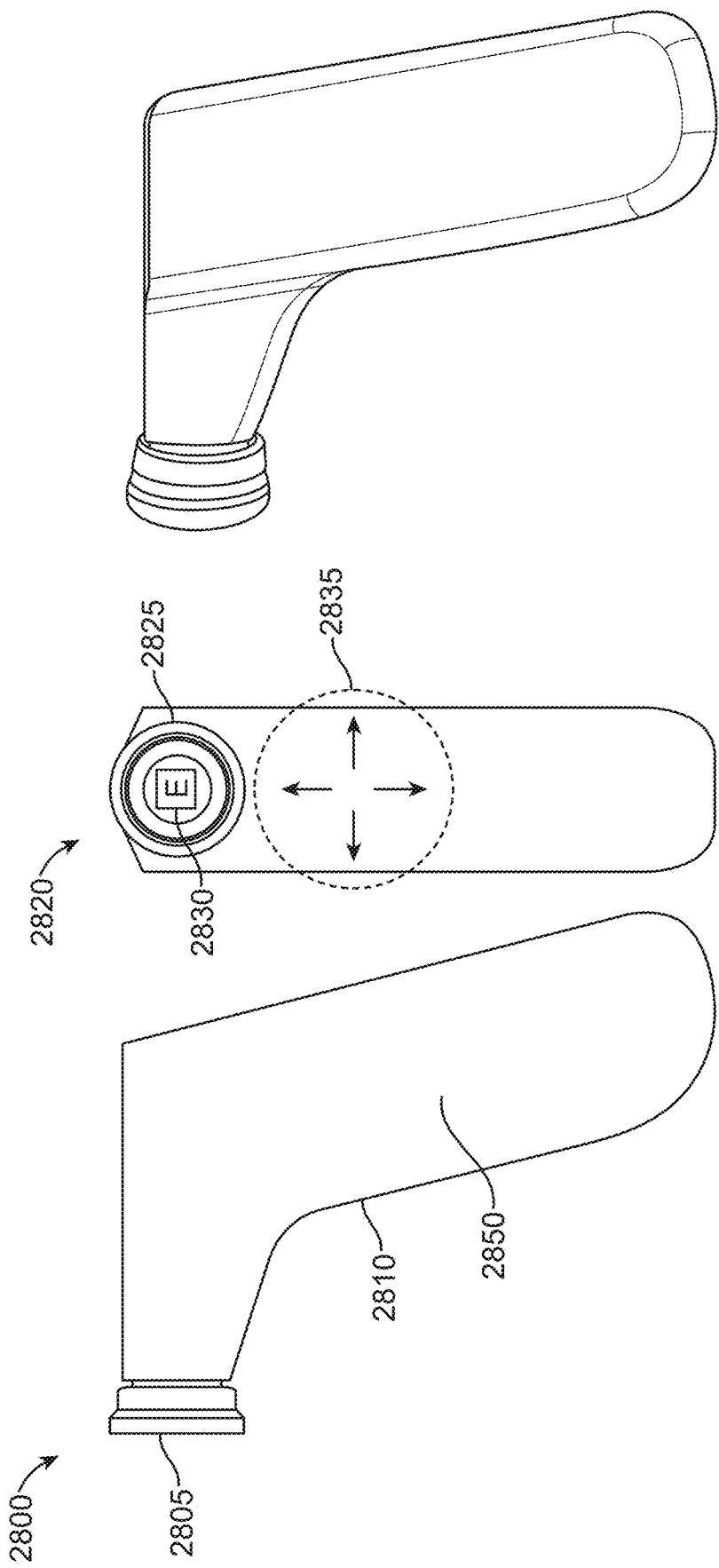

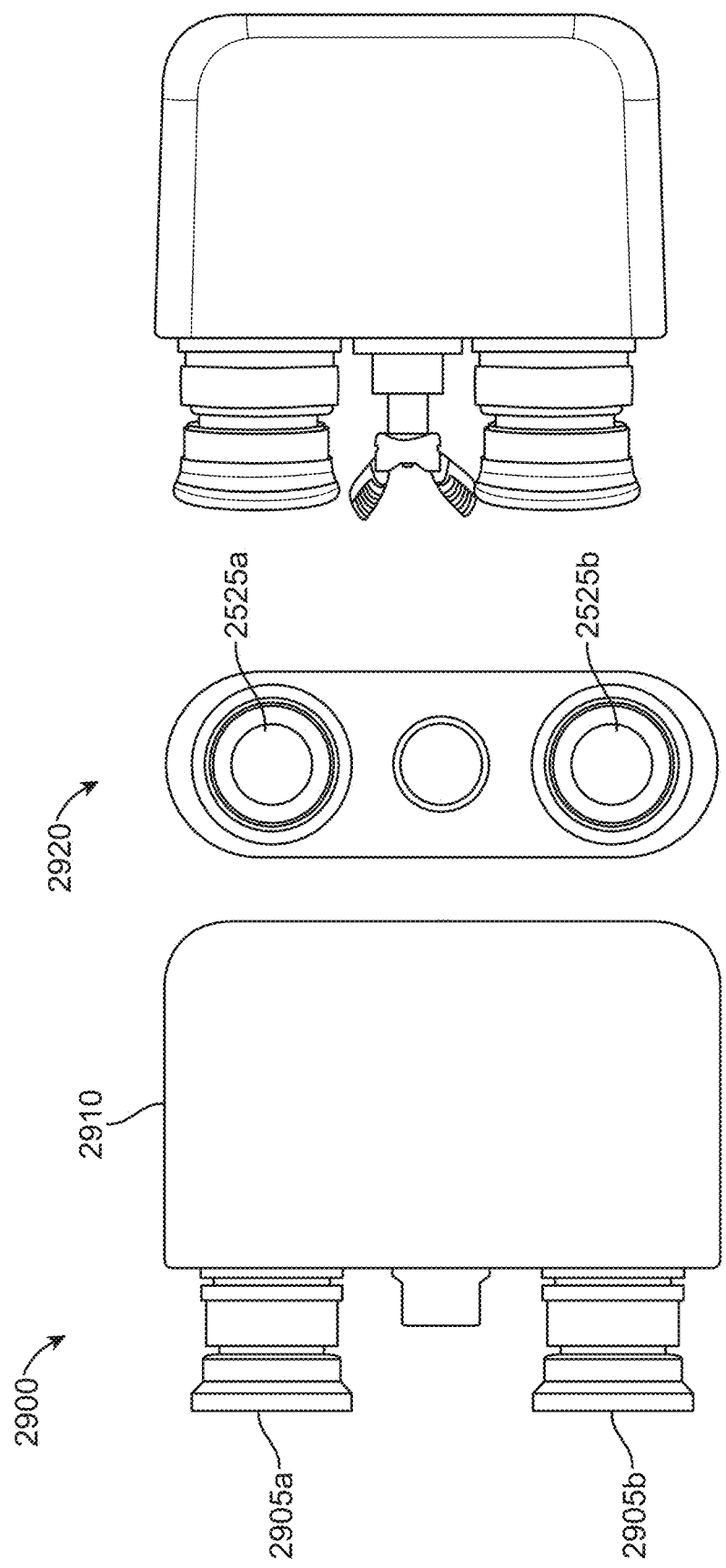

Detector Image: Coherent Irradiance

Detector Image: Coherent Irradiance

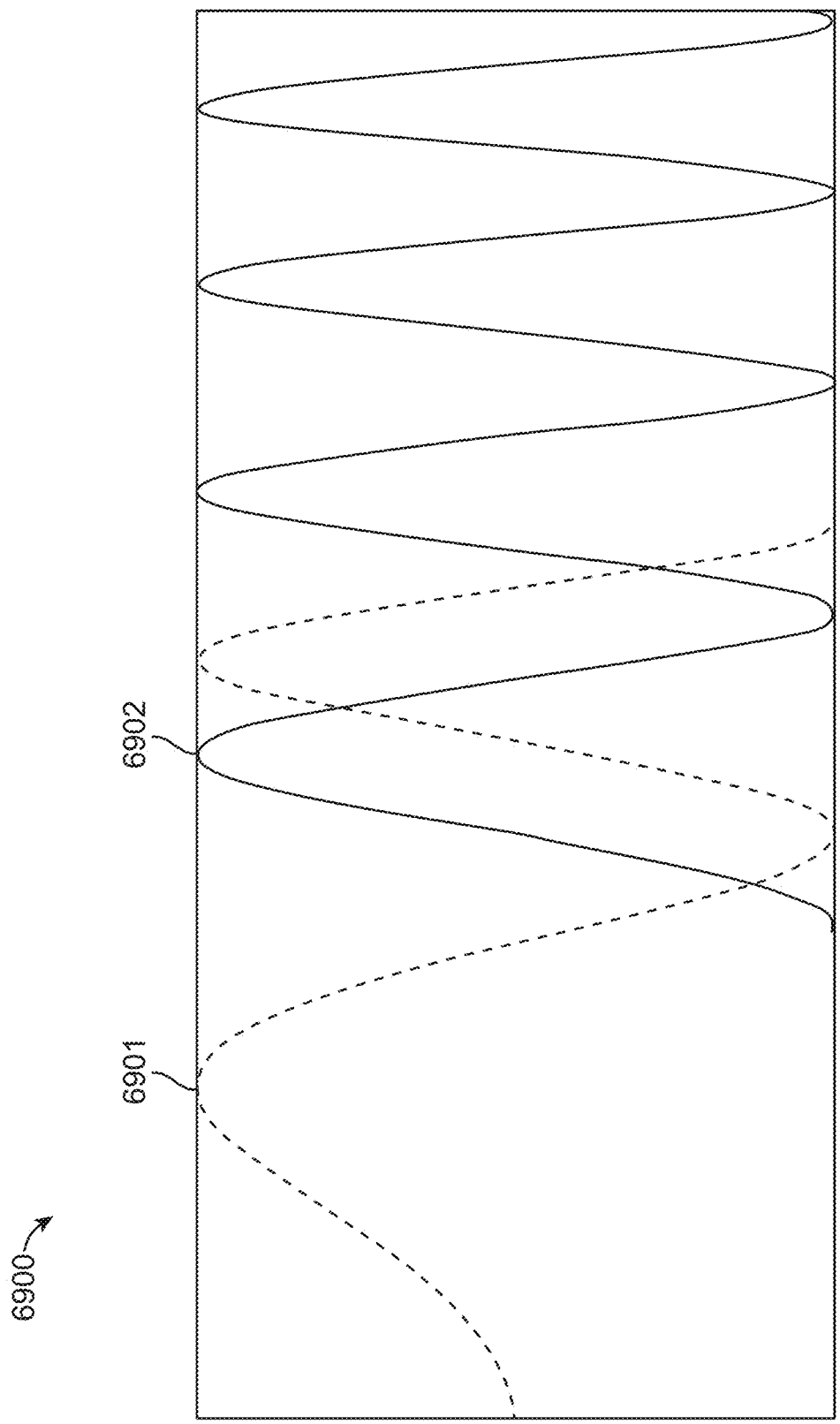

Raw clock signals

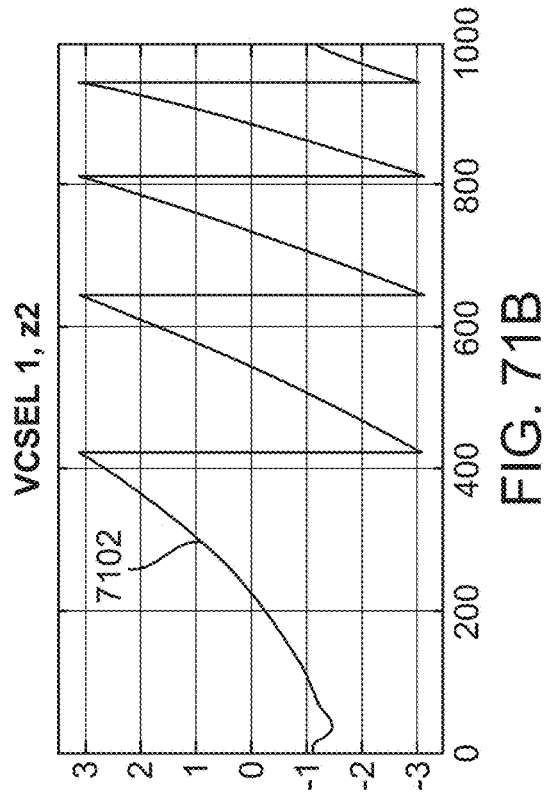
FIG. 71A
FIG. 71B
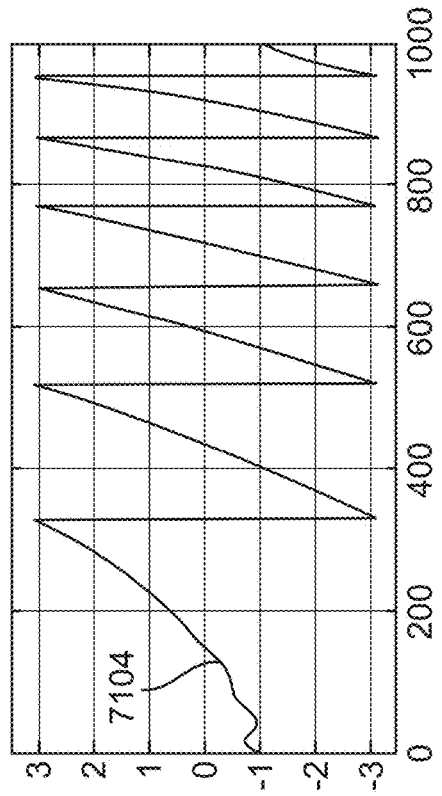
FIG. 71C
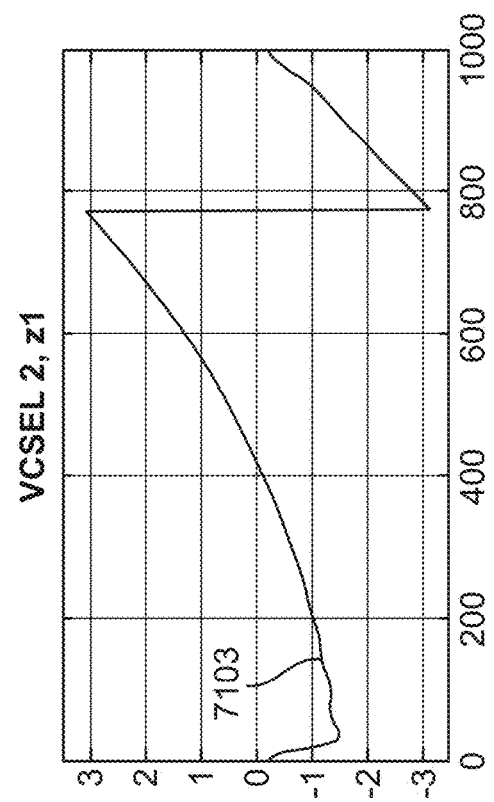
FIG. 71D

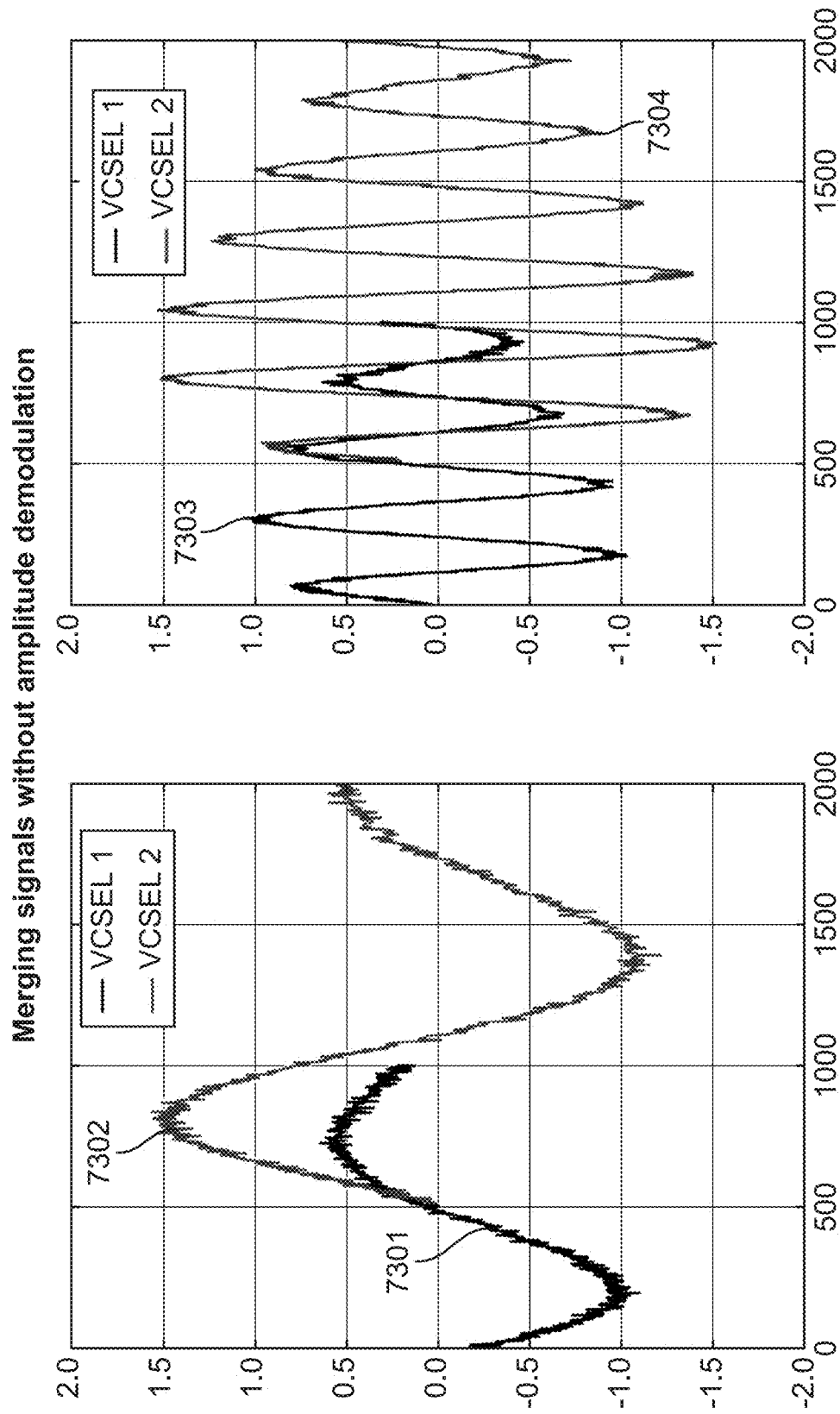

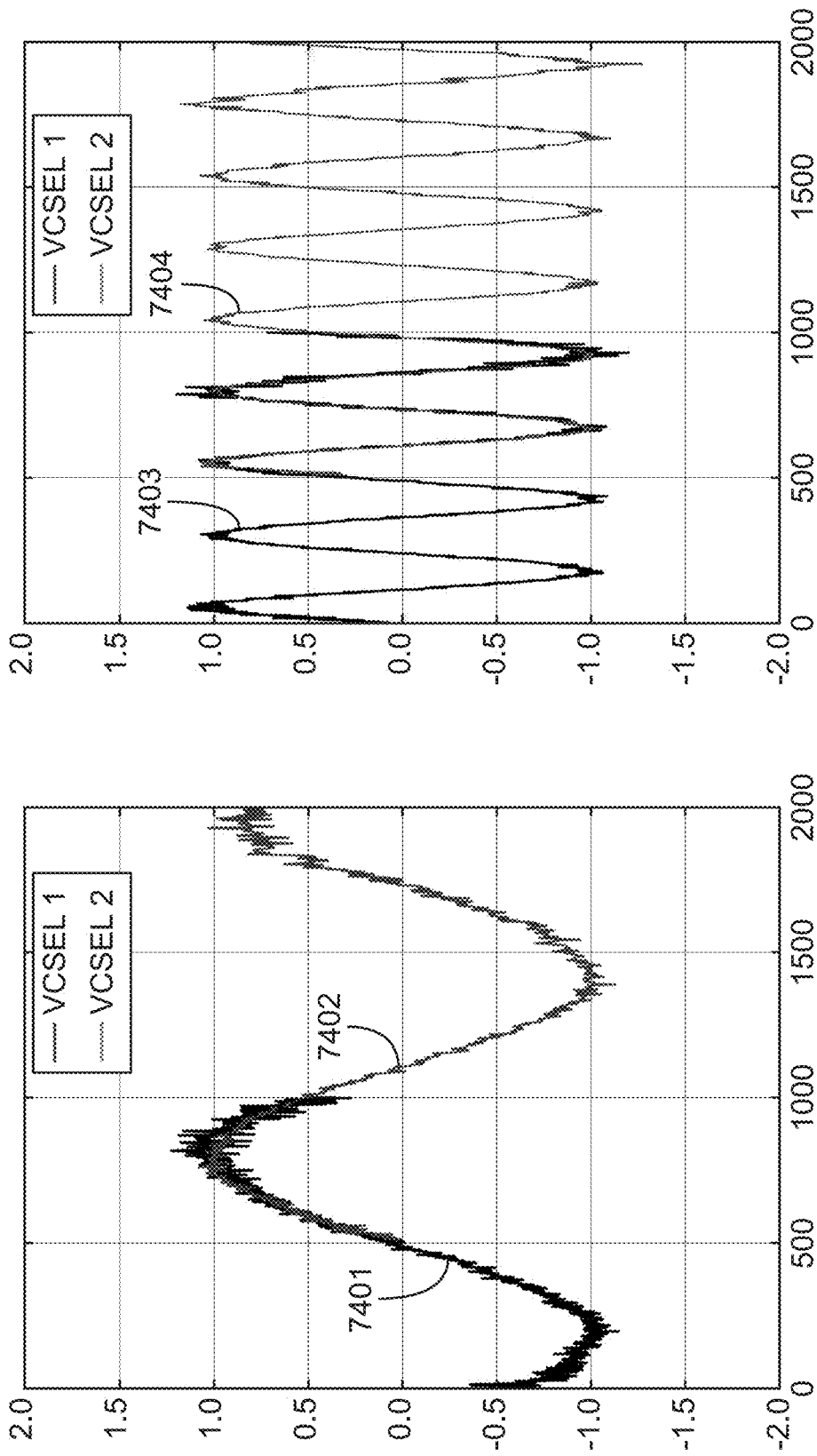

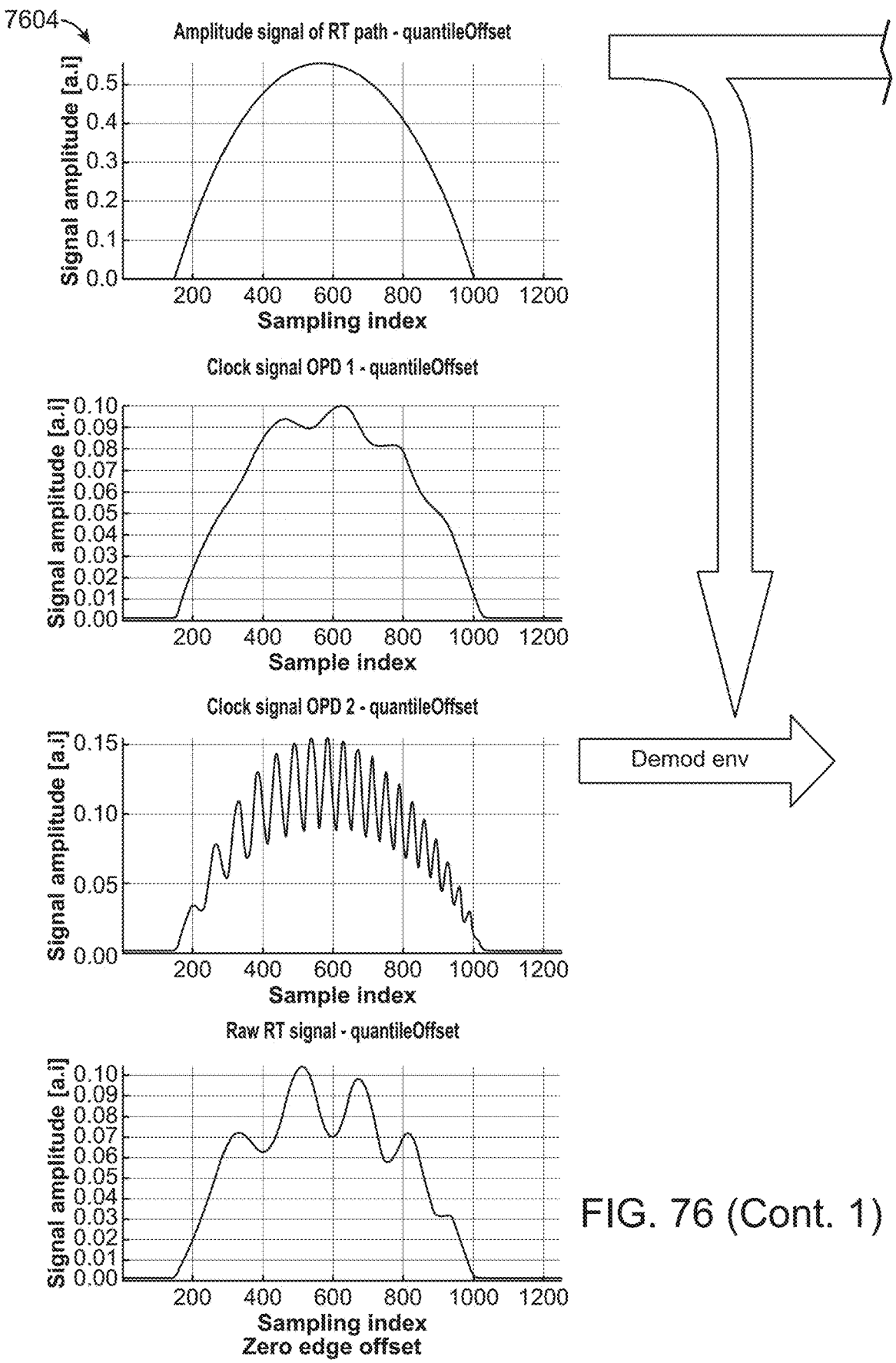
FIG. 76 (Cont. 1)

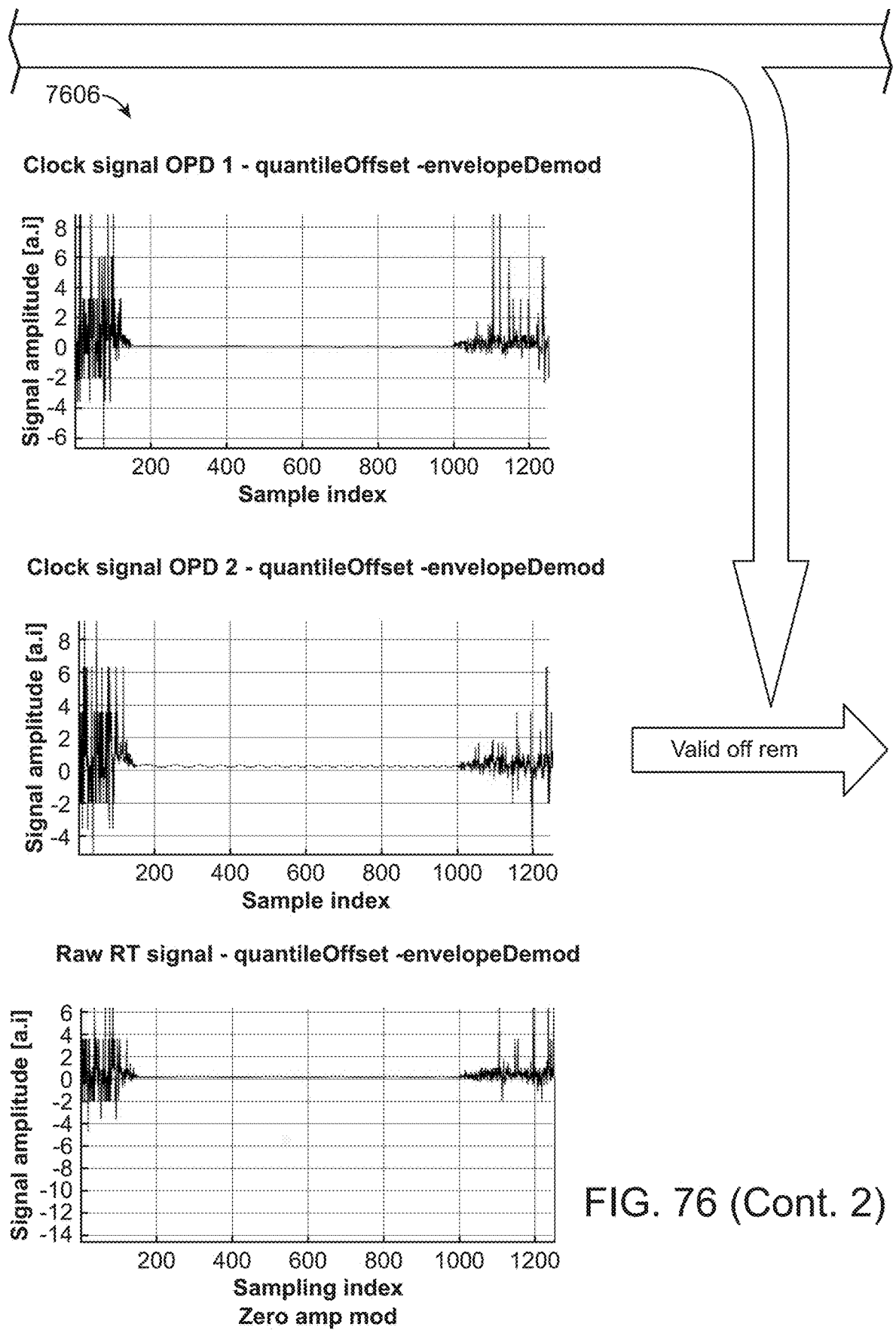
FIG. 76 (Cont. 2)

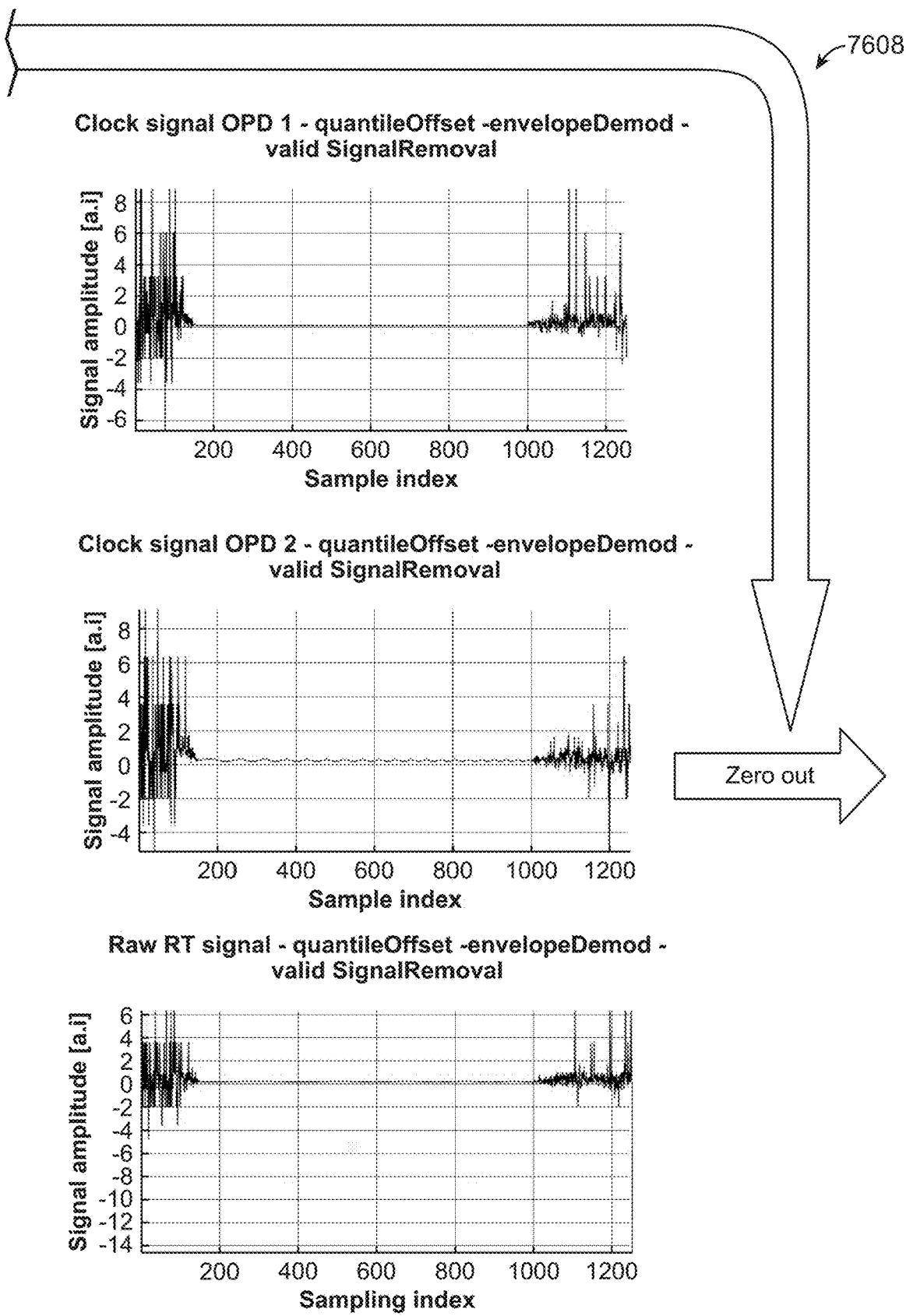
FIG. 76 (Cont. 3)

7610
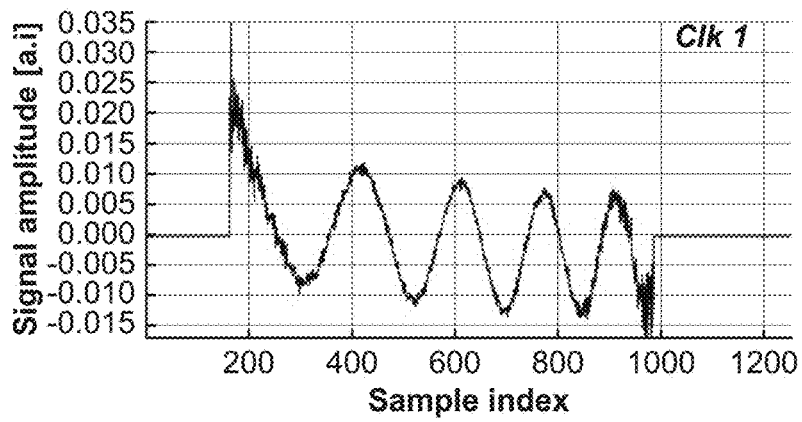
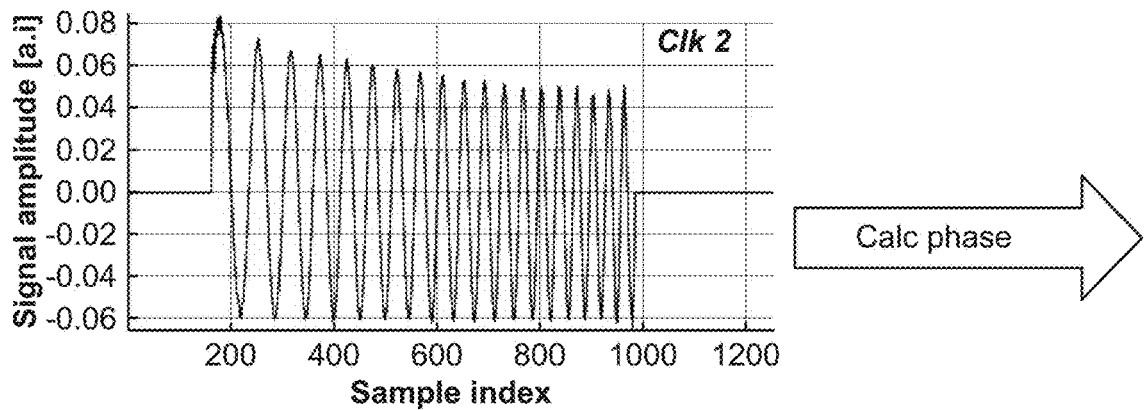
Calc phase →
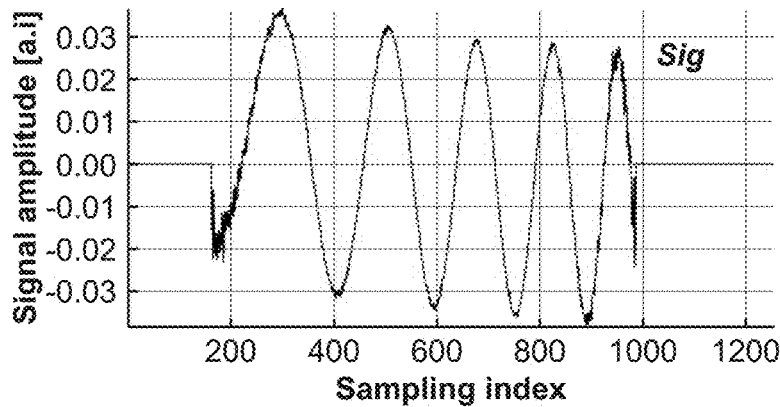
Valid scope zoom
FIG. 76 (Cont. 4)

7612
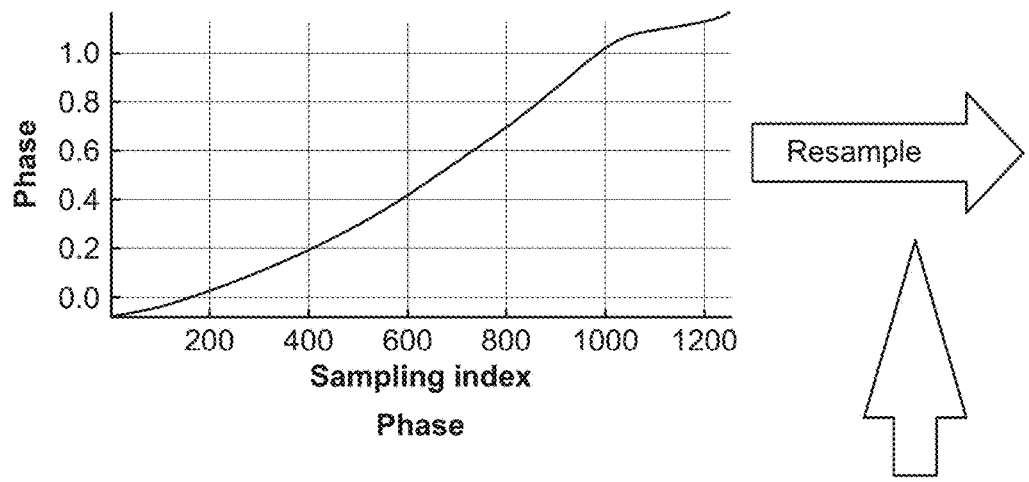
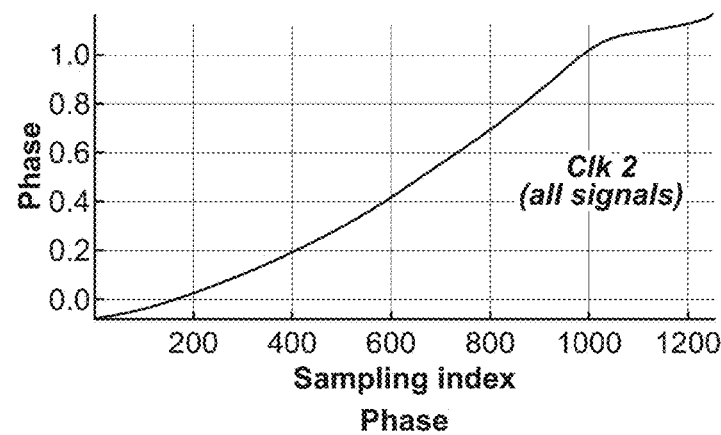
FIG. 76 (Cont. 5)

Amplitude signal of RT path - quantileOffset 7614
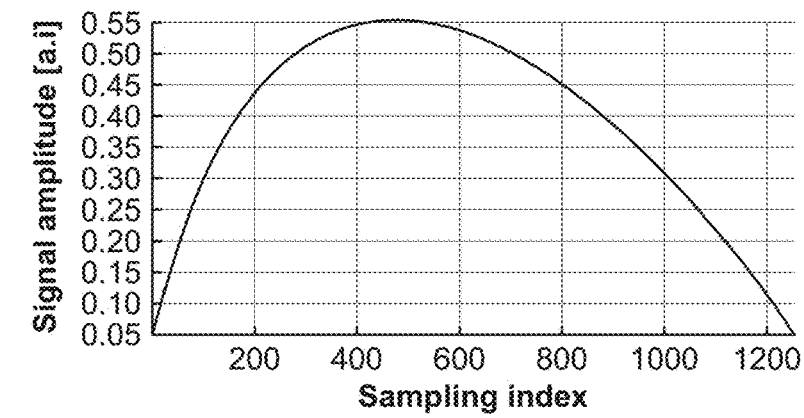
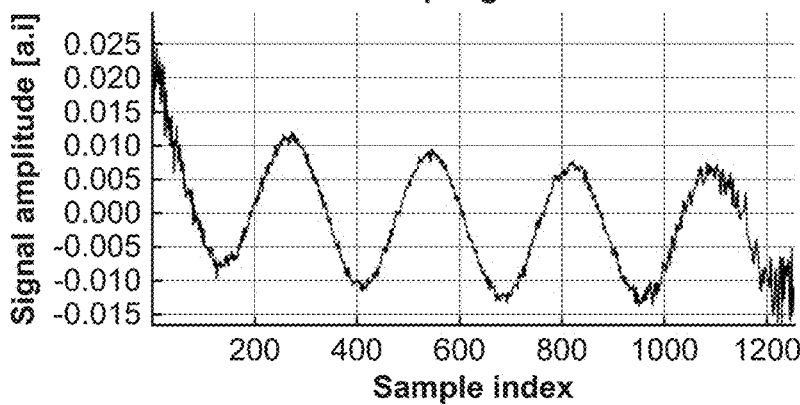
Calc phase →
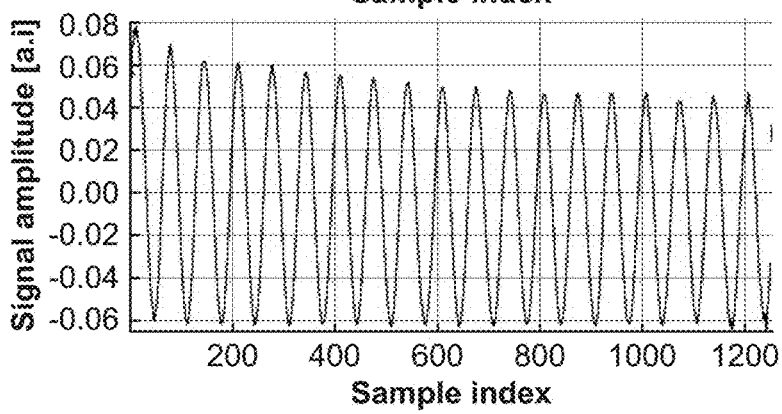
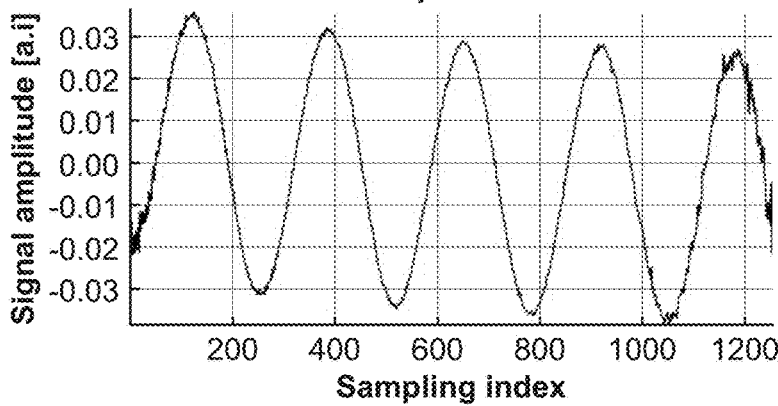
Resampled
FIG. 76 (Cont. 6)

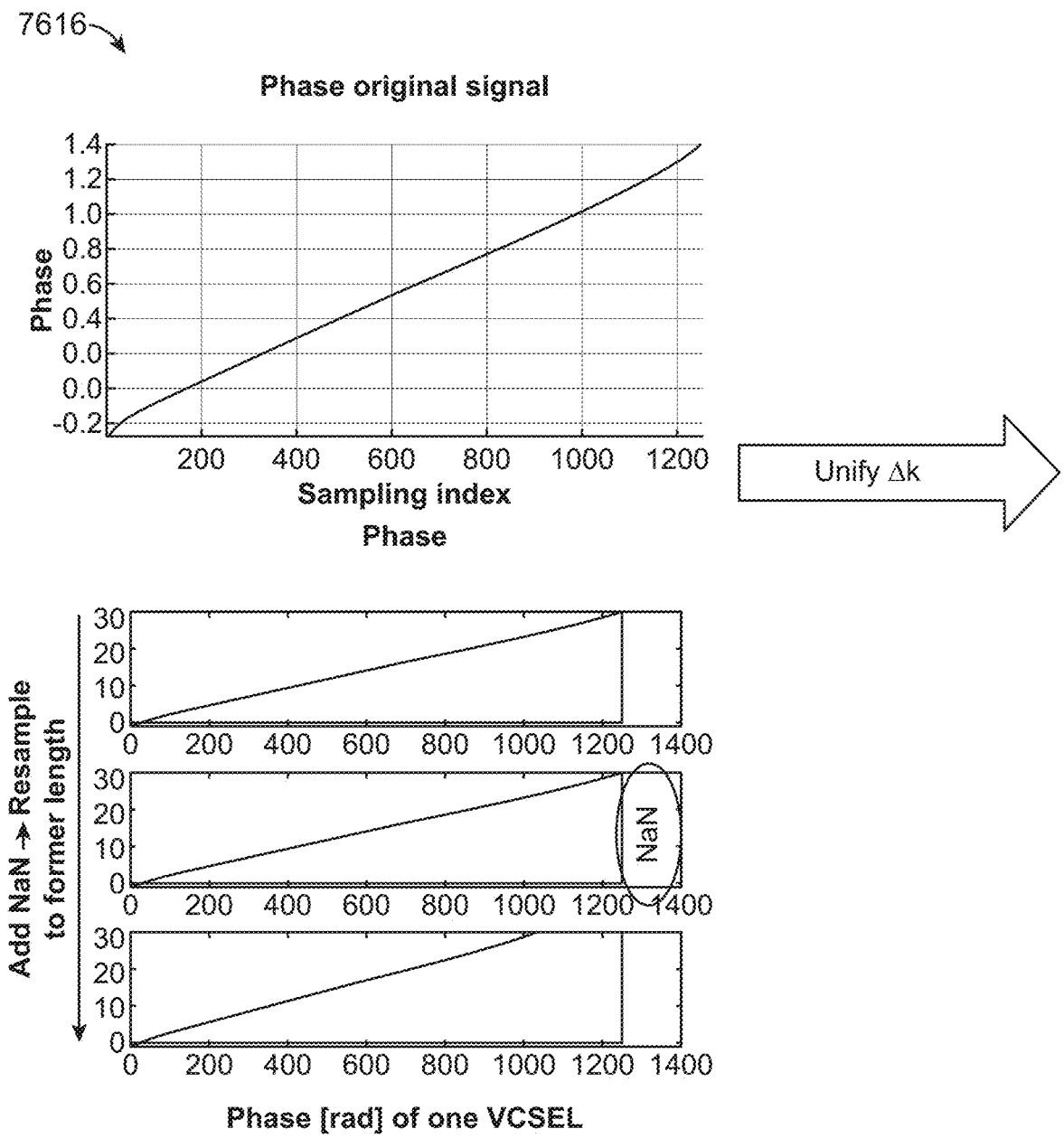
FIG. 76 (Cont. 7)

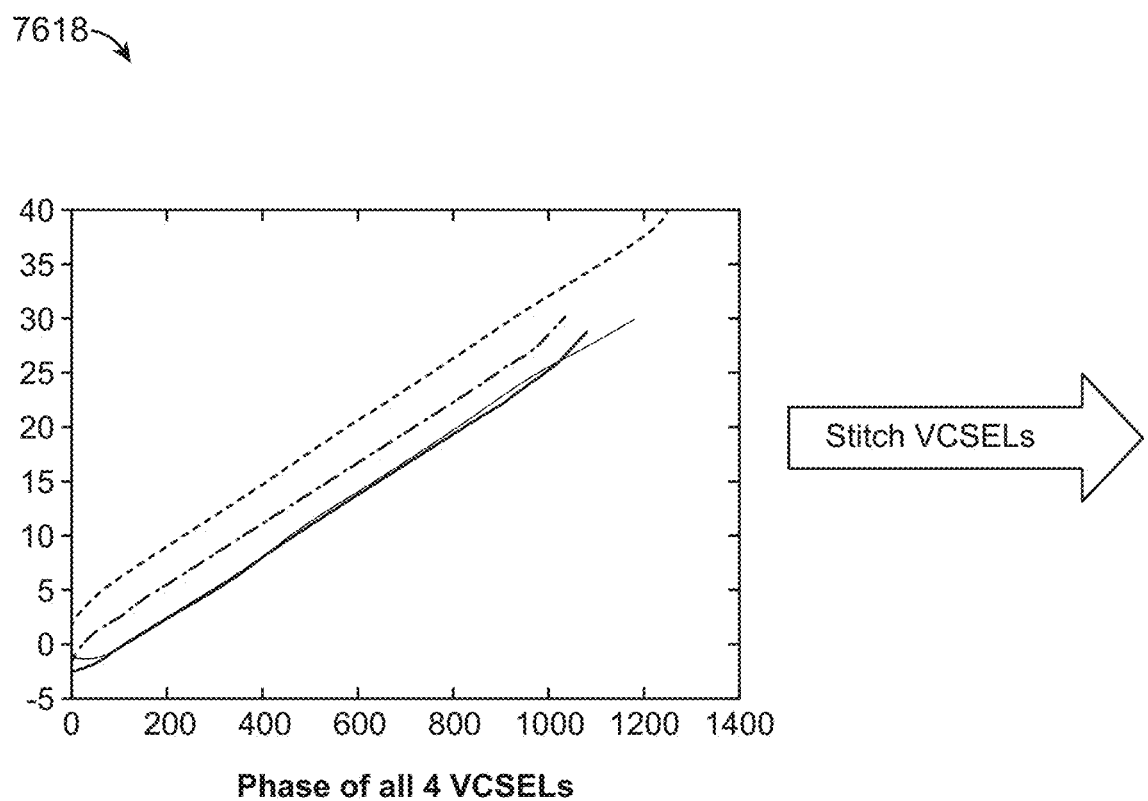
FIG. 76 (Cont. 8)

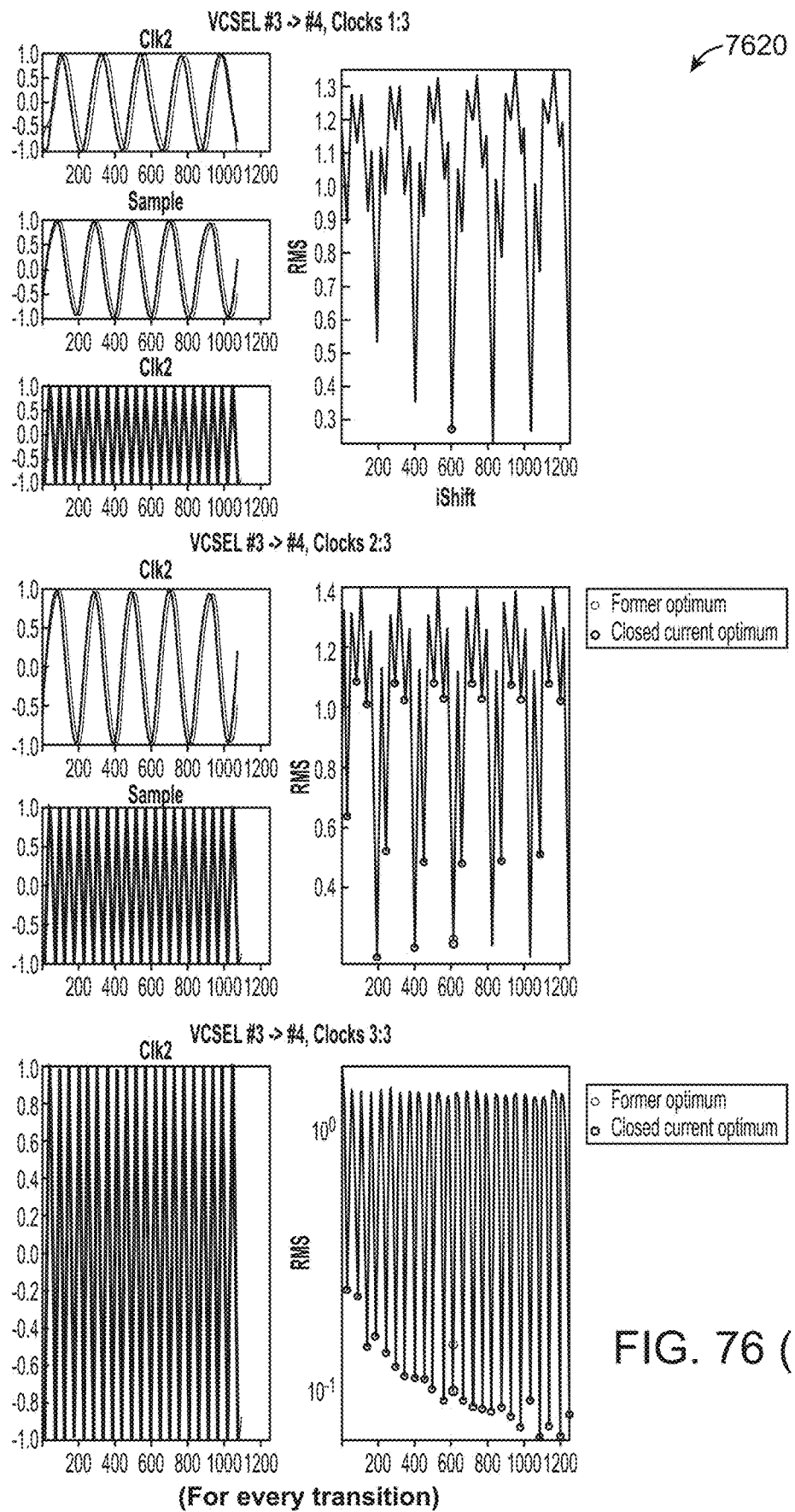
FIG. 76 (Cont. 9)

MINIATURIZED MOBILE, LOW COST OPTICAL COHERENCE TOMOGRAPHY SYSTEM FOR HOME BASED OPHTHALMIC APPLICATIONS

RELATED APPLICATIONS

This application is a continuation of International Application No. PCT/US2019/038270, filed Jun. 20, 2019, published as WO 2019/246412, on Dec. 26, 2019, which claims the benefit under 35 U.S.C. § 119(e) of U.S. Provisional Application No. 62/687,686, filed Jun. 20, 2018, entitled "Miniaturized Mobile, Low Cost Optical Coherence Tomography System for Home Based Ophthalmic Applications", the entire disclosures of which are incorporated herein by reference.

BACKGROUND

The eye is critical for vision, and people need to see. The eye has a cornea and lens that refract light and form an image on the retina. The retina generates electrical signals in response to the image formed thereon, and these electrical signals are transmitted to the brain via the optic nerve. The fovea and macula of the retina have an increased density of cones in relation to other areas of the retina and provide crisp, sharp vision. Unfortunately, diseases of the retina can adversely affect vision even though other parts of the eye, such as the cornea and lens are healthy.

Retinal thickness can be used to diagnose and monitor the health of the retina. Many patients who have been diagnosed with retinal vascular diseases and other diseases or conditions have an elevated retinal thickness and take or are treated with medications. Macular edema is an example of elevated retinal thickness which is often related to other diseases such as diabetes. Macular edema can be related to other diseases such as age related macular degeneration, uveitis, blockage of retinal vasculature, and glaucoma, for example. It would be helpful to know quickly if a medication is not working or requires re-administration so that treatment can be modified accordingly and vision preserved. One approach used to measure the thickness of the retina is optical coherence tomography (OCT).

Unfortunately, many prior OCT systems are overly complex and expensive and not well-suited to monitoring retinal thickness regularly, such as on a weekly or daily basis. The prior standard of eye care involves a visit to a health care provider who measures retinal thickness, but such visits require scheduling and appointments and can become expensive, especially if conducted on a weekly or daily basis. Many of the prior OCT systems are not well-suited for in-home monitoring or mobile health care. Such prior systems typically weigh more than a person can easily carry and are not-well suited to travel with the patient. In addition, the prior OCT systems are more complex than would be ideal, and not well-suited for everyday use and hazards such as being dropped. The prior cost of an OCT system may exceed what a typical patient can afford. Furthermore, use of a prior OCT system may require a trained operator. For the above reasons, in-home monitoring of retinal thickness has not been adopted as the prior standard of care and prior care of patients with retinal disease can be less than ideal in many instances.

In light of the above, it would be helpful to have improved OCT systems and methods to measure thickness of the retina. Ideally, such systems would be compact, handheld, provide in-home monitoring, allow the patient to measure himself or herself, and be robust enough to be dropped while still measuring the retina reliably.

SUMMARY

The compact optical coherence tomography (OCT) system and methods disclosed herein allow in-home and mobile monitoring of retinal thickness. Although specific reference is made to measuring retinal thickness, the compact OCT system and methods disclosed herein will find application in many fields, such as microscopy, metrology, aerospace, astronomy, telecommunications, medicine, pharmaceuticals, dermatology, dentistry, and cardiology.

In some embodiments, the compact OCT system comprises a plurality of light sources such as a plurality of VCSELs in order to extend a spectral range an increase resolution of the OCT system. The plurality of light sources can be sequentially activated to measure a sample structure such as a retinal layer of the eye with a plurality of light beams, each comprising a different spectral range. The measurement signals from each of the plurality of light beams can be combined. The OCT system may comprise a plurality of phase compensation modules that generate periodic signals in response to wavelength changes, and these periodic signals can be used by the processor circuitry and instructions in order to more accurately combine measurements from each of the plurality of light sources. Each of the plurality of light beams generated by each of the plurality of light sources travels along an optical path, and optics can be configured to at least partially overlap the optical paths of the light beams. While the plurality of light sources can be arranged in many ways, in some embodiments the plurality of light sources is arranged on a support to direct the plurality of light beams toward the optics. Although the optical paths of the plurality of light beams may not fully overlap, the circuitry can be coupled to a scanner and configured to activate the light beams so to increase overlap of the illuminate regions as compared to the overlap of the illuminated regions without scanning.

The compact OCT system comprises a plurality of components arranged to provide a decreased optical path and weight. In many embodiments, the compact OCT system is configured to measure changes in retinal thickness that are less than a resolution value of the OCT system, which allows the size, cost and complexity to be decreased significantly. The system comprises sufficient repeatability and reproducibility to accurately detect changes in retinal thickness smaller than the system axial resolution value. The compact OCT system is capable of scanning the wavelength range and acquiring OCT data with sufficient speed in order to decrease errors associated with movement of the system in relation to the eye. In many embodiments, the compact OCT system is calibrated for a specific patient with a clinical reference system having a higher resolution than the compact OCT system, and the compact OCT system is calibrated to the specific patient based on the retinal thickness measured with the clinical reference system. In some cases, the compact OCT system comprises a calibration kit or fixture, which allows the system to be tested to ensure that the repeatability and reproducibility remain within acceptable tolerances.

In some instances, the compact OCT system is configured to be held in the hand of user for the patient to measure himself or herself. Alternatively, the compact OCT system may be configured to be mounted to a table stand or to the head of the user. In some embodiments, the compact OCT system comprises a visible target for the patient to align himself or herself with the compact spectrometer while the patient holds the measurement components of the system with his hand. The compact OCT system comprises a housing to contain the measurement components, and the housing is sized, in some instances, such that the user can readily grasp the housing and lift the measurement components within the housing and align the OCT system with his eye. The compactness and decreased mass of the OCT system allows the system to be easily held in the hand of the patient and transported with the patient. In many embodiments, the tomography system comprises a maximum dimension across within a range from about 80 mm to about 160 mm, and a mass within a range from about 100 grams to about 500 grams. In many embodiments, the OCT system is configured without internal moving parts in order to increase the reliability of the system. The compact OCT system is optionally configured to be dropped from a distance of about one foot, and provide a change in measurement repeatability and accuracy of retinal thickness of no more than about 25 µm, for example.

In some embodiments, the compact OCT system comprises a light source configured to emit a plurality of wavelengths, a detector, optical elements arranged to generate an optical interference signal on the detector, and circuitry coupled to the detector and light source. In some embodiments, the light source comprises a light source configured to emit a light beam of varying wavelength in order to sweep the wavelength over a range of wavelengths. In some instances, the wavelengths are swept over a range from about 3 nm to 10 nm in order to measure the thickness of the retina. This range can provide decreased system complexity and cost with sufficient axial resolution, repeatability, and reproducibility to determine changes in retinal thickness by 25 µm or less, although longer wavelength sweeps can be used. In some embodiments, the sweeping range of the OCT system within a range from 3 nm to 10 nm allows detection of retinal thickness larger than about 150 µm and changes in retinal thickness as small as 25 µm, for example, with the compact OCT system, although longer wavelength sweeps can be used. The circuitry is configured, in some embodiments, to drive the light source with a waveform having a characteristic period and sweeping frequency, such as a saw tooth waveform. In some instances, the circuitry is coupled to the detector to measure frequencies of an interference signal from the light returned from eye to determine retinal thickness of the eye, although the thickness of other objects can be measured. In some embodiments, the circuitry is configured to drive the light source over a maximum rated current threshold for a portion of the waveform and below the maximum rated current threshold for another portion of the waveform, in which the light source emits light during both portions of the waveform. This overdriving of the light source within a portion of the waveform allows for an extended wavelength range of the light source and increased measurement range with decreased complexity, size, and weight of the OCT system.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6A shows a schematic for a SS-OCT device lacking a reference mirror, in accordance with some embodiments.

FIG. 6B shows the wavelength range over which the vertical cavity surface emitting laser (VCSEL) operates in the SS-OCT device lacking a reference mirror, in accordance with some embodiments.

FIG. 16 shows oscilloscope signals for two different configurations of the optical setup.

FIG. 28A and FIG. 28B show a configuration for a handheld monocular OCT system, in accordance with some embodiments;

FIG. 29A, FIG. 29B, and FIG. 29C show a configuration for an exemplary handheld binocular OCT system, in accordance with some embodiments;

FIG. 69 shows waveforms of two VCSELs that are out of phase and suitable for being stitched together into a single signal, in accordance with some embodiments;

FIG. 71A, FIG. 71B, FIG. 71C, and FIG. 71D show plots of the phase wrapping of the raw clock signals of FIGS. 70A to 70D, in accordance with some embodiments;

FIG. 73A and FIG. 73B show plots of clockbox waveform signals generated by first and second VCSELs being merged without amplitude demodulation, in accordance with some embodiments;

FIG. 74A and FIG. 74B show plots of waveforms generated by first and second VCSELs being merged with amplitude demodulation, in accordance with some embodiments;

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed. For example, although reference is made to measuring a thickness of a sample such as the retina, the methods and apparatus disclosed herein can be used to measure many types of samples, such as other tissues of the body and non-tissue material. While reference is made to generating maps of retinal thickness, the methods and apparatus disclosed herein can be used to generate images of retinal samples, such as cross sectional or tomographic images.

The compact OCT system disclosed herein is well-suited for use with many prior clinical tests, such as retinal thickness measurements. In some cases, the OCT system is used by the patient, or by a health care provider. In many instances the patient can align himself with the system, although another user can align the patient with the system and take the measurement. In some embodiments, the OCT system is integrated with prior software and systems to provide additional information to healthcare providers, and can provide alerts in response to changes in retinal thickness. The alerts are optionally sent to the patient, caregiver, and health care providers when corrective action should be taken such as a change in medication, dosage, or a reminder to take medication.

As used herein, the term "retinal thickness (RT)" refers to a thickness of the retina between layers used to evaluate the thickness of a retina of a patient. The RT may correspond to a thickness of the retina between an anterior surface of the retina and external limiting membrane, for example.

As used herein, the term "retinal layer thickness (RLT)" refers to the thickness of one or more optically detectable layers of the retina. The optically detectable layers of the retina may comprise a thickness of the retina extending between the external limiting membrane and the retinal pigment epithelium, for example.

As used herein, the term "high resolution" refers to a measurement system capable of optically resolving structures that are smaller in at least one linear dimension than structures that can be a resolved by a measurement system of lower resolution.

Figure 1:
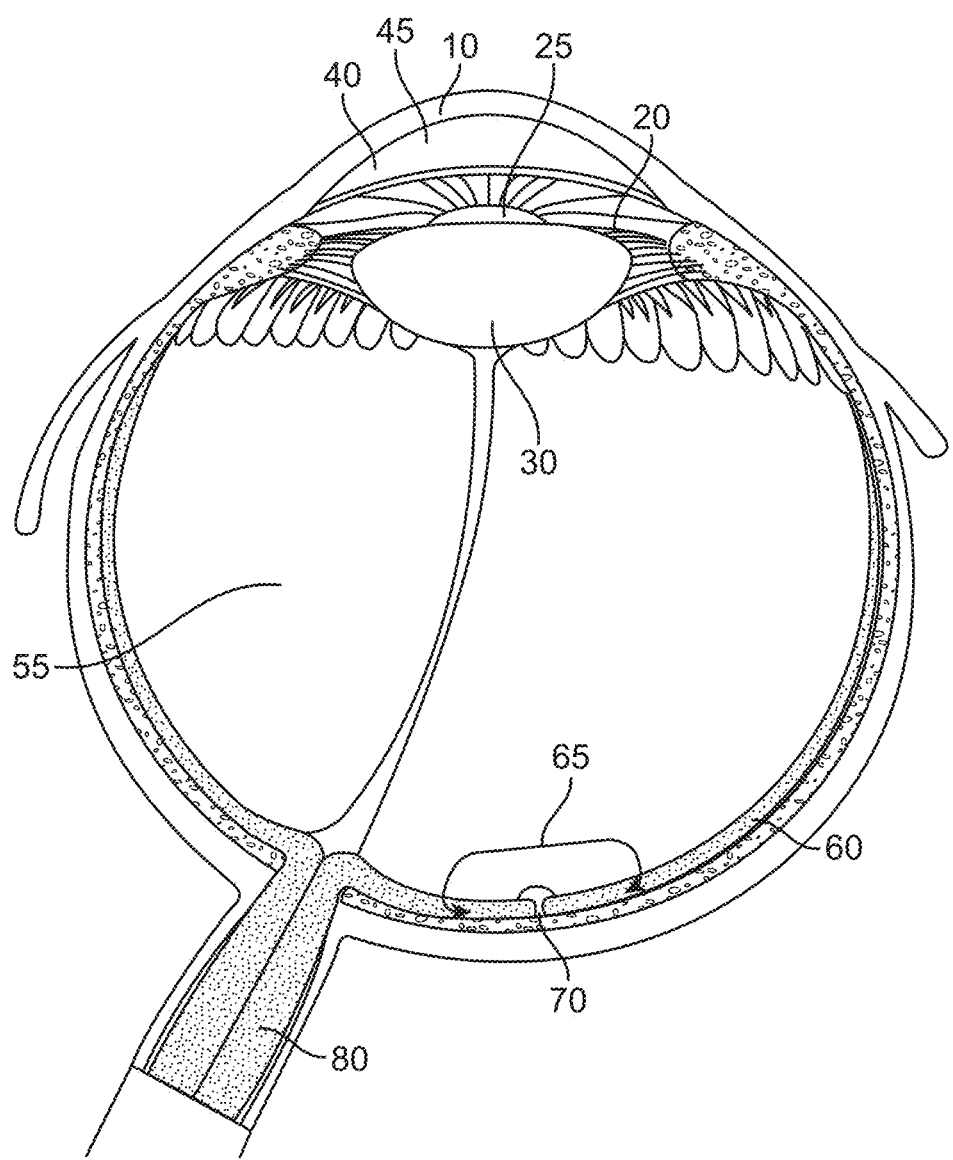
FIG. 1 shows a simplified diagram of the human eye.

FIG. 1 shows a simplified diagram of the human eye. Light enters the eye through the cornea 10. The iris 20 controls the amount of light allowed to pass by varying the size of the pupil 25 that allows light to proceed to the lens 30. The anterior chamber 40 contains aqueous humor 45 which determines the intraocular pressure (TOP). The lens 30 focuses light for imaging. The focal properties of the lens are controlled by muscles which reshape the lens. Focused light passes through the vitreous chamber 50, which is filled with vitreous humor 55. The vitreous humor maintains the overall shape and structure of the eye. Light then falls upon the retina 60, which has photosensitive regions. In particular, the macula 65 is the area of the retina responsible for receiving light in the center of the visual plane. Within the macula, the fovea 70 is the area of the retina most sensitive to light. Light falling on the retina generates electrical signals which are passed to the optic nerve 80 and then to the brain for processing.

Several disorders give rise to reduced optical performance of the eye. In some cases, the intraocular pressure (TOP) is either too high or too low. This is caused, for instance, by too high or too low of a production rate of aqueous humor in the anterior chamber. In other cases, the retina is too thin or too thick. This arises, for instance, due to the buildup of fluid in the retina. Diseases related to an abnormal retinal thickness (RT) include glaucoma and macular edema, for example. In some cases, a healthy range of RT is from 175 µm thick to 225 µm thick. In general, abnormalities in either the TOP or the RT are indicative of the presence of many ophthalmological diseases. Additionally, the IOP or the RT vary in response to ophthalmological treatments or other procedures. Therefore, it is desirable to have a means to measure the IOP and/or RT for diagnosis of ophthalmological diseases and to assess the effectiveness of treatments for a given patient. In some cases, it is desirable to measure the thickness of one or more retinal layers, for example the thickness of a plurality of layers.

The systems and methods disclosed herein relate to the use of optical coherence tomography (OCT) to measure the RT or RLT at multiple points in time. For instance, a patient measures their RT or RLT at multiple time points to track the progression of an ophthalmological disease such as glaucoma or macular edema over time. As another example, a patient measures their RT or RLT at multiple time points to track their response to a pharmaceutical or other treatment. In some cases, the system produces an alert when one or more recent measurements of the RT or RLT deviate significantly from previous measurements. In some cases, the system alerts the patient or the patient's physician of the change. In some instances, this information is be used to schedule a follow-up appointment between the patient and physician to, for instance, attempt a treatment of an ophthalmological illness, discontinue a prescribed treatment, or conduct additional testing.

Figure 2:
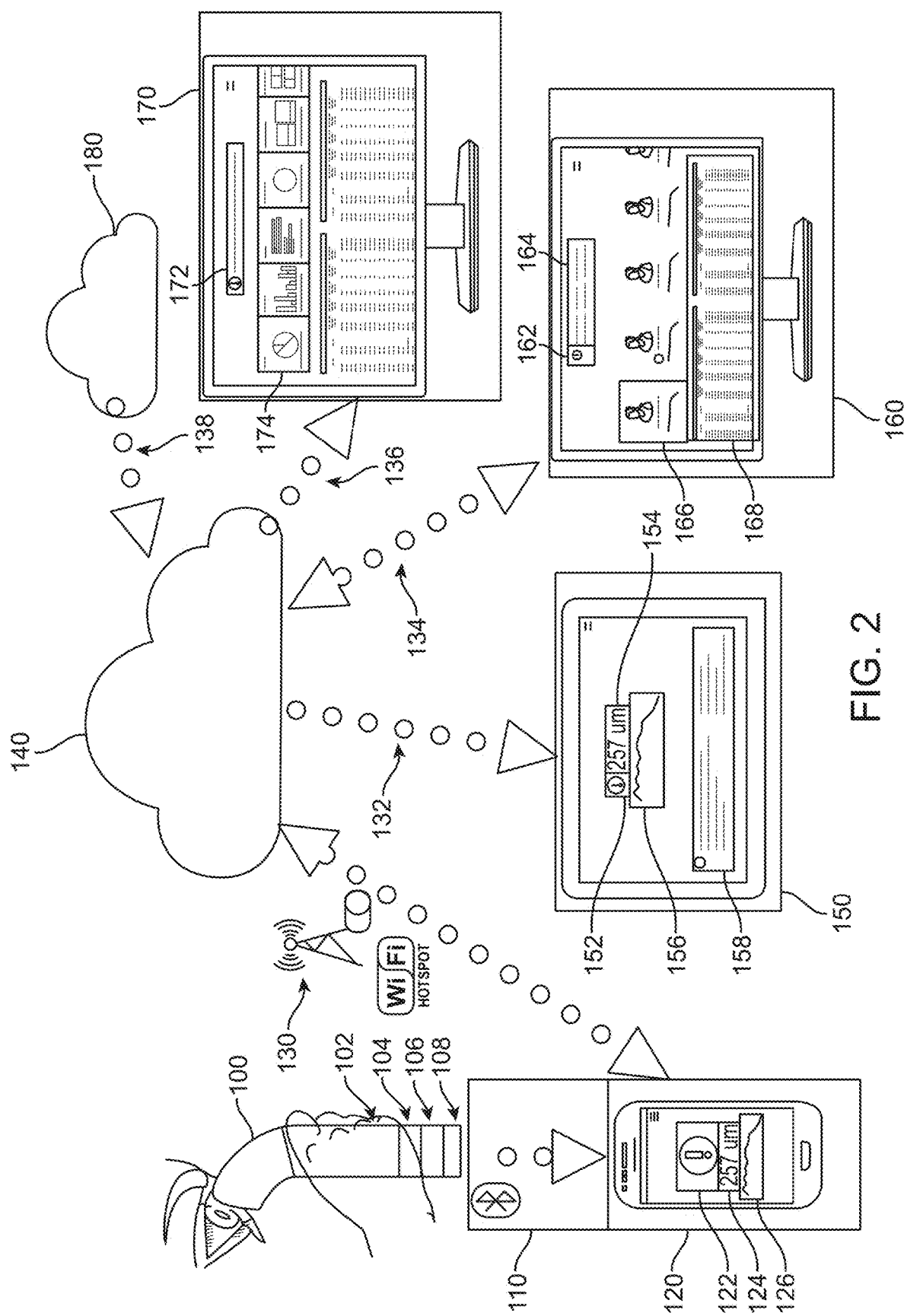
FIG. 2 shows a schematic of a system allowing a patient to measure retinal thickness (RT) at multiple time points and to communicate the results, in accordance with some embodiments.

FIG. 2 shows a schematic of a system allowing a patient to measure RT or RLT at multiple time points and to communicate the results, in accordance with some embodiments. The patient looks into a handheld OCT device 100 to obtain a measurement of the RT or RLT. In some embodiments, the handheld OCT device comprises optics 102, electronics 104 to control and communicate with the optics, a battery 106, and a transmitter 108. In some instances, the transmitter is a wired transmitter. In some cases, the transmitter is a wireless transmitter. In some cases, the handheld OCT device communicates the results via a wireless communication channel 110 to a mobile patient device 120 on the patient's smartphone or other portable electronic device. In some cases, the wireless communication is via Bluetooth communication. In some embodiments, the wireless communication is via Wi-Fi communication. In other embodiments, the wireless communication is via any other wireless communication known to one having skill in the art.

In some cases, the results are fully processed measurements of the RT. In some cases, all processing of the OCT data is performed on the handheld OCT device. For instance, in some embodiments, the handheld OCT device includes hardware or software elements that allow the OCT optical waveforms to be converted into electronic representations. In some cases, the handheld OCT device further includes hardware or software elements that allow processing of the electronic representations to extract, for instance, a measurement of the RT.

In some cases, the results are electronic representations of the raw optical waveforms obtained from the OCT measurement. For instance, in some embodiments, the handheld OCT device includes hardware or software elements that allow the OCT optical waveforms to be converted into electronic representations. In some cases, these electronic representations are then passed to the mobile patient device for further processing to extract, for instance, a measurement of the RT.

In some cases, the patient receives results and analysis of the RT or RLT measurement on the patient mobile app. In some embodiments, the results include an alert 122 alerting the patient that the results of the measurement fall outside of a normal or healthy range. In some cases, the results also include a display of the measured value 124. For instance, in some cases a measurement of the RT or RLT produces a result of 257 µm. In some instances, this result falls outside of a normal or healthy range. This causes the system to produce an alert and to display the measured value of 257 µm on the patient mobile app. In some embodiments, the results also include a chart 126 showing a history of the patient's RT or RLT over multiple points in time.

In some instances, the patient mobile device communicates the results of the measurement via a communication means 130 to a cloud-based or other network-based storage and communications system 140. In some embodiments, the communication means is a wired communication means. In some embodiments, the communication means is a wireless communication means. In some cases, the wireless communication is via Wi-Fi communication. In other cases, the wireless communication is via a cellular network. In still other cases, the wireless communication is via any other wireless communication known to one having skill in the art. In specific embodiments, the wireless communication means is configured to allow transmission to or reception from the cloud-based or other network-based storage and communications system.

Once stored in the cloud, the results are then transmitted to other devices, in specific embodiments. In some cases, the results are transmitted via a first communication channel 132 to a patient device 150 on the patient's computer, tablet, or other electronic device. In some embodiments, the results are transmitted via a second communication channel 134 to a physician device 160 on the patient's physician's computer, tablet, or other electronic device. In some instances, the results are transmitted via a third communication channel 136 to an analytics device 170 on another user's computer, tablet, or other electronic device. In some embodiments, the results are transmitted via a fourth communication channel 138 to a patient administration system or hospital administration system 180. In some cases, each of the devices has appropriate software instructions to perform the associate function as described herein.

In specific embodiments, the first communication channel is a wired communication channel or a wireless communication channel. In some cases, the communication is via Ethernet. In other cases, the communication is via a local area network (LAN) or wide area network (WAN). In still other cases, the communication is via Wi-Fi. In yet other cases, the communication is via any other wired or wireless communication known to one having skill in the art. In some embodiments, the first communication channel is configured to allow transmission to or reception from the cloud-based or other network-based storage and communications system. In some cases, the first communication channel is configured to only allow reception from the cloud-based or other network-based storage and communications system.

In some cases, the second communication channel is a wired communication channel or a wireless communication channel. In some instances, the communication is via Ethernet. In specific embodiments, the communication is via a local area network (LAN) or wide area network (WAN). In other embodiments, the communication is via Wi-Fi. In still other embodiments, the communication is via any other wired or wireless communication known to one having skill in the art. In some cases, the second communication channel is configured to allow transmission to or reception from the cloud-based or other network-based storage and communications system. In some embodiments, the second communication channel is configured to only allow reception from the cloud-based or other network-based storage and communications system.

In specific cases, the third communication channel is a wired communication channel or a wireless communication channel. In some instances, the communication is via Ethernet. In other instances, the communication is via a local area network (LAN) or wide area network (WAN). In still other instances, the communication is via Wi-Fi. In yet other instances, the communication is via any other wired or wireless communication known to one having skill in the art. In some embodiments, the third communication channel is configured to allow transmission to or reception from the cloud-based or other network-based storage and communications system. In some cases, the third communication channel is configured to only allow reception from the cloud-based or other network-based storage and communications system.

In some embodiments, the fourth communication channel is a wired communication channel or a wireless communication channel. In some cases, the communication is via Ethernet. In other cases, the communication is via a local area network (LAN) or wide area network (WAN). In still other cases, the communication is via Wi-Fi. In yet other cases, the communication is any other wired or wireless communication known to one having skill in the art. In some instances, the fourth communication channel is configured to allow transmission to or reception from the cloud-based or other network-based storage and communications system. In other cases, the fourth communication channel is configured to only allow reception from the cloud-based or other network-based storage and communications system.

A determination of the RT or RLT can be performed at many locations. For instance, a determination of the RT or RLT is performed on the handheld OCT device. In some cases, a determination of the RT or RLT is performed at a location near to the handheld OCT device, such as by a smartphone or other portable electronic device. In some embodiments, a determination of the RT or RLT is performed on the cloud-based storage and communications system. In some instances, the handheld OCT device is configured to compress measurement data and transmit the compressed measurement data to the cloud-based storage and communications system.

In some embodiments, the patient receives results and analysis of the RT or RLT measurement on the patient device 150. In some instances, the results include an alert 152 alerting the patient that the results of the measurement fall outside of a normal or healthy range. In some cases, the results also include a display of the measured value 154. For instance, in some cases, a measurement of the RT or RLT produces a result of 257 µm. This result falls outside of a normal or healthy range. In some cases, this causes the system to produce an alert and to display the measured value of 257 µm on the patient app. In specific cases, the results also include a chart 156 showing a history of the patient's RT or RLT over multiple points in time. In some cases, the patient device also displays instructions 158 for the patient to follow. In some instances, the instructions instruct the patient to visit their physician. In some embodiments, the instructions include the patient's name, date of most recent RT or RLT measurement, and next scheduled visit to their physician. In other cases, the instructions include more information. In still other cases, the instructions include less information.

In some embodiments, the patient's physician receives the results and analysis of the RT or RLT measurement on the physician device 160. In some instances, the results include an alert 162 alerting the physician that the results of the measurement fall outside of a normal or healthy range. In some cases, the results also include an alert 164 informing the physician that the patient's measurement falls outside of a normal or healthy range. In some embodiments, the alert includes a suggestion that the physician call the patient to schedule an appointment or to provide medical assistance. In some embodiments, the results also include a display 166 showing the most recent measurements and historical measurements for each of the physician's patients. For instance, in some instances, a measurement of the RT or RLT produces a result of 257 µm. This result falls outside of a normal or healthy range. In some cases, this causes the system to produce an alert and to display the measured value of 257 µm on the physician app. In specific cases, the physician device also displays contact and historical information 168 for each of the physician's patients.

In some embodiments, the other user receives results and analysis of the RT or RLT measurement on the analytics device 170. In some instances, the other user is a researcher investigating the efficacy of a new form of treatment. In other cases, the other user is an auditor monitoring the outcomes of a particular physician or care facility. To protect the patient's privacy, in some cases the analytics device is restricted to receive only a subset of a given patient's information. For instance, the subset is restricted so as not to include any personally identifying information about a given patient. In some cases, the results include an alert 172 alerting that a large number of abnormal or unhealthy measurements have been obtained in a specific period of time. In some cases, the results include one or more graphical representations 174 of the measurements across a population of patients.

In some cases, the results and analysis on the analytics device comprise disease information such as a physician-confirmed diagnosis. In some cases, the results and analysis comprise anonymized patient data such as age, gender, genetic information, information about the patient's environment, smoking history, other diseases suffered by the patient, etc. In some cases, the results and analysis comprise anonymized treatment plans for the patient, such as a list of prescribed medications, treatment history, etc. In some cases, the results and analysis comprise measurement results, such as the results of an RT or RLT measurement, a visual function test, or the patient's compliance with a course of treatment. In some cases, the results and analysis comprise data from an electronic medical record. In some cases, the results and analysis comprise diagnostic information from visits to a patient's medical provider, such as the results of an OCT scan acquired by the patient's medical provider.

In some embodiments, the patient's clinical, hospital, or other health provider receives results and analysis of the RT or RLT measurement on the patient administration system or hospital administration system 180. In some cases, this system contains the patient's electronic medical record. In some cases, the results and analysis provide the patient's health provider with data allowing the provider to update the treatment plan for the patient. In some instances, the results and analysis allow the provider to decide to call the patient in for an early office visit. In some instances, the results and analysis allow the provider to decide to postpone an office visit.

In some embodiments, one or more of the patient device, physician device, and analytics device includes a software app comprising instructions to perform the functions of the patient device, physician device, or analytics device, respectively, as described herein.

Figure 3A:
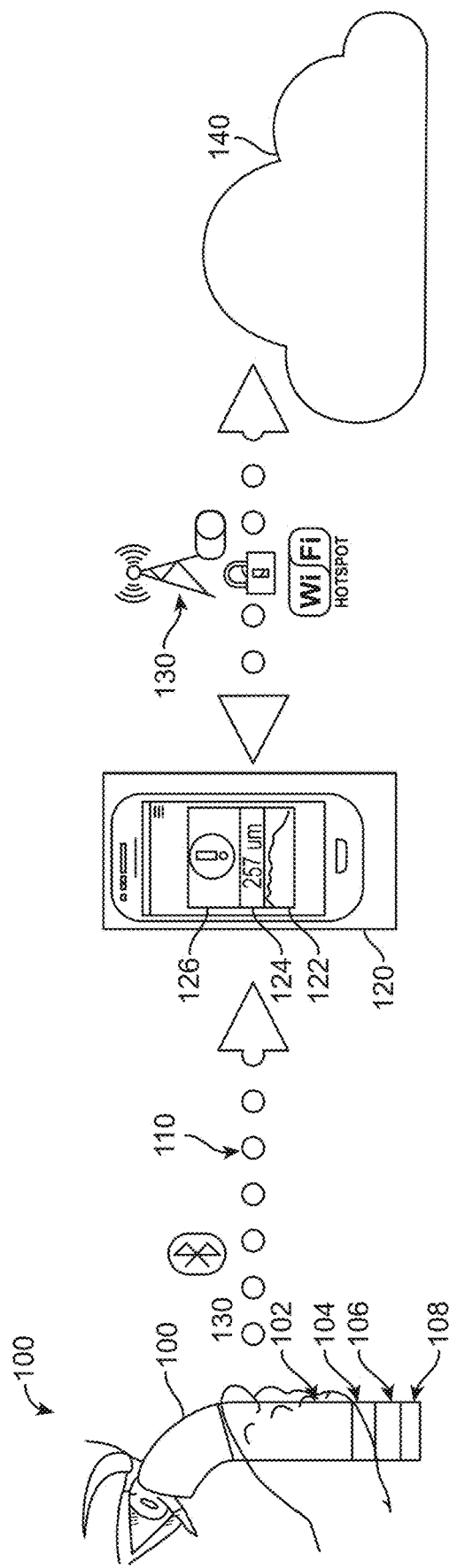
FIG. 3A shows a handheld optical coherence tomography (OCT) device utilizing Bluetooth communication, in accordance with some embodiments.

FIG. 3A shows a handheld OCT device utilizing short-range wireless communication, in accordance with some embodiments. In some embodiments, the handheld OCT device 100 comprises optics 102, electronics to control and communicate with the optics 104, a battery 106, and a wireless transmitter 108. In some cases, the wireless transmitter is a Bluetooth transmitter. In some instances, the results from one or more RT or RLT measurements are stored on the handheld OCT device until an authorized user, such as the patient or another person designated by the patient, opens the patient mobile device on a smartphone or other portable electronic device. Once opened, the patient mobile device establishes wireless communication with the handheld OCT device. In some cases, the communication is via a Bluetooth wireless communication channel 110. In some instances, the handheld OCT device communicates the results via the Bluetooth channel to a mobile patient device 120 on the patient's smartphone or other portable electronic device.

In some instances, the results include an alert 122 alerting the patient that the results of the measurement fall outside of a normal or healthy range. In specific embodiments, the results also include a display of the measured value 124. For instance, a measurement of the RT or RLT produces a result of 257 μm in some cases. This result falls outside of a normal or healthy range. In some cases, this causes the system to produce an alert and to display the measured value of 257 μm on the patient mobile app. In specific embodiments, the results also include a chart 126 showing a history of the patient's RT or RLT over multiple points in time.

In some cases, the patient mobile device communicates the results of the measurement via a wireless communication means 130 to a cloud-based or other network-based storage and communications system 140. In some instances, the wireless communication is via Wi-Fi communication. In other cases, the Wi-Fi communication is via a secure Wi-Fi channel. In still other cases, the wireless communication is via a cellular network. In specific embodiments, the cellular network is a secure cellular network. In other embodiments, the transmitted information is encrypted. In some cases, the communication channel is configured to allow transmission to or reception from the cloud-based or other network-based storage and communications system. In some cases, data is stored on the smartphone or other portable electronic device until the smartphone or other portable electronic device connects to a Wi-Fi or cellular network.

In some cases, the patient mobile device has a feature which notifies the patient or another person designated by the patient when too much time has elapsed since the patient mobile device was last opened. For instance, in some cases this notification occurs because the patient has not acquired measurements of the RT or RLT as recently as required by measuring schedule set by their physician or other healthcare provider. In other cases, the notification occurs because the handheld OCT device has been storing the results of too many measurements and needs to transmit the data to the patient's smartphone. In specific embodiments, the patient mobile device communicates with the cloud-based or other network-based storage and communications system to display a complete set of patient data.

Figure 3B:
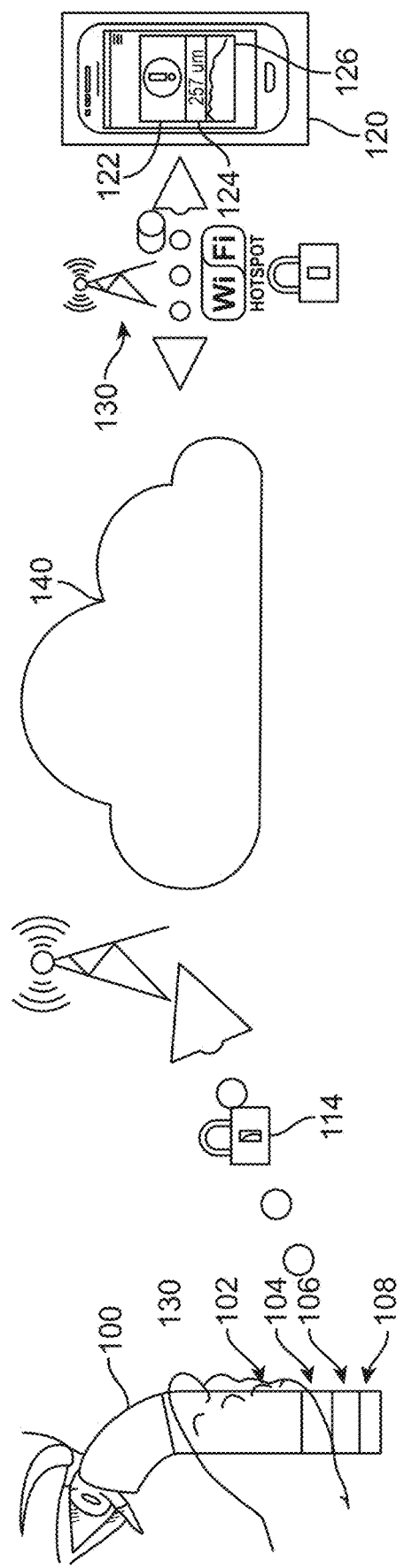
FIG. 3B shows a handheld OCT device utilizing the Global System for Mobile Communications (GSM), in accordance with some embodiments.

FIG. 3B shows a handheld OCT device capable of communicating directly with a cloud-based storage and communication system without reliance on a user device such as a smartphone, in accordance with some embodiments. In some embodiments, the handheld OCT device 100 comprises optics 102, electronics to control and communicate with the optics 104, a battery 106, and a wireless transmitter 108. In some cases, the wireless transmitter is a GSM transmitter. In some instances, the results from one or more RT or RLT measurements are stored on the handheld OCT device. In some cases, the GSM transmitter establishes wireless communication with a cloud-based or other network-based storage and communications system 140 via a wireless communication channel 114. In specific cases, the wireless communication is via a GSM wireless communication channel. In other embodiments, the system utilizes third generation (3G) or fourth generation (4G) mobile communications standards. In such cases, the wireless communication is via a 3G or 4G communication channel.

In specific embodiments, the patient mobile device 120 receives the results of the measurement via a wireless communication means 130 from the cloud-based or other network-based storage and communications system 140. In some cases, the wireless communication is via Wi-Fi communication. In some cases, the Wi-Fi communication is via a secure Wi-Fi channel. In other cases, the wireless communication is via a cellular network. In some cases, the cellular network is a secure cellular network. In specific instances, the transmitted information is encrypted. In some embodiments, the communication channel is configured to allow transmission to or reception from the cloud-based or other network-based storage and communications system.

Once obtained from the cloud-based or other network-based storage and communications system, the results of the RT or RLT measurement are viewed in the patient mobile app, in some instances. In some cases, the results include an alert 122 alerting the patient that the results of the measurement fall outside of a normal or healthy range. In some instances, the results also include a display of the measured value 124. For instance, in some cases a measurement of the RT or RLT produces a result of 257 μm. This result falls outside of a normal or healthy range. In specific embodiments, this causes the system to produce an alert and to display the measured value of 257 μm on the patient mobile app. In some embodiments, the results also include a chart 126 showing a history of the patient's RT or RLT over multiple points in time.

In some cases, the patient mobile device has a feature which notifies the patient or another person designated by the patient when too much time has elapsed since the patient mobile device was last opened. For instance, in some cases this notification occurs because the patient has not acquired measurements of the RT or RLT as recently as required by measuring schedule set by their physician or other healthcare provider. In other cases, the notification occurs because the handheld OCT device has been storing the results of too many measurements and needs to transmit the data to the patient's smartphone. In specific embodiments, the patient mobile device communicates with the cloud-based or other network-based storage and communications system to display a complete set of patient data.

In some cases, the handheld OCT device comprises both a short-range transmitter and a GSM, 3G, or 4G transmitter. In some instances, the short-range transmitter is a Bluetooth transmitter. In some cases, the handheld OCT device communicates directly with the patient mobile device on a smartphone or other portable electronic device through the Bluetooth wireless communication channel. In some embodiments, the handheld OCT also communicates with the cloud-based or other network-based storage and communications system through the GSM, 3G, or 4G wireless communication channel. In specific cases, the cloud-based system then communicates with the patient mobile device through a Wi-Fi, cellular, or other wireless communication channel. Alternatively, the Bluetooth transmitter is built into a docking station. In some instances, this allows for the use of older devices for patients who lack a smartphone. In some cases, the docking station also includes a means for charging the battery of the handheld OCT device.

In some cases, the handheld OCT device of FIGS. 3A and 3B is configured to be held in close proximity to the eye. For instance, in specific embodiments, the device is configured to be held in front of the eye with the detector at a distance of no more than 200 mm from the eye. In other embodiments, the devices are configured to be held in front of the eye with the detector at a distance of no more than 150 mm, no more than 100 mm, or no more than 50 mm from the eye. In specific instances, the handheld OCT devices further comprise housing to support the light source, optical elements, detector, and circuitry. In some cases, the housing is configured to be held in a hand of a user. In some cases, the user holds the devices in front of the eye to direct the light beam into the eye. In some instances, the devices include a sensor to measure which eye is being measured. For instance, in specific embodiments, the devices include an accelerometer or gyroscope to determine which eye is measured in response to an orientation of the housing. The devices optionally include an occlusion structure coupled to the housing and the sensor that determines which eye is measured. The occlusion structure occludes one eye while the other eye is measured. In some cases, the devices include a viewing target to align the light beams with a portion of the retina. For instance, in specific embodiments, the devices include a viewing target to align the light beams with a fovea of the eye. In some cases, the viewing target is a light beam. In some cases, the viewing target is a light emitting diode. In other cases, the viewing target is a vertical cavity surface emitting laser (VCSEL). In still further cases, the viewing target is any viewing target known to one having skill in the art.

The optical components described herein are capable of being miniaturized so as to provide the handheld OCT device with a reduced physical size and mass, as described herein, as will be appreciated by one of ordinary skill in the art.

In many embodiments, the handheld OCT devices of FIGS. 3A and 3B are small enough and light enough to be easily manipulated with one hand by a user. For instance, in many embodiments, the device has a mass within a range from about 100 grams to about 500 grams. In many embodiments, the device has a mass within a range from about 200 grams to about 400 grams. In many embodiments, the device has a mass within a range from about 250 grams to about 350 grams. In specific embodiments, the device has a maximum distance across within a range from about 80 mm to about 160 mm. In specific embodiments, the device has a maximum distance across within a range from about 100 mm to about 140 mm. In specific embodiments, the device has a width within a range from about 110 mm to about 130 mm. In some embodiments, the maximum distance across comprises a length. In some embodiments, the device has a width less than its length. In specific embodiments, the device has a width within a range from about 40 mm to about 80 mm. In specific embodiments, the device has a width within a range from about 50 mm to about 70 mm. In specific embodiments, the device has a width within a range from about 55 mm to about 65 mm.

Figure 4:
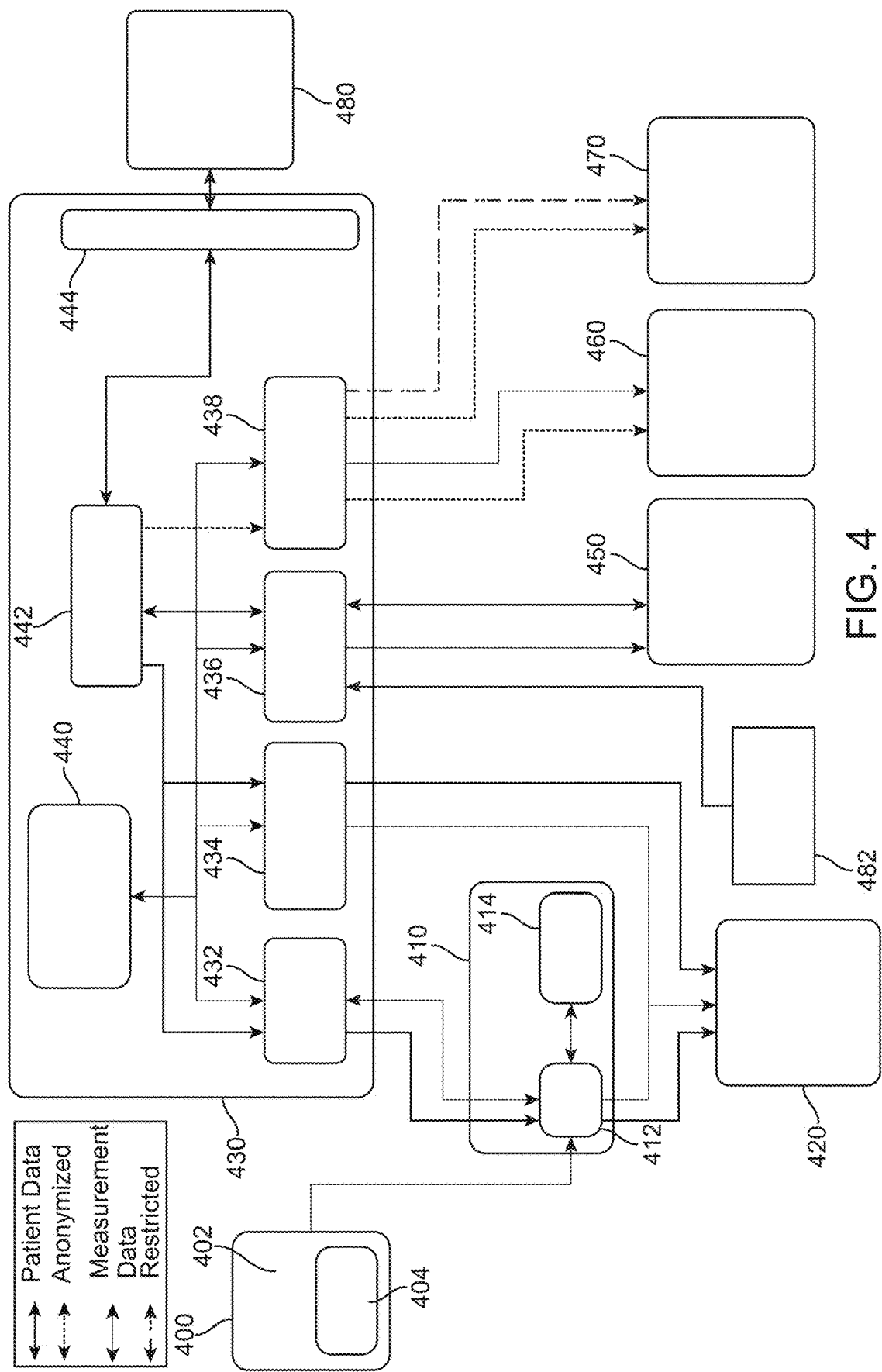
FIG. 4 shows a diagram of the flow of information in the handheld OCT system, in accordance with some embodiments.

FIG. 4 shows a diagram of the flow of information in the handheld OCT system, in accordance with some embodiments. In some cases, the handheld OCT device 400 further comprises a subsystem 402 for measuring RT or RLT and a device storage system 404. In some embodiments, the device storage system comprises any form of volatile or non-volatile memory, including but not limited to Flash memory or random access memory (RAM). In some instances, the subsystem for measuring RT or RLT is communicatively coupled to the device storage system. In some cases, the handheld OCT device transmits measurement data to a smartphone or any other computing device 410. For example, in some cases the smartphone or another handheld device further comprises a smartphone storage system 414 and run a smartphone app 412.

In some cases, the computing device sends patient data and measurement data to a patient device 420. In some embodiments, the smartphone device is communicatively coupled to a cloud-based or other network-based storage and communications system 430. In some instances, the cloud-based or other network-based storage system further comprises any of a mobile application programming interface (API) 432, a patient device 434, a physician device 436, an analytics device 438, a measurement and treatment storage system 440, a patient data storage system 442, and an API 444 interfacing with a patient administration system or a hospital administration system.

In some cases, the mobile API is communicatively couple to the smartphone app. In some embodiments, the mobile API is configured to send and receive measurement information (e.g. measurements of the RT) to and from the smartphone app. In some instances, the mobile API is configured to send patient data (e.g. identifying information or demographic information) to the smartphone device but not to receive this information from the smartphone app. In some cases, this configuration is designed to reduce the likelihood of compromising patient data. In some embodiments, the mobile API is configured to send measurement data and patient data to the patient device and to receive measurement data and patient data from the patient app. In some instances, the patient device is further configured to send measurement data and patient data to the patient and to receive measurement data and patient data from the patient.

In some cases, the mobile API is configured to send measurement data and patient data to the physician device and to receive measurement data and patient data from the physician app. In other cases, the mobile API is configured to send measurement data to the physician device and to receive measurement data and from the physician device but require patient data to first pass through a patient data storage system. In such a case, the patient data storage system is configured to send patient data to the physician device and receive patient data from the physician app. In some embodiments, the patient data storage system is configured to send patient data to the API interfacing with a patient administration system or a hospital administration system and to receive patient data from the API interfacing with a patient administration system or a hospital administration system. In some instances, the API interfacing with a patient administration system or a hospital administration system is configured to send patient data to a patient administration system or hospital administration system 480 and to receive patient data from the patient administration system or hospital administration system. In some cases, the physician device is further configured to send measurement data and patient data to a physician 450 and to receive measurement data and patient data from the physician.

In some cases, the mobile API is configured to send measurement data to the analytics apps and to receive measurement data from the analytics app. In some embodiments, the analytics device is configured to send measurement data to the manufacturer or developer of the handheld OCT system 460. In some instances, the analytics device is configured to send anonymized patient data to the manufacturer or developer of the handheld OCT system. In some cases, the analytics device is configured to send a subset of the measurement data to other parties 470. In some embodiments, the analytics device is configured to send anonymized patient data to other parties 470.

In some embodiments, the cloud-based or other network-based storage and communications system further comprise a measurement and treatment storage system. In some instances, the measurement and treatment storage system are configured to send measurement data to any of the mobile API, the patient app, the physician app, and the analytics app. In some cases, the measurement and treatment storage system are configured to receive measurement data from any of the mobile API, the patient app, the physician app, and the analytics app.

In addition to the patient administration system or hospital information system, in some cases the cloud-based or other network-based storage and communications system is communicatively coupled to a local patient administration system 482. In some embodiments, the local patient administration system is configured to send patient data to the physician app.

The handheld OCT device may utilize any method for optical coherence tomography. In some cases, the handheld OCT device utilizes time domain OCT. In some embodiments, the handheld OCT device utilizes frequency domain OCT. In some instances, the handheld OCT device utilizes spatially encoded frequency domain OCT. In some cases, the handheld OCT device utilizes time encoded frequency domain OCT, also known as swept source OCT (SS-OCT).

Figure 5:
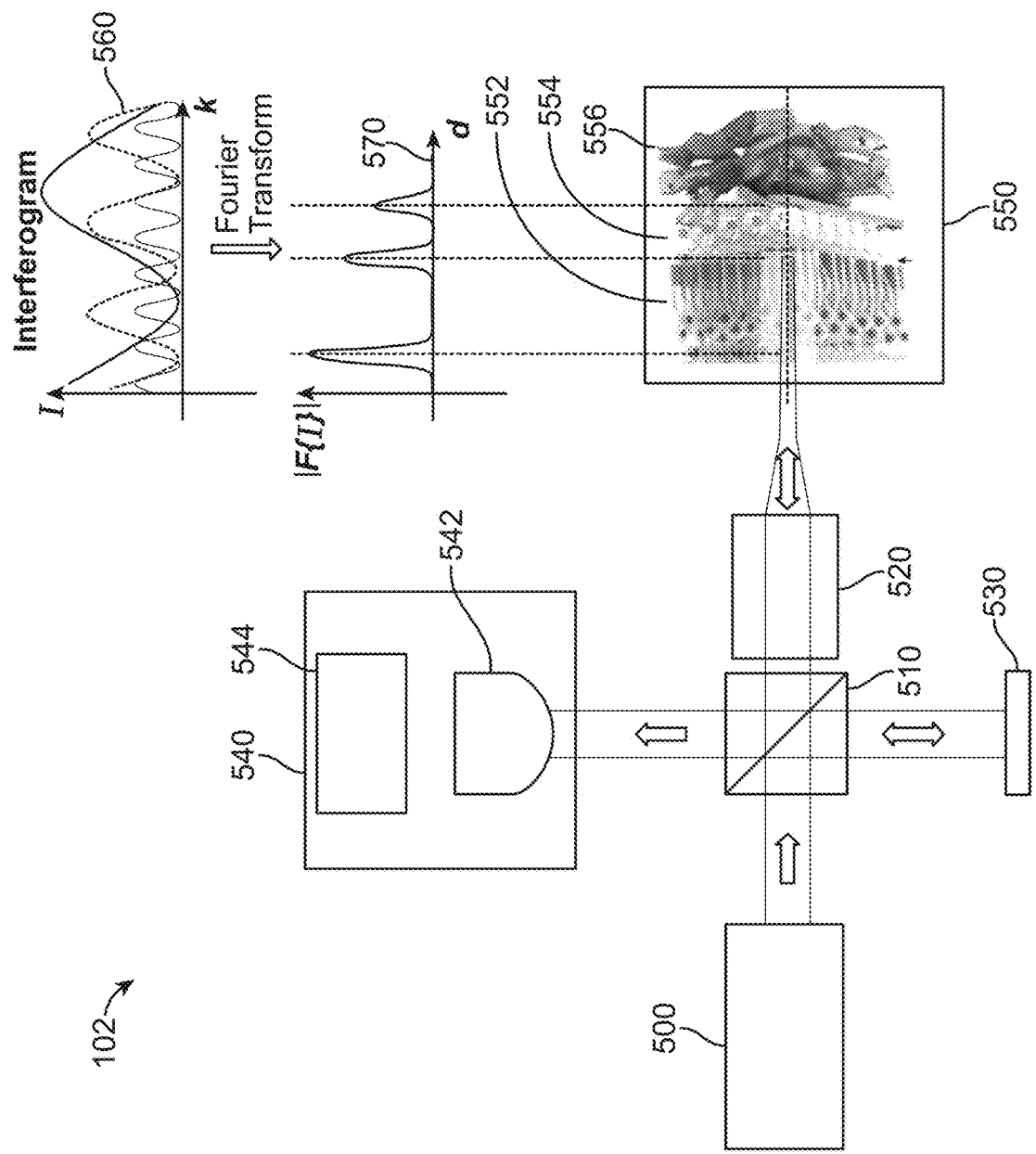
FIG. 5 shows a schematic for a swept source optical coherence tomography (SS-OCT) device, in accordance with some embodiments.

FIG. 5 shows a schematic for the optics of a swept source optical coherence tomography (SS-OCT) device, in accordance with some embodiments. In some cases, the optics 102 comprises a light source 500, a beamsplitter 510, front-end optics 520, a reference mirror 530, and a processing unit 540. In some embodiments, the processing unit further comprises a photodetector 542 and a signal processing module 544. Light from the light source impinges upon the beamsplitter. A portion of the light is directed along a reference arm to a reference mirror and a portion of the light is directed to the front-end optics and then to the sample 550. In some instances, the sample comprises an eye. In some cases, the sample comprises a retina. In some embodiments, the retina comprises a number of layers of tissue. In some instances, the layers of tissue comprise a layer of light-sensitive rod and cone cells 552, the retinal pigment epithelium (RPE) 554, and the choroid 556. In other instances, the layers of tissue comprise other layers of the retina, such as the nerve fiber layer, the ganglion cell layer, the inner plexiform layer, the inner nuclear layer, the outer plexiform layer, the outer nuclear layer, the inner limiting membrane, the external limiting membrane, and/or Bruch's membrane. Light is reflected back to the device at each boundary of each of the layers. Light reflected from each boundary interferes with light reflected from the reference mirror and with light reflected from any other boundary. The interference signal is detected at the photodetector. In some instances, light is reflected from the posterior surface of the layer of rod and cone cells, the anterior surface of the layer of rod and cone cells, the posterior surface of the inner limiting membrane, the anterior surface of the inner limiting membrane, the posterior surface of the choroid, and/or the anterior surface of the choroid. Light may be reflected from any surface of any other layer, such as the nerve fiber layer, the ganglion cell layer, the inner plexiform layer, the inner nuclear layer, the outer plexiform layer, the outer nuclear layer, the external limiting membrane, and/or the retinal pigment epithelium. In some cases, an RLT corresponds to a thickness of any of these retinal layers, or a thickness between any two such layers.

This process is repeated over the range of wavelengths emitted by the light source. The amplitude of the interference signal varies with wavelength and attains a maximum value when the light reflected from a boundary and the light reflected from the reference mirror are in phase or when the light reflected from a boundary is in phase with light reflected from another boundary. This condition is attained at one or more particular wavelengths of light for each boundary and is characterized by one or more maxima in the interference signal. At other wavelengths, the interference signal displays partial constructive interference or destructive interference. The interference signals at all wavelengths are compiled to form an interferogram 560. The interferogram is subjected to a signal analysis procedure. In some cases, the interferogram is subjected to a frequency analysis procedure, such as a fast Fourier transform (FFT), to form a spectrum 570. The spectrum comprises peaks corresponding to the interference signals associated with the thickness of various retinal layers. In some embodiments, the SS-OCT utilizes a light source with a relatively long coherence length (typically greater than a few millimeters). In some instances, the amplitude of the interference signal decreases as the distance between two retinal layers increases. In some cases, the position of a peak is indicative of the thickness of each layer of the tissue.

In some cases, the light source comprises a laser source. In some embodiments, the laser source produces laser light having a wavelength that may be tuned. In some instances, the laser source is scanned over a range of wavelengths in order to obtain an OCT signal. In some cases, the laser source is capable of being scanned rapidly to allow rapid attainment of the OCT signal. In some cases, the laser source comprises a vertical cavity surface emitting laser (VCSEL) laser. In some embodiments, the VCSEL is tuned by varying the electrical current provided to the VCSEL. In some instances, the VCSEL is scanned continuously across a range of wavelengths by continuously varying the electrical current. In some cases, the VCSEL is periodically scanned across a range of wavelengths by periodically varying the electrical current. In some embodiments, the VCSEL is provided with a sinusoidally varying electrical current to produce a sinusoidally varying wavelength.

In some embodiments, the VCSEL is a commercially available VCSEL. In some instances, the VCSEL is a VCSEL modified from a commercially available VCSEL based on the teachings described herein. In some cases, the VCSEL is a VCSEL obtained from manufacturers such as Phillips Photonics, Frankfurt Laser Company, Hamamatsu Corporation, New Focus, Power Technology, Avago Technologies, Masimo Semiconductor, Finisar, Oclaro, or any other manufacturer known to one having skill in the art.

In some instances, the VCSEL has a maximum recommended current for continuous use or for pulsed use. In some cases, the maximum continuous current rating limits the range of wavelengths over which the VCSEL may be swept. For instance, the VCSEL may be limited to a continuous operating current no more than 1 mA, 2 mA, 3 mA, 4 mA, 5 mA, 6 mA, 7 mA, 8 mA, 9 mA, or 10 mA. In some embodiments, the wavelength emitted by the VCSEL varies linearly with the operating current with a proportionality constant of 0.3 nm/mA. In some cases, this limits the range of wavelengths over which the VCSEL may be swept to 0.3 nm, 0.6 nm, 0.9 nm, 1.2 nm, 1.5 nm, 1.8 nm, 2.1 nm, 2.4 nm, 2.7 nm, or 3.0 nm. In some embodiments, this limits the attainable axial resolution of the VCSEL-based SS-OCT device. Assuming a Gaussian spectrum from the light source, the attainable axial resolution is determined according to:

$$\delta z = 2 \ln 2 \lambda_0^2 / \pi \Delta \lambda \quad (1)$$

Here, δz is the attainable axial resolution, $\lambda_0$ is the central emission wavelength of the VCSEL, and $\Delta\lambda$ is the range of wavelengths over which the VCSEL operates.

Thus, in some cases, the limited operating range of the VCSEL limits the attainable axial resolution. In some embodiments, for a VCSEL with a central operating wavelength of 850 nm, the attainable axial resolution is no better than 1062 μm, 531 μm, 354 μm, 266 μm, 213 μm, 177 μm, 152 μm, 133 μm, 118 μm, or 106 μm for operating ranges of 0.3 nm, 0.6 nm, 0.9 nm, 1.2 nm, 1.5 nm, 1.8 nm, 2.1 nm, 2.4 nm, 2.7 nm, and 3.0 nm, respectively. In some instances, the VCSEL emits no more than 0.01 mW, 0.025 mW, 0.05 mW, 0.1 mW, 0.25 mW, 0.5 mW 1 mW, 2.5 mW, 5 mW, 10 mW, 25 mW, 50 mW, 100 mW, 250 mW, 500 mW, 1 W, 2.5 W, 5 W, 10 W, 25 W, 50 W, or 100 W of optical power.

Table 1 shows axial resolution for the corresponding wavelength range of the swept source for a central operating wavelength of 850 nm.

| Wavelength Range (nm) | Axial Resolution (μm) |
|---|---|
| 0.3 | 1062.7 |
| 0.6 | 531.4 |
| 0.9 | 354.2 |
| 1.2 | 265.7 |
| 1.5 | 212.5 |
| 1.8 | 177.1 |
| 2.1 | 151.8 |
| 2.4 | 132.8 |
| 2.7 | 118.1 |
| 3.0 | 106.3 |
| 4.0 | 79.7 |
| 5.0 | 63.8 |
| 6.0 | 53.1 |
| 7.0 | 45.5 |
| 8.0 | 39.9 |
| 9.0 | 35.4 |
| 10.0 | 31.9 |

Although Table 1 makes reference to a central wavelength of 850 nm, a person of ordinary skill in the art can construct a compact OCT system operating at a different central wavelength with similar sweep ranges and similar resolutions in accordance with the disclosure provided herein. Also, a person of ordinary skill in the art can readily correct the above values in accordance with the index of refraction of the retina, which is generally between about 1.3 and 1.4.

In some cases, additional VSCELs are used to extend the swept wavelength range as described herein.

In some cases, the limited operating range of the VCSEL also limits the ability to extract information from the OCT signal due to a limited phase shift imparted by a limited optical path difference (OPD). The phase shift between light reflected from a first interface and light reflected from a second interface is given by:

$$\Delta\Phi = \frac{4\pi}{\lambda_0^2}n\Delta z\Delta\lambda \quad (2)$$

Here, $\Delta\Phi$ is the phase shift, $\lambda_0$ is the central emission wavelength of the VCSEL, n is the index of refraction of the medium between the first and second reflecting interfaces, $\Delta z$ is the distance between the first and second reflecting interfaces, $n\Delta z$ is the OPD, and $\Delta\lambda$ is the range of wavelengths over which the VCSEL operates.

In some cases, it is useful to extract frequency information from the interference signal arising from the interaction of light reflected from the first interface and light reflected from the second interface. In order to extract this information, it may be helpful to attain two signal periods of the interferogram. This corresponds to a phase shift of $4\pi$. Thus, a VCSEL should operate over a minimum range of wavelengths $\Delta\lambda_{min}$ given by:

$$\Delta\lambda_{min} = \frac{\lambda_0^2}{n\Delta z} \quad (3)$$

Thus, in some cases, the limited operating range of the VCSEL limits the ability to attain sufficient phase shifts to extract frequency information from an interference signal in some cases, for example. In some embodiments, for a VCSEL with a central operating wavelength of 850 nm, forming interference patterns between reflecting interfaces separated by 150 μm in a medium with an index of refraction of 1.3, similar to a retina, a minimum range of wavelengths is 3.7 nm. In some instances, this range of wavelengths is greater than the range of wavelengths that is typically emitted by a VCSEL operated within its maximum recommended current for continuous use. Thus, in some cases, it is be helpful to extend the range of wavelengths emitted by the VCSEL in order to produce a sufficient phase shift.

The light source need not be a VCSEL. In some cases, the light source is doped fiber amplifier utilizing amplified spontaneous emission (ASE). In some cases, the light source is a superluminescent diode (SLD). Additionally, in some embodiments, the light source comprises multiple light sources.

In some cases, the front-end optics comprise optical elements such as lenses. In some embodiments, the front-end optics comprise any reflective, refractive, or diffractive elements. In some instances, the front-end optics comprise more than one reflective, refractive, or diffractive elements. In some cases, the front-end optics comprise electro-optic, magneto-optic, acousto-optic, or mechano-optic devices. In some embodiments, the front-end optics comprise any optical elements known to one having skill in the art.

In some embodiments, the front end optics comprise a scanning optical element to allow the light source to be moved to different locations on the retina. In some instances, this allows multiple measurements to be conducted to determine a RT or RLT at different locations on the retina. In some cases, determining a RT or RLT at different locations on the retina further allows the location of the fovea to be ascertained. In some embodiments, the scanning optical element is selected from the group consisting of a mirror, a plurality of mirrors, a gimbal, a lens, a galvanometer, an acousto-optic modulator, an electro-optic modulator, a translating optical element, an optical element translating transverse to the light beam, a deformable mirror and an xy translation stage. In some instances, the scanning optical element comprises any scanning optical element as is known to one having skill in the art.

In some instances, the device further comprises a scanning optical element as described herein.

FIG. 6A shows a schematic for the optics of a swept source optical coherence tomography (SS-OCT) device lacking a reference mirror, in accordance with some embodiments. In some cases, the optics 102 comprise a VCSEL or other light source 600, a beamsplitter 610, front-end optics 620, and a processing unit 640. In some embodiments, the processing unit further comprises a photodetector 642 and a signal processing module 644. Light from the broadband source impinges upon the beamsplitter. Light is directed to the front-end optics and then to the sample 650. Light is reflected back to the device at each boundary of each layer. Light reflected from a boundary of one layer interferes with light reflected from a boundary of another layer. The interference signal is detected at the photodetector.

This process is repeated over the range of wavelengths emitted by the light source. The amplitude of the interference signal varies with wavelength and attains a maximum value when the light reflected from a boundary is in phase with light reflected from another boundary. This condition is attained at one or more particular wavelengths of light for each boundary and is characterized by one or more maxima in the interference signal. At other wavelengths, the interference signal displays partial constructive interference or destructive interference. The interference signals at all wavelengths are compiled to form an interferogram. The interferogram is subjected to a signal analysis procedure. In some cases, the interferogram is subjected to a frequency analysis procedure, such as a fast Fourier transform (FFT), to form a spectrum. The spectrum comprises peaks corresponding to the wavelengths associated with an interference maximum for each boundary. In some embodiments, the SS-OCT utilizes a light source with a relatively long coherence length (typically greater than a few millimeters). In some instances, the amplitude of the interference signal decreases as the distance between two retinal layers increases. In some cases, the position of a peak is indicative of the thickness of each layer of the tissue.

In some cases, the light source comprises a laser source. In some embodiments, the laser source produces laser light having a wavelength that may be tuned. In some instances, the laser source is scanned over a range of wavelengths in order to obtain an OCT signal. In some cases, the laser source is capable of being scanned rapidly to allow rapid attainment of the OCT signal. In some embodiments, the laser source comprises a vertical cavity surface emitting laser (VCSEL) laser. In some instances, the VCSEL is tuned by varying the electrical current provided to the VCSEL. In some cases, the VCSEL is scanned continuously across a range of wavelengths by continuously varying the electrical current. In some embodiments, the VCSEL is periodically scanned across a range of wavelengths by periodically varying the electrical current. For instance, the VCSEL may be provided with a sinusoidally varying electrical current to produce a sinusoidally varying wavelength.

In some embodiments, the front-end optics comprise optical elements such as lenses. In some instances, the front-end optics comprise any reflective, refractive, or diffractive elements. In some cases, the front-end optics comprise more than one reflective, refractive, or diffractive elements. In some embodiments, the front-end optics comprise electro-optic, magneto-optic, acousto-optic, or mechano-optic devices. The front-end optics may comprise any optical elements known to one having skill in the art.

FIG. 6B shows the wavelength range over which the VCSEL operates in the swept source optical coherence tomography (SS-OCT) device lacking a reference mirror, in accordance with some embodiments. In some cases, the VCSEL has a maximum recommended current for continuous use. In some embodiments, the maximum continuous current rating limits the range of wavelengths over which the VCSEL may be swept. In some instances, the VCSEL is limited to a continuous operating current no more than 1 mA, 2 mA, 3 mA, 4 mA, 5 mA, 6 mA, 7 mA, 8 mA, 9 mA, or 10 mA. In some cases, the wavelength emitted by the VCSEL varies linearly with the operating current with a proportionality constant of 0.3 nm/mA. In some embodiments, this limits the range of wavelengths over which the VCSEL may be swept to 0.3 nm, 0.6 nm, 0.9 nm, 1.2 nm, 1.5 nm, 1.8 nm, 2.1 nm, 2.4 nm, 2.7 nm, or 3.0 nm. In some instances, this limits the attainable axial resolution of the VCSEL-based SS-OCT device.

Thus, in some cases, the limited operating range of the VCSEL limits the attainable axial resolution. For instance, for a VCSEL with a central operating wavelength of 850 nm, the attainable axial resolution is no better than 1062 µm, 531 µm, 354 µm, 266 µm, 213 µm, 177 µm, 152 µm, 133 µm, 118 µm, or 106 µm for operating ranges of 0.3 nm, 0.6 nm, 0.9 nm, 1.2 nm, 1.5 nm, 1.8 nm, 2.1 nm, 2.4 nm, 2.7 nm, and 3.0 nm, respectively. In some embodiments, the VCSEL emits no more than 0.01 mW, 0.025 mW, 0.05 mW, 0.1 mW, 0.25 mW, 0.5 mW 1 mW, 2.5 mW, 5 mW, 10 mW, 25 mW, 50 mW, 100 mW, 250 mW, 500 mW, 1 W, 2.5 W, 5 W, 10 W, 25 W, 50 W, or 100 W of optical power.

The light source need not be a VCSEL. In some cases, the light source is a doped fiber amplifier utilizing amplified spontaneous emission (ASE). In some cases, the light source is a superluminescent diode (SLD). Additionally, in some embodiments, the light source comprises multiple light sources.

Regardless of whether the SS-OCT device utilizes a reference mirror or not, the limited frequency range of the VCSEL causes the SS-OCT device to have an attainable axial resolution value less than about 100 µm.

Figure 7A:
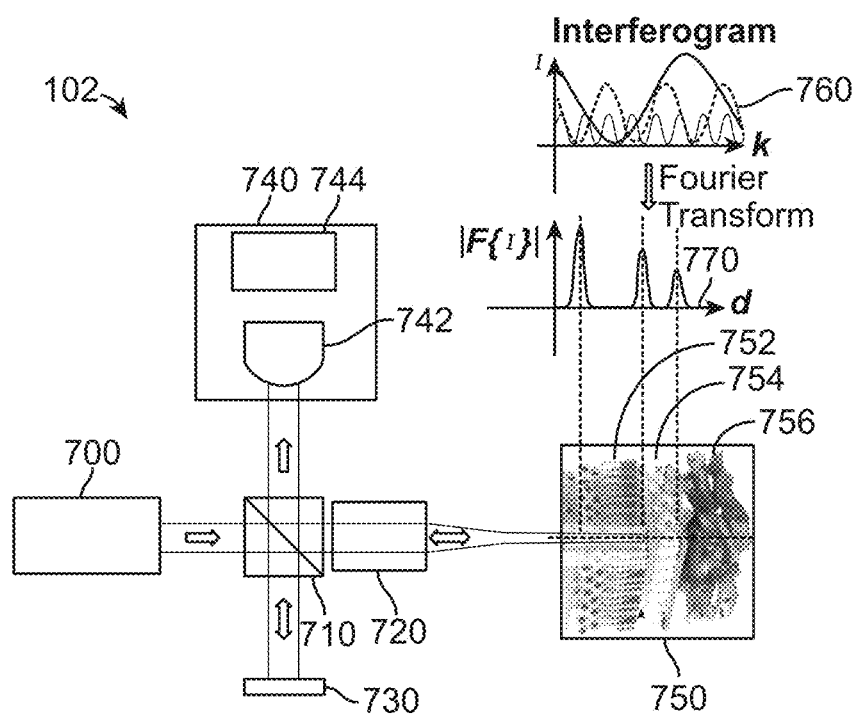
FIG. 7A shows a schematic for a SS-OCT device utilizing an external cavity, in accordance with some embodiments.

FIG. 7A shows a schematic for the optics of a swept source optical coherence tomography (SS-OCT) device utilizing a reference mirror, in accordance with some embodiments. In some cases, the optics 102 comprise a VCSEL or other light source 700, a beamsplitter 710, front-end optics 720, a reference mirror 730, and a processing unit 740. In some embodiments, the processing unit further comprises a photodetector 742 and a signal processing module 744. Light from the light source impinges upon the beamsplitter. A portion of the light is directed along a reference arm to a reference mirror and a portion of the light is directed to the front-end optics and then to the sample 750. Light is reflected back to the device at each boundary of each layer. Light reflected from each boundary interferes with light reflected from the reference mirror and with light reflected from any other boundary. The interference signal is detected at the photodetector.

This process is repeated over the range of wavelengths emitted by the light source. The amplitude of the interference signal varies with wavelength and attains a maximum value when the light reflected from a boundary and the light reflected from the reference mirror are in phase or when the light reflected from a boundary is in phase with light reflected from another boundary. This condition is attained at one or more particular wavelengths of light for each boundary and is characterized by one or more maxima in the interference signal. At other wavelengths, the interference signal displays partial constructive interference or destructive interference. The interference signals at all wavelengths are compiled to form an interferogram. The interferogram is subjected to a signal analysis procedure. In some cases, the interferogram is subjected to a frequency analysis procedure, such as a fast Fourier transform (FFT), to form a spectrum. The spectrum comprises peaks corresponding to the wavelengths associated with an interference maximum for each boundary. In some cases, the SS-OCT utilizes a light source with a relatively long coherence length (typically greater than a few millimeters). In some embodiments, the amplitude of the interference signal decreases as the distance between two retinal layers increases. In some instances, the position of a peak is indicative of the thickness of each layer of the tissue. The reference mirror allows longer optical path lengths for the light traveling to the sample. In some cases, this has the effect of shifting the frequency at which the maximum interference signal is attained to a higher frequency. In some embodiments, this shift to higher frequency allows for detection of the OCT signal in a manner that is more robust to noise.

In some cases, the light source comprises a laser source. In some embodiments, the laser source produces laser light having a wavelength that may be tuned. In some instances, the laser source is scanned over a range of wavelengths in order to obtain an OCT signal. In some cases, the laser source is capable of being scanned rapidly to allow rapid attainment of the OCT signal. In some embodiments, the laser source comprises a vertical cavity surface emitting laser (VCSEL) laser. In some instances, the VCSEL is tuned by varying the electrical current provided to the VCSEL. In some cases, the VCSEL is scanned continuously across a range of wavelengths by continuously varying the electrical current. In some embodiments, the VCSEL is periodically scanned across a range of wavelengths by periodically varying the electrical current. For instance, the VCSEL may be provided with a sinusoidally varying electrical current to produce a sinusoidally varying wavelength.

In some embodiments, the front-end optics comprise optical elements such as lenses. In some instances, the front-end optics comprise any reflective, refractive, or diffractive elements. In some cases, the front-end optics comprise more than one reflective, refractive, or diffractive elements. In some embodiments, the front-end optics comprise electro-optic, magneto-optic, acousto-optic, or mechano-optic devices. The front-end optics may comprise any optical elements known to one having skill in the art.

In some cases, the front end optics comprise a scanning optical element as described herein.

Figure 7B:
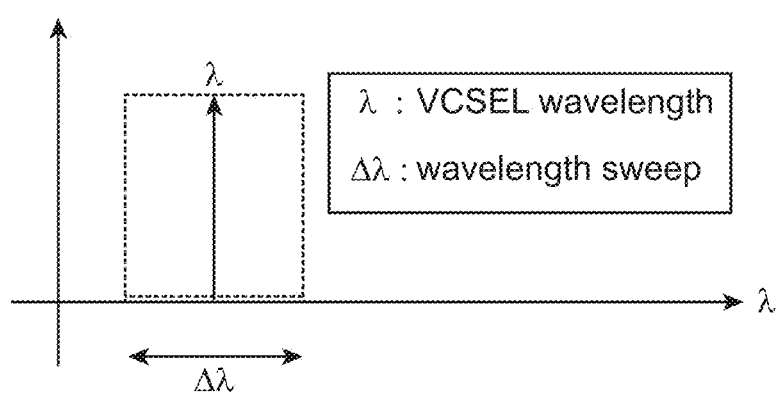
FIG. 7B shows the wavelength range over which the VCSEL operates in the SS-OCT device lacking a reference mirror, in accordance with some embodiments.

FIG. 7B shows the wavelength range over which the VCSEL operates in the swept source optical coherence tomography (SS-OCT) device lacking a reference mirror, in accordance with some embodiments. The light source emits light with a central wavelength $\lambda$. The central wavelength is varied over a range of wavelengths $\Delta\lambda$.

Figure 7C:
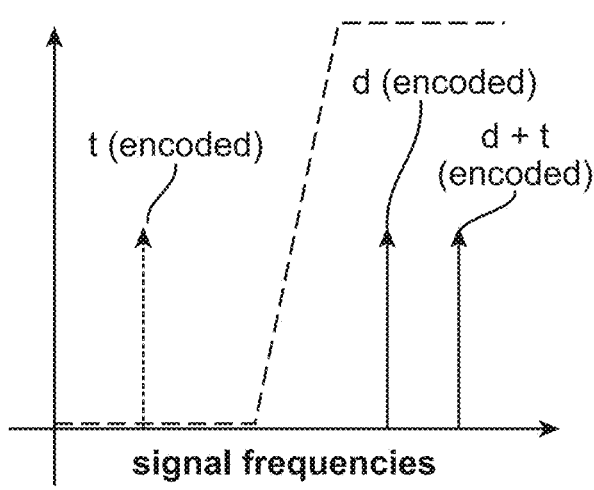
FIG. 7C shows how the use of an external cavity mirror may shift the OCT peaks to a higher optical frequency compared to the frequency of the OCT peak in the absence of the external cavity mirror.

FIG. 7C shows how a reference mirror may shift the OCT peaks to a higher optical frequency compared to the frequency of the OCT peak in the absence of the reference mirror. In the absence of the reference mirror, the OCT peak of a given sample is obtained at a relatively low frequency, indicated by t(encoded). This frequency corresponds to the optical path difference in the sample. The present of the reference mirror has the effect that each boundary of a sample interferes with the reference mirror. For a sample with two boundaries, this effect gives rise to two relatively high frequency components in the OCT signal, denoted as d(encoded) and d+t(encoded) in FIG. 7C. The difference between these two frequencies corresponds to the distance between the boundaries of the sample. For a retina or retinal layer, the different thus corresponds to a RT or RLT, respectively.

In some cases, the VCSEL has a maximum recommended current for continuous use. In some embodiments, the maximum continuous current rating limits the range of wavelengths over which the VCSEL may be swept. In some instances, the VCSEL is limited to a continuous operating current no more than 1 mA, 2 mA, 3 mA, 4 mA, 5 mA, 6 mA, 7 mA, 8 mA, 9 mA, or 10 mA. In some cases, the wavelength emitted by the VCSEL varies linearly with the operating current with a proportionality constant of 0.3 nm/mA. In some embodiments, this current limit limits the range of wavelengths over which the VCSEL may be swept. In some instances, the VCSEL is swept over a range defined by any two of the following numbers: 0.3 nm, 0.6 nm, 0.9 nm, 1.2 nm, 1.5 nm, 1.8 nm, 2.1 nm, 2.4 nm, 2.7 nm, or 3.0 nm. In some cases, this sweeping range limit limits the attainable axial resolution of the VCSEL-based SS-OCT device. In some embodiments, the sweep range is increased by driving the current beyond the maximum current rating, as described herein.

Thus, in some cases, the limited operating range of the VCSEL limits the attainable axial resolution. In some embodiments, for a VCSEL with a central operating wavelength of 850 nm, the attainable axial resolution is no better than 1062 µm, 531 µm, 354 µm, 266 µm, 213 µm, 177 µm, 152 µm, 133 µm, 118 µm, or 106 µm for operating ranges of 0.3 nm, 0.6 nm, 0.9 nm, 1.2 nm, 1.5 nm, 1.8 nm, 2.1 nm, 2.4 nm, 2.7 nm, and 3.0 nm, respectively. In some instances, the VCSEL emits no more than 0.01 mW, 0.025 mW, 0.05 mW, 0.1 mW, 0.25 mW, 0.5 mW 1 mW, 2.5 mW, 5 mW, 10 mW, 25 mW, 50 mW, 100 mW, 250 mW, 500 mW, 1 W, 2.5 W, 5 W, 10 W, 25 W, 50 W, or 100 W of optical power.

The light source need not be a VCSEL. In some cases, the light source is a doped fiber amplifier utilizing amplified spontaneous emission (ASE). In some cases, the light source is a superluminescent diode (SLD). Additionally, in some embodiments, the light source comprises multiple light sources.

In some cases, the limited attainable axial resolution is improved by utilizing two or more VCSELs or other light sources in the SS-OCT system. In some embodiments, each of the two or more VCSELs or other light sources has an emission spectrum which is distinct from the emission spectra of each of the other VCSELs or other light sources. In some cases, the emission spectra of the two or more VCSELs partially overlap. In some cases, the emission spectra of the two or more VCSELs do not overlap. In this manner, in some embodiments, the two or more VCSELs or other light sources combine to produce a wider range of emission wavelengths for the SS-OCT measurement. In some instances, this enhances the attainable axial resolution of the SS-OCT measurement.

Figure 8A:
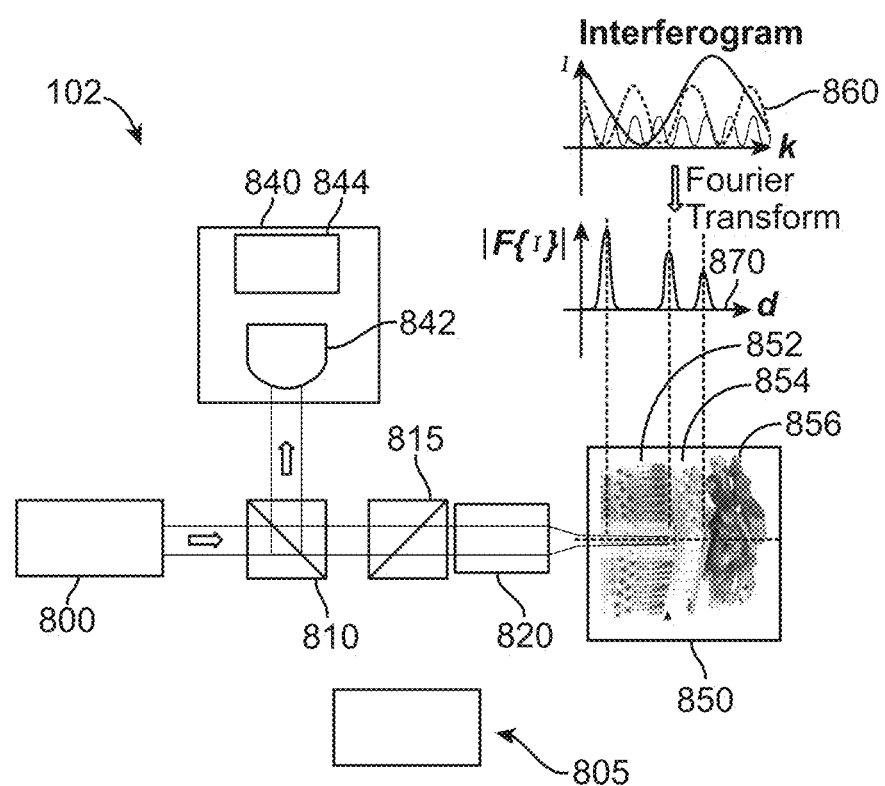
FIG. 8A shows a schematic for a SS-OCT device utilizing two VCSELs and lacking a reference mirror at a first particular point in time, in accordance with some embodiments.

FIG. 8A shows the optics of a swept source optical coherence tomography (SS-OCT) device utilizing two VCSELs and lacking a reference mirror at a first particular point in time, in accordance with some embodiments. In some cases, the optics 102 comprise a first VCSEL or other light source 800, a second VCSEL or other light source 805, a first beamsplitter 810, a second beamsplitter 815, front-end optics 820 as described herein, and a processing unit 840. In some embodiments, the processing unit further comprises a photodetector 842 and a signal processing module 844. Light from the first source impinges upon the beamsplitter. The light is then directed to the front-end optics and then to the sample 850. In some instances, at a first particular point in time, the first VCSEL or other light source is on (sending laser light to the sample) while the second VCSEL or other light source is off (not sending laser light to the sample). Light is reflected back to the device at each boundary of each layer. Light reflected from a boundary of a first layer interferes with light reflected from a back boundary of a second layer. The interference signal is detected at the photodetector.

Figure 8B:
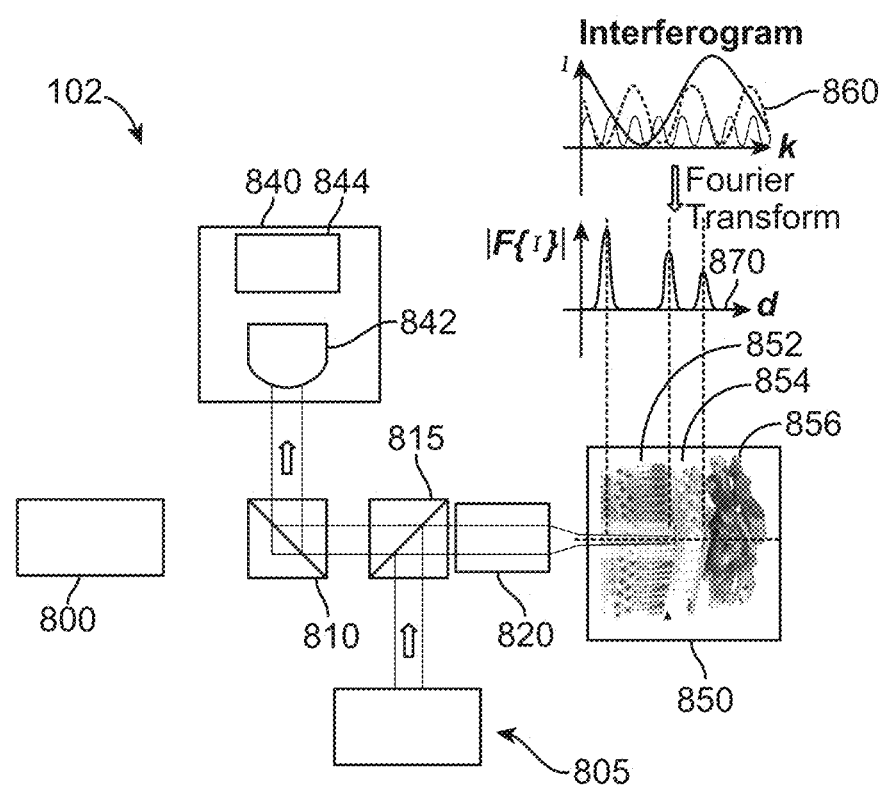
FIG. 8B shows a schematic for a SS-OCT device utilizing two VCSELs and lacking a reference mirror at second particular point in time, in accordance with some embodiments.

FIG. 8B shows a schematic for a swept source optical coherence tomography (SS-OCT) device utilizing two VCSELs and lacking a reference mirror at second particular point in time, in accordance with some embodiments. In some instances, at a second particular point in time, the first VCSEL or other light source is off (not sending laser light to the sample) while the second VCSEL or other light source is on (sending laser light to the sample). Light is reflected back to the device at each boundary of each layer. Light reflected from a boundary of a first layer interferes with light reflected from a boundary of a second layer. The interference signal is detected at the photodetector.

This process is repeated over the entire range of wavelengths emitted by the first and second light sources. The amplitude of the interference signal varies with wavelength and attains a maximum value when the light reflected from a boundary and the light reflected from the reference mirror are in phase or when the light reflected from a boundary is in phase with light reflected from another boundary. This condition is attained at one or more particular wavelengths of light for each boundary and is characterized by one or more maxima in the interference signal. At other wavelengths, the interference signal displays partial constructive interference or destructive interference. The interference signals at all wavelengths are compiled to form an interferogram. The interferogram is subjected to a signal analysis procedure. In some cases, the interferogram is subjected to a frequency analysis procedure, such as a fast Fourier transform (FFT), to form a spectrum. The spectrum comprises peaks corresponding to the wavelengths associated with an interference maximum for each boundary. In some cases, the SS-OCT utilizes light sources with a short coherence length (typically less than a few millimeters). In such a case, the amplitude of the interference signal decreases rapidly as the wavelength is moved away from the wavelength associated with the interference maximum. In some embodiments, this yields narrow peaks in the frequency spectrum. In some instances, the distances between peaks are indicative of the thickness of each layer of the tissue.

In some cases, the light sources comprise laser sources. In some embodiments, the laser sources produce laser light having a wavelength that may be tuned. In some instances, the laser sources are scanned over a range of wavelengths in order to obtain an OCT signal. In some cases, the laser sources are capable of being scanned rapidly to allow rapid attainment of the OCT signal. In some embodiments, the laser sources comprise vertical cavity surface emitting laser (VCSEL) lasers. In some instances, the VCSELs are tuned by varying the electrical current provided to the VCSELs. In some cases, the VCSELs are scanned continuously across a range of wavelengths by continuously varying the electrical current. In some embodiments, the VCSELs are periodically scanned across a range of wavelengths by periodically varying the electrical current. For instance, the VCSELs may be provided with a sinusoidally varying electrical current to produce a sinusoidally varying wavelength.

In some embodiments, the front-end optics comprise optical elements such as lenses. In some instances, the front-end optics comprise any reflective, refractive, or diffractive elements. In some cases, the front-end optics comprise more than one reflective, refractive, or diffractive elements. In some embodiments, the front-end optics comprise electro-optic, magneto-optic, acousto-optic, or mechano-optic devices. In some instances, the front-end optics comprise any optical elements known to one having skill in the art.

In some instances, the front end optics comprise a scanning optical element to allow the light source to be moved to different locations on the retina. In some cases, this allows multiple measurements to be conducted to determine a RT or RLT at different locations on the retina. In some embodiments, the scanning optical element comprises a galvanometer. In some instances, the scanning optical element comprises an acousto-optic modulator. In some cases, the scanning optical element comprises an electro-optic modulator. In some embodiments, the scanning optical element comprises an xy stage. The scanning optical element may comprise any scanning optical element as is known to one having skill in the art.

Figure 8C:
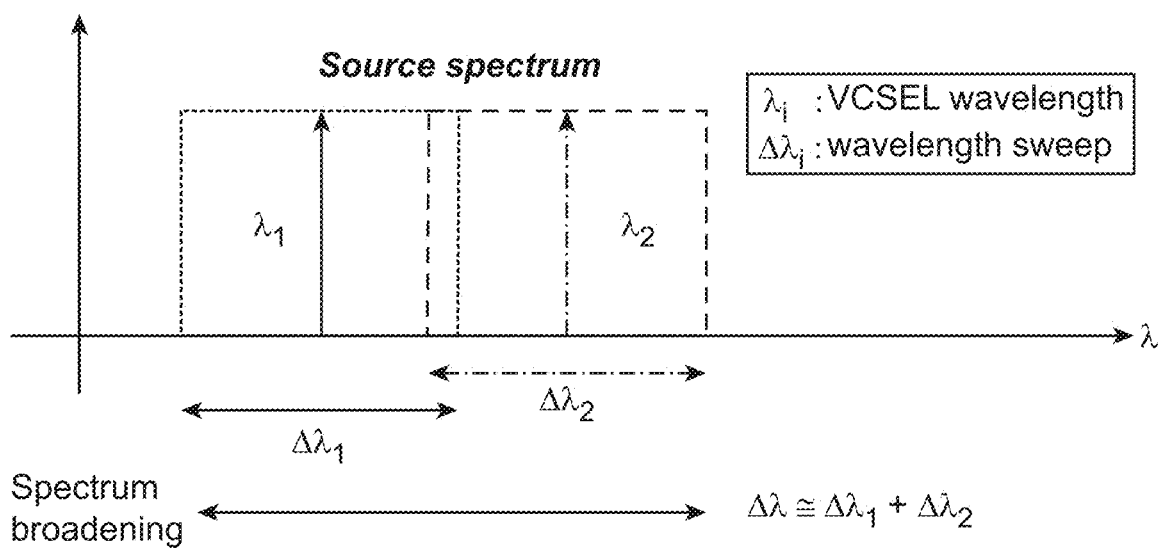
FIG. 8C shows the wavelength range over which the VCSELs operate in the SS-OCT device utilizing two VCSELs and lacking a reference mirror, in accordance with some embodiments.

FIG. 8C shows the wavelength range over which the VCSELs operate in the swept source optical coherence tomography (SS-OCT) device utilizing two VCSELs and lacking a reference mirror, in accordance with some embodiments.

The wavelength sweep may be coordinated between the two or more VCSELs or other light sources in a variety of manners. In one embodiment, the first VCSEL or other light source is swept over its entire wavelength range while the second VCSEL or other light source is off. The second VCSEL or other light source is then swept over its entire wavelength range while the first VCSEL or other light source is off. The wavelength sweep alternates between the two VCSELs or other light sources until the entire SS-OCT signal has been acquired. In some cases, the second VCSEL is configured to emit light having a wavelength within about 0.1 nm of the first VCSEL when the first VCSEL is turned off. In some embodiments, the VCSELs are swept at a rate between about 50 Hz and about 10 kHz. In some instances, the VCSELs are swept at a rate between about 1 kHz and about 5 kHz.

In another embodiment, the two or more VCSELs undergo their wavelength sweeps simultaneously and at the same rate. In such a setup it may be helpful to remove the temporal correlation between the OCT signals arising from the first VCSEL or other light source and the OCT signals arising from the second VCSEL or other light source. This may be accomplished, for instance, by modifying the optical setup of FIG. 8A to include a spectrometer in place of the photodetector, as will be readily understood be a person having skill in the art. In some cases, the sweep frequencies of the two VCSELs are substantially the same. In some embodiments, the sweep rates of the two VCSELs are within 5% of each other. In some instances, the sweep rates of the two VCSELs are within 1% of each other. In some cases, the VCSELs are swept at a rate between about 50 Hz and about 10 kHz. In some embodiments, the VCSELs are swept at a rate between about 1 kHz and about 5 kHz.

In another embodiment, the two or more VCSELs undergo their wavelength sweeps simultaneously but at different rates. For instance, the first VCSEL or other light source may be swept over its range of emission wavelengths at a first rate, so that it completes its wavelength sweep in a first amount of time. The second VCSEL or other light source is swept over its range of emission wavelengths at a second rate that is different from the first rate, so that it completes its wavelength sweep in a second amount of time that is different from the first amount of time. In this manner, the SS-OCT signals arising from the first VCSEL or other light source are encoded in time in a manner that is different from the temporal encoding of the SS-OCT signals arising from the second VCSEL or other light source. The SS-OCT signals arising from the first VCSEL or other light source are then distinguished from the SS-OCT signals arising from the second VCSEL or other light source through signal processing means. In some cases, the VCSELs are swept at a rate between about 50 Hz and about 10 kHz. In some embodiments, the VCSELs are swept at a rate between about 1 kHz and about 5 kHz.

In some embodiments, the system comprises 2, 3, 4, 5, 6, 7, 8, 9, 10, or more VCSELs or other light sources. In some instances, each VCSEL has a maximum recommended current for continuous use. In some cases, the maximum continuous operating current rating limits the range of wavelengths over which each VCSEL may be swept. For instance, each VCSEL may be limited to a continuous operating current no more than 1 mA, 2 mA, 3 mA, 4 mA, 5 mA, 6 mA, 7 mA, 8 mA, 9 mA, or 10 mA. In some cases, the wavelength emitted by each VCSEL varies linearly with the operating current with a proportionality constant of 0.3 nm/mA. In some embodiments, this limits the range of wavelengths over which each VCSEL may be swept to 0.3 nm, 0.6 nm, 0.9 nm, 1.2 nm, 1.5 nm, 1.8 nm, 2.1 nm, 2.4 nm, 2.7 nm, or 3.0 nm. In some instances, the combination of 2, 3, 4, 5, 6, 7, 8, 9, 10, or VCSELs or other light sources produces a total range of wavelengths of up to 30 nm or more. In some cases, the use of multiple VCSELs allows a swept wavelength range within the range of 5 nm to 10 nm, for example.

Thus, in some cases, the larger total operating range of the 2, 3, 4, 5, 6, 7, 8, 9, 10, or more VCSELs enhances the attainable axial resolution. In some embodiments, for a set of 2 VCSELs, each with a central operating wavelength of approximately 850 nm, the attainable axial resolution is 53 µm if each VCSEL has an operating range of 3.0 nm. With 3 VCSELs, the attainable axial resolution is 35 µm if each VCSEL has an operating range of 3.0 nm. With 4 VCSELs, the attainable axial resolution is 27 µm if each VCSEL has an operating range of 3.0 nm. In some cases, with greater and greater numbers of VCSELs, the attainable axial resolution is further enhanced. In some embodiments, each VCSEL emits no more than 0.01 mW, 0.025 mW, 0.05 mW, 0.1 mW, 0.25 mW, 0.5 mW 1 mW, 2.5 mW, 5 mW, 10 mW, 25 mW, 50 mW, 100 mW, 250 mW, 500 mW, 1 W, 2.5 W, 5 W, 10 W, 25 W, 50 W, or 100 W of optical power.

Obtaining an overall OCT signal with an enhanced resolution using a plurality of OCT light sources may introduce a desire to correct the OCT signals obtained from each of the individual OCT light sources in order to account for variations in the amplitudes, phases, or other optical parameters associated with the individual OCT light sources. Such variations may be corrected using the systems and methods described herein. For instance, the variations may be corrected using the optical systems and methods described herein with respect to FIGS. 45A-B and FIGS. 46A-G, for example.

Figure 45A:
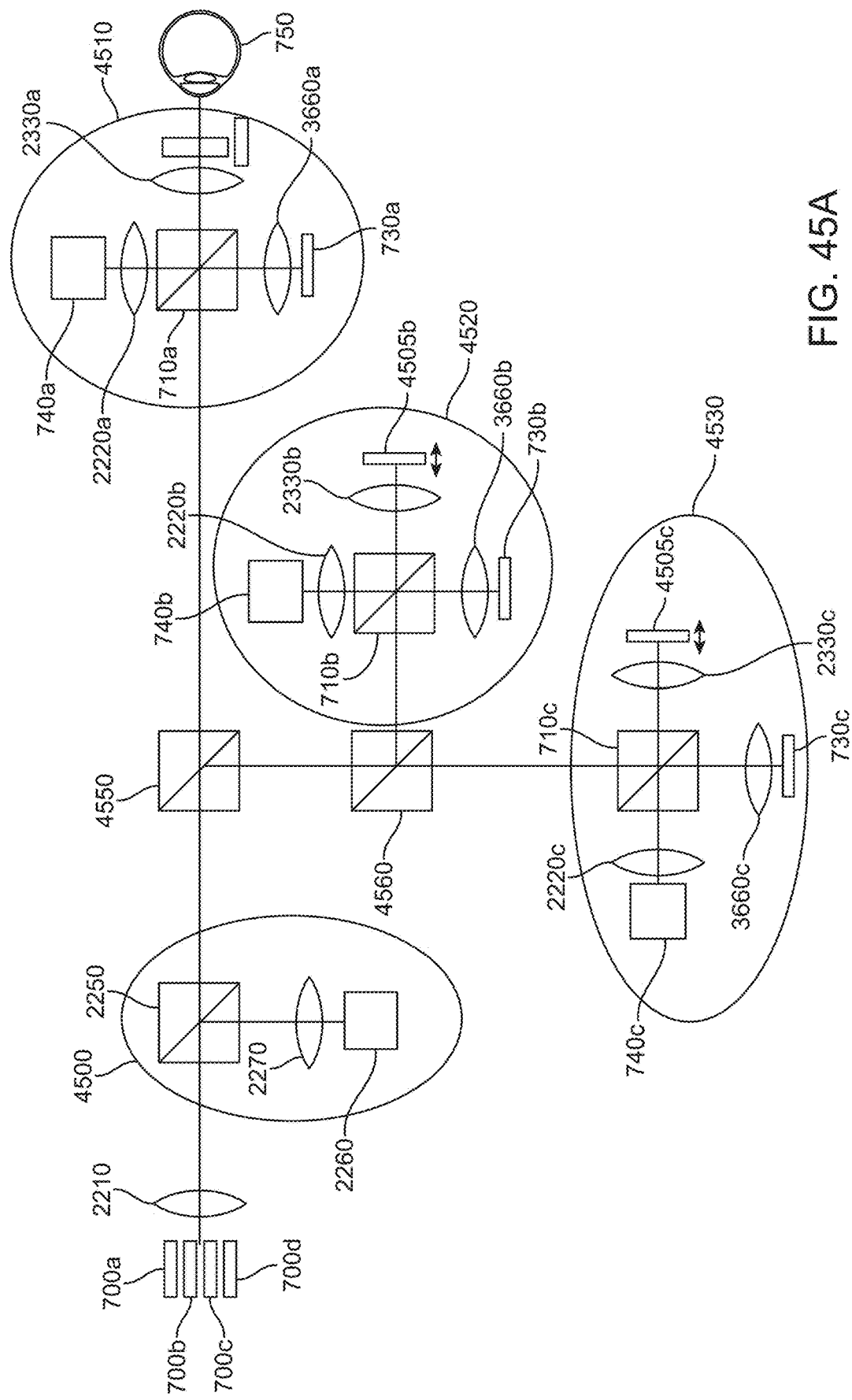
FIG. 45A shows a schematic for optics configured to characterize the wavelengths of light emitted by a plurality of OCT light sources, in accordance with some embodiments.

FIG. 45A shows a schematic for optics configured to characterize the wavelengths of light emitted by a plurality of OCT light sources, in accordance with some embodiments. As shown in FIG. 45A, the optics may comprise first, second, third, and fourth light sources 700a, 700b, 700c, and 700d, respectively. Each of the first, second, third, and fourth light sources may be similar to any light source described herein, such as light source 700 described herein. The first, second, third, and fourth light sources may emit first, second, third, and fourth emitted light, respectively. Any two, three, or four of the first, second, third, and fourth light sources may emit light at different points in time. Alternatively or in combination, any two, three, or four of the first, second, third, and fourth light sources may emit light simultaneously. Light emitted by the first, second, third, and fourth light sources may be directed to a collimating lens 2210.

The optics may further comprise a power measurement module 4500. Light emitted by the first, second, third, or fourth light sources may be collimated and directed to the power measurement module. The power measurement module may comprise a beamsplitter 2250 configured to direct a portion of the light emitted by the first, second, third, or fourth light source to a lens 2270 and photodetector 2260, as described herein. The power measurement module may be configured to measure an optical power emitted by the first, second, third, or fourth light source.

The optics may further comprise a sample measurement module 4510. A beamsplitter 4550 may be configured to direct a portion of the light emitted by the first, second, third, or fourth light sources to the sample measurement module. The sample measurement module may be configured to measure an OCT signal from a sample, such as an eye 750. The sample measurement module may comprise a beamsplitter 710a, a focusing lens 3660a, a reference mirror 730a, a focusing lens 2330a, a detector 740a, and a lens 2330a. The beamsplitter 710a, focusing lens 3660a, reference mirror 730a, focusing lens 2330a, detector 740a, and lens 2330a may be similar to beamsplitter 710, focusing lens 3660, reference mirror 730, focusing lens 2330, detector 740, and lens 2330, respectively, described herein. The elements of the sample measurement module may be configured to measure an OCT signal as described herein. In some embodiments, the sample measurement module is coupled to a scanner such as a scanning mirror as described herein, for example.

The optics may further comprise a first wavelength characterization module 4520. A beamsplitter 4560 may be configured to direct a portion of the light emitted by the first, second, third, or fourth light sources to the first wavelength characterization module. The first wavelength characterization module may be configured to characterize the wavelength of light emitted by the first, second, third, or fourth light sources. The first wavelength characterization module may comprise a beamsplitter 710b, a focusing lens 3660b, a reference mirror 730b, a focusing lens 2330b, a detector 740b, and a lens 2330b. The beamsplitter 710b, focusing lens 3660b, reference mirror 730b, focusing lens 2330b, detector 740b, and lens 2330b may be similar to beamsplitter 710, focusing lens 3660, reference mirror 730, focusing lens 2330, detector 740, and lens 2330, respectively, described herein. The first wavelength characterization module may further comprise a mirror 4505b. The mirror may be a scanning mirror configured to move (for instance, in a left to right manner as depicted in FIG. 45A) to alter an optical path difference between light reflected from the reference mirror 730b and the scanning mirror 4505b. Alternatively, the mirror 4505b may be fixed in location.

The optics may further comprise a second wavelength characterization module 4530. The beamsplitter 4560 may be configured to direct a portion of the light emitted by the first, second, third, or fourth light sources to the second wavelength characterization module. The second wavelength characterization module may be configured to characterize the wavelength of light emitted by the first, second, third, or fourth light sources. The second wavelength characterization module may comprise a beamsplitter 710c, a focusing lens 3660c, a reference mirror 730c, a focusing lens 2330c, a detector 740c, and a lens 2330c. The beamsplitter 710c, focusing lens 3660c, reference mirror 730c, focusing lens 2330c, detector 740c, and lens 2330c may be similar to beamsplitter 710, focusing lens 3660, reference mirror 730, focusing lens 2330, detector 740, and lens 2330, respectively, described herein. The second wavelength characterization module may further comprise a mirror 4505c. The mirror may be a scanning mirror configured to move (for instance, in a left to right manner as depicted in FIG. 45A) to alter an optical path difference between light reflected from the reference mirror 730c and the scanning mirror 4505c. Alternatively, the mirror 4505c may be fixed in location.

Though depicted as comprising 4 light sources in FIG. 45A, the system may comprise any number of light sources, such as at least 2, at least 3, at least 4, at least 5, at least 6, at least 7, at least 8, at least 9, at least 10, at least 20, at least 30, at least 40, at least 50, at least 60, at least 70, at least 80, at least 90, or at least 100 light sources, or a number of light sources that is within a range defined by any two of the preceding values. Though depicted as comprising 2 wavelength characterization modules in FIG. 45A, the system may comprise any number of wavelength characterization modules (and elements thereof), such as at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, or at least 100 wavelength characterization modules (and elements thereof), or a number of wavelength characterization modules (and elements thereof) that is within a range defined by any two of the preceding values.

Figure 45B:
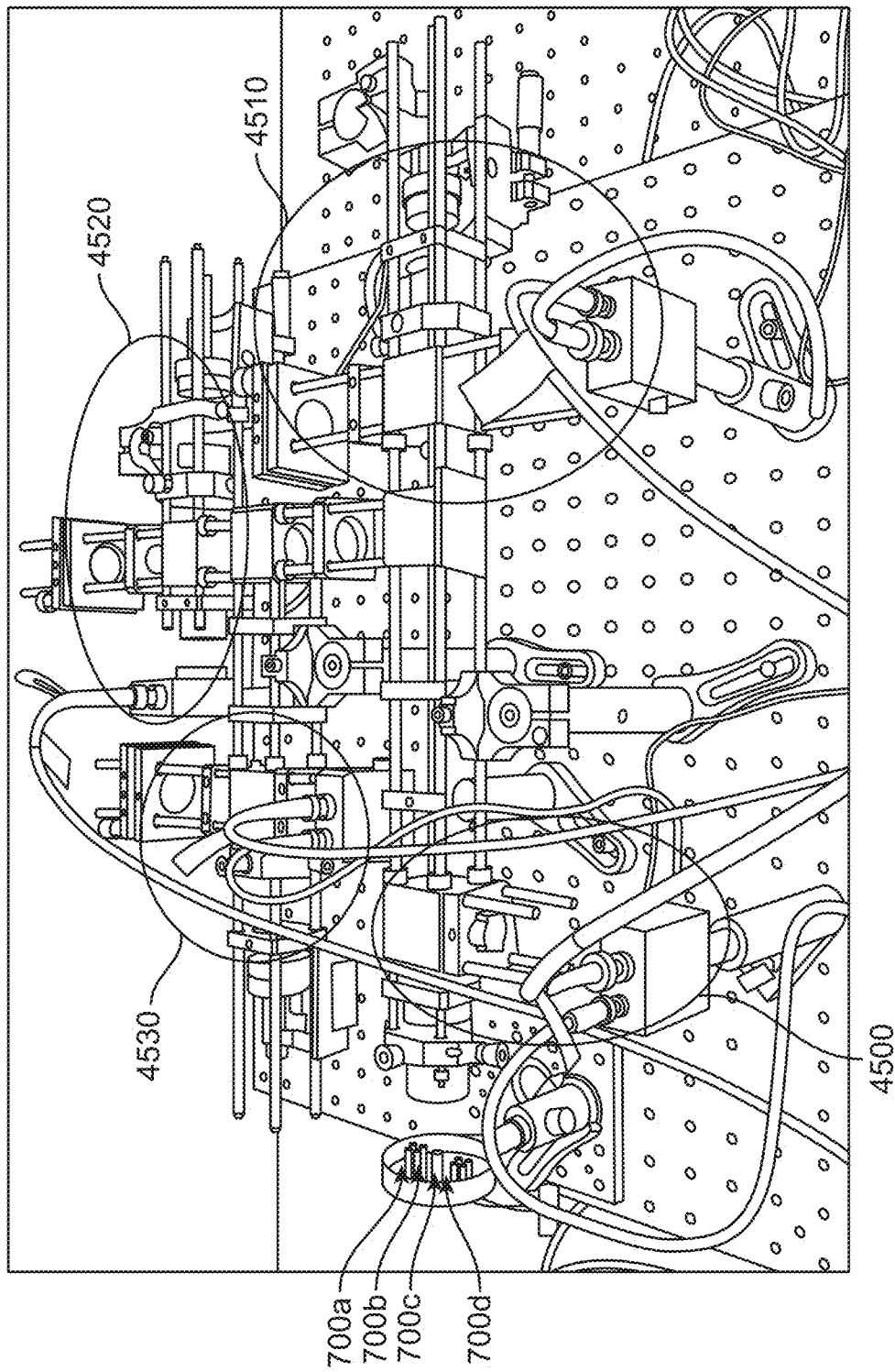
FIG. 45B shows an optical breadboard comprising optics configured to characterize the wavelengths of light emitted by a plurality of OCT light sources, in accordance with some embodiments.

FIG. 45B shows an optical breadboard comprising optics configured to characterize the wavelengths of light emitted by a plurality of OCT light sources, in accordance with some embodiments. As shown in FIG. 45B, the optics comprise first, second, third, and fourth light sources 700a, 700b, 700c, and 700d, respectively, power measurement module 4500, sample measurement module 4510, and first and second wavelength characterization modules 4520 and 4530, respectively.

The signals obtained by wavelength characterization optics (such as the first and second wavelength characterization modules described herein) or from the sample measurement module may allow the stitching together of clock signals from a plurality of light sources.

Figure 46A:
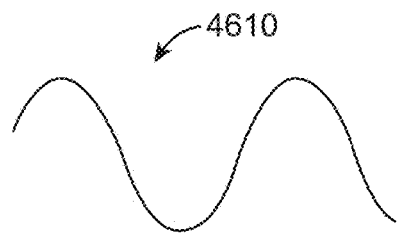
FIG. 46A shows a clock signal from a first light source as measured by a first wavelength characterization module, in accordance with some embodiments.

FIG. 46A shows a clock signal 4610 from a first light source as measured by a first wavelength characterization module described herein, in accordance with some embodiments. The clock signal 4610 may be a relatively low-frequency clock signal. The clock signal may comprise a measured intensity signal of interfering light measured with a detector of the wavelength characterization module. In some embodiments, the frequency of the clock signal is determined in response to an optical path distance between mirrors of the interferometer. Shorter distances between mirrors may generally correspond to lower frequencies, and greater distances between mirrors may correspond to higher frequencies. The frequencies from the modules can differ by a factor of 0.1, 0.25, 0.5, 1, 2, 5, 10, 20, 50, 100 and a range defined by any two of the preceding values. The lower frequency signal may reduce ambiguity when stitching a first measurement signal from a first VCSEL with a second measurement signal from a second VCSEL. The higher frequency component may increase precision and accuracy of the stitching.

Figure 46B:
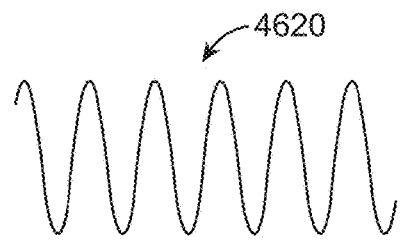
FIG. 46B shows a clock signal from a first light source as measured by a second wavelength characterization module, in accordance with some embodiments.

FIG. 46B shows a clock signal 4620 from a first light source as measured by a second wavelength characterization module described herein, in accordance with some embodiments. The clock signal 4620 may comprise a relatively high-frequency clock signal.

Figure 46C:
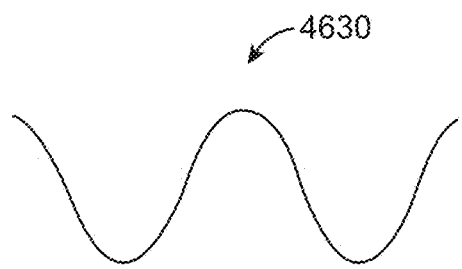
FIG. 46C shows a clock signal from a second light source as measured by a first wavelength characterization module, in accordance with some embodiments.

FIG. 46C shows a clock signal 4630 from a second light source as measured by a first wavelength characterization module described herein, in accordance with some embodiments. The clock signal 4630 may comprise a relatively low-frequency clock signal. As shown in FIG. 46C, the clock signal 4630 from the second light source may be out of phase with the clock signal 4610 from the first light source.

Figure 46D:
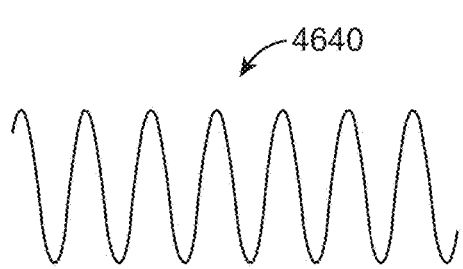
FIG. 46D shows a clock signal from a second light source as measured by a second wavelength characterization module, in accordance with some embodiments.

FIG. 46D shows a clock signal 4640 from a second light source as measured by a second wavelength characterization module described herein, in accordance with some embodiments. The clock signal 4640 may be a relatively high-frequency clock signal. As shown in FIG. 46D, the clock signal 4640 from the second light source may be out of phase from the clock signal 4620 from the first light source.

Figures 46E, 46F:
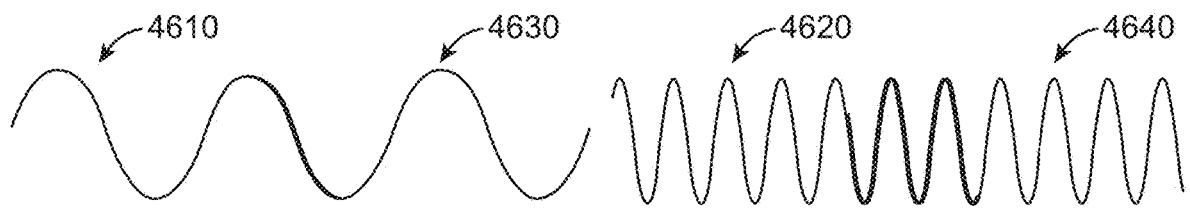
FIG. 46E shows the stitching together of the clock signal from the first light source as measured by the first wavelength characterization module and the clock signal from the second light source as measured by the first wavelength characterization module, in accordance with some embodiments.
FIG. 46F shows the stitching together of the clock signal from the first light source as measured by the second wavelength characterization module and the clock signal from the second light source as measured by the second wavelength characterization module, in accordance with some embodiments.

FIG. 46E shows the stitching together of the clock signal from the first light source as measured by the first wavelength characterization module and the clock signal from the second light source as measured by the first wavelength characterization module, in accordance with some embodiments. The low-frequency clock signals 4610 and 4630 from the first and second light sources, respectively, may be stitched together in a time series by partially overlapping a portion of the clock signal 4610 (such as a portion occurring near the end of the clock signal 4610) and a portion of the clock signal 4630 (such as a portion occurring near the beginning of the clock signal 4630). The partial overlapping may be achieved by shifting the clock signal 4610. In this manner, the clock signal 4610 and 4630 may be stitched into a continuous signal in time.

FIG. 46F shows the stitching together of the clock signal from the first light source as measured by the second wavelength characterization module and the clock signal from the second light source as measured by the second wavelength characterization module, in accordance with some embodiments. The high-frequency clock signals 4620 and 4640 from the first and second light sources, respectively, may be stitched together in a time series by partially overlapping a portion of the clock signal 4620 (such as a portion occurring near the end of the clock signal 4620) and a portion of the clock signal 4640 (such as a portion occurring near the beginning of the clock signal 4640). The partial overlapping may be achieved by shifting the clock signal 4620. In this manner, the clock signal 4620 and 4640 may be stitched into a continuous signal in time.

Though FIGS. 46A-F depict the stitching together of clock signals from two light sources, signals may be stitched together from any number of light sources. For instance, signals may be stitched together from at least 2, at least 3, at least 4, at least 5, at least 6, at least 7, at least 8, at least 9, or at least 10 light sources, or a number of light sources that is within a range defined by any two of the preceding values.

Figure 46G:
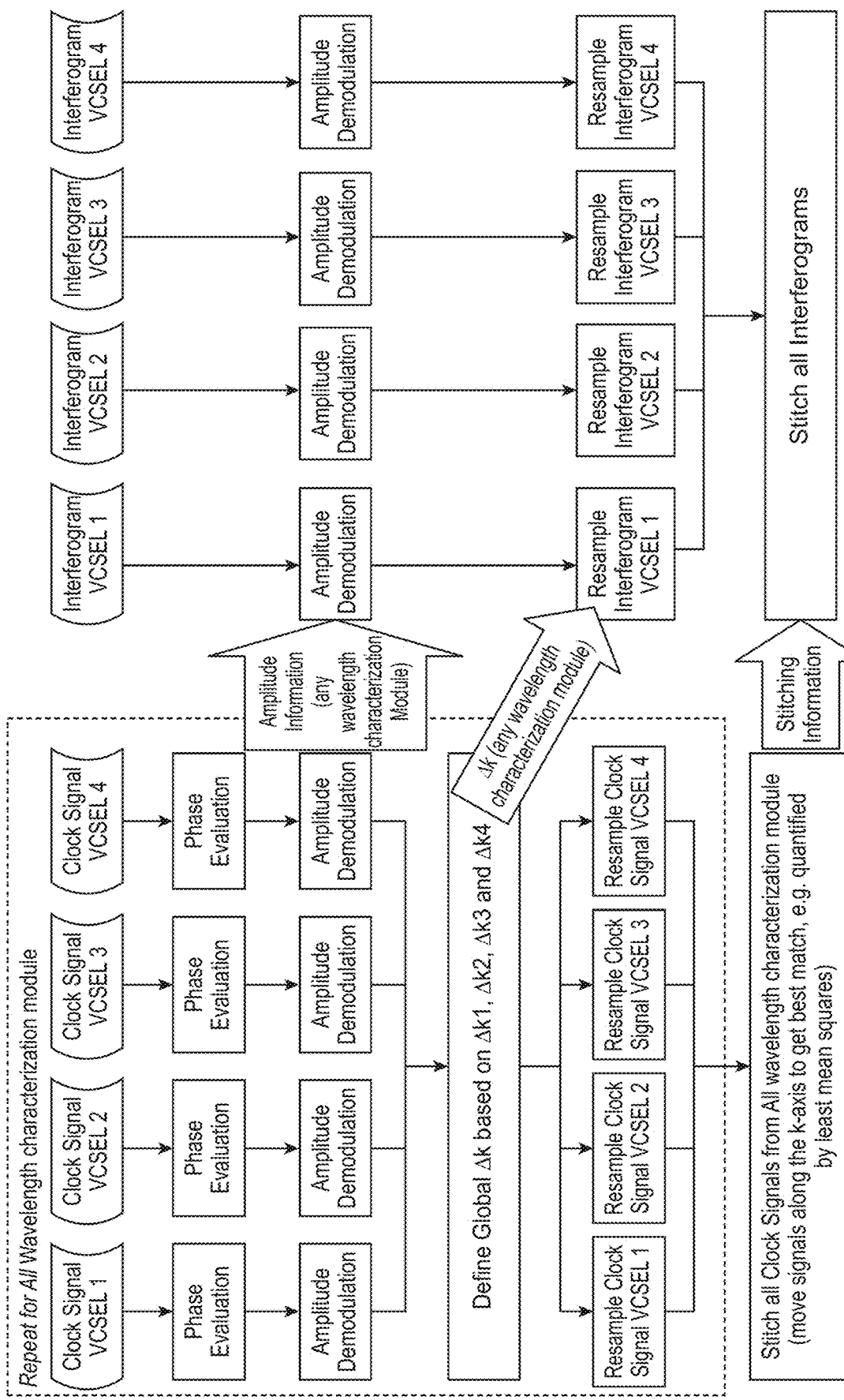
FIG. 46G shows a schematic for the stitching together of clock signals from a plurality of light sources, in accordance with some embodiments.

FIG. 46G shows a schematic for the stitching together of clock signals or interferometer signals from a plurality of light sources, in accordance with some embodiments. As shown in FIG. 46G, clock signals from first, second, third, and fourth light sources may be subjected to phase evaluation and amplitude demodulation procedures. The phase evaluation and amplitude demodulation procedures may be implemented using the systems and methods described herein. For instance, the phase evaluation procedure may be implemented using the wavelength characterization modules described herein. The phase evaluation and amplitude demodulation procedures may be implemented to determine a first phase shift $\Delta k1$ associated with the first light source, a second phase shift $\Delta k2$ associated with the second light source, a third phase shift $\Delta k3$ associated with the third light source, and a fourth phase shift $\Delta k4$ associated with the fourth light source. The first, second, third, and fourth phase shifts may be combined to define a global phase shift Δk. The clock signals associated with the first, second, third, and fourth light sources may be resampled with respect to the global phase shift. The clock signals may then be stitched together, as described herein. This procedure may be repeated for clock signals obtained from each wavelength characterization module. For instance, the procedure may be repeated for the first and second wavelength characterization modules described herein. The procedure may be repeated for at least 2, at least 3, at least 4, at least 5, at least 6, at least 7, at least 8, at least 9, or at least 10 wavelength characterization modules, or a number of wavelength characterization modules that is within a range defined by any two of the preceding values.

The stitched clock signals may be used to stitch together the OCT interferometer signals obtained by the first, second, third, and fourth light sources. Information obtained from the amplitude demodulation procedure may be utilized to perform amplitude demodulation of the OCT signals obtained by the first, second, third, and fourth light sources. The OCT interferometry signals associated with the first, second, third, and fourth light sources may be resampled with respect to the global phase shift Δk. The resampled OCT interferometry signals may then be stitched together using the stitching information from the stitched clock signals.

Obtaining an overall OCT signal with an enhanced resolution using a plurality of OCT light sources may also introduce a need to correct the OCT signals obtained from each of the individual OCT light sources in order to account for variations in the physical locations of the individual OCT light sources and how those physical locations influence the manner in which the light emitted by the individual OCT light sources interacts with other optical elements of the OCT systems. Such variations may be corrected using the systems and methods described herein. For instance, the variations may be corrected using the optical systems and methods described herein with respect to FIGS. 47A-J.

Figure 47A:
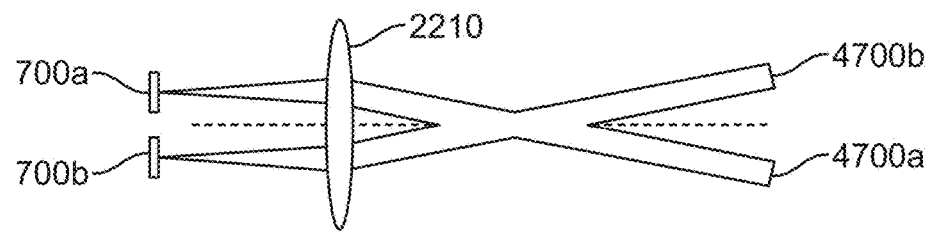
FIG. 47A shows optical beams associated with variations in the physical locations of a plurality of OCT light sources, in accordance with some embodiments.

FIG. 47A shows optical beams associated with variations in the physical locations of a plurality of OCT light sources, in accordance with some embodiments. First and second OCT light sources 700a and 700b, respectively, may emit first and second light beams 4700a and 4700b, respectively. The first and second light sources may be similar to light source 700 described herein. Because the first and second light sources each occupies a finite amount of physical space, one or both of the first and second light sources may be located at a position that is off the central axis of collimating lens 2210. For instance, as shown in FIG. 47A, the first light source may be located above the optical axis of the collimating lens while the second light source may be located below the optical axis of the collimating lens. In such a case, the collimating lens may produce non-ideal collimation of the first or second light. For instance, the collimating lens may produce collimated first and second light that are not parallel to one another, as shown in FIG. 47A. As a consequence, it may be non-ideal to align elements on an OCT optical system such that the first and second light sources create interference patterns on the same detector. This may be corrected using the systems and methods described herein with respect to FIGS. 47B-J.

Figure 47B:
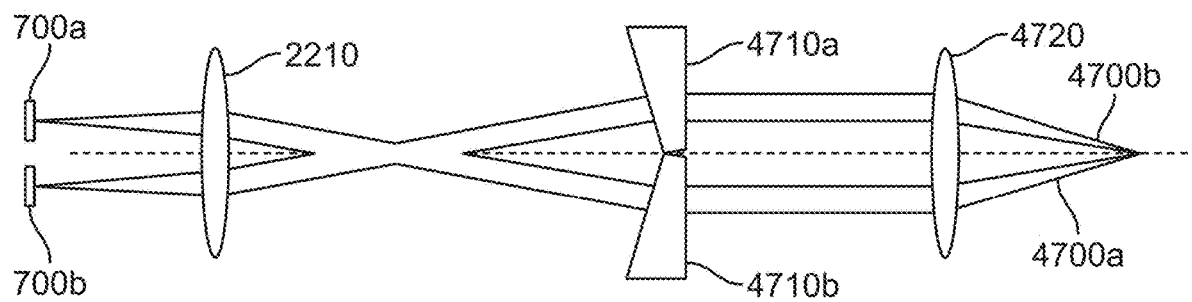
FIG. 47B shows a first schematic for optics configured to correct optical beams associated with variations in the physical locations of a plurality of OCT light sources, in accordance with some embodiments.

FIG. 47B shows a first schematic for optics configured to correct optical beams associated with variations in the physical locations of a plurality of OCT light sources, in accordance with some embodiments. As shown in FIG. 47B, the collimating lens 2210 may produce non-ideal collimation of the first and second light 4700a and 4700b, respectively, emitted by the first and second light sources 700a and 700b, respectively (such as the non-parallel first and second light depicted in FIG. 47A). The optics may comprise first and second prisms 4710a and 4710b, respectively, to correct the non-ideal collimation of the first and second light (such as the non-parallel first and second light depicted in FIG. 47A), respectively. For instance, the first and second prisms may correct the non-parallel paths of the first and second light, as depicted in FIG. 47B. The first and second light may then be focused to the same location (such as an eye, a retina of an eye, or a detector) by a focusing lens 4720. Though depicted as comprising 2 light sources and 2 prisms in FIG. 47B, the optics may comprise any number of light sources and any number of prisms. For instance, the optics may comprise at least 2, at least 3, at least 4, at least 5, at least 6, at least 7, at least 8, at least 9, or at least 10 light sources, or a number of light sources that is within a range defined by any two of the preceding values. The optics may comprise at least 2, at least 3, at least 4, at least 5, at least 6, at least 7, at least 8, at least 9, or at least 10 prisms, or a number of prisms that is within a range defined by any two of the preceding values.

Figure 47C:
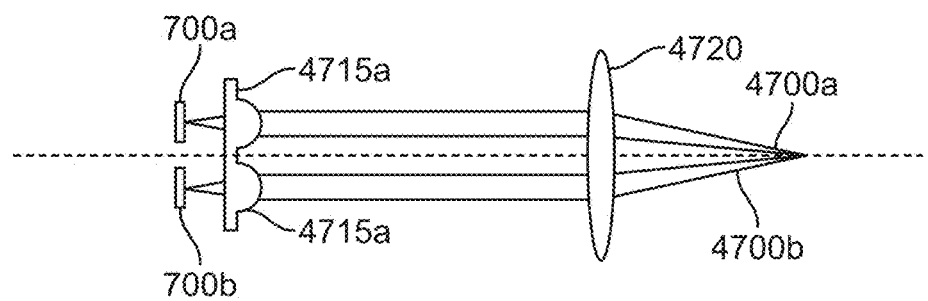
FIG. 47C shows a second schematic for optics configured to correct optical beams associated with variations in the physical locations of a plurality of OCT light sources, in accordance with some embodiments.

FIG. 47C shows a second schematic for optics configured to correct optical beams associated with variations in the physical locations of a plurality of OCT light sources, in accordance with some embodiments. As shown in FIG. 47C, a collimating lens that acts on both the first and second light 4700a and 4700b, respectively, emitted by the first and second light sources 700a and 700b, respectively, may be foregone. In place of the collimating lens, the optics may comprise first and second microlenses 4715a and 4715b, respectively, to individually collimate the first and second light, respectively. The first and second light may then be focused to the same location (such as an eye, a retina of an eye, or a detector) by a focusing lens 4720. Though depicted as comprising 2 light sources and 2 microlenses in FIG. 47C, the optics may comprise any number of light sources and any number of microlenses. For instance, the optics may comprise at least 2, at least 3, at least 4, at least 5, at least 6, at least 7, at least 8, at least 9, or at least 10 light sources, or a number of light sources that is within a range defined by any two of the preceding values. The optics may comprise at least 2, at least 3, at least 4, at least 5, at least 6, at least 7, at least 8, at least 9, or at least 10 prisms, or a number of microlenses that is within a range defined by any two of the preceding values.

Figure 47D:
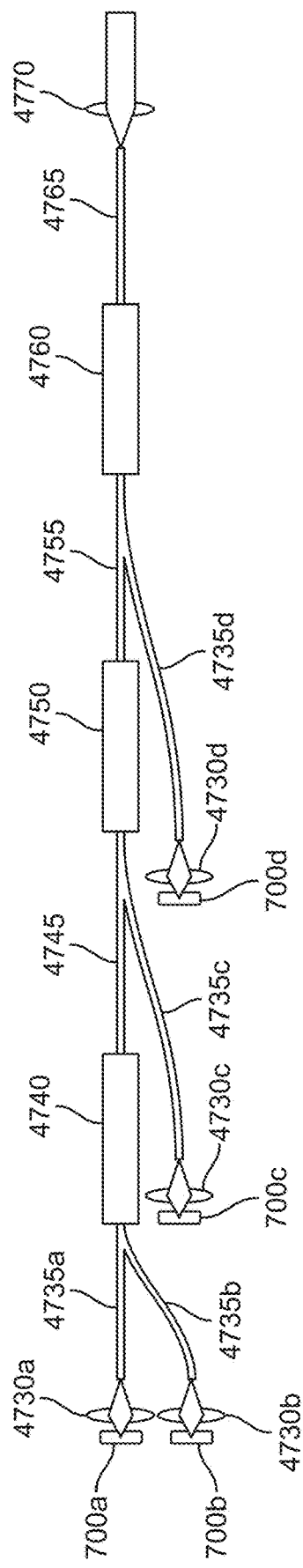
FIG. 47D shows a third schematic for optics configured to correct optical beams associated with variations in the physical locations of a plurality of OCT light sources, in accordance with some embodiments.

FIG. 47D shows a third schematic for optics configured to correct optical beams associated with variations in the physical locations of a plurality of OCT light sources, in accordance with some embodiments. As shown in FIG. 47D, first light emitted by a first light source 700a (which may be similar to light source 700 described herein) may be coupled into a first input optical fiber 4735a through a first coupling lens 4730a. Second light emitted by a second light source 700b (which may be similar to light source 700 described herein) may be coupled into a second input optical fiber 4735b through a second coupling lens 4730b. The first and second input optical fibers may be coupled to a first multiplexer 4740. Multiplexed light from the first multiplexer may be output to a first multiplexed optical fiber 4745. Third light emitted by a third light source 700c (which may be similar to light source 700 described herein) may be coupled into a third input optical fiber 4735c through a third coupling lens 4730c. The third input optical fiber and first multiplexed optical fiber may be coupled to a second multiplexer 4750. Multiplexed light from the second multiplexer may be output to a second multiplexed optical fiber 4755. Fourth light emitted by a third light source 700*d* (which may be similar to light source 700 described herein) may be coupled into a fourth input optical fiber 4735*d* through a fourth coupling lens 4730*d*. The fourth input optical fiber and second multiplexed optical fiber may be coupled to a third multiplexer 4760. Multiplexed light from the third multiplexer may be output to a third multiplexed optical fiber 4765. The third multiplexed optical fiber may be coupled to an output fiber coupling lens 4770 to produce collimated light from the first, second, third, and fourth light sources.

Though depicted as comprising 4 light sources, 4 coupling lenses, 4 input optical fibers, 3 multiplexers, and 3 multiplexed optical fibers in FIG. 47D, the optics may comprise any number of light sources, any number of coupling lenses, any number of input optical fibers, any number of multiplexers, and any number of multiplexed optical fibers. For instance, the optics may comprise at least 2, at least 3, at least 4, at least 5, at least 6, at least 7, at least 8, at least 9, or at least 10 light sources, or a number of light sources that is within a range defined by any two of the preceding values. The optics may comprise at least 2, at least 3, at least 4, at least 5, at least 6, at least 7, at least 8, at least 9, or at least 10 coupling lenses, or a number of coupling lenses that is within a range defined by any two of the preceding values. The optics may comprise at least 2, at least 3, at least 4, at least 5, at least 6, at least 7, at least 8, at least 9, or at least 10 input optical fibers, or a number of input optical fibers that is within a range defined by any two of the preceding values. The optics may comprise at least 2, at least 3, at least 4, at least 5, at least 6, at least 7, at least 8, at least 9, or at least 10 multiplexers, or a number of multiplexers that is within a range defined by any two of the preceding values. The optics may comprise at least 2, at least 3, at least 4, at least 5, at least 6, at least 7, at least 8, at least 9, or at least 10 multiplexed optical fibers, or a number of multiplexed optical fibers that is within a range defined by any two of the preceding values.

Figure 47E:
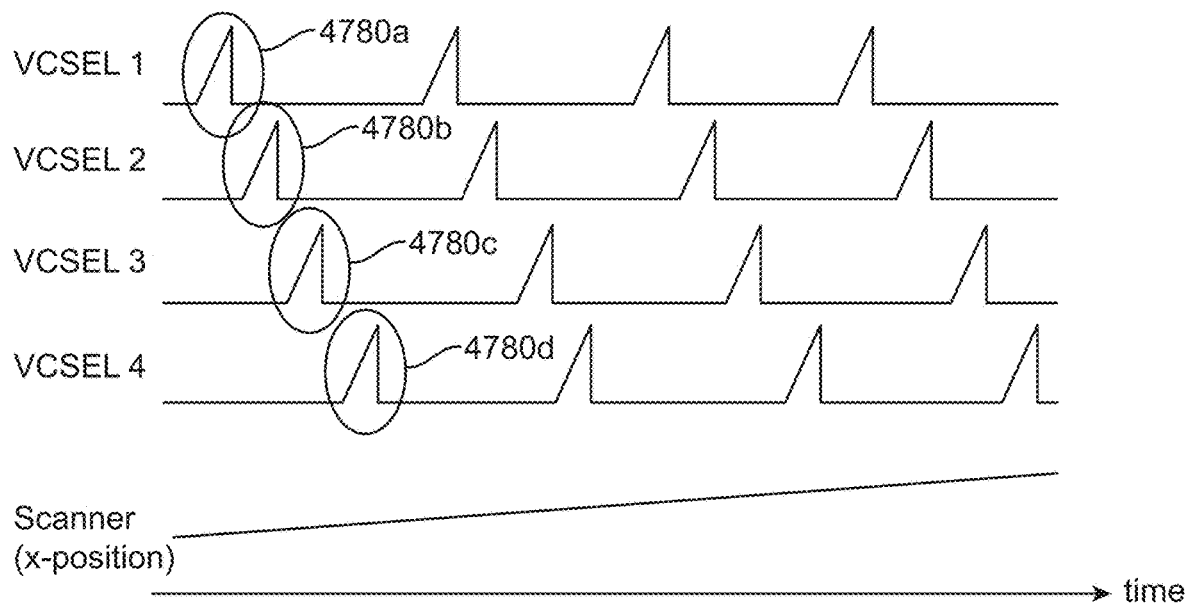
FIG. 47E shows a first retinal scan pattern for correcting optical beams associated with variations in the physical locations of a plurality of OCT light sources, in accordance with some embodiments.

FIG. 47E shows a first retinal scan pattern for correcting optical beams associated with variations in the physical locations of a plurality of OCT light sources, in accordance with some embodiments. As shown in FIG. 47E, the OCT signals may be combined by combining first, second, third, and fourth OCT signals associated with first, second, third, and fourth light sources, respectively, by acquiring the first, second, third, and fourth OCT signals with decreased temporal separation between the first, second, third, and fourth OCT signals. For instance, a first OCT signal 4780*a* associated with a first light source may be obtained at a first time. A second OCT signal 4780*b* associated with a second light source may be obtained at a second time, with the second time following very closely after the first time. For instance, the second time may follow at least 0.001 ms, at least 0.002 ms, at least 0.005 ms, at least 0.01 ms, at least 0.02 ms, at least 0.05 ms, at least 0.1 ms, at least 0.2 ms, at least 0.5 ms, or at least 1 ms after the first time. The second time may follow at most 1 ms, at most 0.5 ms, at most 0.2 ms, at most 0.1 ms, at most 0.05 ms, at most 0.02 ms, at most 0.01 ms, at most 0.005 ms, at most 0.002 ms, or at most 0.001 ms after the first time. The second time may follow the first time by a period of time that is within a range defined by any two of the preceding values. A third OCT signal 4780*c* associated with a third light source may be obtained at a third time, with the third time following very closely after the second time. For instance, the third time may follow at least 0.001 ms, at least 0.002 ms, at least 0.005 ms, at least 0.01 ms, at least 0.02 ms, at least 0.05 ms, at least 0.1 ms, at least 0.2 ms, at least 0.5 ms, or at least 1 ms after the second time. The third time may follow at most 1 ms, at most 0.5 ms, at most 0.2 ms, at most 0.1 ms, at most 0.05 ms, at most 0.02 ms, at most 0.01 ms, at most 0.005 ms, at most 0.002 ms, or at most 0.001 ms after the second time. The third time may follow the second time by a period of time that is within a range defined by any two of the preceding values. A fourth OCT signal 4780*d* associated with a fourth light source may be obtained at a fourth time, with the fourth time following very closely after the third time. For instance, the fourth time may follow at least 0.001 ms, at least 0.002 ms, at least 0.005 ms, at least 0.01 ms, at least 0.02 ms, at least 0.05 ms, at least 0.1 ms, at least 0.2 ms, at least 0.5 ms, or at least 1 ms after the third time. The fourth time may follow at most 1 ms, at most 0.5 ms, at most 0.2 ms, at most 0.1 ms, at most 0.05 ms, at most 0.02 ms, at most 0.01 ms, at most 0.005 ms, at most 0.002 ms, or at most 0.001 ms after the third time. The fourth time may follow the third time by a period of time that is within a range defined by any two of the preceding values.

Figure 47F:
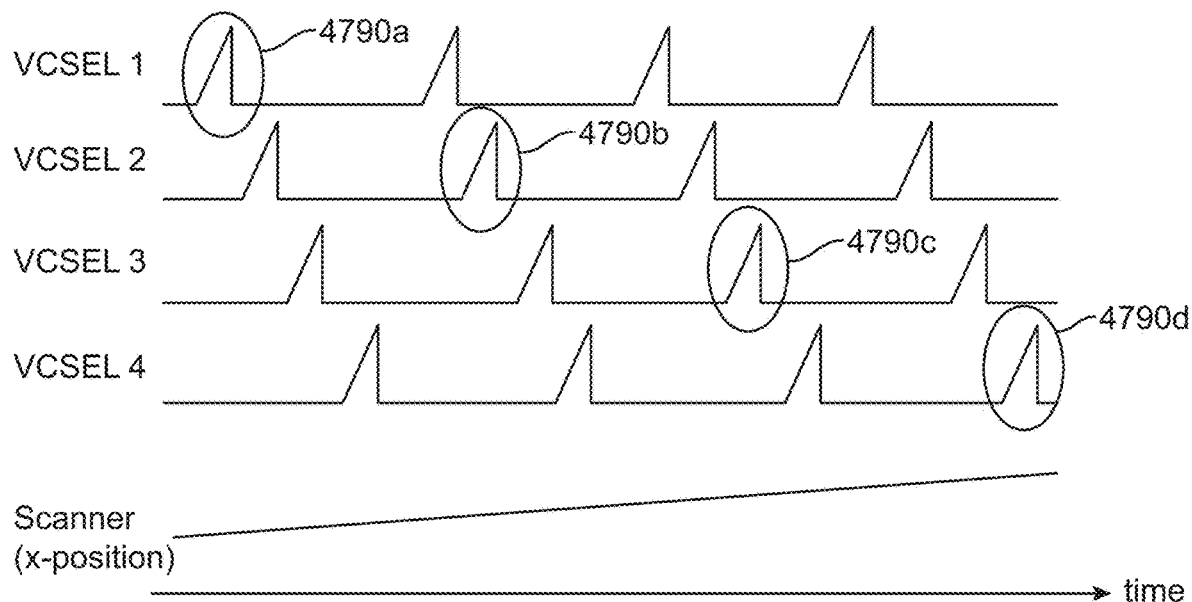
FIG. 47F shows a second retinal scan pattern for correcting optical beams associated with variations in the physical locations of a plurality of OCT light sources, in accordance with some embodiments.

FIG. 47F shows a second retinal scan pattern for correcting optical beams associated with variations in the physical locations of a plurality of OCT light sources, in accordance with some embodiments. As shown in FIG. 47F, the OCT signals may be combined by combining first, second, third, and fourth OCT signals associated with first, second, third, and fourth light sources, respectively, by acquiring the first, second, third, and fourth OCT signals at points in time at which first, second, third, and fourth light from the first, second, third, and fourth light sources, respectively, are directed to approximately the same location on a sample (such as an eye or a retina of an eye). For instance, a first OCT signal 4790*a* associated with a first light source may be obtained at a first time. At the first time, first light from the first light source may be directed to a particular location on a sample (such as an eye or a retina of an eye). A second OCT signal 4790*b* associated with a second light source may be obtained at a second time. At the second time, second light from the second light source may be directed to the same particular location on the sample. A third OCT signal 4790*c* associated with a third light source may be obtained at a third time. At the second time, third light from the third light source may be directed to the same particular location on the sample. A fourth OCT signal 4790*d* associated with a fourth light source may be obtained at a fourth time. At the fourth time, fourth light from the fourth light source may be directed to the same particular location on the sample.

Figure 47G:
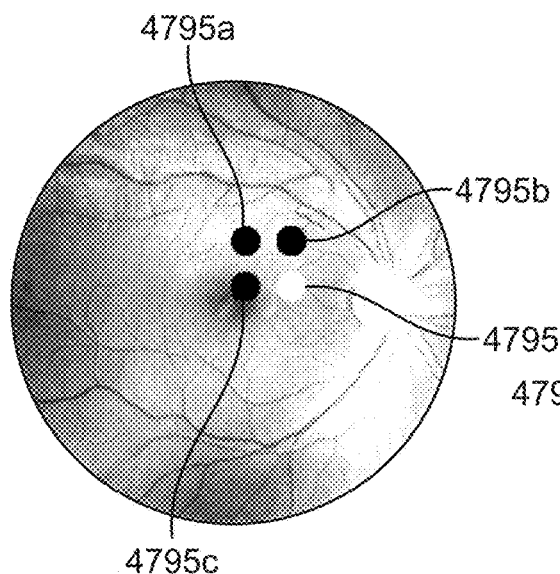
FIG. 47G shows the locations of light generated by a plurality of OCT light sources on a retina at a first time during a scan, in accordance with some embodiments.

FIG. 47G shows the illumination regions of light generated by a plurality of OCT light sources on a retina at a first time during a scan, in accordance with some embodiments. At the first point of the scan, first light associated with a first light source is at an illumination region 4795*a* on a retina. Second light associated with a second light source is at an illumination region 4795*b* on the retina. Third light associated with a third light source is at an illumination region 4795*c* on the retina. Fourth light associated with a fourth light source is at an illumination region 4795*d* on the retina.

Figure 47H:
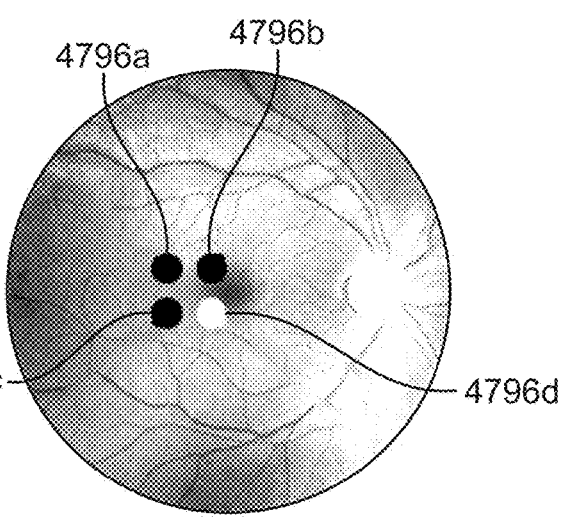
FIG. 47H shows the locations of light generated by a plurality of OCT light sources on a retina at a second time during a scan, in accordance with some embodiments.

FIG. 47H shows the illumination regions of light generated by a plurality of OCT light sources on a retina at a second time during a scan, in accordance with some embodiments. At the second point of the scan, first light beam associated with a first light source is at an illumination region 4796*a* on a retina. Second light beam associated with a second light source is at an illumination region 4796*b* on the retina. Third light beam associated with a third light source is at an illumination region 4796*c* on the retina. Fourth light beam associated with a fourth light source is at an illumination region 4796*d* on the retina.

Figure 47I:
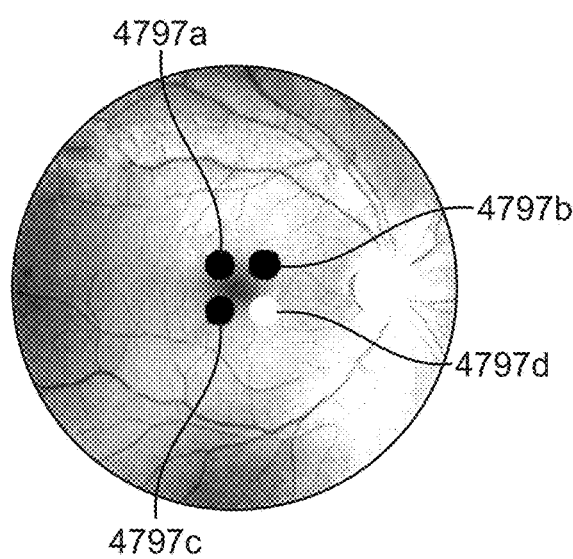
FIG. 47I shows the locations of light generated by a plurality of OCT light sources on a retina at a third time during a scan, in accordance with some embodiments.

FIG. 47I shows the illumination regions of light generated by a plurality of OCT light sources on a retina at a second time during a scan, in accordance with some embodiments. At the third point of the scan, first light beam associated with a first light source is at an illumination region 4797a on a retina. Second light beam associated with a second light source is at an illumination region 4797b on the retina. Third light beam associated with a third light source is at an illumination region 4797c on the retina. Fourth light beam associated with a fourth light source is at an illumination region 4797d on the retina.

Figure 47J:
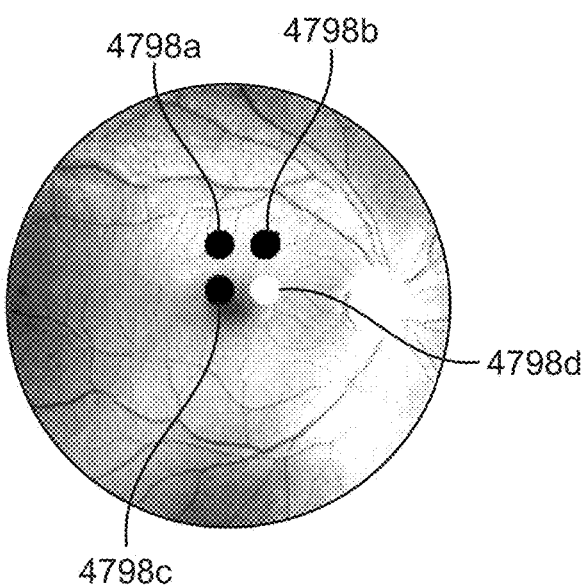
FIG. 47J shows the locations of light generated by a plurality of OCT light sources on a retina at a fourth time during a scan, in accordance with some embodiments.

FIG. 47J shows the illumination regions of light generated by a plurality of OCT light sources on a retina at a fourth time during a scan, in accordance with some embodiments. At the fourth point of the scan, first light associated with a first light source is at an illumination region 4798a on a retina. Second light associated with a second light source is at an illumination region 4798b on the retina. Third light associated with a third light source is at an illumination region 4798c on the retina. Fourth light associated with a fourth light source is at an illumination region 4798d on the retina.

It should be noted, with reference to FIGS. 47G-47J, that the timing of the sequential light source activation and scanning pattern can be arranged such that the illuminated areas from each beam overlap on the eye, so as to improve measurement accuracy. For example, the light sources can be sequentially activated and the scanner moved under computer control with instructions as described herein so that the illumination regions 4795c, 4796b, 4797b, and 4798c, which are associated with the third, second, second, and third light sources, respectively, substantially or partially overlap. In some embodiments, the scanner and timing may be configured to substantially overlap light from each of the light sources at each of a plurality of regions on the retina.

In some cases, the limited attainable axial resolution is also improved by providing the VCSEL or other light sources with a maximum electric current greater than that for which it is rated. A VCSEL is typically rated for a maximum electric current on the assumption that it will experience a high duty cycle. However, a VCSEL may be able to tolerate an electric current greater than the rated current for short periods of time. In a handheld SS-OCT device, a VCSEL may only be driven at an operating current outside of its rated range for a period required to obtain an OCT measurement. In some cases, the VCSEL is driven at an operating current outside of its rated range for less than one minute at a time. In some instances, the VCSEL is driven at an operating current outside of its rated range infrequently. For instance, in some cases, the VCSEL is driven at an operating current outside of its rated range once ever few hours. In some cases, the VCSEL is driven at an operating current outside of its rated range once every few days. In some embodiments, the VCSEL is turned off for periods in which it is not driven at an operating current outside of its rated range. In other embodiments, the VCSEL is driven at a lower operating current that is within its rated range for such periods. Thus, in some instances, a VCSEL is able to withstand being driven at a higher electric current than it is rated for under the operating conditions expected for a handheld SS-OCT device.

Figure 9:
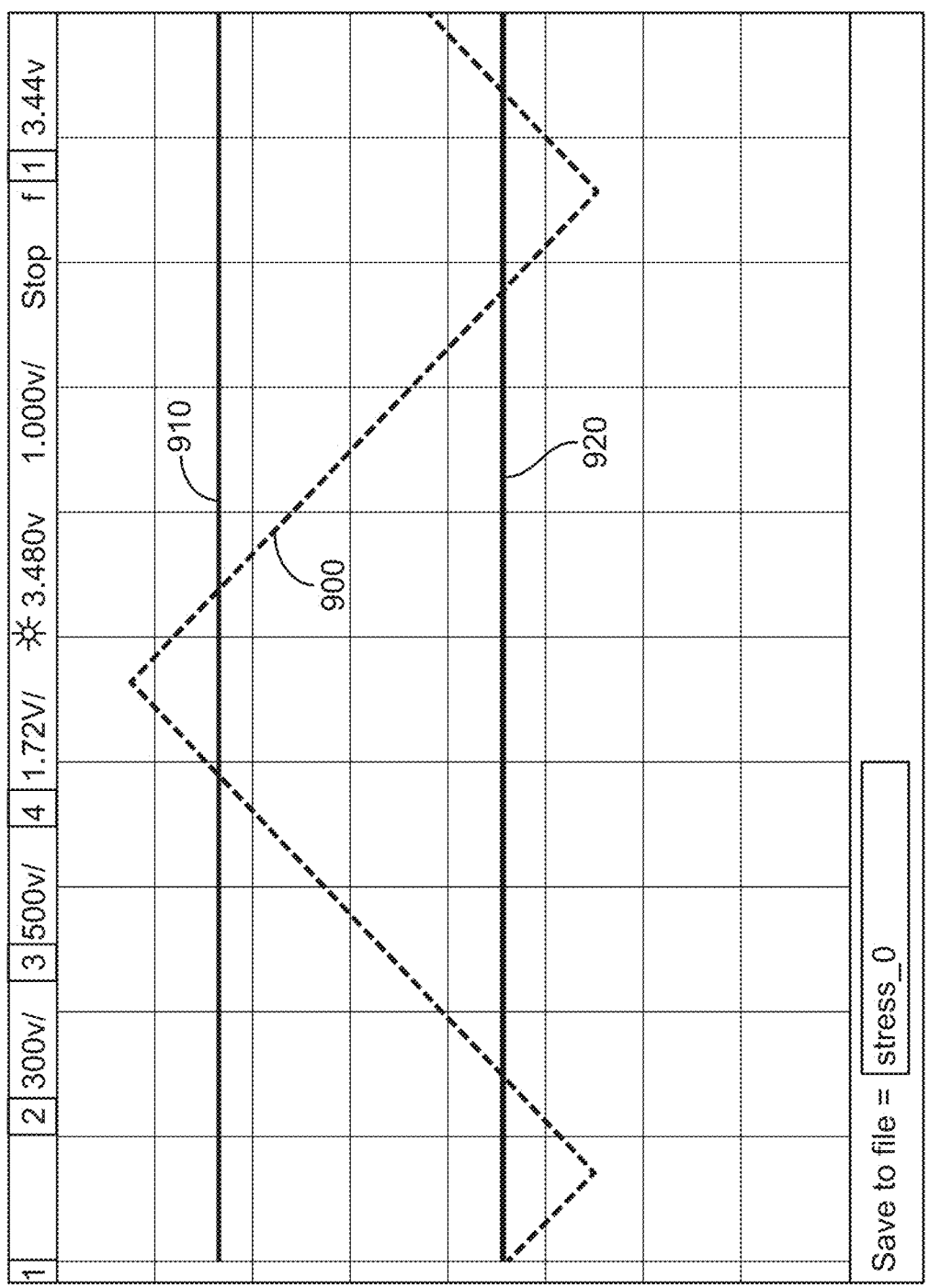
FIG. 9 shows the operation of a VCSEL beyond its maximum current rating, in accordance with some embodiments.

FIG. 9 shows the operation of a VCSEL beyond its maximum current rating. In some cases, the electric current supplied to the VCSEL is varied over time according to some waveform 900. The waveform may be triangular, sinusoidal, or any other waveform known to one having skill in the art. In some embodiments, the VCSEL has a recommended continuous electric current range specified by an upper current threshold 910 and/or a lower current threshold 920. At different time points in the waveform, the VCSEL is supplied with an electric current exceeding the upper current threshold or falling below the lower current threshold. In some cases, the maximum current exceeds the upper current threshold by more than 10%, more than 20%, more than 50%, more than 100%, more than 200%, more than 300%, more than 400%, or more than 500%. In some embodiments, the VCSEL is swept at a rate between about 50 Hz and about 10 kHz. In some instances, the VCSEL is swept at a rate between about 1 kHz and about 5 kHz.

In some cases, exceeding the maximum current allows the VCSEL to be driven beyond a specified maximum wavelength range directly related to its maximum recommend current for continuous use. In some cases, the VCSEL is driven beyond its specified wavelength range by at least about 1 nm. In some cases, the VCSEL is driven beyond its specified wavelength range by an amount within a range of 1 nm to 5 nm. In some embodiments, driving the VCSEL beyond its specified wavelength range allows a wavelength range within the range of 5 nm to 10 nm. In some instances, the VCSEL is driven beyond its maximum wavelength range for each of a plurality of measurements. To avoid overheating of the VCSEL, there may be a delay implemented between successive measurements. In some cases, the delay ranges from about 1 ms to about 100 ms. In some cases, the delay ranges from about 5 ms to about 20 ms.

In some cases, the limited attainable axial resolution afforded by a single VCSEL with a limited operating range does not present a problem for a technique that comprises measuring the thickness of a specific structure but not attempting to measure substructures within the structure. For instance, it may be of interest to attain a measurement of the RT or RLT without concern about imaging substructures within the retina. It may be of further interest to be concerned primarily with measured changes in the RT or RLT. In some cases, it is possible to obtain measurements of the RT or RLT with greater precision than may be expected from the attainable axial resolution.

Figure 10A:
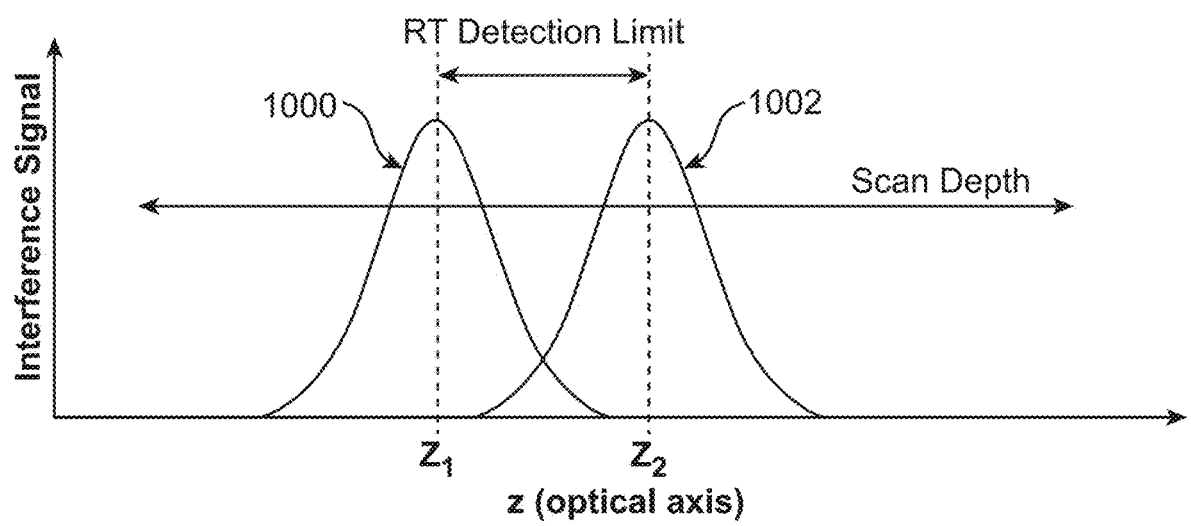
FIG. 10A shows a graphical representation of axial resolution.

FIG. 10A shows a graphical representation of axial resolution. An SS-OCT device used to measure RT or RLT produces a first interference signal 1000 associated with light reflected from a first boundary of a layer of tissue and a second interference signal 1002 associated with light reflected from a second boundary of a layer of tissue. The interference signals 1000 and 1002 are represented in the frequency domain. The first signal has a maximum at an optical path difference $\Delta z_1$. The second signal has a maximum at an optical path difference $\Delta z_2$. Each of the signal peaks has an associated width. The first and second interference signals may be said to be resolved if the two signals do not completely overlap and provide discernable peaks. A maximum overlap occurs when the two signals would no longer be distinguishable if they further overlapped. The distance between the first peak and the second peak at the point of maximum overlap is the axial resolution. The width is inversely related to the range of wavelengths over which the SS-OCT light source is swept. Thus, for SS-OCT devices utilizing a relatively narrow range of wavelengths, the axial resolution can be less than ideal.

For measurements of the RT, the axial resolution should be sufficient to distinguish a first interference signal associated with a first interfacial boundary of a layer of tissue and a second interference signal associated with a second interfacial boundary of the layer of tissue. Since a retina typically has a RT of greater than 150 µm, an SS-OCT device capable of measuring a RT can achieve an axial resolution value of less than about 150 µm.

Figure 10B:
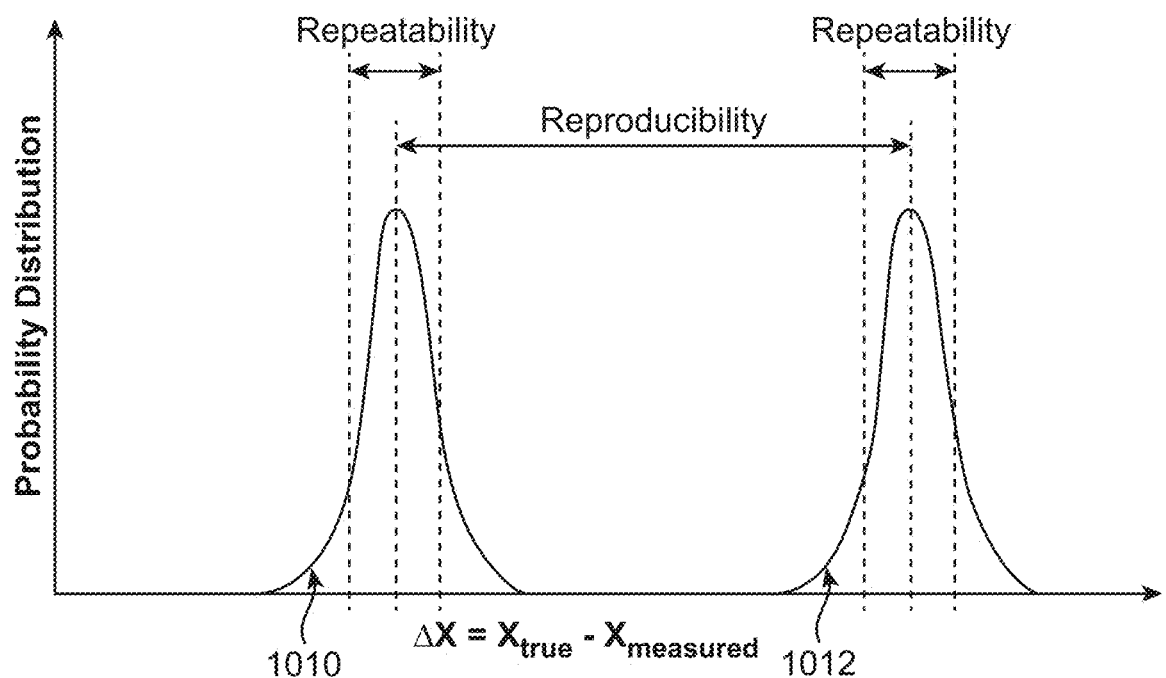
FIG. 10B shows a graphical representation of repeatability and reproducibility.

FIG. 10B shows a graphical representation of repeatability and reproducibility. Repeatability refers to the variation in measurements taken by a single instrument on the same item, under similar conditions, within a short period of time (e.g. within a minute, within an hour, or within a day). Reproducibility refers to the variation in measurements taken by a single instrument on the same sample, under similar conditions but over a longer period of time (e.g. after more than a day, more than a week, more than a month, more than 3 months, or more than 6 months). Repeatability may be quantitatively expressed as the full-width at half maximum (FWHM) value of the distribution of values obtained during repeated measurements by a single instrument, under similar conditions, within the relatively short period of time. Reproducibility may be quantitatively expressed as a difference between the central value of a first distribution of values obtained by a single instrument, under a first set of conditions, conducted within a first short period of time, and the central value of a second distribution of values obtained by the single instrument, under a second set of conditions, conducted within the second short period of time. For measurements of the RT, the combination of repeatability and reproducibility can be used to set tolerances for determining determines whether a change in the measured value of the RT or RLT is due to noise or due to an actual change in the thickness of the retina.

Figure 10C:
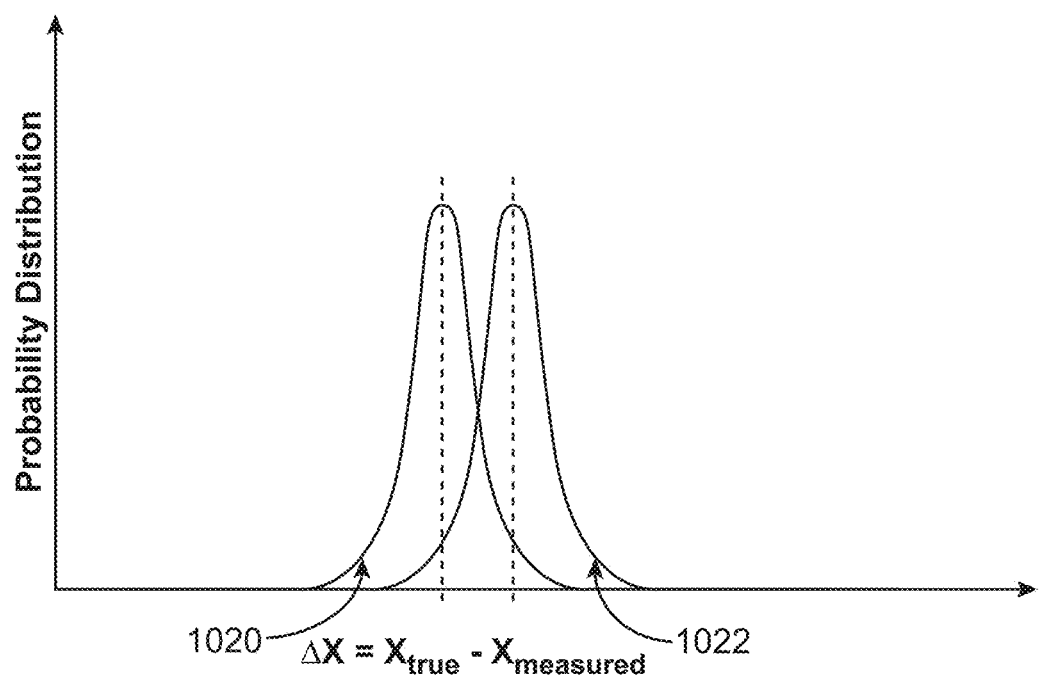
FIG. 10C shows a graphical representation of the repeatability and reproducibility associated with measurements of the RT of a retina that has not exhibited a change in RT.

FIG. 10C shows a graphical representation of the repeatability and reproducibility associated with measurements of the RT or RLT of a retina that has not exhibited a change in RT or RLT. At a first point in time, a measured value of the RT follows a distribution 1020 determined by the repeatability. At a later point in time, a measured value of the RT or RLT is obtained from a distribution 1022, as determined by the repeatability and reproducibility. For a retina which has not exhibited a change in RT or RLT, the two distributions 1020 and 1022 lie within close proximity of one another, such that Δx is within the combined repeatability and reproducibility. If however, Δx is greater than the combined repeatability and reproducibility an increase in retinal thickness is identified and reported to the patient and health care provider, for example with an alert, as explained more fully in FIG. 10D. In many embodiments, the compact OCT device has a combined repeatability and reproducibility of less than about 35 µm. In some embodiments, the SS-OCT device has a combined repeatability and reproducibility of less than 25 µm with a 95% confidence level.

Figure 10D:
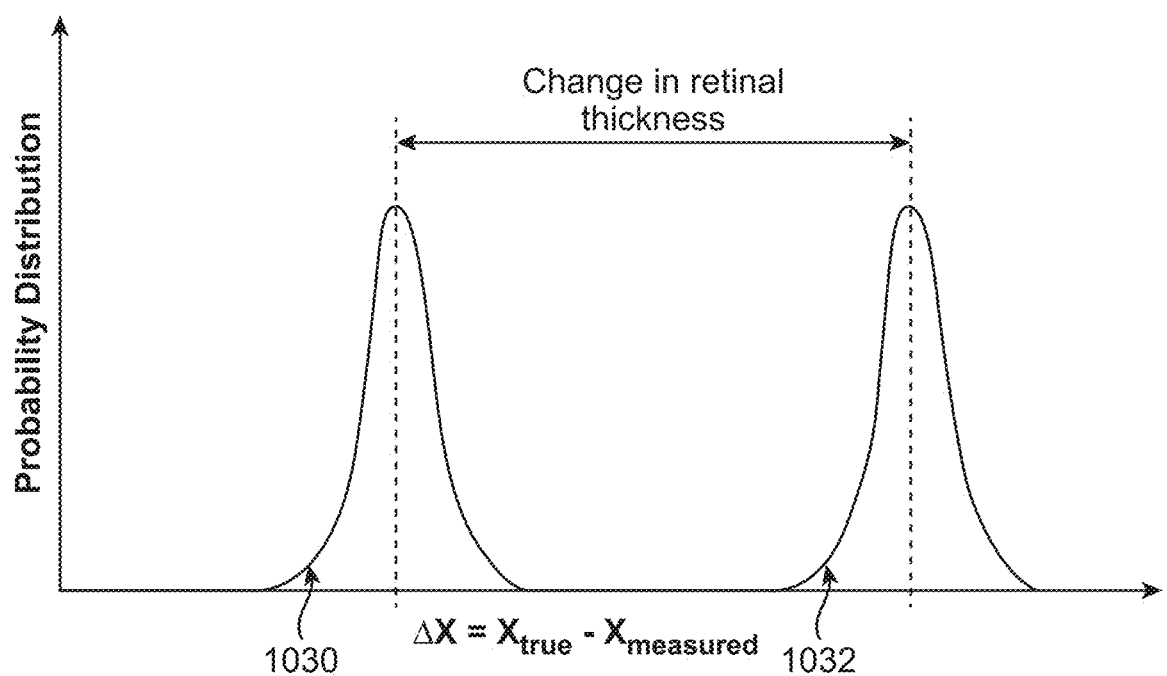
FIG. 10D shows a graphical representation of the repeatability and reproducibility associated with measurements of the RT of a retina that has exhibited a change in RT.

FIG. 10D shows a graphical representation of the repeatability and reproducibility associated with measurements of the RT or RLT of a retina that has exhibited a change in RT or RLT. At a first point in time, a RT or RLT is obtained within a first distribution 1030 determined by the repeatability. At a later point in time, the RT or RLT is obtained within a second distribution 1032, also determined by the repeatability. For a retina which has exhibited a change in RT or RLT, the two distributions 1030 and 1032 no longer lie within close proximity of one another. When the distance between the two distributions 1030 and 1032 exceeds the combination of the repeatability and reproducibility, it may be determined that the RT or RLT has changed. The distance between the two distributions can be determined by determining a difference between the respective means of the two distributions. The system can determine that a change in RT or RLT has occurred when the measured values are separated by more than the combination of the repeatability and reproducibility. For example, this would be approximately 35 µm for a reproducibility of 25 µm and a repeatability of 25 µm. Alternatively, with systematic errors or long-term drift, the combined error could be larger than 35 µm for a reproducibility of 25 µm and a repeatability of 25 µm. Therefore, the peaks of the distributions for a first RT measurement of 150 µm and a second RT measurement of 200 µm would be 50 µm apart. Although the first measurement and the second measurement are shown to have non-overlapping distributions, the methods and apparatuses described herein are capable of determining RT or RLT for partially overlapping distributions of measurements.

In some cases, a measured value of the RT or RLT obtained by the handheld OCT device is compared to a reference measurement. In some embodiments, the reference measurement is obtained from a measurement conducted by a clinical OCT device. In some instances, the reference measurement is obtained during a visit to a patient's health care provider. In some cases, the reference measurement is stored on the handheld OCT device, the patient device (such as a smartphone or other portable electronic device), or the cloud-based storage and communications system. In some embodiments, the reference measurement is used to adjust the measured value from the compact OCT device to account for any systematic errors in the measured value, for example.

Thus, when it is desired to attain measured changes in the RT or RLT, it may be possible to obtain a limit of detection which is substantially better than the attainable axial resolution for OCT imaging set by Equation 1. In some cases, the handheld OCT devices described herein attains a repeatability of approximately 25 µm. In some embodiments, the handheld OCT devices described herein is capable of detecting a change in RT or RLT of approximately 25 µm. In some cases, the handheld OCT devices described herein is capable of detecting a change in RT or RLT of in the range of 10 µm to 40 µm with a confidence better than 95%. In some cases, the handheld OCT devices described herein is capable of detecting a change in RT or RLT of in the range of 20 µm to 30 µm with a confidence better than 95%.

In many embodiments, the compact OCT system is calibrated for a specific patient with a high resolution clinical OCT reference system having a resolution value less than the compact OCT system. For example, the patient can visit an ophthalmologist and the retinal thickness measured with a high resolution ultrasound system at the physician's office. The compact OCT system can be calibrated to the specific patient based on the retinal thickness measured with the clinical reference system. This calibration of the compact OCT system based on the high resolution OCT system can be performed within a day of the high resolution ultrasound system measurement, preferably within about two hours of the clinical high resolution ultrasound measurement, and in many instances while the patient is at the clinic.

In some embodiments, the devices described herein are capable of continued operation after being dropped. In some instances, the devices described herein are capable of withstanding drops with a 95% survival rate during a drop test. In some cases, the drop test consists of dropping a device from 1 foot (0.305 m), 2 feet (0.610 m), 3 feet (0.914 m), and 4 feet (1.219 m). In some embodiments, the devices described herein are capable of continued operation with a change in repeatability of no more than 30 µm following the drop test. In some embodiments, the devices are capable of continued operation with a change in repeatability of no more than 20 µm following the drop test. In some embodiments, the devices are capable of continued operation with a change in repeatability of no more than 15 µm following the drop test. In some embodiments, the devices are capable of continued operation with a change in repeatability of no more than 10 µm following the drop test. In some embodiments, the devices are capable of continued operation with a change in repeatability of no more than 5 µm following the drop test.

Figure 11:
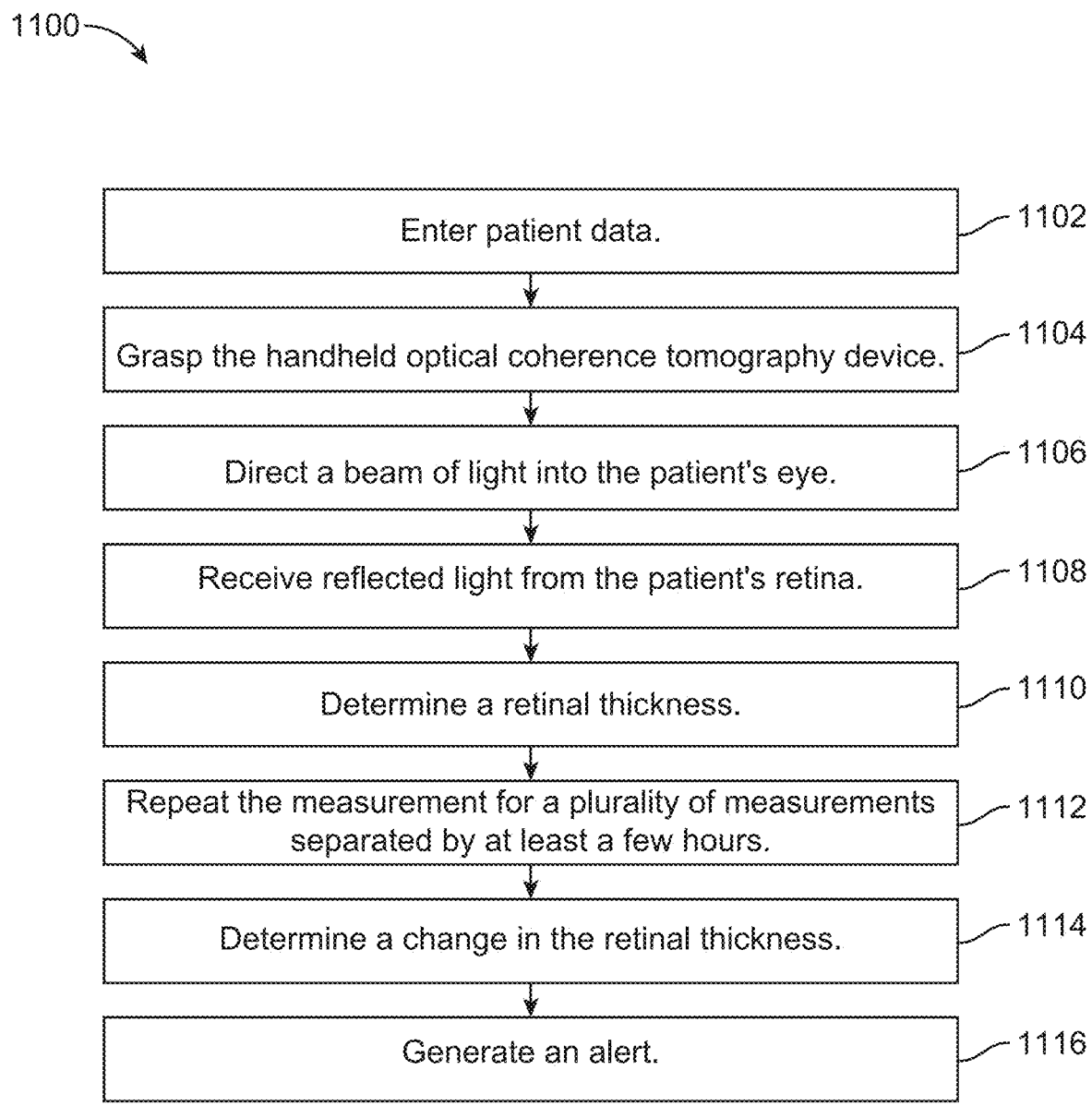
FIG. 11 is a flowchart of a method for conducting repeated measurements of a patient's RT over time and noting changes that may correspond to adverse outcomes.

FIG. 11 is a flowchart of a method for conducting repeated measurements of a patient's retinal thickness (RT) over time and noting changes that may correspond to undesirable outcomes. The method 1100 consists of entering patient data, grasping a handheld OCT device, directing a beam of light into the patient's eye, receiving reflected light from the patient's retina, determining a retinal thickness, repeating the measurement for a plurality of measurements separated by at least a few hours, determining a change in the RT, and generating an alert.

In step 1102, patient data is entered into the handheld OCT device described herein. In some cases, the patient data includes any of the patient's name, age, gender, height, weight, current ophthalmological issues, and current medical issues.

In step 1104, the patient grasps the handheld OCT device described herein. The patient looks into the handheld OCT device.

In step 1106, the handheld OCT device directs a beam of light into the patient's eye. The light is reflected from boundaries of the various layers of the patient's retina.

In step 1108, the handheld OCT receives light reflected from the various layers of the patient's retina. The reflected light forms an interference signal which is detected by a photodetector. In some cases, the interference signal is generated by the interference of the reflected light with light which has traversed the reference arms of the handheld OCT device. In some cases, the interference signal is generated by the interference between light reflected from two or more boundaries of the various layers of the retina. The handheld OCT device varies the wavelength of light directed to the eye and records an interference signal for each wavelength.

In step 1110, a patient's RT or RLT is determined. In some cases, the RT or RLT is determined by a mathematical analysis of the OCT signal. For instance, the RT or RLT may be determined from a fast Fourier transformation of the OCT signal. The RT or RLT may be determined from any other frequency analysis of the OCT signal. The RT or RLT may be determined by comparing the frequency content of the OCT signal to a calibration curve which maps RT or RLT to frequency. In some embodiments, the calibration curve is generic to all patients. In some instances, the calibration curve is specific to an individual patient.

In step 1112, the measurement is repeated for a plurality of measurements separated by at least a few hours. For each measurement, the steps 1102, 1104, 1106, 1108, and 1110 are repeated.

In step 1114, a change in the RT or RLT is determined. In some cases, the value of the RT or RLT determined in the most recent measurement is compared to any previous measurement. In some embodiments, the change in the value of the RT or RLT is recorded and tracked over the course of many measurements.

In step 1116, an alert is generated if the RT or RLT has changed significantly or if the RT or RLT falls outside of a normal or healthy range. In some cases, the alert comprises a notification displayed on the mobile patient device described herein. In some embodiments, the alert may comprise a notification sent to the patient's physician or other medical provider, as described herein.

In some cases, a first RT or RLT is measured with a handheld OCT device within 24 hours of a visit to an ophthalmologist. In some embodiments, a second RT or RLT is measured within a range from one day to twenty days after the first measurement. In some instances, the RT or RLT are measured each day for a plurality of days within a range from about 5 days to about 20 days. In some cases, the RT or RLT are measured more often than once per day. In some embodiments, the RT or RLT are measured for a period longer than 20 days. A change in RT or RLT is determined in response to the baseline thickness and the plurality of later thicknesses. In some cases, the change in RT or RLT is measured with a confidence interval of at least 90%, at least 95%, or at least 99%.

Figure 12:
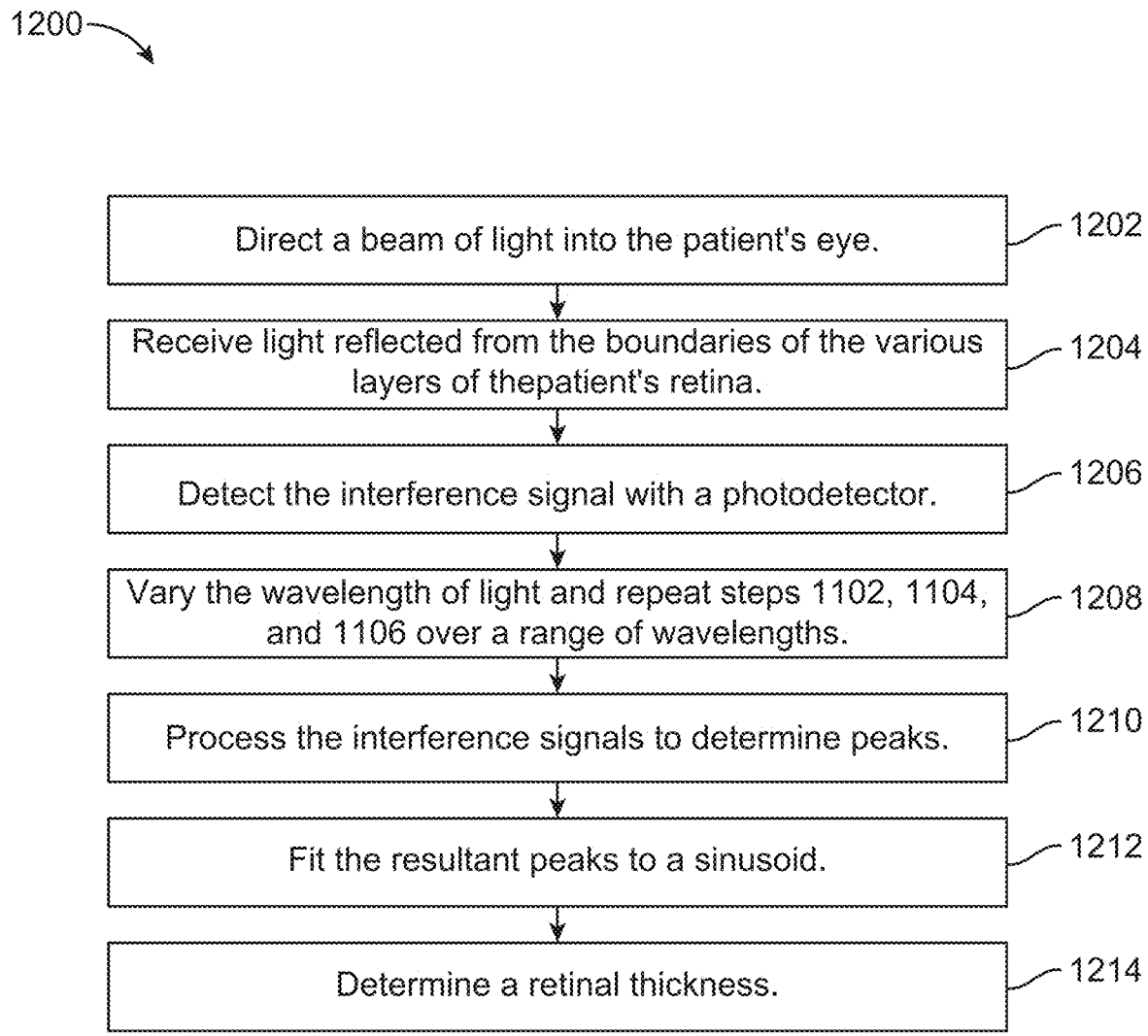
FIG. 12 shows a flowchart of a method for determining the RT from a measurement using the handheld OCT device.

FIG. 12 shows a flowchart of a method for determining the RT from a measurement using the handheld OCT device. The method 1200 comprises the steps of directing a light beam to the retina, generating an interference signal, capturing the interference pattern with a detector, varying the wavelength of the light directed to the retina, processing the interference signals to determine peaks, fitting the resultant peaks to a sinusoid, and determining a RT or RLT.

In step 1202, the handheld OCT device directs a beam of light into the patient's eye. The light is reflected from boundaries of the various layers of the patient's retina.

In step 1204, the handheld OCT receives light reflected from the boundaries of the various layers of the patient's retina. The reflected light forms an interference signal. In some cases, the interference signal is generated by the interference of the reflected light with light which has traversed the reference arms of the handheld OCT device. In some cases, the interference signal is generated by the interference between light reflected from two or more boundaries of the various layers of the retina.

In step 1206, the interference signal is detected by a photodetector.

In step 1208, the handheld OCT device varies the wavelength of light directed to the retina. For each wavelength, the steps 1202, 1204, and 1206 are repeated. An interference signal is recorded for each wavelength.

In step 1210, the interference signals are processed to determine peaks. In some cases, the peaks correspond to interference maxima between light reflected from the various layers of the retina and light which has traversed a reference arm of the handheld OCT device. In some cases, the peaks correspond to interference maxima between light reflected from the boundaries of the various layers of the retina and light which has traversed the reference arms of the handheld OCT device. In some cases, the peaks correspond to interference maxima between light reflected from two or more boundaries of the various layers of the retina.

In step 1212, the resultant peaks are fit to a sinusoid. In some cases, the fitting is via a non-linear least squares fitting. In some embodiments, the fitting is via any other fitting method known to one having skill in the art.

In step 1214, the RT or RLT is determined. In some cases, the RT or RLT is determined by extracting the frequency of the fitted sinusoid. In some embodiments, the RT or RLT is determined by comparing the frequency content of the OCT signal to a calibration curve which maps RT to frequency. In some instances, the calibration curve is generic to all patients. In some cases, the calibration curve is specific to an individual patient.

A person of ordinary skill in the art will recognize many variations, alterations and adaptations based on the disclosure provided herein. For example, the order of the steps of the methods 1100 and/or 1200 can be changed, some of the steps removed, some of the steps duplicated, and additional steps added as appropriate. The methods of 1100 and 1200 may be combined. Some of the steps may comprise sub-steps. Some of the steps may be automated and some of the steps may be manual. The processor as described herein may comprise one or more instructions to perform at least a portion of one or more steps of the methods 1100 and/or 1200.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 13:
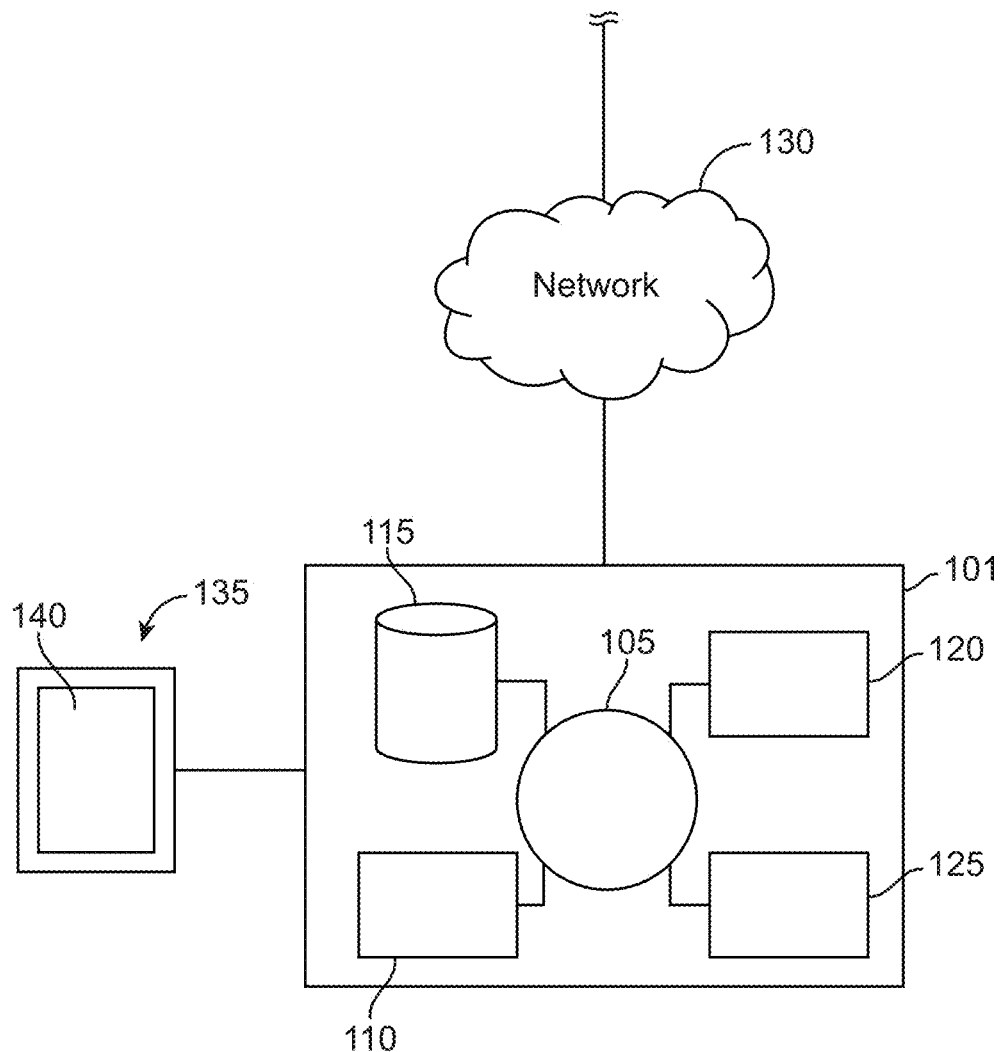
FIG. 13 shows an exemplary digital processing device programmed or otherwise configured to determine a RT or RLT.

Referring to FIG. 13, in a particular embodiment, an exemplary digital processing device 1301 is programmed or otherwise configured to determine a RT or RLT. The device 1301 can regulate various aspects of the RT or RLT determination of the present disclosure, such as, for example, performing processing steps. In this embodiment, the digital processing device 1301 includes a central processing unit (CPU, also "processor" and "computer processor" herein) 1305, which can be a single core or multi core processor, or a plurality of processors for parallel processing. The digital processing device 1301 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The digital processing device 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the device 1301, can implement a peer-to-peer network, which may enable devices coupled to the device 1301 to behave as a client or a server.

Continuing to refer to FIG. 13, the CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and write back. The CPU 1305 can be part of a circuit, such as an integrated circuit. One or more other components of the device 1301 can be included in the circuit. In some cases, the circuit is an application specific integrated circuit (ASIC) or a field programmable gate array (FPGA).

Continuing to refer to FIG. 13, the storage unit 1315 can store files, such as drivers, libraries and saved programs. The storage unit 1315 can store user data, e.g., user preferences and user programs. The digital processing device 1301 in some cases can include one or more additional data storage units that are external, such as located on a remote server that is in communication through an intranet or the Internet.

Continuing to refer to FIG. 13, the digital processing device 1301 can communicate with one or more remote computer systems through the network 1330. For instance, the device 1301 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1301, such as, for example, on the memory 1310 or electronic storage unit 1315. The machine executable or machine readable code can be provided in the form of software. During use, the code can be executed by the processor 1305. In some cases, the code can be retrieved from the storage unit 1315 and stored on the memory 1310 for ready access by the processor 105. In some situations, the electronic storage unit 1315 can be precluded, and machine-executable instructions are stored on memory 1310.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB.NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Figure 20A:
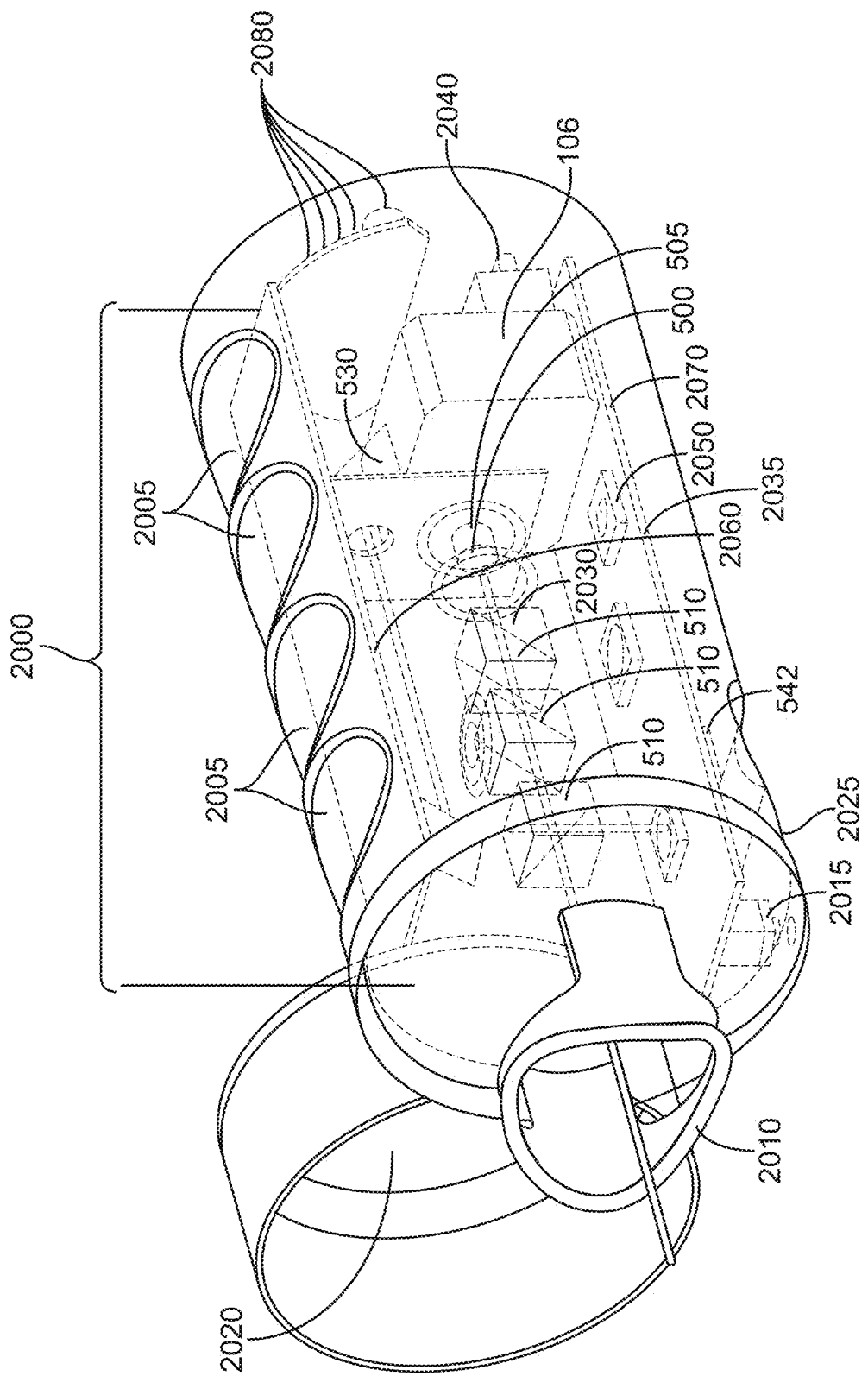
FIG. 20A shows a diagram of a handheld OCT system with an eye adapter.

FIG. 20A shows a diagram of a handheld OCT system with an eye adapter. In some cases, the system comprises a main body 2000. In some embodiments, the main body features a surface adapted to provide an ergonomic grip of the system. In some instances, the surface adapted to provide an ergonomic grip comprises one or more finger holds 2005. In some cases, the system further comprises a measurement end with an adapter 2010 configured to interface the orbital of a user's eye. In some embodiments, the system further comprises a detector which detects the orientation of the system and determines whether the user's left eye or right eye is being measured. In some instances, the system comprises a cap 2020. In some cases, the cap is utilized to cover an eye not being measured. For instance, when the left eye is being measured, the cap covers the right eye. When the right eye is being measured, the cap covers the left eye. In some embodiments, when neither eye is being measured, the cap is placed over the measurement end of the system in order to protect system components from damage.

In some cases, within the main body, the system comprises optics 104. In some embodiments, the system comprises a laser source 500. In some instances, the laser source directs laser light to a collimating lens 505. In some cases, the collimating lens shapes the laser source into a collimated beam of light. In some embodiments, the laser light is directed to a beamsplitter 2030. In some instances, the beamsplitter 2030 directs a portion of the laser light to an optical power meter 2035. In some cases, the optical power meter makes continuous measurements of the emitted laser power, allowing for correction of OCT signals based on the measured power or for the implementation of optical feedback techniques. In some embodiments, the portion of light that passes through the beamsplitter 2030 without being directed to the optical power meter impinges upon one or more beamsplitters 510. In some instances, the one or more beamsplitters 510 direct a portion of the light to a user's eye and another portion of the light to a reference mirror 530. In some cases, the reference mirror comprises a reference surface that is built into the main body of the system. In some embodiments, the system further comprises a detector 542 for detecting OCT signals.

In some embodiments, the system comprises a battery 106. In some instances, the battery is a rechargeable battery. In some cases, the battery is a lithium ion battery. In some embodiments, the battery is a nickel metal hydride battery. In some instances, the battery is a nickel cadmium battery. In some instances, the battery is operatively coupled to a charging device 2040. In some cases, the charging device is a connective charging device. The charging device may be any connective charging device as is known to one having skill in the art. In some cases, the charging device is an inductively coupled charging device. The charging device may be any inductively coupled charging device as is known to one having skill in the art.

In some instances, wireless communication circuitry and a processor as described herein are coupled to the battery to power the compact OCT system and acquire OCT data and transmit the data wirelessly.

In some cases, the system comprises additional components to allow proper operation of the system by a user. In some embodiments, the system comprises an orientation or motion sensor 2050. In some instances, the orientation or motion sensor comprises a gyroscope for measuring an orientation of the device to determine which eye is measured. In some cases, the orientation or motion sensor comprises an accelerometer for measuring a movement of the device. In some embodiments, the orientation or motion sensor comprises any orientation or motion sensor as is known to one having skill in the art. In some instances, the system comprises a visual fixation target 2060 that is viewed when the compact OCT system measures the retina. In some cases, the system comprises a mechanical feature 2070 for providing electrical safety. In some embodiments, the system comprises one or more status indicators 2080.

Figure 20B:
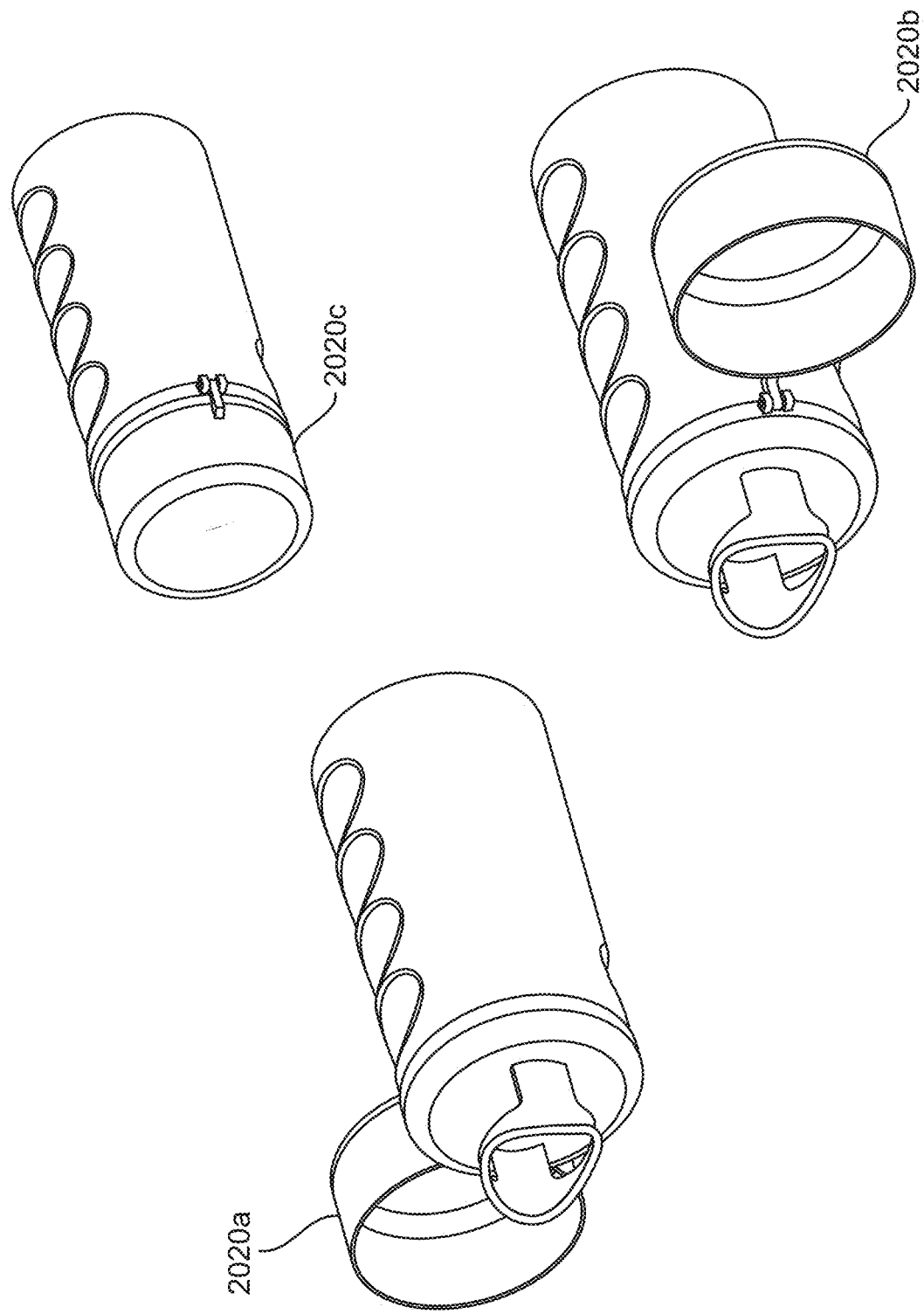
FIG. 20B shows a handheld OCT system adapted to measure a right eye or a left eye.

FIG. 20B shows a handheld OCT system adapted to measure a right eye or a left eye. When operated to provide a right eye measurement, the handheld OCT system 100 is operated in a configuration 2020a having the eye cap 2020 positioned to the left side of a measurement end of the handheld OCT system. When operated to provide a left eye measurement, the handheld OCT system is operated in a configuration 2020b having the eye cap to the right side of a measurement end of the handheld OCT system. When neither eye is being measured, the handheld OCT system is operated in a configuration 2020c having the eye cap positioned to cover the measurement end of the handheld OCT system. In this configuration, the eye cap provides protection of the internal components of the handheld OCT system when the system is not in use. The eye cap is transitioned from the configuration 2020a to the configuration 2020b by a 180 degree rotation of the eye cap. In some cases, the handheld OCT system comprises a switch that detects which eye is to be examined using the OCT system.

Figure 20C:
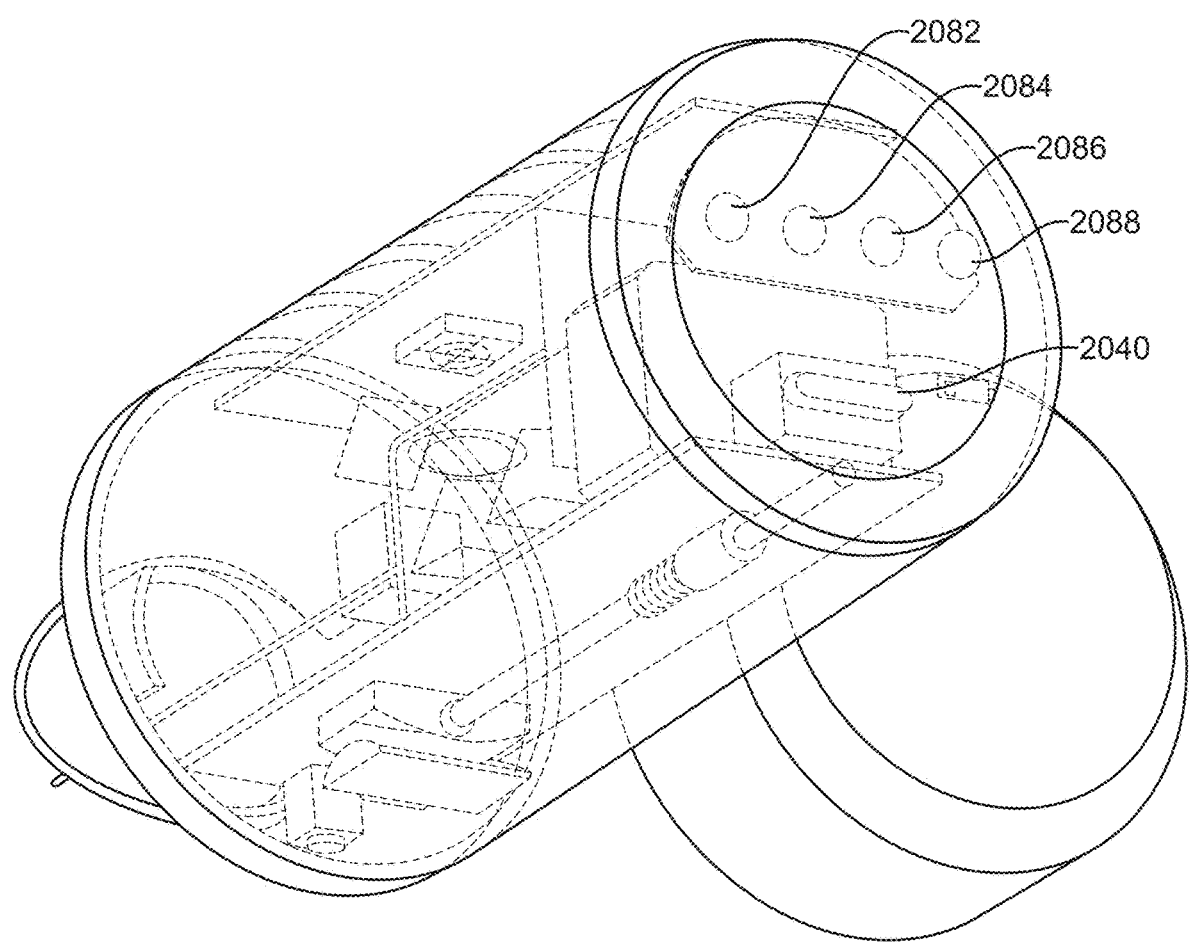
FIG. 20C shows a handheld OCT system with indicator lights and communications adapters.

FIG. 20C shows a handheld OCT system with indicator lights and power adapter. In some cases, the end of the handheld OCT device opposite the measurement end comprises one or more visual vindicators 2080. In some embodiments, the visual indicators comprise light sources. In some instances, the light sources are light emitting diodes (LEDs). In some cases, the visual indicators comprise a first visual indicator 2082 to indicate whether or not the handheld OCT device is in operation. In some embodiments, the visual indicators comprise a second visual indicator 2084 to indicate whether or not the handheld OCT device is utilizing battery power. In some instances, the visual indicators comprise a third visual indicator 2086 to indicate whether or not the handheld OCT device is utilizing an external power source. In some cases, the visual indicators comprise a fourth visual indicator 2088 to indicate whether or not the handheld OCT device is not suitable for use. In some embodiments, the end of the handheld OCT device opposite the measurement end comprises an adapter 2040 to receive electrical power.

Figure 20D:
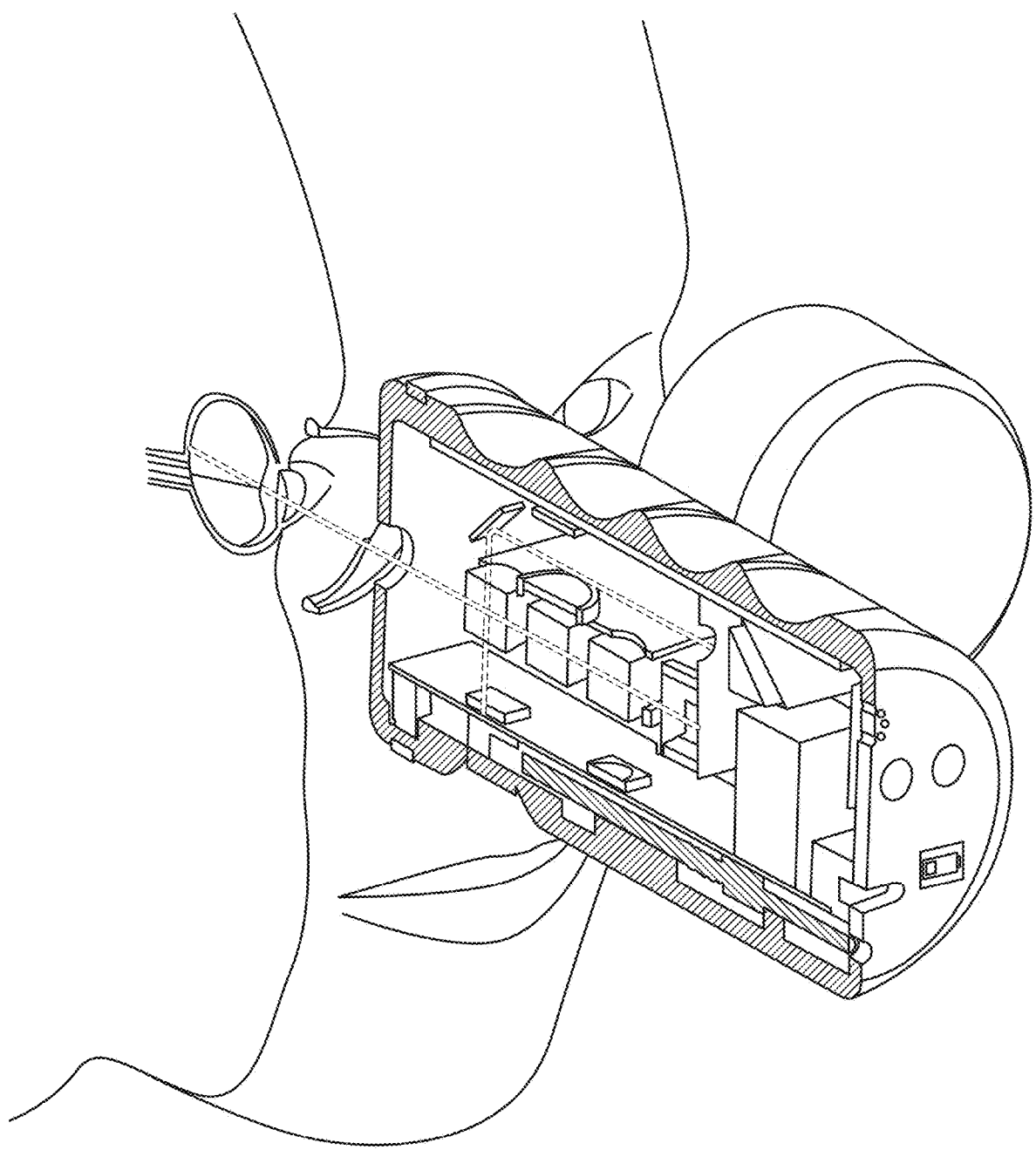
FIG. 20D shows a handheld OCT placed proximate to an eye to provide an OCT measurement.

FIG. 20D shows a handheld OCT placed proximate to an eye to provide an OCT measurement. In some cases, the measurement end of the handheld OCT system is shaped to conform to an eye socket. In some embodiments, the eye cap is positioned to cover the eye that is not being measured. In some instances, the handheld OCT system directs light into the eye in order to obtain an OCT measurement.

In some cases, the handheld OCT device is configured to obtain information sufficient to determine a single measurement of a RT or RLT in a period of time no more than that associated with motion of the eye relative to the device. In some embodiments, the motion of the eye relative to the device is due to motion of the user's hand while holding the device. In some cases, the motion of the eye relative to the device is due to motion of the eye. In some instances, the handheld OCT device is configured to obtain a measurement of a RT or RLT in a period of time no more than 100 ms, no more than 50 ms, or no more than 10 ms. In some cases, the handheld OCT device is configured to obtain a measurements of a RT or RLT in a period of time that lies within a range defined by any two of the preceding values.

Figure 21:
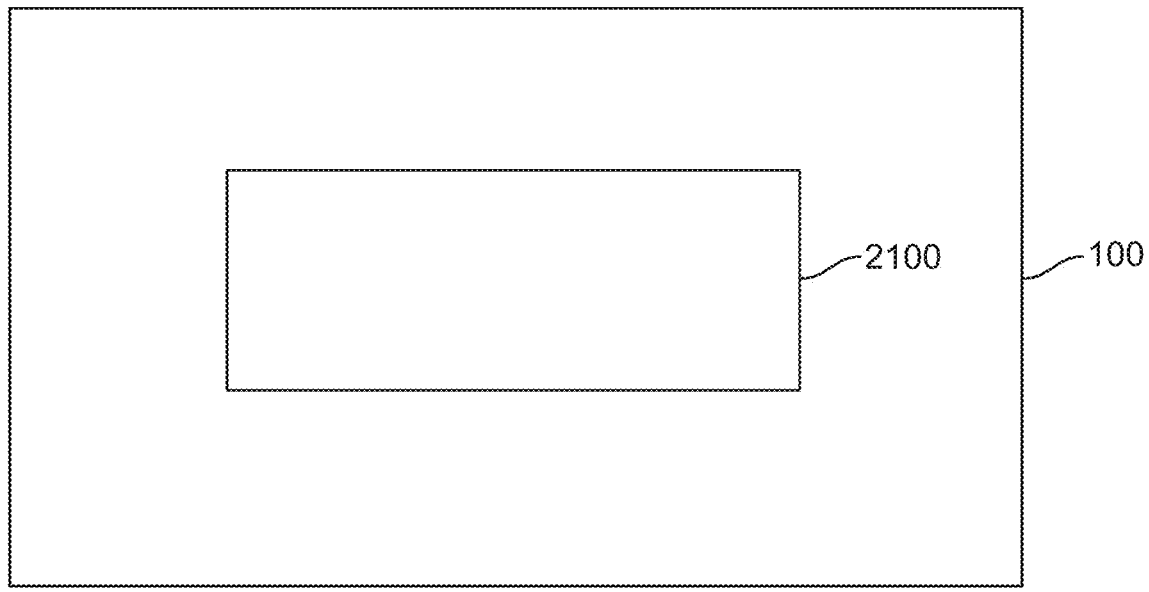
FIG. 21 shows a calibration kit for a handheld OCT device.

FIG. 21 shows a calibration kit for a handheld OCT device. In some cases, the handheld OCT device 100 comprises a calibration fixture 2100. In some embodiments, the calibration fixture is located on an inside surface of the cap 2020 of FIG. 20.

Figure 22:
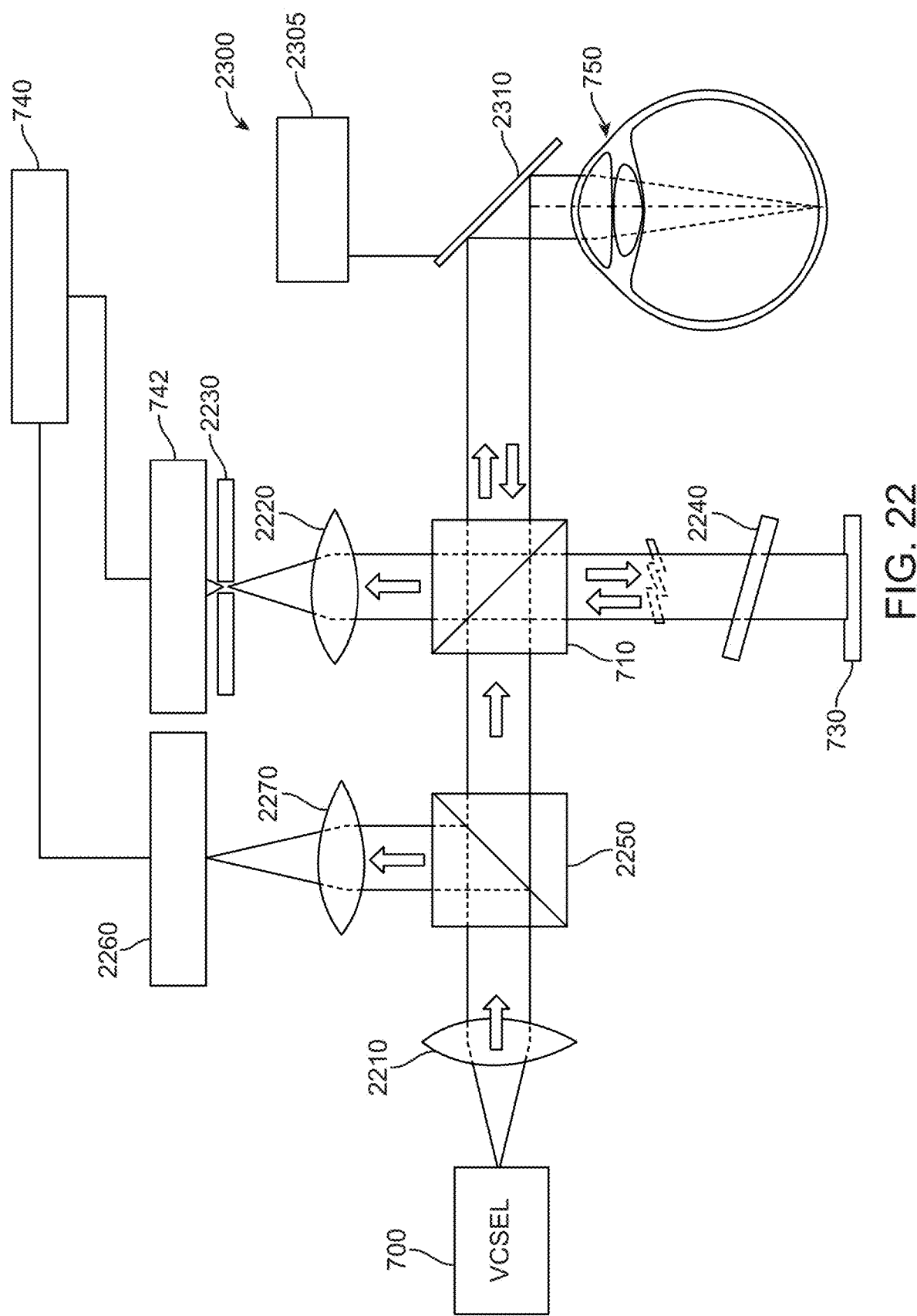
FIG. 22 shows a schematic for a SS-OCT device utilizing a scanning mechanism, in accordance with some embodiments.

FIG. 22 shows a schematic for the optics of a swept source optical coherence tomography (SS-OCT) device utilizing a scanning mechanism, in accordance with some embodiments. The optics 102 comprises a light source 700, a first beamsplitter 710, and a reference mirror 730 as described herein. The first processing unit 740 is coupled to a detector 742 to detect the swept source interference signal. The first processing unit may comprise a first photodetector 742 as described herein and a first signal processing unit 742, as described herein.

The optics may further comprise a collimating optical element 2210. The collimating optical element may comprise a collimating lens, for example. The collimating optical element may collimate light emitted from the light source prior to the interaction of the light with other optical elements. The optics may further comprise a lens 2220 that focuses an interference signal onto the photodetector 742. The optics may further comprise a pinhole 2230 through which light focused by the first lens is passed prior to detection by the first processing unit. The optics may further comprise a neutral density filter 2240 that reduces the intensity of light incident on the reference mirror.

The optics may further comprise a beamsplitter 2250. The beamsplitter may comprise any beamsplitter as described herein. The second beamsplitter may direct a portion of the light emitted by the light source to a second photodetector 2260, which may be similar to the first processing unit 740, or other circuitry configured to control the amount of energy emitted by the VCSEL. The second processing unit may comprise a second photodetector (not shown) and a second signal processing unit (not shown), which may be similar to the first photodetector and first signal processing unit. The second processing unit may detect fluctuations in the intensity of light emitted by the light source. The detected fluctuations in the intensity of light emitted by the light source may be utilized to correct the SS-OCT signal detected by the first processing unit for errors associated with fluctuations in the intensity of light emitted by the light source. The optics may further comprise a lens 2270 that focuses the portion of the light emitted by the light source onto the second photodetector 2260.

The light source 700 may be configured in many ways. For example, light source 700 may comprise a swept source VCSEL driven as described herein. Alternatively or in combination, the VCSEL may be cooled in order to increase the sweep range. For example, the VCSEL may be cooled with a chiller such as a thermo electric chiller in order to allow the VCSEL to be driven over a broader sweep range. The VCSEL may comprise a MEMS actuator coupled to a mirror in order to increase a range of swept wavelengths to about 20 nm or more. The VCSEL may be coupled to an external mirror and an actuator to change a position of the mirror in order to increase the range of swept wavelengths, for example. The VCSEL coupled to movable mirror may be swept over a range of wavelengths within a range from about 10 to 30 nm, or more.

Table 2 shows sweep ranges and resolutions that may be obtained for 10 to 30 nm of sweeping of the VCSEL of the compact SS-OCT system as described herein.

| Wavelength Range (nm) | Axial Resolution (μm) |
| --- | --- |
| 10 | 31.9 |
| 11 | 29.0 |
| 12 | 26.6 |
| 13 | 24.5 |
| 14 | 22.8 |
| 15 | 21.3 |
| 16 | 19.9 |
| 17 | 18.8 |
| 18 | 17.7 |
| 19 | 16.8 |
| 20 | 15.9 |
| 21 | 15.2 |
| 22 | 14.5 |
| 23 | 13.9 |
| 24 | 13.3 |
| 25 | 12.8 |
| 26 | 12.3 |
| 26 | 12.3 |
| 28 | 11.4 |
| 29 | 11.0 |
| 30 | 10.6 |

The light source 700 may be swept by an amount within a range defined by any two values in Table 1 and Table 2, for example over a range from 9 nm to 20 nm, so as to provide a corresponding resolution, for example a corresponding resolution within a range from 35.4 um to 15.9 um.

In some embodiments, the compact SS-OCT system further comprises a scanning mechanism 2300. The scanning mechanism 2300 may comprise an actuator 2305 and a mirror 2310, which is deflected by the actuator in order to scan the light beam on the eye. The actuator 2305 may comprise any actuator known to one of ordinary skill in the art, such as a microelectromechanical system (MEMS) actuator, a galvanometer, or a piezo electric crystal, for example. The scanning mechanism 2300 may be coupled to the control unit as described herein.

Figure 23:
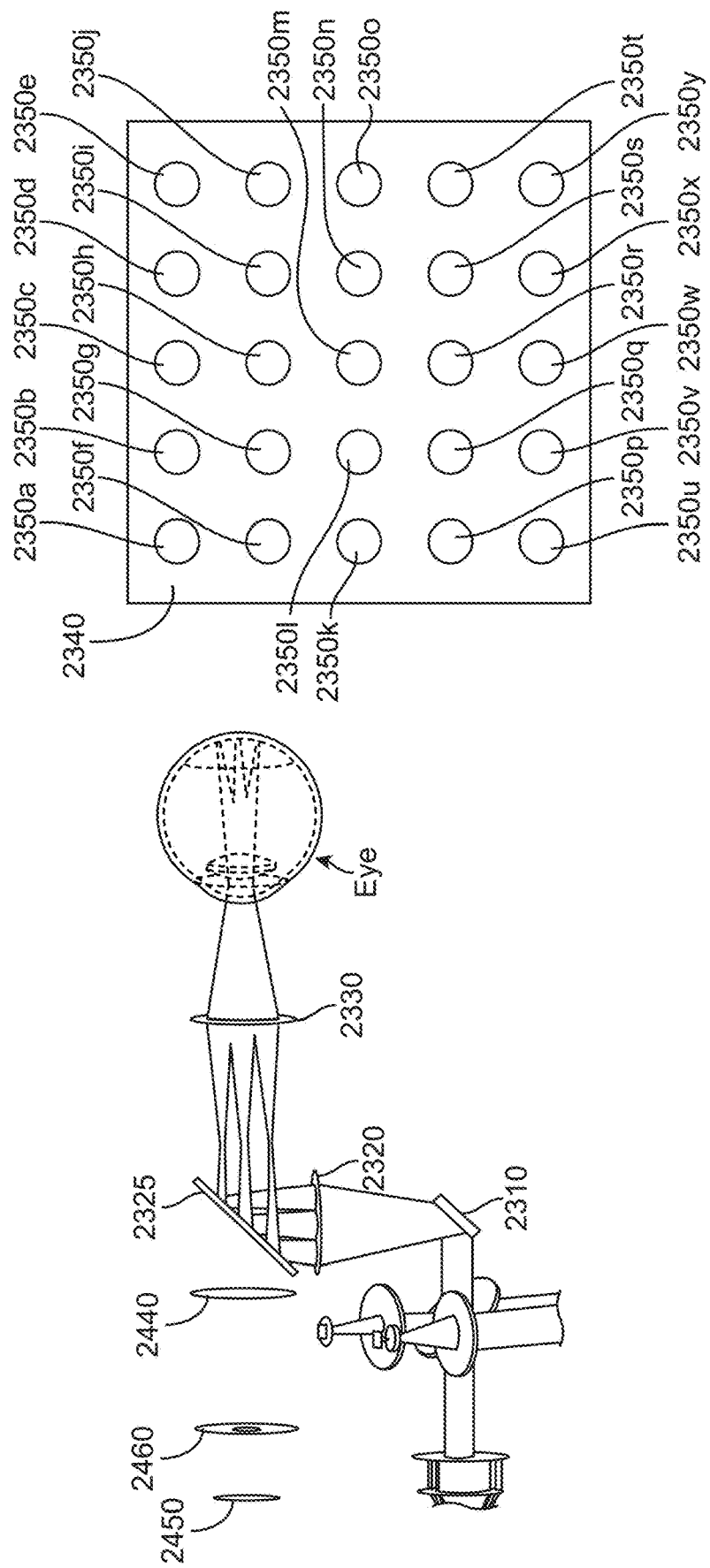
FIG. 23A shows a schematic for a scanning mechanism, in accordance with some embodiments.
FIG. 23B shows an array of retinal layer thickness measurement sites, in accordance with some embodiments.

FIG. 23A shows scanning mechanism 2300 optically coupled to an eye with the compact SS-OCT system, in accordance with some embodiments. The scanning mechanism 2300 may comprise a first scanning optical element, such as a mirror 2310, and a telescope system comprising a first telescope lens 2320 and a second telescope lens 2330. The telescope system may comprise a 4-f telescope system, for example. The telescope system may further comprise a mirror 2325 to deflect the scanned light beam toward the eye. The second telescope lens 2330 may comprise an aspheric lens.

In some embodiments, the mirror 2325 couples an optical path of a patient visualization system with the optical path of the scanned light beam. In some cases, the mirror 2325 comprises a short pass mirror. The patient visualization system may comprise a lens 2440, an aperture 2460 and a lens 2450, is further described in FIG. 24.

The scanning optical element may comprise any type of scanning optical element known to one of ordinary skill in the art, such as mirror, a prism, a polygonal mirror, or a lens, for example. The scanning element may be a galvanometer. The scanning element may permit the measurement of a RT or RLT at more than one location on a retina by scanning the measurement beam across a plurality of locations on the retina.

FIG. 23B shows an array of retinal thickness (RT) or retinal layer thickness (RLT) measurement sites, in accordance with some embodiments. The scanning mechanism described herein may direct measurement light to a plurality of measurement locations 2350a, 2350b, 2350c, 2350d, 2350e, 2350f, 2350g, 2350h, 2350i, 2350j, 2350k, 2350l, 2350m, 2350n, 2350o, 2350p, 2350q, 2350r, 2350s, 2350t, 2350u, 2350v, 2350w, 2350x, and 2350y on a retina 2340. Although 25 measurement locations are depicted, the scanning mechanism may direct the measurement light to 2 or more measurement locations, 5 or more measurement locations, 10 or more measurement locations, 20 or more measurement locations, 50 or more measurement locations, 100 or more measurement locations, 200 or more measurement locations, 500 or more measurement locations, or 1000 or more measurement locations. A measurement of a RT or RLT may be obtained at each of the measurement locations to obtain a plurality of RT or RLT measurements. The plurality of RT or RLT measurements may allow the construction of a spatial map of RT or RLT measurements. The plurality of RT or RLT measurements may span a first distance on the retina in a first direction and a second distance on the retina in a second direction transverse to the first direction. The first distance may comprise a length of less than 0.5 mm, less than 1.0 mm, less than 1.5 mm, less than 2.0 mm, less than 2.5 mm, less than 3.0 mm, less than 3.5 mm, less than 4.0 mm, less than 4.5 mm, or less than 5.0 mm. The second distance may comprise a length of less than 0.5 mm, less than 1.0 mm, less than 1.5 mm, less than 2.0 mm, less than 2.5 mm, less than 3.0 mm, less than 3.5 mm, less than 4.0 mm, less than 4.5 mm, or less than 5.0 mm.

Figure 24:
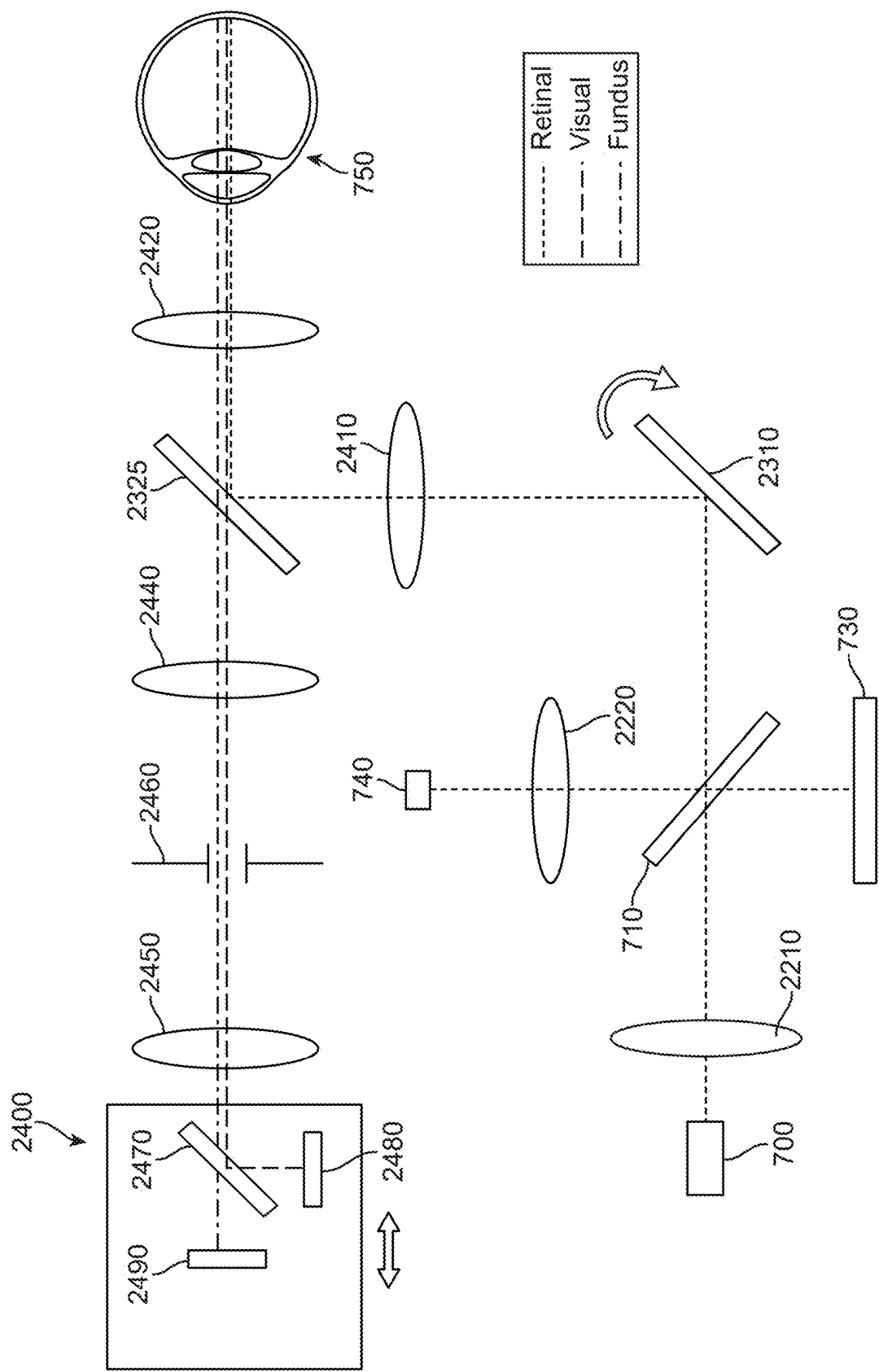
FIG. 24 shows a schematic for a SS-OCT device utilizing a scanning mechanism and one or more cameras, in accordance with some embodiments.

FIG. 24 shows a schematic for the optics of a compact swept source optical coherence tomography (SS-OCT) device comprising a patient visualization system 2400. The patient visualization system 2400 may comprise a camera to view the fundus and a display to measure patient visual acuity. The display to measure patient visual acuity may configured for the patient to fixate on a viewing target, for example by displaying a small object visible to the patient. The optics 102 may comprise a light source 700, a collimating optical element 2210, a first beamsplitter 710, a reference mirror 730, and a first lens 2200 coupled to photodetector 742 as described herein.

The optics may further comprise a scanning mechanism as described herein. The scanning mechanism may comprise a scanning optical element 2310 and a telescope system comprising a first telescope lens 2320 and a second telescope lens 2330. The optics may further comprise mirror 2435, such as a hot mirror. The hot mirror may be configured to reflect infrared light. The hot mirror may be configured to transmit visible light. The hot mirror may be configured to reflect OCT measurement light to an eye and to transmit visible light to the patient in order to display images shown on the display to the subject and to image the fundus with a detector.

The visual function measurement apparatus of the compact SS-OCT system may comprise a Badal lens and imaging system to compensate for the refraction of the patient. The lens 2450 may be coupled to an actuator to move the lens along the optical axis to correct for refractive error of the subject, in order to bring the image of the fundus into focus on the detector array and to bring the image on the display as seen by the subject into focus. The Badal lens may be configured to provide a virtual image seen by the patient with a constant viewing angle, and lens may provide a refractive error compensation that is linear with microdisplay displacement (e.g. +−5 diopter).

The visual function measurement apparatus presents one or more visual cues to a patient.

The compact SS-OCT system may further comprise one or more camera apparatuses, such as a fundus camera. The compact SS-OCT system may comprise a visual camera apparatus configured to measure an anterior portion of the eye, for example. The optics coupled to the fundus camera and visual display may further comprise a telescope comprising a first telescope lens 2440 and a second telescope lens 2450. The optics may further comprise an aperture 2460 comprising a stop. The stop may comprise a ring stop, for example. The optics may further comprise a second beamsplitter 2470. The second beamsplitter may direct a portion of incident from the eye light toward a detector array 2480 and a portion of incident light from a micro-display 2490 toward the eye for patient visualization. The detector array may be a charge coupled device (CCD). The detector array may be a complementary metal oxide semiconductor (CMOS) detector array, for example.

The visual camera apparatus may obtain images of an eye while the OCT system obtains RT or RLT measurements of the eye. The visual camera apparatus may obtain images of an eye before, during, or after the OCT system obtains RT or RLT measurements of the eye as described herein. The fundus camera apparatus may obtain images of a fundus of an eye while the OCT system obtains RT or RLT measurements of the eye. The fundus camera apparatus may obtain images of an eye before, during, or after the OCT system obtains RT or RLT measurements of the eye. The images of the fundus obtained by the fundus camera apparatus may be subjected to image processing to determine whether and by how much an OCT measurement location has moved between two consecutive measurements (such as due to voluntary or involuntary motion of the eye or due to voluntary or involuntary motion of the handheld OCT system).

The scanning of the OCT beam may be adjusted in response to eye movements in order to compensate for eye movements.

Figure 25:
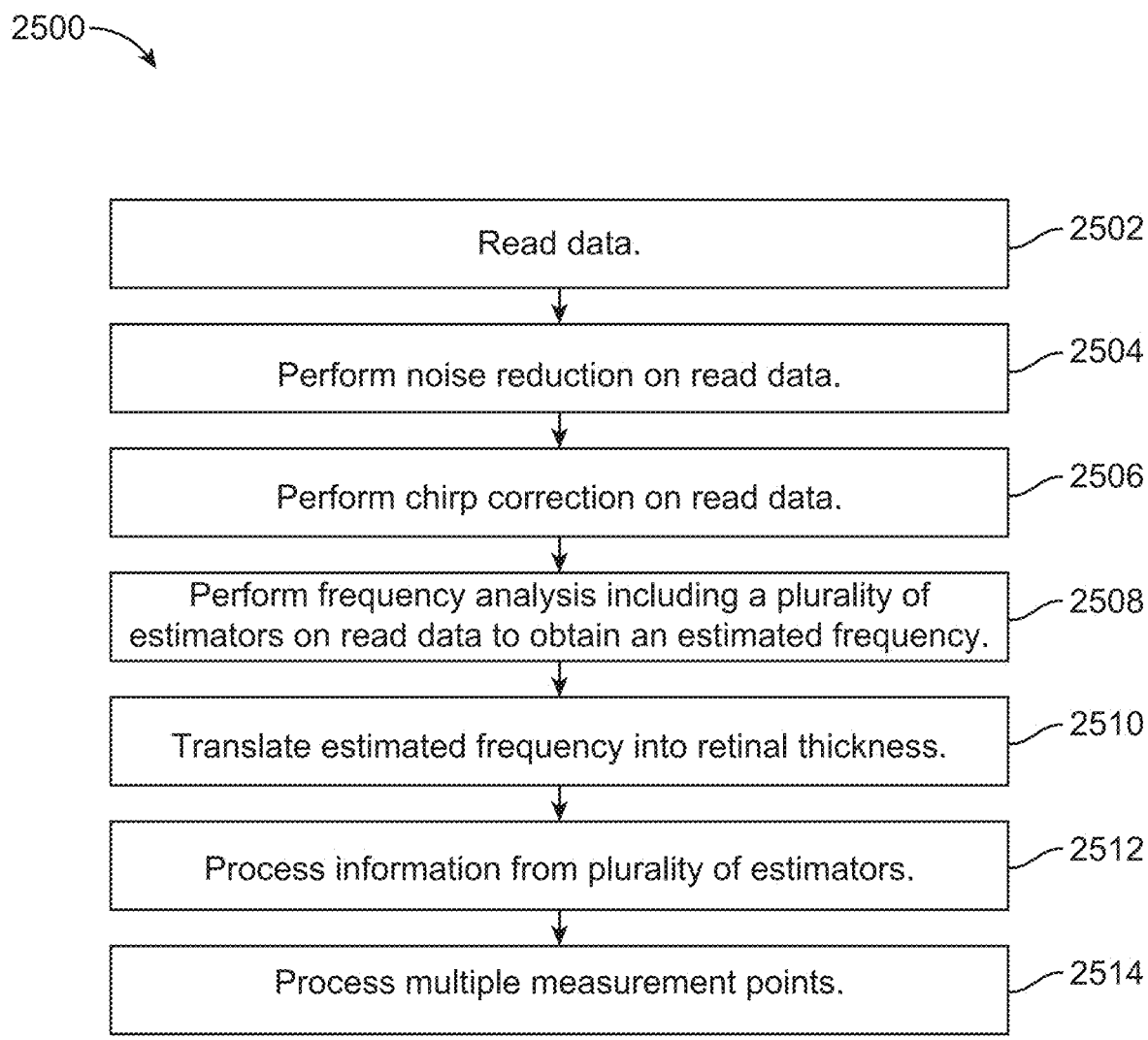
FIG. 25 shows a method for extracting a measurement of a retinal thickness (RT) or retinal layer thickness (RLT) from an OCT measurement, in accordance with some embodiments.

FIG. 25 shows a method 2500 for extracting a measurement of a retinal thickness (RT) or retinal layer thickness (RLT) from an OCT measurement, in accordance with some embodiments. The method 2500 comprises reading data, performing noise reduction on the read data, performing chirp correction on the read data, performing frequency analysis on the read data to obtain an estimated frequency, translating the estimated frequency into a retinal thickness, processing information from a plurality of estimators, and processing multiple measurement points.

In step 2502, OCT data obtained by the OCT measurement system is read to form read data. In some cases, the read data comprises OCT interference intensities.

In step 2504, noise reduction is performed on the read data.

In step 2506, chirp correction is performed on the read data. The chirp correction may comprise re-sampling the OCT signal in the time domain. Re-sampling the OCT signal may transform a linear time signal into a linear wave-vector signal. The re-sampling may compensate for phase instabilities arising due to non-linearities in the relationship between the wavelength of light emitted by a VCSEL or other light source and the drive current of the VCSEL or other light source, variations in temperature, aging of optical components, vibrations, or other environmental conditions. The re-sampling may be based on a phase measurement of the light source, such as the phase measurement methods as described herein. The re-sampling may be carried out during post-processing of an SS-OCT signal described herein.

The re-sampling may comprise first and second correction operations. In the first correction operation, the re-sampling may correct for an average non-linearity in the phase of light emitted by the VCSEL or other light source based on an average behavior of the light emitted by the light source over a period of time. In the second correction operation, the re-sampling may correct for deviations from the average behavior of the light source. The second correction operation may be based on a simultaneous acquisition of the phase signal and the SS-OCT signal and may therefore correct for variations associated with changes in temperature, humidity, aging of optical or electronics components, and other sources of drift of the SS-OCT signal.

In step 2508, frequency analysis is performed on the read data to obtain an estimated frequency. The frequency analysis may be performed using one or more estimators. The frequency may be performed using one, two, three, four, five, or more than five estimators. The estimators may utilize eigenspace techniques. The estimators may utilize eigen decomposition techniques. The estimators may utilize Pisarenko decomposition techniques. The estimators may utilize multiple signal classification (MUSIC) techniques. Each estimator of the one or more estimators may utilize a MUSIC technique with a unique filter. Each estimator may obtain an estimated frequency from the read OCT data.

In step 2510, one or more estimated frequencies are used to determine an estimated RT or RLT. A RT or RLT may be obtained from an analysis of terms of the interference signal. The terms used to determine the RT or RLT may comprise auto terms or cross terms of the interference signal, and combinations thereof. Auto terms may be generated by back-reflected signals from a sample (e.g. a retina or retinal layer), independent of a reference arm of the SS-OCT system. An auto term may correspond to a single frequency at a relatively low frequency. The frequency associated with the auto term may directly relate to a RT or RLT. A RT or RLT may be obtained from an analysis of a cross term of the interference signal. Cross terms may be generated by back-reflected signals from a sample and a reference mirror. A cross term may correspond to a pair of frequencies at relatively high frequencies. The difference between the two frequencies of the pair of frequencies may directly relate to a RT or RLT. The terms can be combined to determine a thickness of the retina, thicknesses of a plurality of layers, and relative locations of each of a plurality of layers of the retina.

Alternatively or in combination, a RT or RLT may be obtained from an analysis of the envelope of the OCT signal in the time domain. The envelope of the OCT signal may be calculated by performing a mathematical transform on the OCT signal, such as a Hilbert transform. The envelope may be subjected to a filtering operation to obtain a filtered envelope. The RT or RLT may relate to a beat frequency of the filtered envelope. Estimations of a RT or RLT using the envelope of the OCT signal may be less susceptible to noise such as that associated with motion (of the SS-OCT device or a user of the SS-OCT device).

In step 2512, the information from the plurality of estimators is processed. The processing of the multiple estimators may utilize a statistical analysis procedure. The processing of the multiple estimators may utilize an artificial intelligence or machine learning procedure, for example.

In step 2514, multiple measurement points are processed. The multiple measurement points may be processed from multiple measurements taken at a single location on a retina. The multiple measurement points may be processed from measurements taken at a plurality of location on the retina.

Although FIG. 25 shows a method 2500 for extracting a measurement of a retinal thickness (RT) or retinal layer thickness (RLT) from an OCT measurement in accordance with some embodiments, a person of ordinary skill in the art will recognize many variations and adaptations. For example, some of the steps may be deleted, some of the steps may be repeated, and some of the steps may comprise sub-steps. The steps may be performed in a different order, for example.

Figure 26:
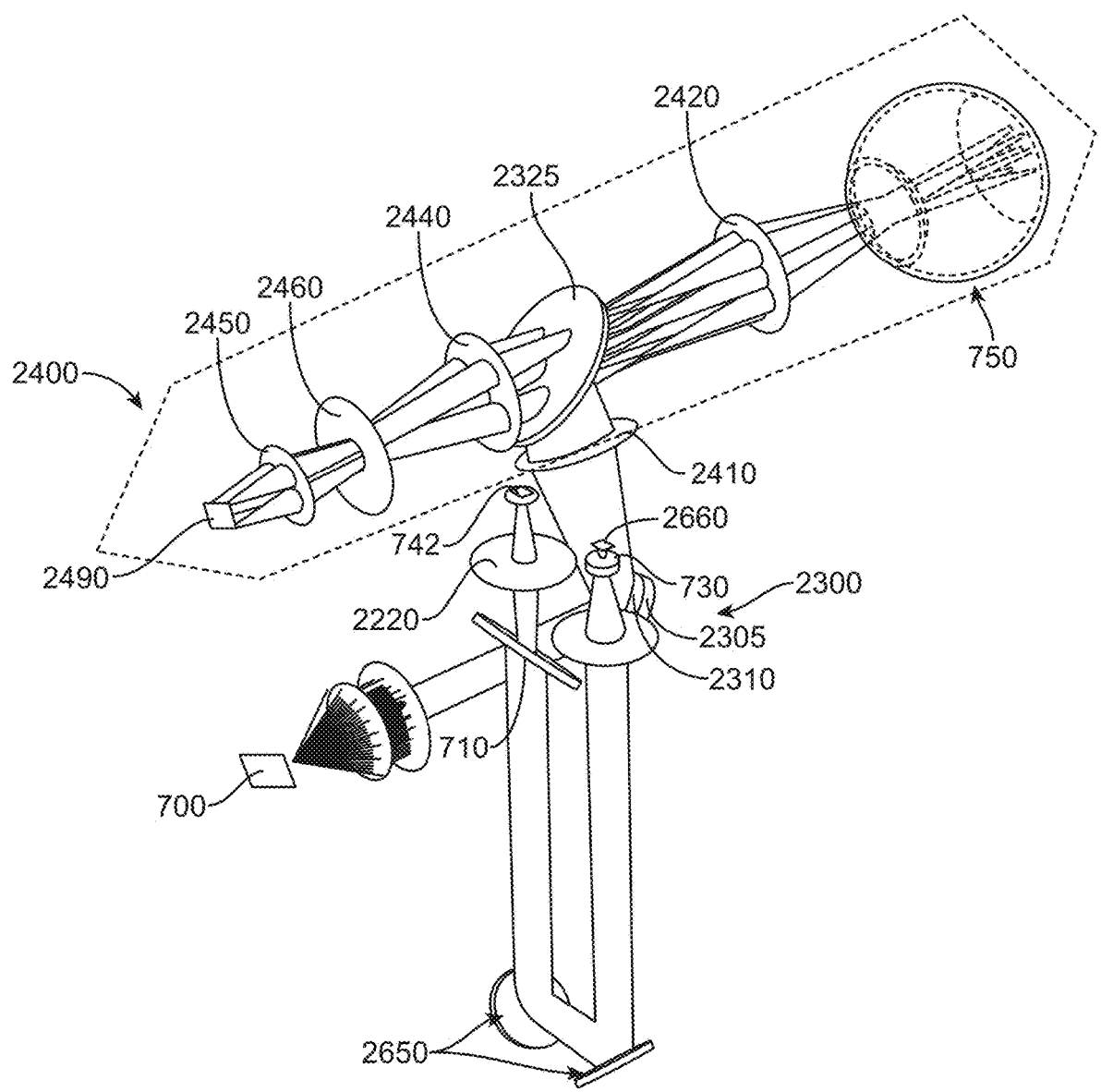
FIG. 26 shows a schematic for a SS-OCT device incorporating a visual function measurement apparatus, in accordance with some embodiments.

FIG. 26 shows a schematic for a SS-OCT incorporating a visual function measurement apparatus, in accordance with some embodiments. The system may be sized for the patient to lift the system and may comprise a weight sufficient to allow the patient to lift the system for measurements, for example. The system may comprise patient visualization system 2400, and the optical components may be arranged to provide a compact system that may be held by the patient during measurements, for example. The system may comprise display 2490, and may comprise the fundus camera as described herein. The light from the light source 700 may be directed toward a mirror 710 that splits the light into a measurement leg directed toward eye 750 and a reference leg directed toward reference mirror 730. Reference mirror 730 may be coupled to an optical detector 2660 that may detect a portion of light transmitted by the reference mirror. Optical detector 2660 may measure fluctuations in light output from the light source. Reference mirror 730 may be coupled to an actuator (not shown) to adjust the distance of the reference mirror in order to adjust the distance of the reference mirror to compensate for varying distances from patient contacting structure to the retina of the subject. The reference leg may comprise a mirror to deflect the beam. The reference mirror may comprise a plurality of mirrors such as mirror pair 2650. Locations of mirror pair 2650 may be adjusted so as adjust the optical path length of the reference leg. For example, actuators may be coupled to the mirror pair 2650 to adjust the mirrors in a trombone configuration, so as to adjust the optical path length of the reference leg.

The scanning mechanism 2300 may scan the measurement beam and receive light from retina and direct light to the retina in a confocal configuration as described herein.

Figure 34:
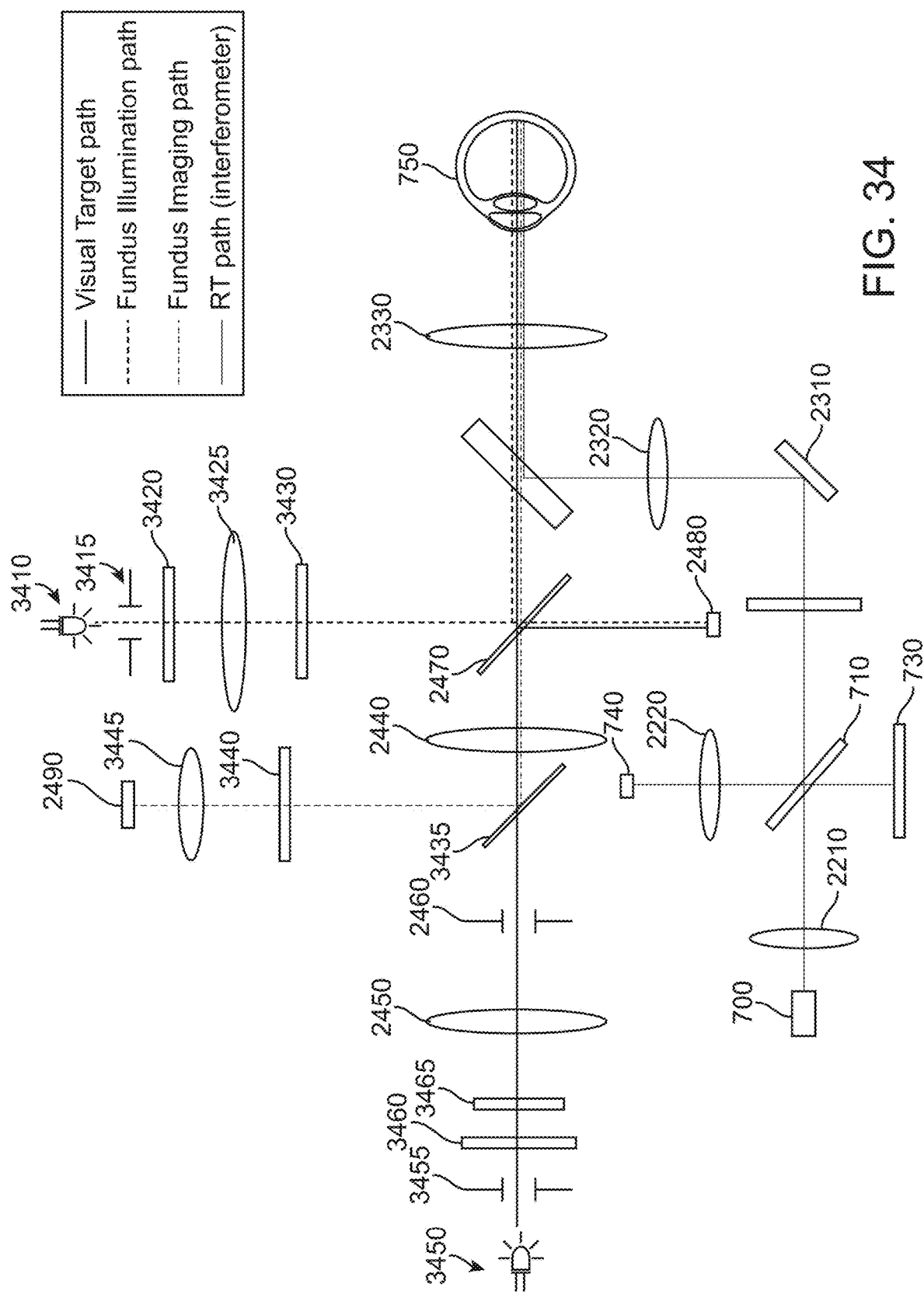
FIG. 34 shows a schematic for the optics of a SS-OCT device incorporating a visual fixation target apparatus and a fundus imaging apparatus, in accordance with some embodiments.

FIG. 34 shows a schematic 3400 for the optics of a SS-OCT device incorporating a visual fixation target apparatus and a fundus imaging apparatus, in accordance with some embodiments.

The optics may comprise a RT or RLT path comprising an interferometer, as described herein. The interferometer may comprise a light source 700, as described herein. The light source may direct light to an optional collimating lens 2210 and a beamsplitter 710, as described herein. The beamsplitter may direct a first portion of the light incident on the beamsplitter along a reference arm to reference mirror 730 and a second portion of the light incident on the beamsplitter to a measurement arm of the interferometer, as described herein. The second portion of the light may be directed to an optional filter (such as a bandpass filter) 3470 and a scanning mirror 2310 or other scanning mechanism, as described herein. The scanning mirror may direct the second portion of the light to a telescope system comprising a first telescope lens 2320 and a second telescope lens 2330, as described herein. The telescope system may further comprise a mirror 2325 to deflect scanned light deflected by the scanning mirror toward the eye 750, as described herein. Scanned light may be reflected from the eye, the retina, or one or more layers of the retina, as described herein and directed back along the path comprising elements 2330, 2325, 2320, 2310, 3470, and 710. The scanned light may then be passed by the beamsplitter 710 to an optional focusing lens 2220 and a detector 740, as described herein. The detector may detect an interference between the scanned light that has passed through the measurement arm of the interferometer and the reference light that has passed along the reference arm of the interferometer, as described herein.

The optics may further comprise a visual target path. The visual target path may comprise a visual target light source 3450. The visual target light source may comprise a light emitting diode (LED). The LED may emit light having a wavelength that is within the visible portion of the electromagnetic spectrum. For instance, the LED may emit light having a wavelength that is within a range from 400 nm to 700 nm. The LED may emit approximately green light. For instance, the LED may emit light having a wavelength of about 525 nm. The LED may emit light at a plurality of wavelengths that are within the visible portion of the electromagnetic spectrum. The visual target light source may direct light toward an aperture 3455 comprising a stop. The stop may comprise a ring stop, for example. The light may then pass to a diffuser 3460. The light may then pass to a collimating lens 2450 and a stop 2460, as described herein. The light may be directed to a hot mirror 3435. The hot mirror may be configured to pass light from the visual target path to a lens 2440, as described herein. The light may then pass to a beamsplitter 2470, as described herein. The beamsplitter may pass visual target light to the eye 750. The light may be detected by the eye and provide a target for a user to focus upon. Focusing on the target may allow a user to reduce the motion of the user's eye during fundus, RT, or RLT measurements. In some cases, the beamsplitter may pass visual target light to the eye through the mirror 2325 and the second telescope lens 2330, as described herein. The beamsplitter 2470 may be configured to direct a portion of the visual target light to a detector 2480. The portion of the visual target light directed to the detector may allow the optical power delivered to the eye to be monitored over time.

The optics may further comprise a fundus illumination path. The fundus illumination path may comprise a fundus illumination light source. The fundus illumination light source may comprise an LED. The LED may emit light having a wavelength that is within the near infrared portion of the electromagnetic spectrum. For instance, the LED may emit light having a wavelength that is within a range from 700 nm to 2500 nm. For instance, the LED may emit light having a wavelength of about 780 nm. The LED may emit light at a plurality of wavelengths that are within the near infrared portion of the electromagnetic spectrum. The fundus illumination light source may direct light toward an aperture 3415 comprising a stop. The stop may comprise a ring stop, for example. The light may then pass to a diffuser 3420. The light may then pass to a collimating lens 3425. The light may then pass to a first polarizer 3430. The first polarizer may be a linear polarizer. The first polarizer may impart a linear polarization to the light. The first polarizer may be an s-polarizer. The first polarizer may impart an s-polarization to the light. The first polarizer may be a p-polarizer. The first polarizer may impart a p-polarization to the light. The light may then pass to a beamsplitter 2470, as described herein. The beamsplitter may pass fundus illumination light to the eye 750. In some cases, the beamsplitter may pass fundus illumination light to the eye through the mirror 2325 and the second telescope lens 2330, as described herein. The beamsplitter 2470 may be configured to direct a portion of the fundus illumination light to a detector 2480. The portion of the fundus illumination light directed to the detector may allow the optical power delivered to the eye to be monitored over time.

The optics may further comprise a fundus imaging target path. The fundus imaging target path may receive fundus illumination light reflected from the eye. The light may be directed through the elements 2330, 2325, 2470, 2440, and 3435. The hot mirror 3435 may be configured to direct the light to a second polarizer 3440. The second polarizer may be configured to pass light having a polarization similar to the polarization imparted by the first polarizer. The light may be directed to an imaging lens 3445 and a camera 2490, as described herein.

The imaging lens and camera may record one or more images of the fundus of a user's eye. The imaging lens and camera may be configured to record a series of images of the fundus of a user's eye. The camera may be coupled to an image processor. The image processor may be configured to recognize the fundus. For instance, the image processor may be configured to detect a vein of the fundus. The image processor may be configured to detect the vein of the fundus by comparing an image of the fundus to a template. The template may comprise a small region of an image of the eye containing the vein. The image processor may be configured to detect tubular structures of the diameter of the vein. For instance, the image processor may be configured to implement a filter, such as a Hessian multiscale filter, to detect the vein. The filter may enhance the clarity of a region of the fundus image containing the vein and the clarity of the region of the template containing the vein. The image processor may cross-correlate the enhanced region of the fundus image with the enhanced region of the template. In this manner, the location of the vein may be determined. The location of the vein may be determined for each fundus image in a series of fundus images. In this manner, the relative motion of the eye may be measured over time.

Figure 48:
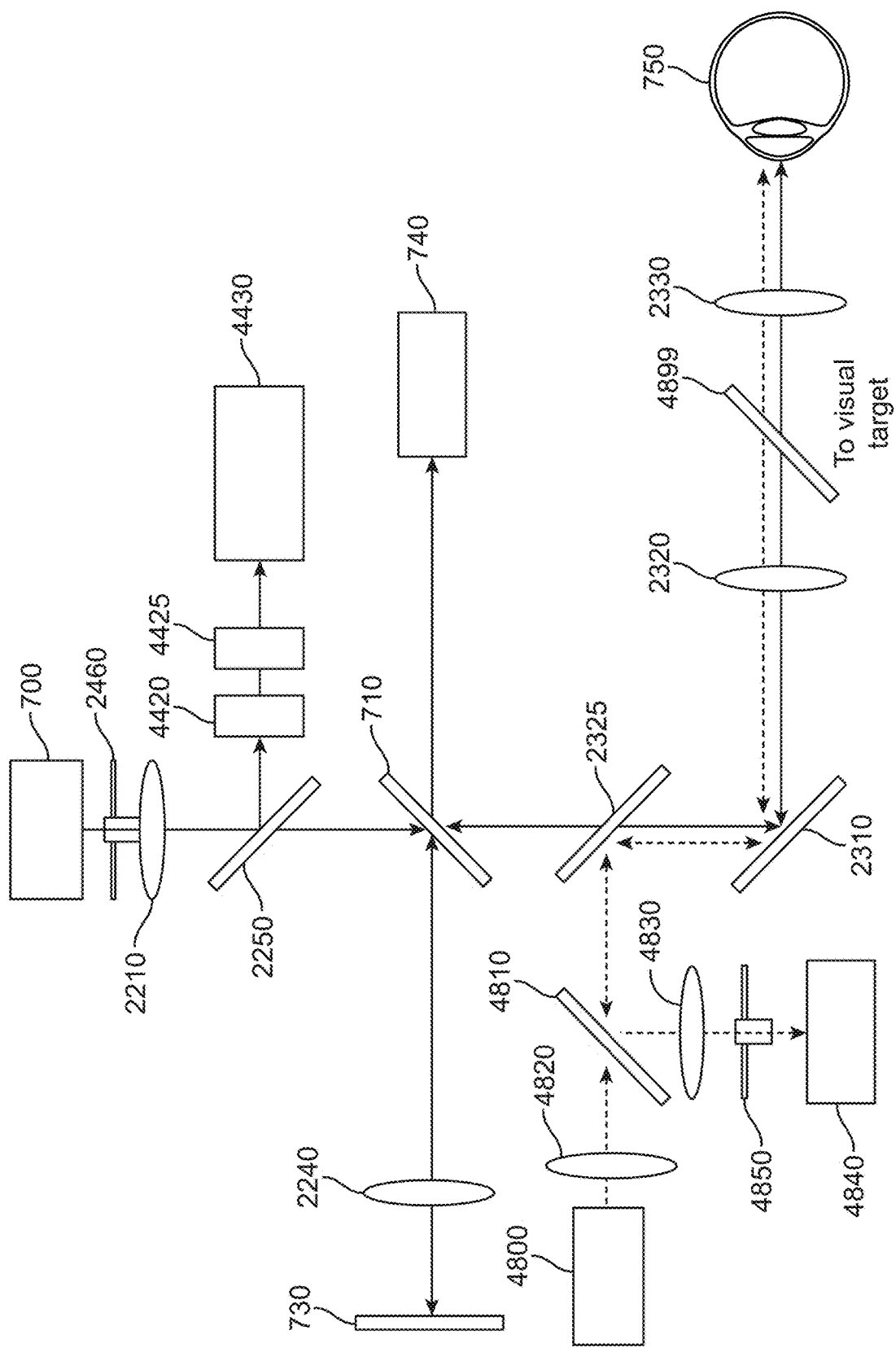
FIG. 48 shows a schematic for the optics of a SS-OCT device incorporating a scanning laser ophthalmoscope (SLO), in accordance with some embodiments.

FIG. 48 shows a schematic for a SS-OCT device incorporating a scanning laser ophthalmoscope (SLO), in accordance with some embodiments. The optics may comprise any OCT components as described herein such as light source 700, stop 2460, collimating lens 2210, beamsplitter 710, focusing lens 2240, reference mirror 730, scanning mirror 2310, first and second telescope lenses 2320 and 2330, respectively, and detector 740 configured to detect an OCT signal from an eye 750, as described herein. The optics may further comprise a beamsplitter 2250 configured to direct a portion of the light emitted by the light source through a Fabry-Perot interferometer comprising first and second Fabry-Perot mirrors 4420 and 4425 and to a detector 4430 configured to characterize an optical phase of light emitted by the light source, as described herein.

The optics may further comprise a SLO light source 4800. The SLO light source may comprise any SLO light sources as is known to one of ordinary skill in the art, and may comprise any light source described herein, such as light source 700. The SLO light source may direct light to a collimating lens 4820 and to a beamsplitter 4810. The beamsplitter 4810 may be similar to beamsplitter 710 described herein. The beamsplitter 4810 may be configured to direct light emitted by the SLO light source along a first optical path comprising a dichroic mirror 2325, the scanning mirror 2310, and the first and second telescope lenses 2320 and 2330, respectively, toward the eye 750. The light may be reflected from the eye in the opposite direction along the beam path comprising the dichroic mirror 2325, the scanning mirror 2310, and the first and second telescope lenses 2320 and 2330, respectively. The light reflected from the eye may be directed to a focusing lens 4830, through a confocal pinhole 4850, and to a SLO detector 4840, where the light reflected from the eye, retina, or retinal layer may form a SLO signal. The SLO detector may comprise a photomultiplier tube or an avalanche photodiode, for example. The SLO signals may be combined to generate an image a fundus of the eye, which can be combined with the OCT measurement to provide combined SLO and OCT maps of the eye.

The optics may further comprise a dichroic mirror 4890 configured to direct light from a visual target optical system toward the eye as described herein.

Figure 35:
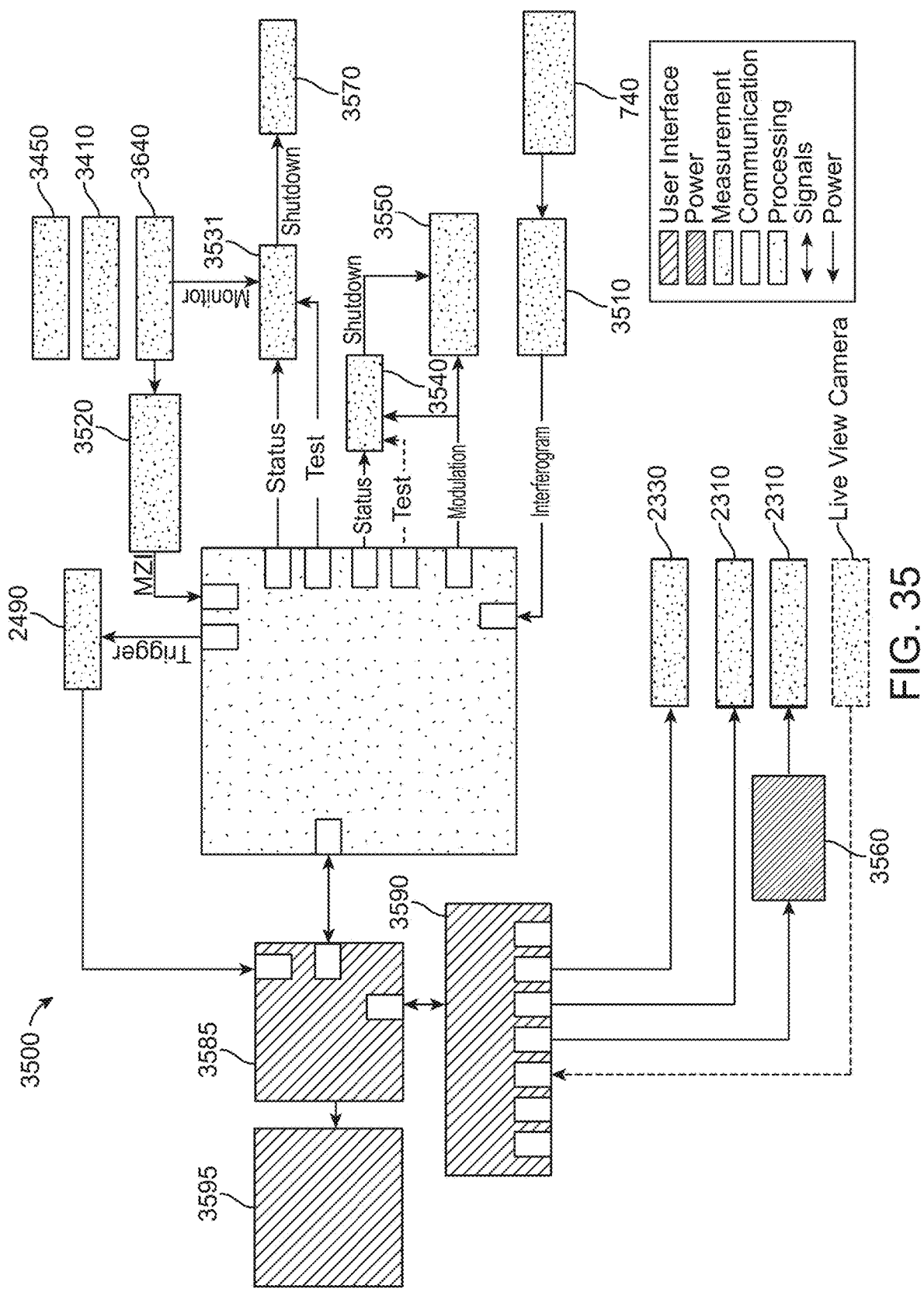
FIG. 35 shows a schematic of an electronic circuit board for controlling the optics of the compact SS-OCT systems described herein, in accordance with some embodiments.

FIG. 35 shows a schematic 3500 of electronic circuitry for controlling the optics of the compact SS-OCT systems described herein. The optics described herein may be coupled to electronic circuitry configured to control the operations of various elements of the optics. For instance, a photodetector 740 described herein may be electronically coupled to a first filter 3510, such as a low pass filter. The first filter may be configured to receive an interference signal described herein from the photodetector, filter the interference signal, and pass the filtered interference signal to a data acquisition module 3580. The data acquisition module may comprise a data acquisition card, such as a data acquisition card provided by National Instruments. The data acquisition module may comprise one or more analog to digital converters (ADCs) or one or more digital to analog converters (DACs). The data acquisition module may be configured to sample the ADCs at a sampling rate of at least 1 kilosample per second (kS/s), at least 2 kS/s, at least 5 kS/s, at least 10 kS/s, at least 20 kS/s, at least 50 kS/s, at least 100 kS/s, at least 200 kS/s, at least 500 kS/s, at least 1,000 kS/s, at least 2,000 kS/s, at least 5,000 kS/S, or at least 10,000 kS/s. The data acquisition module may be configured to sample the ADCs at a sampling rate that is within a range defined by any two of the preceding values. The data acquisition module may be configured to sample the DACs at a sampling rate of at least 1 kilosample per second (kS/s), at least 2 kS/s, at least 5 kS/s, at least 10 kS/s, at least 20 kS/s, at least 50 kS/s, at least 100 kS/s, at least 200 kS/s, at least 500 kS/s, at least 1,000 kS/s, at least 2,000 kS/s, at least 5,000 kS/S, or at least 10,000 kS/s. The data acquisition module may be configured to sample the DACs at a sampling rate that is within a range defined by any two of the preceding values.

An interferometer apparatus 3640 for enhancing phase stability described herein (for instance, with respect to FIG. 36) may be electronically coupled to a second filter 3520, such as a low pass filter. The second filter may be configured to receive a phase measurement from the interferometer apparatus 3640 as described herein, filter the phase measurement, and pass the filtered phase measurement to the data acquisition module.

The electronic circuitry may comprise safety circuitry. The electronic circuitry may comprise a first safety circuit 3530 electronically coupled to the data acquisition module. The first safety circuit may be configured to receive a first status signal from the data acquisition module. The first safety circuit may be configured to monitor a signal from the interferometer apparatus 3640. If a signal from the interferometer apparatus 3640 exceeds a safe level, the first safety circuit may send a signal to activate a first safety device 3570, such as a shutter. Activation of the first safety device may reduce the amount of optical power received by the interferometer apparatus 3640 or an eye of a subject to a safe level. In the event that the first safety device is activated, the first safety circuit may send a status signal to the data acquisition module. This status signal may be passed to an operator of the SS-OCT device to ensure that the operator is informed about the safety status.

The electronic circuitry may comprise a second safety circuit 3540 electronically coupled to the data acquisition module. The second safety circuit may be configured to a receive a second status signal from the data acquisition module. The second safety circuit may be configured to monitor a signal from a light source driver 3550, such as a VCSEL driver. If an output power from the light source driver exceeds a safe level, the second safety circuit may send a signal to shut down the light source driver or otherwise reduce the power supplied by the light source driver. Shutting down or reducing power from the light source driver may reduce the amount of optical power supplied by the light source to a safe level. The data acquisition module 3580 may be configured to send a modulation signal to the light source driver to modulate the operating current of the light source as described herein.

The data acquisition module 3580 may be electronically coupled to a fundus camera 2490 described herein. The data acquisition module may be configured to trigger a measurement from the fundus camera. A signal from the fundus camera may be directed to a computation module 3585. The computation module may comprise an external computer. The computation module may comprise a personal computer or workstation. The computation module may comprise a mobile device, such as a tablet or smartphone. The computation module may be configured to operate a visualization program, such as a graphical user device (GUI). The computation module may be configured to receive one or more fundus images from the fundus camera. The computation module may be configured to display the one or more fundus images on a display 3595. The display may be external to the computation module, such as an external monitor electronically coupled to the computation module. The display may be integrated into the computation module, as may be the case for a computation module configured as a mobile device.

The computation module may be electronically coupled to a control bus module 3590. The control bus module may comprise a universal serial bus (USB) hub. The computation module may direct signals to the control bus module 3590 to control the operation of one or more optical components of the compact SS-OCT system. For instance, the control bus module may direct a signal to a scanner interface module 3560 that controls the operation of the scanning element 2310 described herein. The scanner interface module may comprise a high voltage driver that powers the scanning element at a high voltage, such as a voltage of up to 200 V. The control bus module may direct a signal to a first OCT focusing element, such as any of lenses 2320, 3650, or 3655 described herein, to adjust a focus of the SS-OCT systems described herein. The control bus module may direct a signal to a second OCT focusing element, such as any of lenses 2330, 3650, or 3655 described herein, to adjust a focus of the SS-OCT systems described herein. The first or second focusing elements may comprise tunable lenses. Alternatively or in combination, the first or second focusing elements may comprise moveable lenses. The control bus module may direct a signal to a live view camera. The live view camera may provide one or more images of an eye. The live view camera may provide one or more images of a side view of an eye. Images acquired by the live view camera may assist an operator of an SS-OCT device described herein in correctly aligning the device with a subject's eye. For instance, images acquired by the live view camera may allow the operator to select a proper distance between the eye and the SS-OCT device.

Though not shown in FIG. 35, the electronic circuitry may be configured to control other elements of the compact SS-OCT systems described herein. For instance, the electronic circuitry may be configured to control any or all optical elements described herein with respect to any of FIGS. 5, 6A, 7A, 8A, 8B, 22, 23A, 24, 26, 34, or 36. The computation module 3585 may be configured to implement any steps of any method described herein, such as methods 1100, 1200, or 2500.

Figure 36:
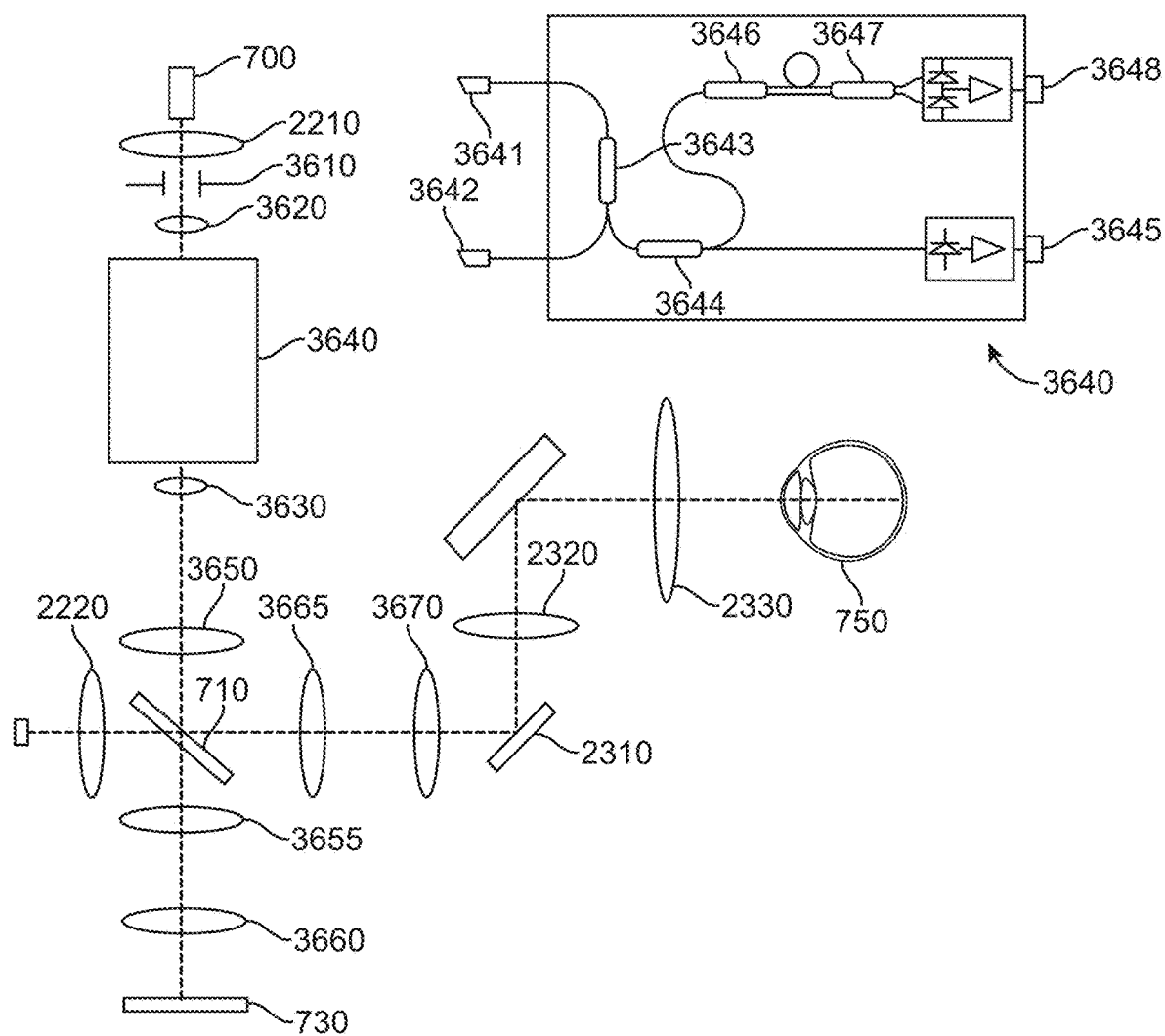
FIG. 36 shows a schematic for the optics of a SS-OCT device incorporating an interferometer for enhancing phase stability.

FIG. 36 shows a schematic 3600 for the optics of a SS-OCT device incorporating an interferometer for enhancing phase stability. The optics may comprise a light source 700, collimating lens 2210, beam splitter 710, reference mirror 730, scanning mirror 2310, telescope lenses 2320 and 2330, mirror 2325, focusing lens 2220, and detector 740, as described herein. The elements 700, 2210, 710, 730, 2310, 2320, 2330, 2325, 2220, and detector 740 may be arranged to produce an OCT signal from an eye 750, as described herein.

The optics may further comprise an aperture 2460 comprising a stop. The stop may comprise a ring stop, for example. The stop may be located between the collimating lens 2210 and a first coupling lens 3620. The first coupling lens may be a fiber coupling lens. The first coupling lens may have a numerical aperture sufficient to direct collimated light emitted by the light source into an optical fiber. The first coupling lens may be configured to direct light to an interferometer apparatus 3640.

The interferometer apparatus may be a fiber-based interferometer apparatus. Alternatively, the interferometer apparatus may be a bulk interferometer apparatus. The interferometer apparatus may be configured to direct a first portion (such as 95% of the light) of the light to a second coupling lens 3630 and a second portion (such as 5% of the light) of the light to a light analysis unit within the interferometer apparatus. The light analysis unit may direct a third portion (such as 50% of the second portion of the light) of the light to a power monitoring apparatus within the interferometer apparatus and a fourth portion (such as 50% of the second portion of the light) of the light to a Mach-Zender interferometer. The power monitoring apparatus may measure an optical power of the light incident on the interferometer apparatus and output the measurement to a power measurement output 3642. Such a measurement may allow monitoring to ensure that the optical power does not exceed a safe level. The Mach-Zender interferometer may measure a phase of the light coupled into the interferometer apparatus and output the measurement to a phase measurement output 3644. The phase may be monitored and phase drifts (such as phase drifts associated with ambient temperature fluctuations, aging of optical components, transient responses of optical or electronic components, or other factors) may be corrected. Correction of the phase drifts may narrow peaks in the frequency domain. This may increase the accuracy of the RT or RLT estimations.

A phase measurement may be obtained by a Mach-Zender interferometer, as described herein. Alternatively or in combination, the phase measurement may be obtained using another optical phase measurement apparatus, such as a Fabry-Perot interferometer, as described herein. The phase of the light source may be acquired simultaneously with an OCT signal.

The second coupling lens may be a fiber coupling lens. The second coupling lens may have a numerical aperture sufficient to accept light emitted by the interferometer apparatus and direct the light to first and second tunable lenses 3650 and 3655 and a focusing lens 3660. The first and second tunable lenses may be configured to vary a spot size of light emitted by the SS-OCT system on a retina.

The optics may further comprise a beam expander comprising first and second beam expander lenses 3665 and 3670.

Figure 44A:
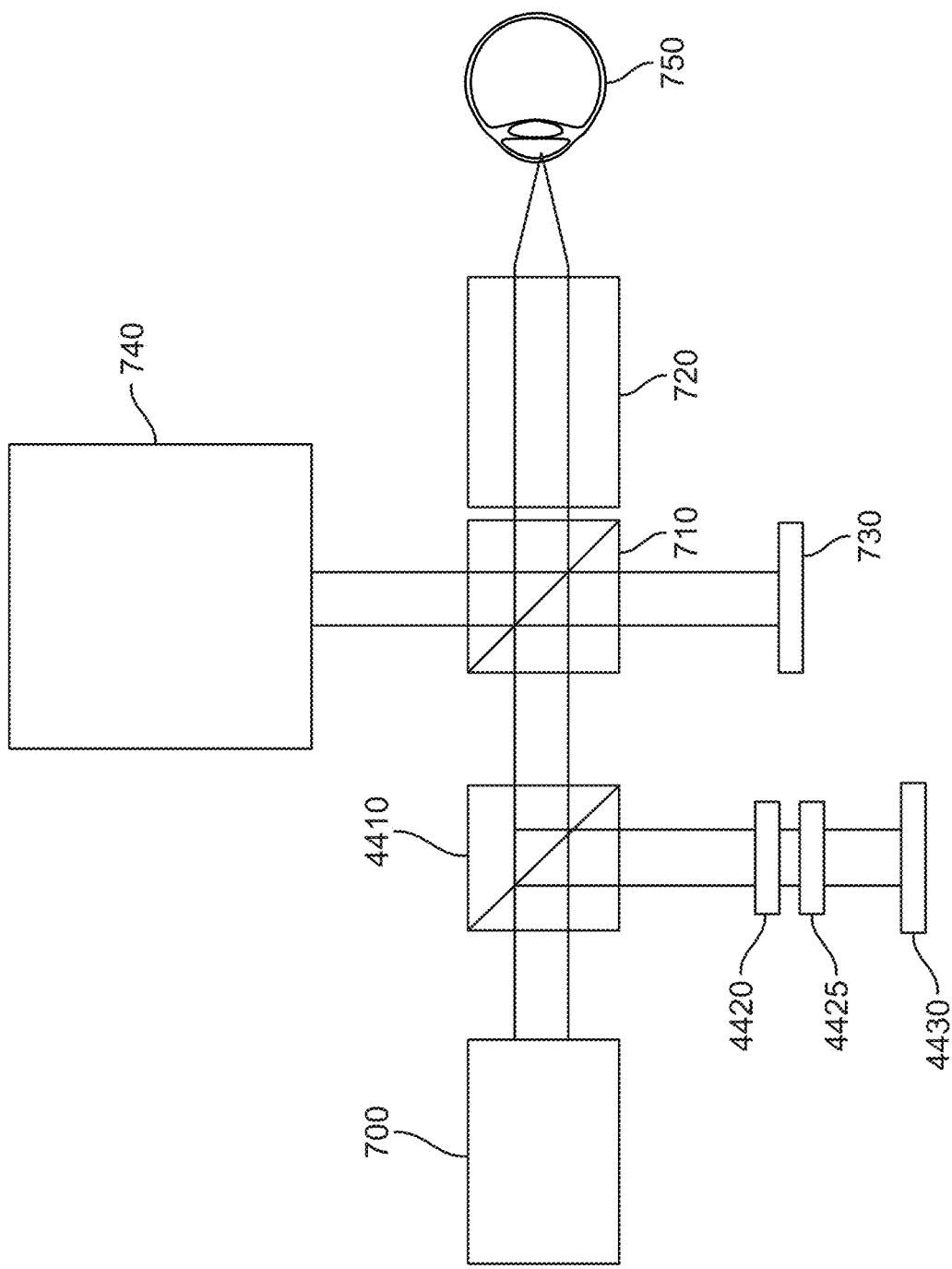
FIG. 44A shows a schematic for the optics of a SS-OCT incorporating a Fabry-Perot interferometer for optical phase measurement, in accordance with some embodiments.

FIG. 44A shows a schematic for the optics of a SS-OCT incorporating a Fabry-Perot interferometer for optical phase measurement, in accordance with some embodiments. The optics may comprise a light source 700, beam splitter 710, front end optics 720, reference mirror 730, and detector 740, as described herein. The elements 700, 710, 720, 730, and 740 may be arranged to produce an OCT signal from an eye 750, as described herein. The optics may further comprise any additional optical elements described herein, such as any one or more of collimating lens 2210 (not shown in FIG. 44A), telescope lenses 2320 and 2330 (not shown in FIG. 44A), mirror 2325 (not shown in FIG. 44A), or focusing lens 2220 (not shown in FIG. 44A).

The optics may further comprise a beamsplitter 4410. The beamsplitter may be configured to direct a portion of light emitted by the light source (such as at least 1%, at least 2%, at least 5%, or at least 10% of the light emitted by the light source, or an amount of the light emitted by the light source that is within a range defined by any two of the preceding values) to first and second Fabry-Perot mirrors 4420 and 4425, respectively. The first and second Fabry-Perot mirrors may be configured to form a Fabry-Perot interferometer. One or both of the first and second Fabry-Perot mirrors may be tilted. The first and second Fabry-Perot mirrors may comprise reflective coatings on opposing surfaces of a substrate such as glass. One or both of the first and second Fabry-Perot mirrors may be oriented at an angle to the light directed toward them, such that the light hits one or both of the first and second Fabry-Perot mirrors at an angle that is slightly different than normal to the first or second Fabry-Perot mirrors. The amount by which the angle is slightly different than normal may be referred to as the tilt angle. The tilt angle may correspond to an angle between opposing reflective surfaces of an optical substrate. One or both of the first and second Fabry-Perot mirrors may have a tilt angle of at least 1 arcsecond, at least 2 arcseconds, at least 5 arcseconds, at least 10 arcseconds, at least 20 arcseconds, at least 50 arcseconds, or at least 100 arcseconds, or a tilt angle that is within a range defined by any two of the preceding values. The tilt angle may alter the efficiency with which a range of wavelengths of light (such as the range of wavelengths swept over by a tunable light source described herein) are transmitted by the Fabry-Perot interferometer by altering the finesse of the Fabry-Perot interferometer. The tilt angle may produce a Fabry-Perot transmission spectrum with a waveform shape that is favorable for phase evaluation (such as an approximately sinusoidal shape). An approximately sinusoidal shape may be favorable for phase evaluation due to the occurrence of only one or a few peaks in the frequency domain that may be associated with such a shape. The light passed by the Fabry-Perot interferometer may be detected by a detector 4430. The detector may comprise any detector as described herein.

Figure 44B:
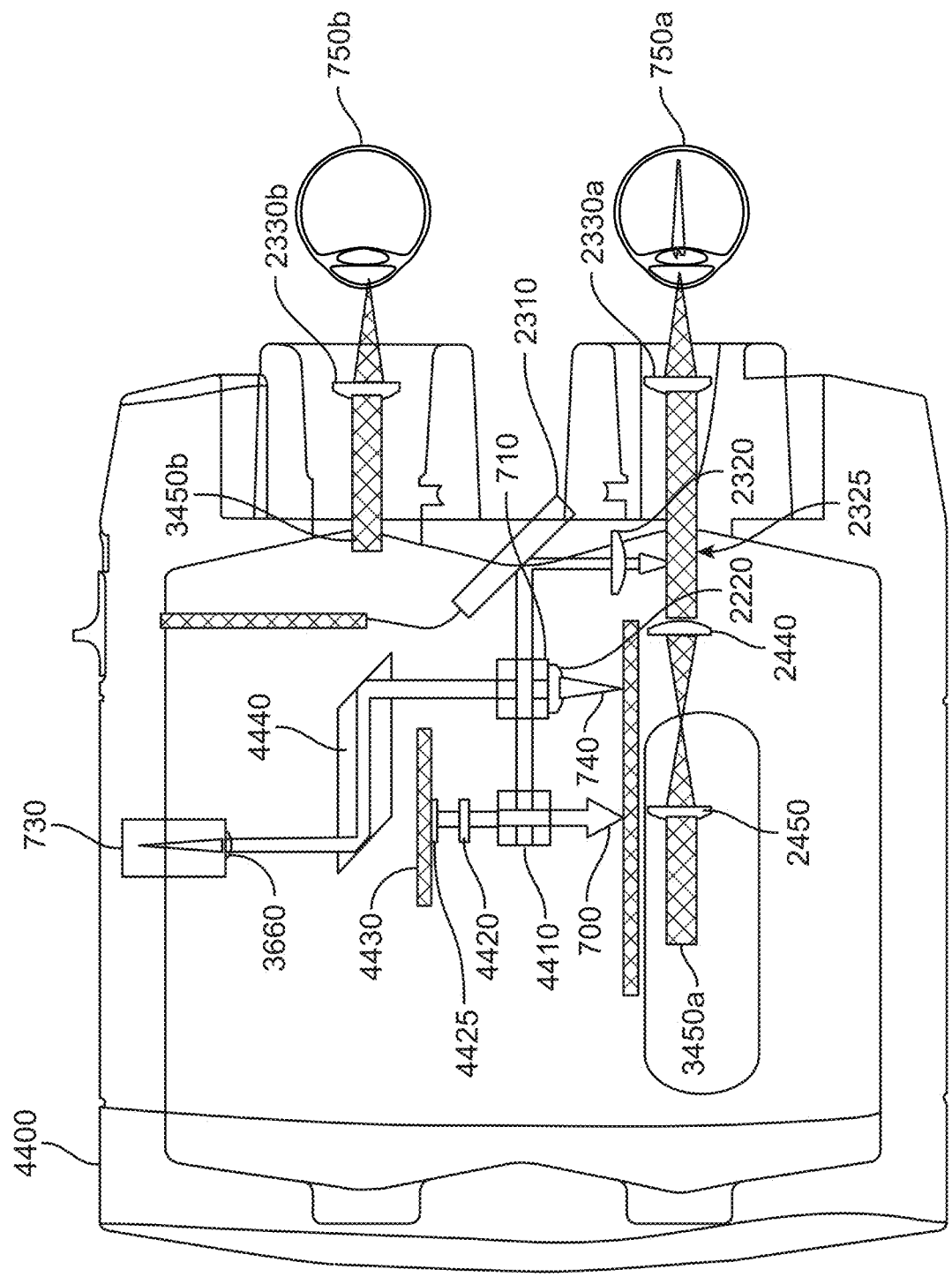
FIG. 44B shows a handheld binocular OCT system comprising a Fabry-Perot interferometer for optical phase measurement, in accordance with some embodiments.

FIG. 44B shows a handheld binocular OCT system comprising a Fabry-Perot interferometer for optical phase measurement, in accordance with some embodiments. As shown in FIG. 44B, the handheld OCT system may have the form factor of a binocular system 4400, as described herein. The binocular system may comprise OCT optics configured to produce an OCT signal from a first eye 750a of a user. The OCT optics may comprise a light source 700, beam splitter 710, front end optics 720, reference mirror 730, and detector 740, as described herein. The elements 700, 710, 720, 730, and 740 may be arranged to produce an OCT signal from a first eye 750a of a user, as described herein. The OCT optics may further comprise a beamsplitter 4410, first and second Fabry-Perot mirrors 4420 and 4425, and a detector 4430 to measure a phase of light emitted by the light source, as described herein. The OCT optics may further comprise a collimating lens 2210, scanning mirror 2310, telescope lenses 2320 and 2330a (which may be similar to lens 2330 described herein), mirror 2325, focusing lens 2220, and focusing lens 3660, as described herein. The OCT optics may further comprise a prism 4440. The prism may be configured to compensate for chromatic dispersion or to fold and compactify the OCT optical path.

The binocular system may further comprise first visual target optics configured to direct a visual target to the first eye. The first visual target optics may comprise a first visual target light source 3450a. The first visual target light source may be similar to visual target light source 3450 described herein. The first visual target optics may further comprise first and second lenses 2450 and 2440, as described herein. The first visual target optics may be configured similarly to any visual target optics described herein.

The binocular system may further comprise second visual target optics configured to direct a visual target to a second eye 750b of a user. The second visual target optics may comprise a second visual target light source 3450b. The second visual target light source may be similar to visual target light source 3450 described herein. The second visual target optics may further comprise a lens 2330b (which may be similar to lens 2330 described herein), as described herein.

Figure 44C:
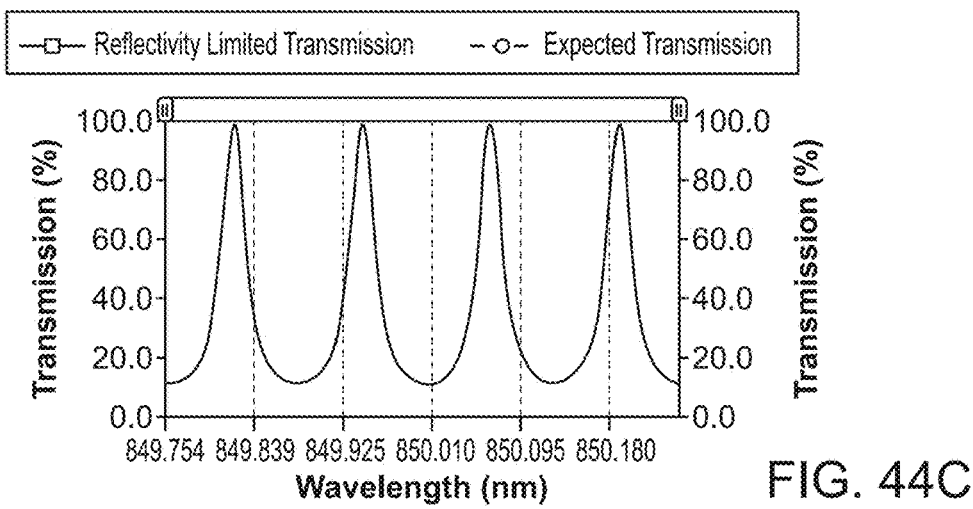
FIG. 44C shows an exemplary simulated transmission spectrum passed by a Fabry-Perot interferometer with no tilt angle, in accordance with some embodiments.

FIG. 44C shows an exemplary simulated transmission spectrum passed by a Fabry-Perot interferometer with no tilt angle, in accordance with some embodiments. As shown in FIG. 44C, the transmission spectrum from the untitled Fabry-Perot interferometer comprises a series of maxima with high transmittance and minima with low transmittance. The transmission spectrum was simulated using 2 mm thick BK7-N glass coated to achieve a transmittance of 50% on each surface. As shown in FIG. 44C, the untitled Fabry-Perot interferometer produces a transmission spectrum that may be unfavorable for phase measurement.

Figure 44D:
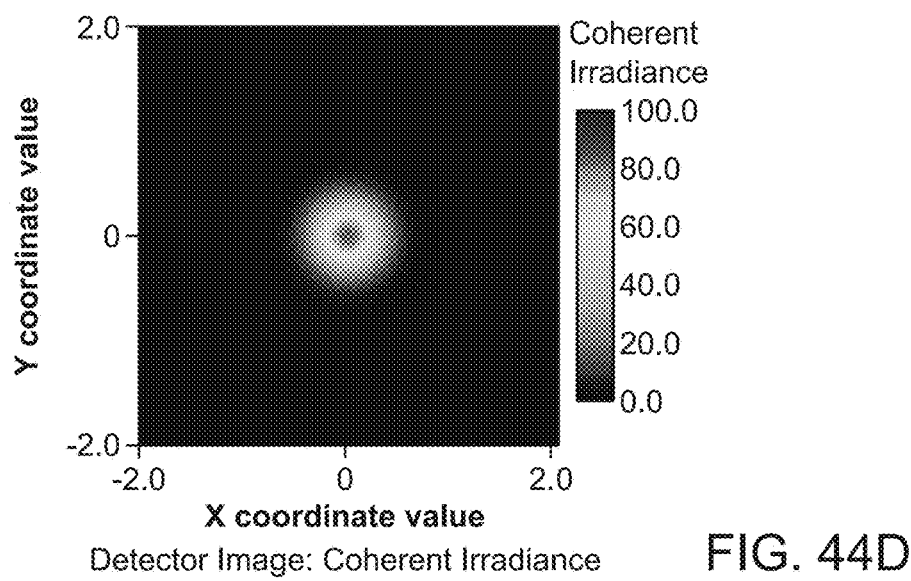
FIG. 44D shows an exemplary maximal transmittance passed by a Fabry-Perot interferometer with no tilt angle, in accordance with some embodiments.

FIG. 44D shows an exemplary maximal transmittance passed by a Fabry-Perot interferometer with no tilt angle, in accordance with some embodiments.

Figure 44E:
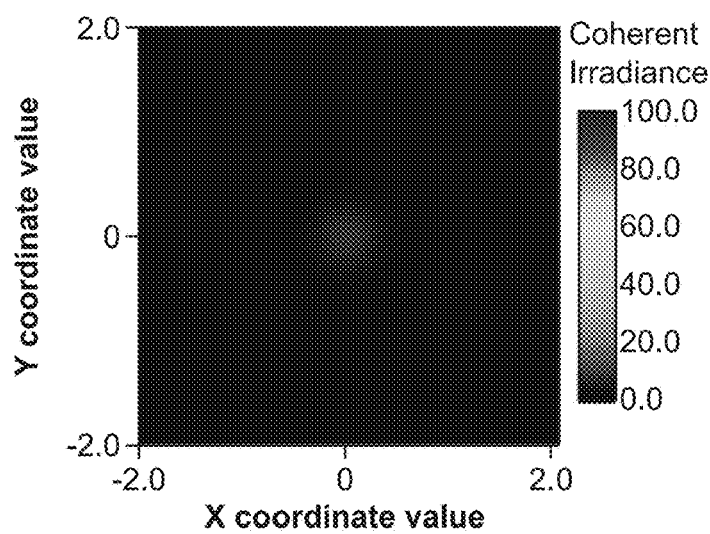
FIG. 44E shows an exemplary minimal transmittance passed by a Fabry-Perot interferometer with no tilt angle, in accordance with some embodiments.

FIG. 44E shows an exemplary minimal transmittance passed by a Fabry-Perot interferometer with no tilt angle, in accordance with some embodiments.

Figure 44F:
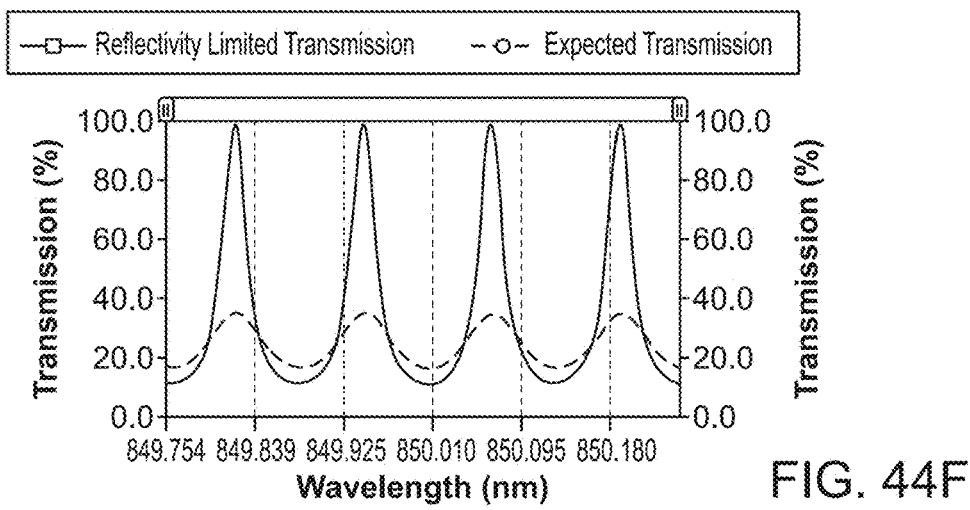
FIG. 44F shows an exemplary simulated transmission spectrum passed by a Fabry-Perot interferometer with a tilt angle of 20 arcseconds, in accordance with some embodiments.

FIG. 44F shows an exemplary simulated transmission spectrum passed by a Fabry-Perot interferometer with a tilt angle of 20 arcseconds, in accordance with some embodiments. As shown in FIG. 44F, the transmission spectrum from the tilted Fabry-Perot interferometer comprises a series of maxima with reduced transmittance (compared to the untilted case) and minima with high transmittance (compared to the untilted case). The transmission spectrum was simulated using 2 mm thick BK7-N glass coated to achieve a transmittance of 50% on each surface. As shown in FIG. 44F, the tilted Fabry-Perot interferometer produces an approximately sinusoidal transmission spectrum, which may be more favorable for phase measurement.

Figure 44G:
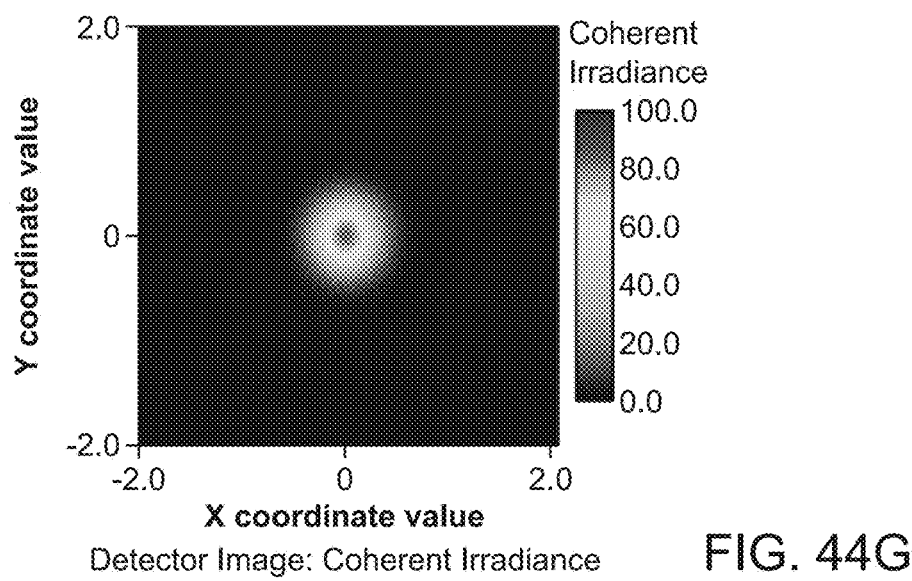
FIG. 44G shows an exemplary maximal transmittance passed by a Fabry-Perot interferometer with a tilt angle of 20 arcseconds, in accordance with some embodiments.

FIG. 44G shows an exemplary maximal transmittance passed by a Fabry-Perot interferometer with a tilt angle of 20 arcseconds, in accordance with some embodiments.

Figure 44H:
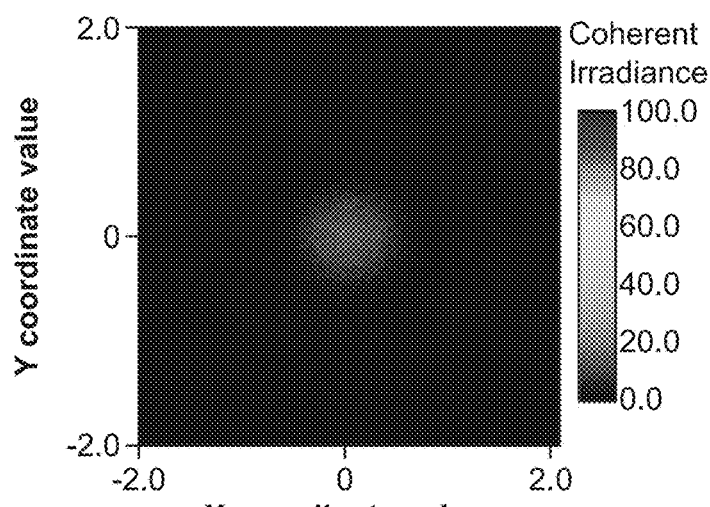
FIG. 44H shows an exemplary minimal transmittance passed by a Fabry-Perot interferometer with a tilt angle of 20 arcseconds, in accordance with some embodiments.

FIG. 44H shows an exemplary minimal transmittance passed by a Fabry-Perot interferometer with a tilt angle of 20 arcseconds, in accordance with some embodiments.

Figure 44I:
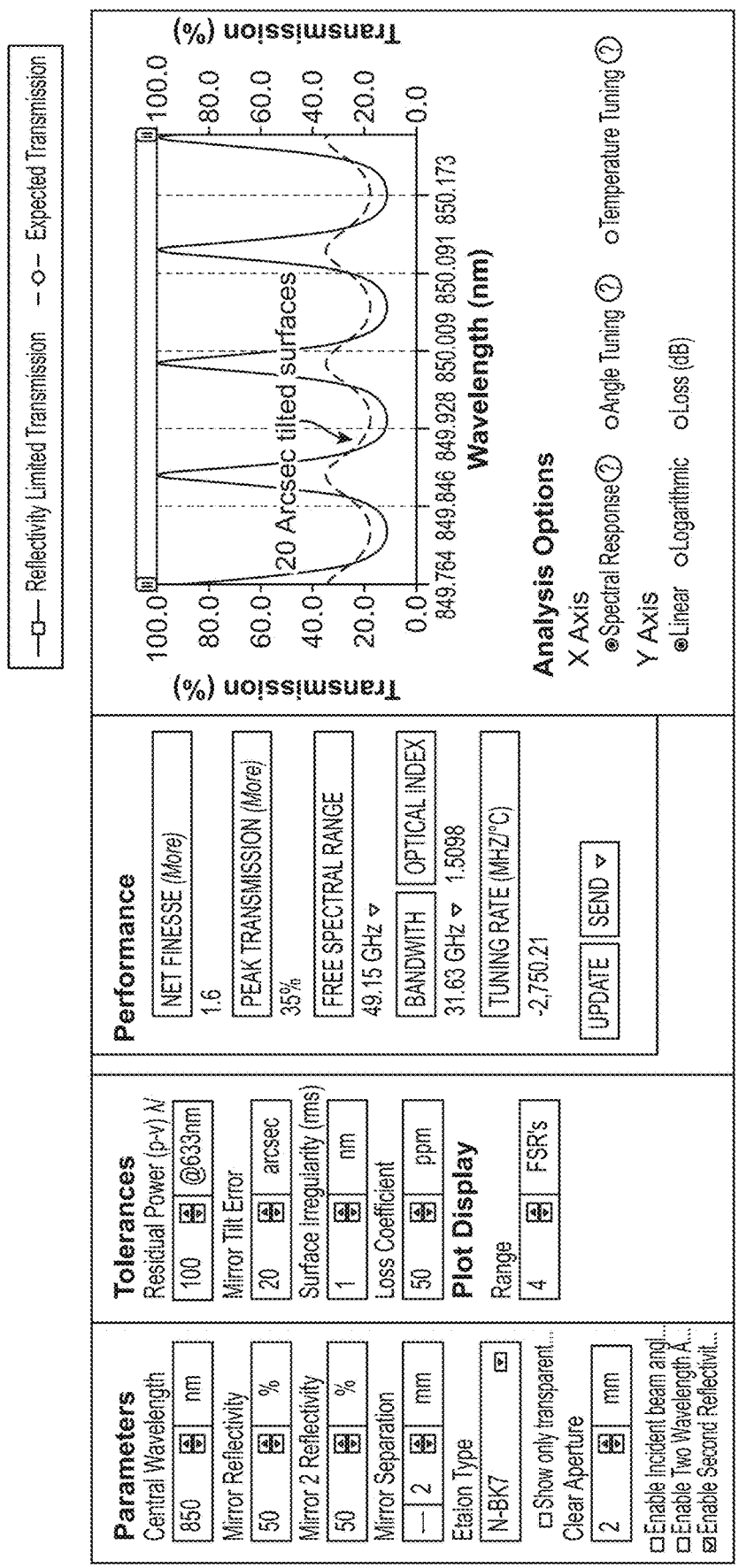
FIG. 44I shows an exemplary simulated transmission spectrum passed by a Fabry-Perot interferometer with a tilt angle of 20 arcseconds and coatings with 50% transmissivity on each plate, in accordance with some embodiments.

FIG. 44I shows an exemplary simulated transmission spectrum passed by a Fabry-Perot interferometer with a tilt angle of 20 arcseconds and coatings with 50% transmissivity on each plate, in accordance with some embodiments. As shown in FIG. 44I, light is passed through the Fabry-Perot interferometer with low efficiency.

Figure 44J:
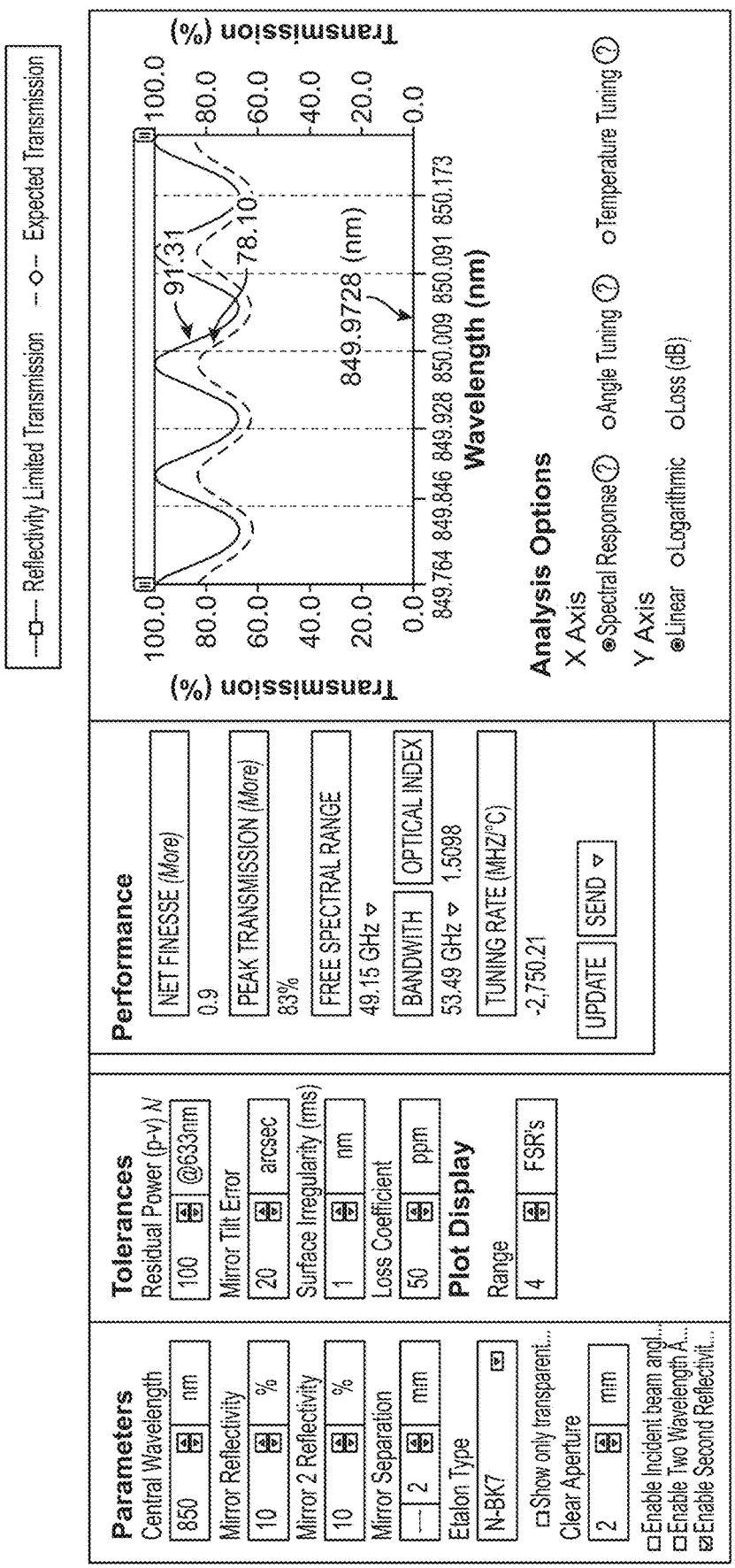
FIG. 44J shows an exemplary simulated transmission spectrum passed by a Fabry-Perot interferometer with a tilt angle of 20 arcseconds and coatings with 10% transmissivity on each plate, in accordance with some embodiments.

FIG. 44J shows an exemplary simulated transmission spectrum passed by a Fabry-Perot interferometer with a tilt angle of 20 arcseconds and coatings with 10% transmissivity on each plate, in accordance with some embodiments. As shown in FIG. 44J, light is passed through the Fabry-Perot interferometer with higher efficiency relative to the case depicted in FIG. 44I.

Figure 27A:
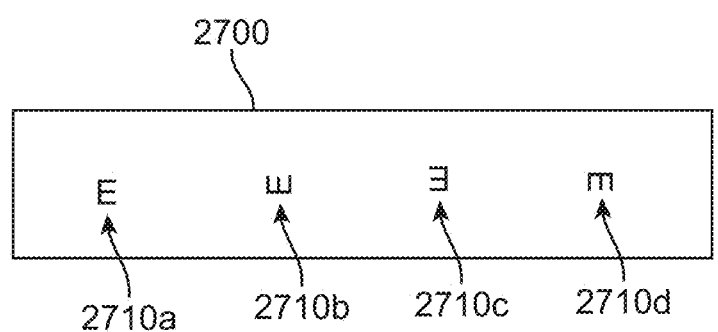
FIG. 27A and FIG. 27B show visual cues on a background, in accordance with some embodiments.

FIG. 27A shows dark visual cues on a light background. The visual cues may be presented alone, or in combination. The visual cue may comprise a letter at an orientation, such as a tumbling E, for example. The subject may input the orientation of the orientation of the letter in order to determine the visual acuity of the subject. The visual cues may comprise a plurality of dark letters 2710a, 2710b, 2710c, and 2710d, such as the letter "E", on a light background 2700. Although four letters are shown, the visual cues may comprise 1, 2, 3, 4, 5, 6, 7, 8, 9, 10, or more than 10 letters. The letters may move along the background, such as downward along the background. Other visual stimuli may be presented, such as an arrow, in which the patient indicates the orientation of the letter.

Figure 27B:
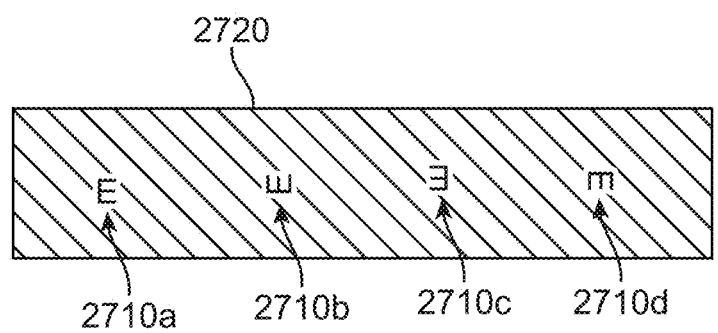

FIG. 27B shows dark visual cues on a dark background. The visual cues may comprise a plurality of dark letters 2710a, 2710b, 2710c, and 2710d, such as the letter "E", on a dark background 2720. Although four letters are shown, the visual cues may comprise 1, 2, 3, 4, 5, 6, 7, 8, 9, 10, or more than 10 letters. The letters may move along the background, such as downward along the background. The letters may be presented in different orientations, such as facing to the left, right, up, or down.

In many embodiments, the visual cues are shown on the display as described herein, and the lens may compensate for the refractive error of the subject in order to test vision of the subject. The compact SS-OCT system may comprise an input for the patient to input an orientation of the letter presented, such that the vision of the patient may be determined. The input may comprise an input configured to receive an orientation of the letter, such as a button or a plurality of buttons, for example.

FIG. 28A shows a schematic of a housing for an exemplary handheld monocular OCT system, in accordance with some embodiments. The left side of the figure shows a side view 2800 of the housing. The housing may comprise and a body 2810. The body of the housing may comprise a handle 2850 for the patient to grasp the system. The body 2810 may be coupled to a structure to contact the patient, such as an eye piece 2805, or foam or other structure. The housing may have an inner volume that contains any of the components of the handheld OCT systems and devices described herein. The reference leg of the interferometer may extend at least partially into the handle 2850, for example.

The eye piece may be configured to dock the housing to an area surrounding a subject's eye, such as the skin surrounding the subject's eye. The body may be configured to be held within a hand of the subject.

The right side of the figure shows a front view 2820 of the housing. The eye piece may comprise an area 2825 configured to dock with an area surrounding a subject's eye and an opening 2830 configured to allow OCT measurement light to travel from the OCT system to the eye and back. The opening may be further configured to present visual cues to the subject (such as one or more of the letter "E"), as described herein. The housing may comprise a mechanism 2835 that allows a subject to indicate the orientation (such as facing left, right, up, or down) of each letter presented to them.

FIG. 28B shows a housing for an exemplary handheld monocular OCT system, in accordance with some embodiments.

FIGS. 29A and 29B show a configuration for a handheld binocular OCT system, in accordance with some embodiments. Alternatively, the system may comprise a monoocular system, in which the non-measured eye is occluded with the measurement system. The left side of the figure shows a side view 2900 of the housing. The housing may comprise eye pieces 2905a and 2905b and a body 2910. The housing may have an inner volume that contains any of the components of the handheld OCT systems and devices described herein. The eye pieces may be configured to dock the housing to an area surrounding a subject's eyes, such as the skin surrounding the subject's eyes. The body may be configured to be held within both hands of the subject.

The right side of the figure shows a front view 2920 of the housing. The eye pieces may comprise areas 2925a and 2925b configured to dock with an area surrounding a subject's eyes and an opening 2930 configured to allow OCT measurement light to travel from the OCT system to one or both of the eyes and back. The opening may be further configured to present visual cues to the subject (such as one or more of the letter "E"), as described herein. The housing may comprise a mechanism 2935 that allows a subject to indicate the orientation (such as facing left, right, up, or down) of each letter presented to them.

FIG. 29C shows a housing for an exemplary handheld binocular OCT system, in accordance with some embodiments.

Figure 30:
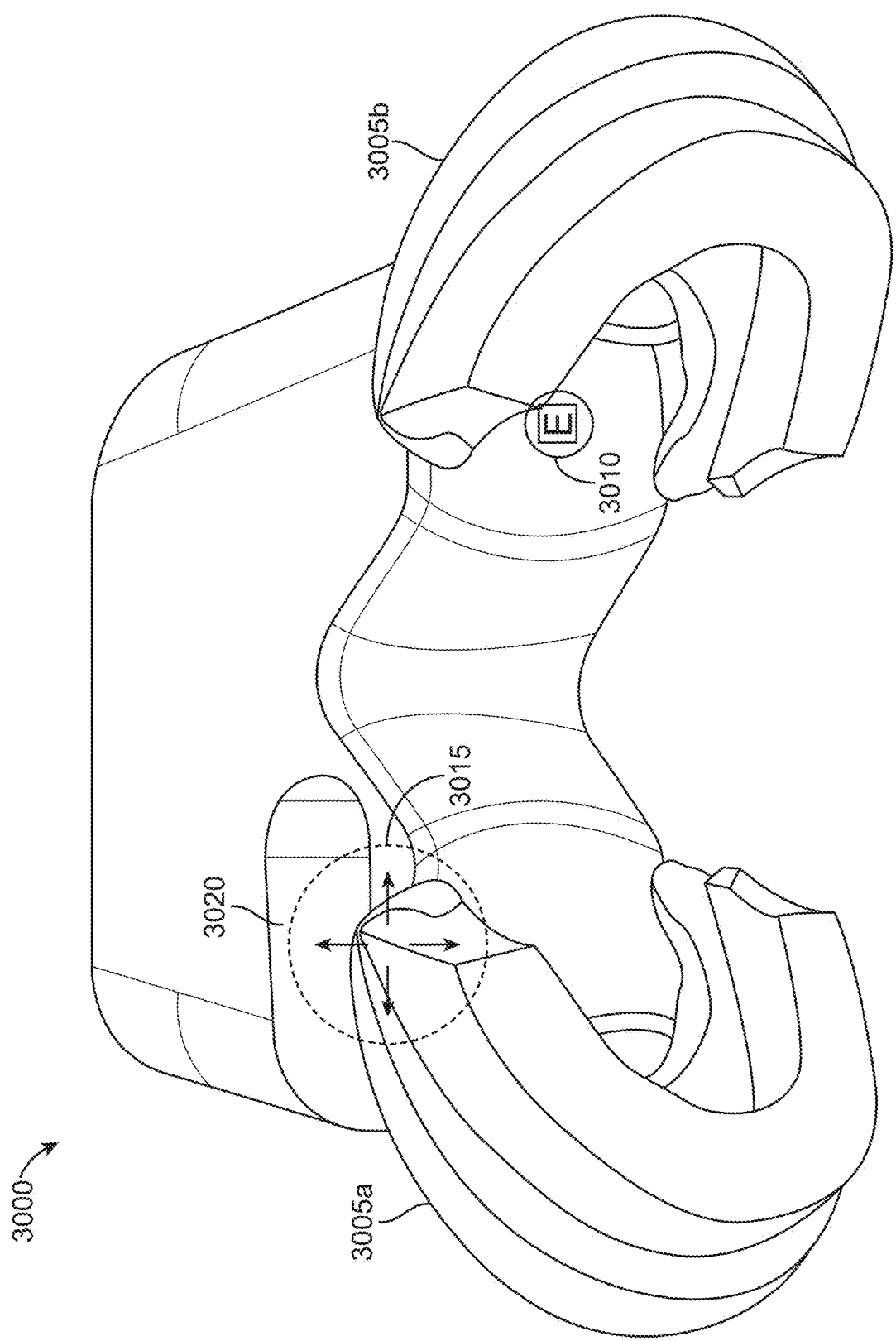
FIG. 30 shows a configuration for an exemplary handheld binocular OCT system, in accordance with some embodiments.

FIG. 30 shows a configuration for an exemplary handheld binocular OCT system, in accordance with some embodiments. The housing 3000 may comprise eye pieces 3005a and 3005b and a body 3020. The housing may have an inner volume that contains any of the components of the handheld OCT systems and devices described herein. The eye pieces may be configured to dock the housing to an area surrounding a subject's eyes, such as the skin surrounding the subject's eyes. The body may be configured to be held within both hands of the subject. One of the eye pieces may comprise an opening 3010 configured to allow OCT measurement light to travel from the OCT system to one of the eyes and back. The opening may be further configured to present visual cues to the subject (such as one or more of the letter "E"), as described herein. The housing may comprise a mechanism 3015 that allows a subject to indicate the orientation (such as facing left, right, up, or down) of each letter presented to them. The body of the housing may comprise a cutout area. The orientation of the cutout area may indicate which eye is to be measured using the OCT system. The cutout area may be located on the opposite side of the housing from the eye to be measured.

An orientation sensor such as an accelerometer may be mechanically coupled to the optics and electronically coupled to the control unit as described herein, in order to measure which eye is measured in response to an orientation of the orientation sensor.

Figure 31A:
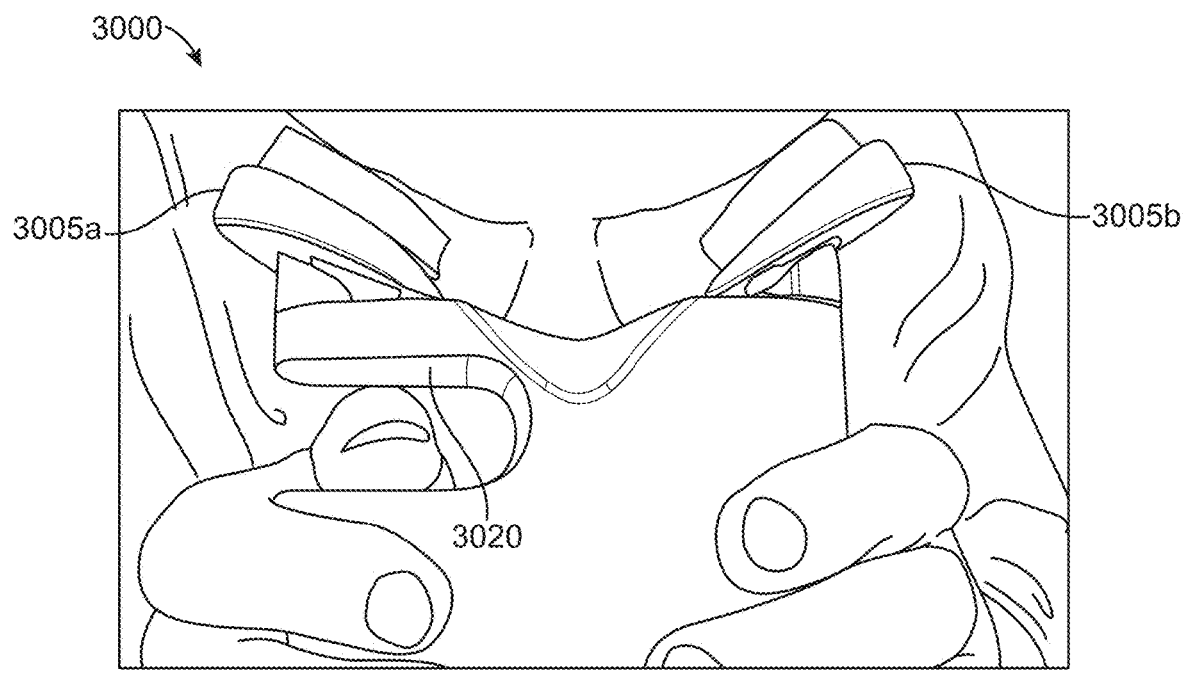
FIG. 31A shows a handheld binocular OCT system oriented to measure a subject's left eye, in accordance with some embodiments.

FIG. 31A shows a handheld binocular OCT system oriented to measure a subject's left eye.

Figure 31B:
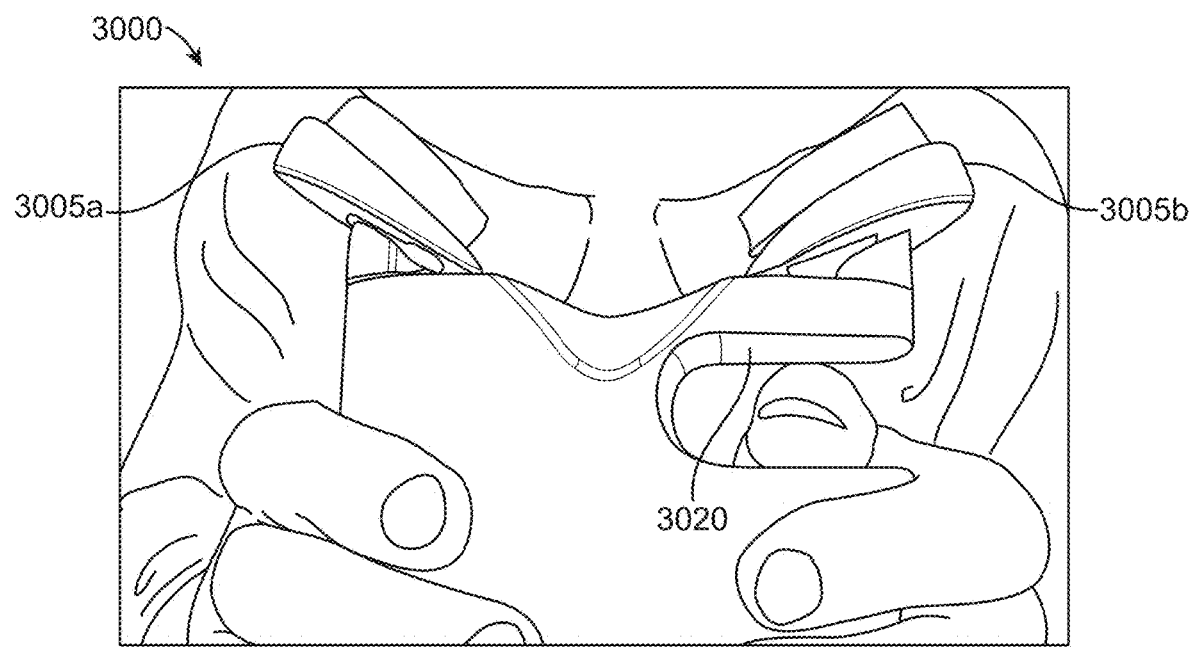
FIG. 31B shows a housing for an exemplary handheld binocular OCT system oriented to measure a subject's right eye, in accordance with some embodiments.

FIG. 31B shows a housing for an exemplary handheld binocular OCT system oriented to measure a subject's right eye.

Figure 32A:
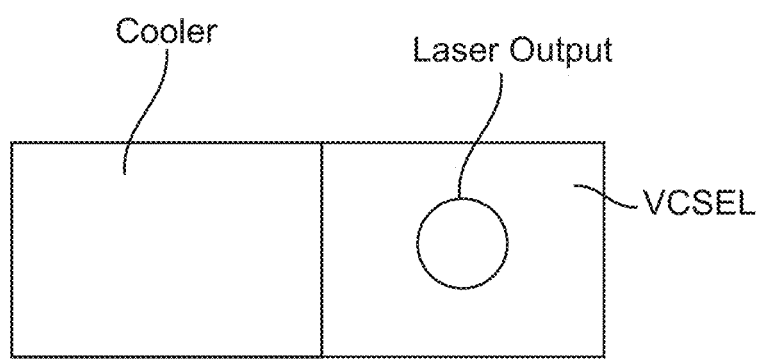
FIG. 32A shows a VCSEL coupled to a cooler to increase the range of wavelengths swept, in accordance with some embodiments.

FIG. 32A shows a VCSEL coupled to a cooler to increase a range of wavelengths swept with the VCSEL, in accordance with some embodiments. The VCSEL of the SS-OCT systems described herein may be subjected to a cooling procedure to reduce the operating temperature of the VCSEL to a temperature that is below the ambient temperature of approximately 37° C., in order to increase the range of wavelengths swept by the VCSEL. The cooling can be combined with overdriving of the VCSEL as described herein, in order to further increase the range of wavelengths swept by the VCSEL. The VCSEL of the SS-OCT systems may be cooled below ambient temperature by 10° C., 20° C., 30° C., 40° C., 50° C., 70° C., 80° C., 90° C. or more. The VCSEL of the SS-OCT systems may be cooled by an amount within a range defined by any two of the preceding values, for example cooled by an amount within a range from 20° C. to 70° C. The range of wavelengths swept can be increased by 1 nm, 2 nm, 3 nm, 4 nm, 5 nm, or increased by an amount within a range defined by any two of the preceding values. For example, a VCSEL with a specified wavelength sweep range of 5 nm can be overdriven to increase the sweep range by about 3 nm and chilled to increase the sweep range by about 2 nm to provide a total sweep range of about 10 nm. The cooler can be configured in many ways, and may comprise a Peltier cooler, a gas based cooler, a chamber comprising a gas such as nitrogen that expands to chill the VCSEL, or a chilled circulating fluid, and combinations thereof. The cooler may comprise a heat sink coupled to the VSCEL, for example.

Figure 32B:
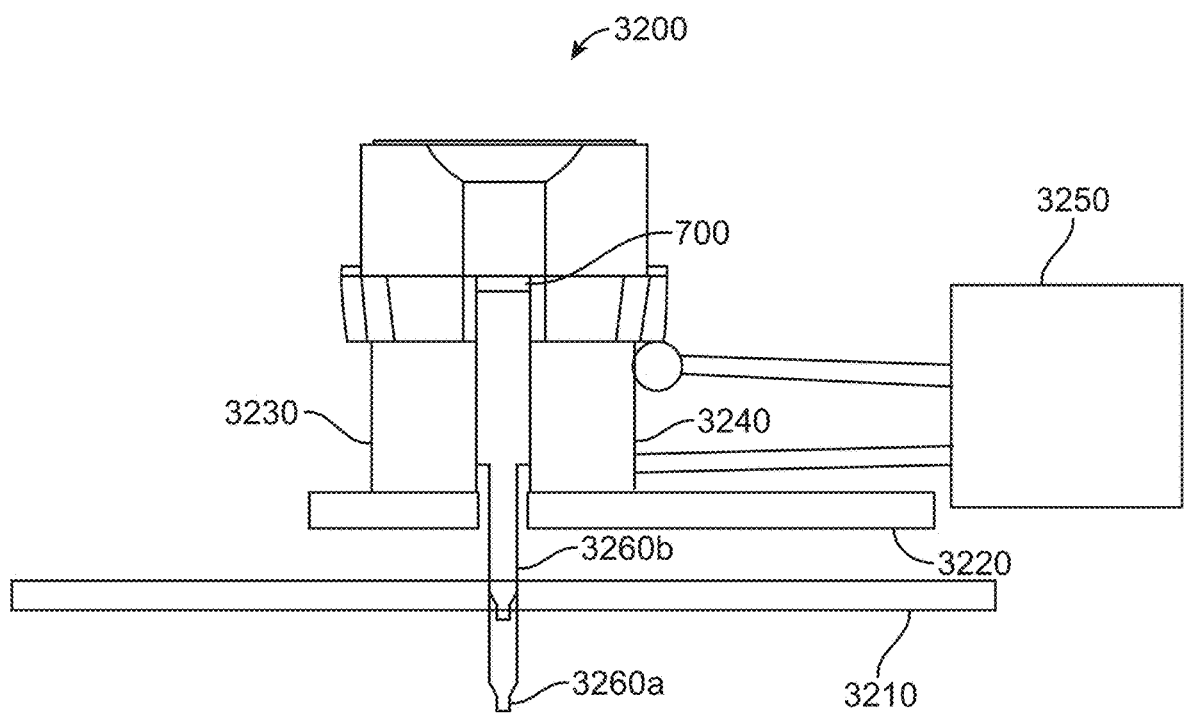
FIG. 32B shows a schematic of a VCSEL coupled to a thermoelectric cooler, in accordance with some embodiments.

FIG. 32B shows a schematic 3200 of a VCSEL coupled to a thermoelectric cooler. The VCSEL 700 may be mounted to a VCSEL driver 3210. The VCSEL driver may comprise a printed circuit board (PCB). The VCSEL may be mounted to the VCSEL driver through one or more electrical connectors, such as electrical connectors 3260a and 3260b. The VCSEL or VCSEL driver may be coupled to a heat sink 3220 configured to draw heat from the VCSEL or VCSEL driver. The VCSEL may be further coupled to a thermoelectric cooler (TEC) 3230. The TEC may comprise a Peltier cooler. The TEC may be configured to cool the VCSEL by 10° C., 20° C., 30° C., 40° C., 50° C., 70° C., 80° C., 90° C. or more. The TEC may be configured to cool the VCSEL by an amount within a range defined by any two of the preceding values. The VCSEL may be further coupled to a temperature sensor 3240. The temperature sensor may comprise a thermistor. The temperature sensor may be configured to measure an operating temperature of the VCSEL. The temperature sensor and TEC may be coupled to a TEC controller 3250. The TEC controller may control a cooling power of the TEC based on a measured temperature of the VCSEL by the temperature sensor. In this manner, the TEC, thermistor, and TEC controller may form a negative feedback system designed to maintain the VCSEL at a stable operating temperature, such as an operating temperature described herein.

Figure 33A:
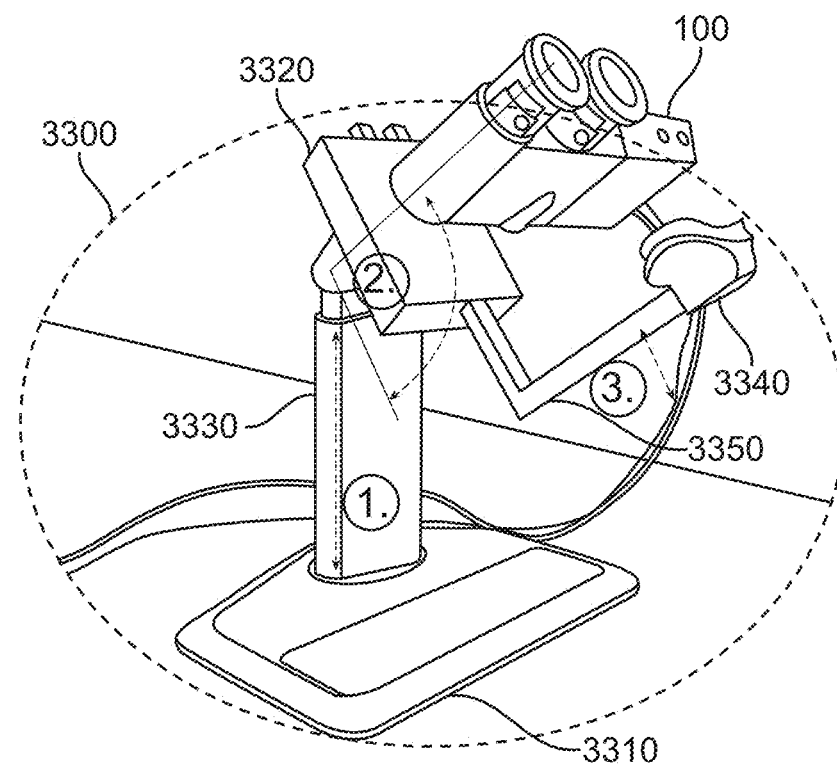
FIG. 33A shows a compact SS-OCT system placed on a support, in accordance with some embodiments

FIG. 33A shows a compact SS-OCT system as described herein placed on a support, such as a desktop mounted support. The compact SS-OCT system 100 may be any compact SS-OCT system described herein. The compact SS-OCT system may comprise any capabilities described herein. For instance, the compact SS-OCT system may comprise an OCT imaging system, an eye-tracking system, a visual fixation target, or a Badal lens, as described herein. The compact SS-OCT system may comprise one or two eyepieces.

The compact SS-OCT system may be placed a support system 3300, for example releasably mounted or attached to the support. The compact SS-OCT system may be fixably attached to the support system. The compact SS-OCT system may be removably attached to the support system. The support system may be mounted to a desktop or other surface. The support system 3300 may comprise a base 3310. The base may be attached to or placed on a desktop or other surface. The base may be fixably attached to the desktop or other surface. The base may be removably attached to the desktop or other surface.

The support system may further comprise a mounting surface 3320 to receive the compact SS-OCT system. The mounting surface may be a mounting plate. The mounting surface may provide a location to which the compact SS-OCT may be mounted. The mounting surface may be coupled to the base by a first coupler 3330. The first coupler may be configured to allow a user to change a distance between the mounting surface and the base, as indicated by the arrow labeled "1" in FIG. 33A. The distance between the mounting surface and the base may be adjustable by 1 cm, 2 cm, 5 cm, 10 cm, 20 cm, or 50 cm. The distance between the mounting surface and the base may be adjustable by a value that is within a range defined by any two of the preceding values. The distance between the mounting surface and the base may be adjusted to increase a user's comfort while using the compact SS-OCT system.

The support system may comprise a second coupler configured to allow a user to change an angle between the mounting surface and the base, as indicated by the arrow labeled "2" in FIG. 33A. The angle between the mounting surface and the base may be adjustable by 1 degree, 2 degrees, 5 degrees, 10 degrees, 20 degrees, 50 degrees, or 100 degrees. The angle between the mounting surface and the base may be adjustable by a value that is within a range defined by any two of the preceding values. The angle between the mounting surface and the base may be adjusted to increase a user's comfort while using the compact SS-OCT system.

The support system may further comprise a chinrest 3340. The chinrest may provide a location for a user to rest his or her chin while operating the compact SS-OCT system. The chinrest may be coupled to the mounting plate by an extension 3350. The support system may comprise a third coupler configured to allow a user to change a distance between the chinrest and the eyepieces, as indicated by the arrow labeled "3" in FIG. 33A. The distance between the chinrest and the eyepieces may be adjustable by a distance of 1 cm, 2 cm, 5 cm, or 10 cm. The distance between the chinrest and eyepieces may be adjustable by a value that is within a range defined by any two of the preceding values. The distance between the chinrest and the mounting surface may be adjusted to increase a user's comfort while using the compact SS-OCT system. The distance between the chinrest and the mounting surface may be adjusted to bring a user's eye into alignment with the eye pieces of the compact SS-OCT system. For instance, the distance between the chinrest and the eyepieces and the mounting surface may be adjusted to bring a user's eye into alignment with an optical axis of the compact SS-OCT system.

The compact SS-OCT system placed on the support may have a length, a width, and a height. The length may comprise a longest dimension across the system, the width may comprise a next longest dimension across the system, and the width may comprise a shortest dimension across the system. The length, width and height may extend transverse to each other, for example perpendicular to each other. The compact SS-OCT system may have a length of 10 cm, 20 cm, or 50 cm. The compact SS-OCT system may have a length that is within a range defined by any two of the preceding values. The compact SS-OCT system may have a width of 5 cm, 10 cm, or 25 cm. The compact SS-OCT system may have a width that is within a range defined by any two of the preceding values. The compact SS-OCT system may have a height of 2.5 cm, 5 cm, or 10 cm. The compact SS-OCT system may have a height that is within a range defined by any two of the preceding values.

The compact SS-OCT placed on the support may comprise a mass of 0.1 kg, 0.2 kg, 0.5 kg, 1 kg, or 2 kg. The support system may comprise a mass that is within a range defined by any two of the preceding values.

Figure 33B:
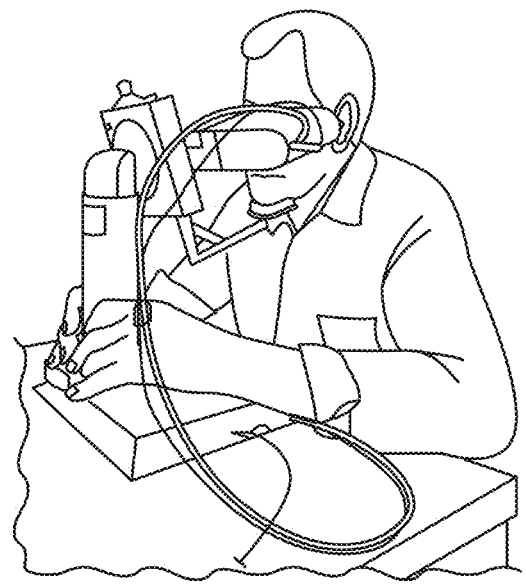
FIG. 33B shows a user using the compact SS-OCT device mounted on a support, in accordance with some embodiments.

FIG. 33B shows a user using the desktop-mounted SS-OCT device.

A stand or other support structure can be helpful to facilitate alignment between the OCT device and the user, for example, when the user self-aligns with the OCT measurement system. In some embodiments, the OCT system may comprise a binocular device, in which the user can hold the system similar to binoculars, or place the OCT system on a stand such as a tripod to facilitate alignment. In some embodiments, the OCT system measures a first eye, e.g. the right eye, and the user inverts the OCT system to measure a second eye, e.g. a left eye by turning the system over.

Although the binocular OCT system described herein may comprise a swept source OCT system, the components, structure, methods and circuitry can be used with other types of OCT systems such as spectral domain OCT imaging, time domain OCT imaging, or multi-reference OCT imaging, for example. These alternative OCT measurement systems are well suited for incorporation into the binocular OCT system as described herein.

Figure 49:
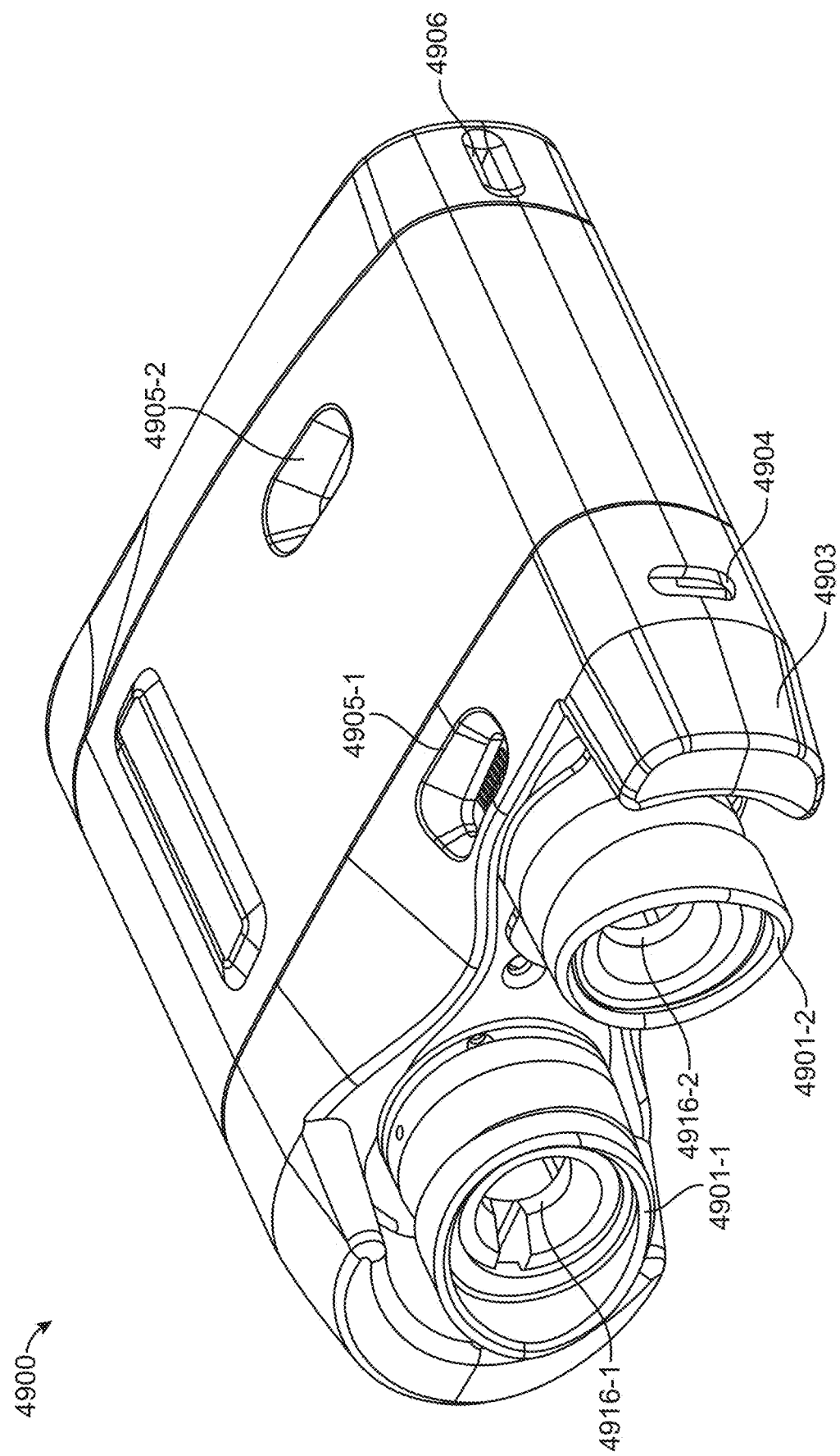
FIG. 49 shows a perspective view of a binocular OCT device for measuring eyes of a user, in accordance with some embodiments.

FIG. 49 shows a perspective view of a binocular OCT device 4900 for measuring eyes of a user, in accordance with some embodiments. The binocular OCT device 4900 comprises a first adjustable lens 4916-1 that is optically coupled to an OCT measurement system and a first fixation target configured within a handheld unit body 4903 (e.g., a housing), both of which are hidden from view in this figure. Similarly, a second adjustable lens 4916-2 may be optically coupled to the OCT measurement system and a second fixation target (hidden). The first adjustable lens 4916-1 may be part of a first free space optics that is configured to provide a fixation target and measure a retinal thickness of the user's eye, whereas the second adjustable and 4916-2 may be part of a second free space optics that is configured to only provide a fixation target so as to reduce a number of components in the binoculars OCT device 4900. For instance, while both free space optics provide the user with a fixation target, only one of the free space optics is used to measure the retinal thickness as the binocular OCT device 4900 may be turned upside down, i.e. inverted, after the user measures a first eye such that the user may measure the other eye.

The binocular OCT device 4900, in this embodiment, comprises an interpupillary distance (IPD) adjustment mechanism 4905 that is accessible on the exterior of the handheld unit body 4903. In this embodiment, the IPD adjustment mechanism 4905 comprises two components, a first component 4905-1 that adjusts the distance between the lenses 4916-1 and 4916-2 to match the IPD of a user's pupils when the user places the binocular OCT device 4900 front of the user's eyes when the eye cups 4901-1 and 4901-2 rest on the user's face.

This IPD can be set by a healthcare professional, and locked into position for the user to measure retinal thickness at home. Alternatively, the IPD can be user adjustable. A switch 4904 may be used to adjust the lenses 4916-1 and 4916-2 to match a user's refraction, i.e. eyeglass prescription. Alternatively, a mobile device, such as a tablet can be used program the refraction of each eye of the patient. For example, the user may fixate on the first fixation target with one eye and a second fixation target with another eye, and the movable lenses adjusted to the user's refraction. The switch 4904 may selectively adjust the assemblies of the lenses 4916-1 and 4916-2 within the handheld unit body 4903 to change the positioning of the lenses 4916-1 and 4916-2. These positions can be input into the device by a health care professional, and stored in a processor along with an orientation from an orientation sensor as described herein. The device can be inverted and the process repeated. Alternatively or additionally, the prescription for each eye can be stored in the processor and the lenses adjusted to the appropriate refraction for each eye in response to the orientation of the orientation sensor.

Both of the components 4905-1 and 4905-5 may be implemented as one or more wheels that the health care professional manually rotates. Alternatively, the IPD adjustment mechanism 4905 may be motorized. In this regard, the components 4905-1 and 4905-5 may be configured as directional switches that actuate motors within the handheld unit body 4903 to rotate gears within the handheld unit body 4903 based on the direction in which the user directs the switch.

The switch 4904 can be used to adjust the focusing of the binocular OCT device 4900. For example, because the focal change effected by adjustment of the lenses 4916-1 and 4916-2 can be measured in a customary unit of refractive power (e.g., the Diopter) by adjustment of the lenses 4916-1 and 4916-2. The Diopter switch 4906 may also comprise a directional switch that actuates a motor within the handheld unit body 4903 to rotate gears within the handheld unit body 4903 based on the direction in which the healthcare professional directs the switch to adjust the refractive power of the binocular OCT device 4900. As the binocular OCT device 4900 may comprise an electronic device, the binocular OCT device 4900 may comprise a power switch 4906 to control powering of the binocular OCT device 4900.

Each of the eyecups 4901-1 and 4901-2 can be threadedly mounted and coupled to the housing to allow adjustment of the position of the eye during measurements. Work in relation to the present disclosure suggests that the eyecups can be adjusted by a healthcare professional and locked in place to allow sufficiently reproducible positioning of the eye for retinal thickness measurements as described herein. Alternatively or in combination, an eye position sensor, such as a Purkinje image sensor can be used to determine a distance from the eye to the OCT measurement system.

The binocular OCT device 4900 may comprise appropriate dimensions and weight for in home measurements and for the user to take the binocular OCT system on trips. For example, the binocular OCT system may comprise a suitable length, a suitable width and a suitable height. The length can extend along an axis corresponding to the users viewing direction. The length can be within a range from about 90 mm to about 150 mm, for example about 130 mm. The width can extend laterally to the length and can be within a range from about 90 mm to about 150 mm for example about 130 mm. The height can be within a range from about 20 mm to about 50 mm, for example. The weight of the binocular OCT system can be within a range from about 1 pound to two pounds, e.g. 0.5 kg to about 1 kg.

The binocular OCT device 4900 can be configured to be dropped. For example, the binocular OCT device can be configured to be dropped from a height of about 30 cm and still function so as to perform retinal thickness measurements accurately, e.g. with a change in measured retinal thickness of no more than the repeatability of the measurements. The binocular OCT system can be configured to be dropped from a height of about 1 meter without presenting a safety hazard, for example from glass breaking.

Figure 50:
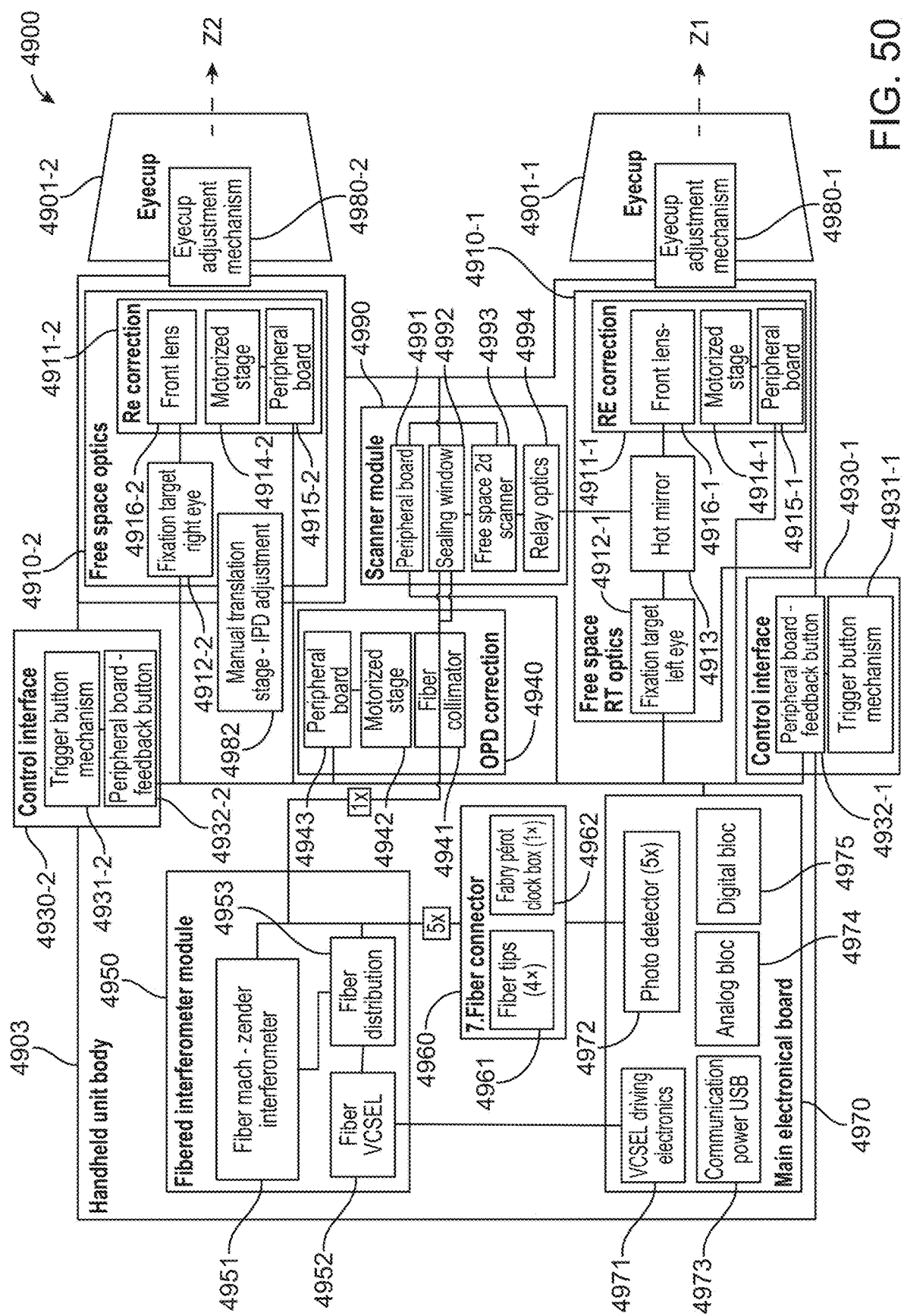
FIG. 50 shows a block diagram of the binocular OCT device illustrating various components within the handheld unit body, in accordance with some embodiments.

FIG. 50 shows a block diagram of the binocular OCT device 4900 illustrating various components within the handheld unit body 4903, in accordance with some embodiments. For instance, the binocular OCT device 4900 comprises free space optics 4910-1 and 4910-2. Each of the free space optics 4910-1 and 4910-2 comprises a fixation target 4912 for its respective eye that allows the user to fixate/gaze on the target while the user's retinal thickness is being measured, and to allow fixation with the other eye, so as to provide binocular fixation. The fixation target may comprise an aperture back illuminated with a light source such as an LED, (e.g., a circular aperture to form a disc shaped illumination target, although a cross or other suitable fixation stimulus may be used. The free space optics 4910-1 and 4910-2 may also comprise refractive error (RE) correction modules 4911-1 and 4911-2, respectively, that comprises the lenses 4916-1 and 4916-2, respectively. These lenses can be moved to preprogrammed positions corresponding to the refractive error of the appropriate eye. A peripheral board 4915-1 and 4915-2 in the free space optics modules 4910-1 and 4910-2 provides electronic control over a motorized stage 4914-1 and 4914-2, respectively to correct for the refractive error of the respective eye viewing the fixation target of the binocular OCT device 4900.

As discussed herein, the binocular OCT device 4900 may comprise eye cups 4901-1 and 4901-2 that may be used to comfortably rest the binocular OCT device 4900 on the user's face. They may also be configured to block out external light as the user gazes into the binocular OCT device 4900. The eye cups 4901 may also comprise eye cup adjustment mechanisms 4980-1 and 4980-2 that allow the health care professional and optionally the user to move the eye cups 4901-1 and 4901-2 back and forth with respect to the handheld unit body 4903 to comfortably position the eye cups on the user's face and appropriately position each eye for measurement.

In some embodiments, the binocular OCT device 4900 comprises a fibered interferometer module 4950 that comprises a single VCSEL or a plurality of VCSELs 4952. The one or more VCSELs 4952 are optically coupled to a fiber distribution module 4953, which is optically coupled to fiber Mach-Zender interferometer 4951. With embodiments comprising a plurality of VCSELs 4952, the VCSELS may each comprise a range of wavelengths different from other VCSEL 4952 in the plurality in order to extend a spectral range of light. For example, each VCSEL 4952 may pulse laser light that is swept over a range of wavelengths for some duration of time. The swept range of each VCSEL 4952 may partially overlap an adjacent swept range of another VCSEL 4952 in the plurality as described herein. Thus, the overall swept range of wavelengths of the plurality of VCSELs 4952 may be extended to a larger wavelength sweep range. Additionally, the firing of the laser light from the plurality of VCSELs 4952 may be sequential. For example, a first VCSEL of the plurality of VCSELs 4952 may sweep a laser pulse over a first wavelength for some duration. Then, a second VCSEL of the plurality of VCSELs 4952 may sweep a laser pulse over a second wavelength for some similar duration, then a third, and so on.

The laser light from the VCSELs 4952 is optically transferred to the fiber distribution module 4953, where a portion of the laser light is optically transferred to a fiber connector 4960 for analysis in a main electronic board 4970. The fiber connector 4960 may connect a plurality of optical fibers from the fiber distribution module 4953 to the fiber connector module 4960. Another portion of the laser light is optically transferred to an optical path distance correction (OPD) module 4940 and ultimately to the free space retinal thickness optics 4910-1 for delivery to a user's eye and measurement of the user's eye with a portion of the measurement arm of the Mach-Zender interferometer. For example, the OPD correction module 4940 may comprise a peripheral board 4943 that is controlled by the main electronic board 4970 to actuate a motorized stage 4942 to change the optical path distance between the user's eye, a coupler of the Mach-Zender interferometer and the one or more VCSELs 4952. The OPD correction module 4940 may also comprise a fiber collimator 4941 that collimates the laser light from the VCSELs 4952 before delivery to the user's eye, and the fiber collimator can be translated with the OPD correction module 4940.

A controller interface 4930 may be used to receive user inputs to control the binocular OCT measurement system. The controller interface may comprise a first controller interface 4930-1 and a second controller interface 4930-2. The controller interface 4930 may comprise a trigger button mechanism that allows a user to initiate a sequence of steps to align the eye and measure the retina as described herein.

Additionally, the binocular OCT device 4900 may comprise a scanner module 4990 that scans the laser light from the one or more VCSELs 4952 in a pattern (e.g., a stop and go trajectory, a star trajectory, a continuous trajectory, and/or a Lissajous trajectory, each of which is explained in greater detail below). For example, a peripheral board 4991 of the scanner module 4990 may be communicatively coupled to the main electronic board 4970 to receive control signals that direct the scanner module 4992 to scan the pulsed laser light from the VCSELs 4952 in a pattern to perform an optical coherence tomography (OCT) on the user's eye. The scanning module 4990 may comprise a sealing window 4992 that receives the laser light from the fiber collimator 4941 and optically transfers the laser light to a free space two-dimensional scanner 4993, which provides the scan pattern of the laser light. The two-dimensional scanner may comprise a scanner as described herein, such as a two axis galvanometer, or a two axis electro-static scanner, for example. When present, the sealing window 4992 may be used to keep the internal components of the binocular OCT device 4900 free of dirt and/or moisture. The laser light is then optically transferred to relay optics 4994 such that the scanned laser light can be input to the user's eye via the free space RT optics 4910-1. In this regard, the scanned laser light may be transferred to a hot mirror 4913 such that infrared light may be reflected back towards the hot mirror, the scanning mirror and focused into an optical fiber tip coupled to the collimation lens. The hot mirror 4913 generally transmits visible light and reflects infrared light, and may comprise a dichroic short pass mirror, for example.

The scanner and associated optics can be configured to scan any suitably sized region of the retina. For example, the scanner can be configured to scan the retina over an area comprising a maximum distance across within a range from about 1.5 to 3 mm, for example. The scanning region of the retina may comprise an area larger than maps of retinal thickness in order to account for slight errors in alignment, e.g. up to 0.5 mm in the lateral positioning of the eye in relation to the OCT system, for example in order to compensate for alignment errors, e.g. by aligning the map based on the measured position of the eye. The size of the OCT measurement beam on the retina can be within a range from about 25 microns to about 75 microns. In some embodiments, the mirror is scanned with a continuous trajectory with a scan rate on the retina within a range from about 50 mm per second to about 200 mm per second. The displacement of the beam during an A-scan can be within a range from about 2 to 10 microns, for example. The beams for each of a plurality of A-scans can overlap. In embodiments where the one or more VCSELs comprises a plurality of VCSELs, the plurality of VCSELs can be sequentially scanned for each A-scan, such that the measurement beams from each of the plurality of VCSELs overlaps on the retina with a prior scan. For example, each of the sequentially generated beams from each of the plurality of VCSELs from a first A-scan can overlap with each of the sequentially generated beams from each of the plurality of VCSELs from a second A-scan along the trajectory.

As described herein, the binocular OCT device 4900 may comprise an IPD adjustment via the components 4905-1 and/or 4905-2. These components may be communicatively coupled to a manual translation stage IP adjustment module 4982 that perform the actuation of the free space optics modules 4910-1 and 4910-2, so as to change a separation distance between the free space optics modules and adjust the IPD.

The main electronic board 4970 may comprise a variety of components. For example, a photodetector 4972 may be used to receive laser light directed from the VCSELs 4952 through the fiber connector 4960 as well interfering light reflected from the user's eye. The fiber connector 4960 may comprise a module 4961 that couples a plurality of optical fibers, for example four optical fibers, to a plurality of detectors, for example five detectors. The fiber connector 4960 may also comprise an interferometer clock box 4962 (e.g. an etalon) that may be used in phase wrapping light reflected back from the user's eyes, as shown and described herein. Once received by the photodetectors 4972, the photodetectors 4972 may convert the light into electronic signals to be processed on the main electronic board 4970 and/or another processing device. The plurality of photo detectors may comprise two detectors of a balanced detector pair coupled to the fiber Mach-Zender interferometer, a clock box detector, and a pair of power measurement detectors, for example.

The main electronic board 4970 may comprise a communication power module 4973 (e.g., a Universal Serial Bus, or "USB") that can communicatively couple the binocular OCT device 4900 to another processing system, provide power to the binocular OCT device 4900, and/or charge a battery of the binoculars OCT device 4900. Of course, the binocular OCT device 4900 may comprise other modules that may be used to communicate information from the binocular OCT device 4900 to another device, including for example, Wi-Fi, Bluetooth, ethernet, FireWire, etc.

The main electronic board 4970 may also comprise VCSEL driving electronics 4971 which direct how and when the VCSELs 4952 are to be fired towards the user's eyes. Other components on the main electronic board 4970 comprise an analog block 4974 and a digital block 4975 which may be used to process and/or generate analog and digital signals, respectively, being transmitted to the binocular OCT device 4900 (e.g., from an external processing system), being received from various components within the binocular OCT device 4900, and/or being received from various components within the binocular OCT device 4900. For example, the peripheral feedback button 4932 may generate an analog signal that is processed by the analog block 4974 and/or digital clock 4975, which may in turn generate a control signal that is used to stimulate the motorized stage module 4942 via the peripheral board 4943. Alternatively or additionally, the analog block 4974 may process analog signals from the photodetectors 4972 such that they may be converted to digital signals by the digital block 4975 for subsequent digital signal processing (e.g., FFTs, phase wrapping analysis, etc.).

Figure 51:
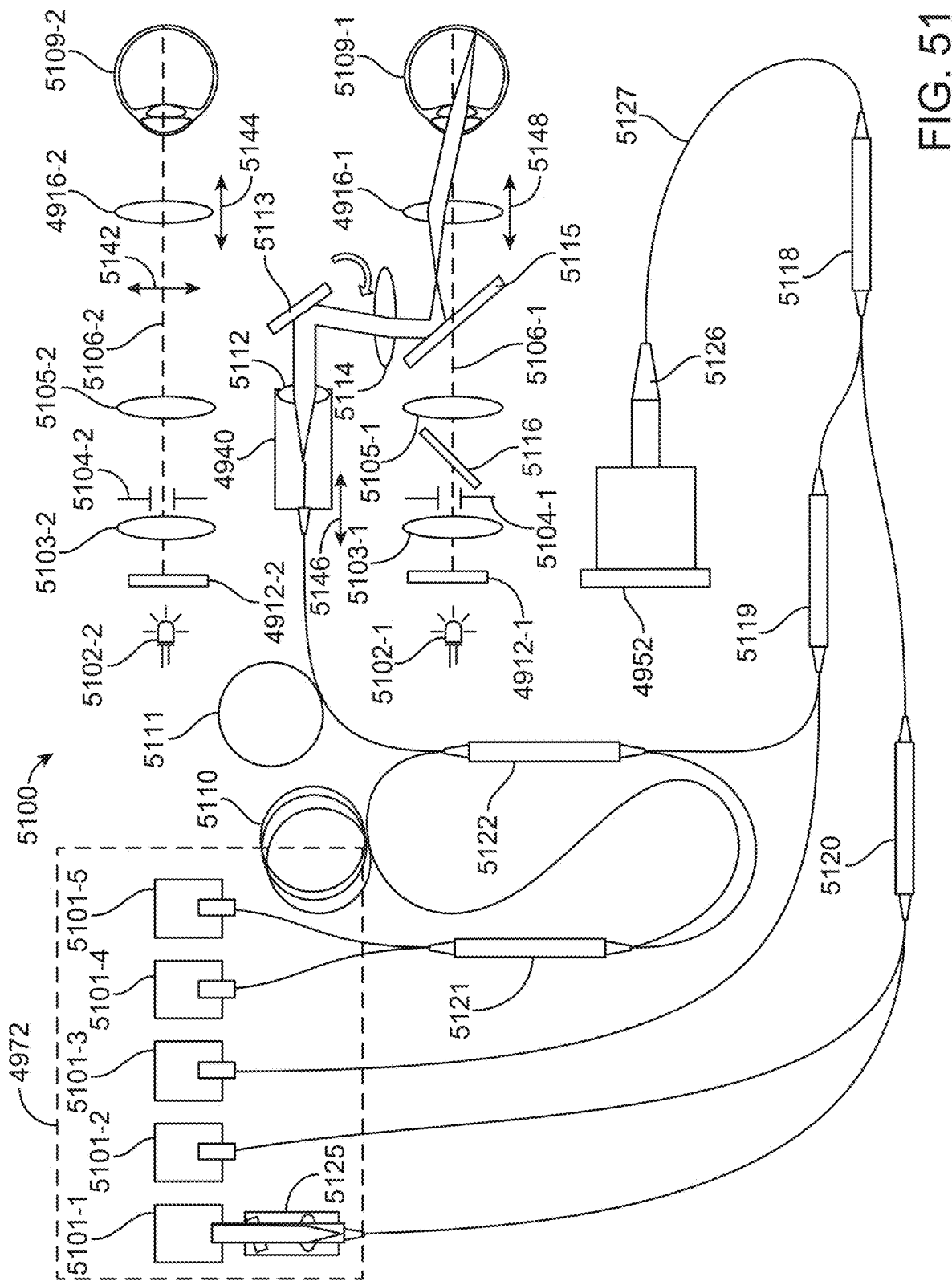
FIG. 51 shows a schematic of an optical configuration that may be implemented with the OCT binocular, in accordance with some embodiments.

FIG. 51 shows a schematic of an optical configuration 5100 that may be implemented with the OCT binocular 4900, in accordance with some embodiments. The optical configuration 5100 comprises one or more VCSELs 4952 that are fiber coupled via an optical coupler 5126. As discussed above, the one or more VCSELs 4952 may be swept over a range of wavelengths when fired. For embodiments with a plurality of VCSELs 4952, the wavelengths may partially overlap a wavelength sweep range of another VCSEL 4952 in the plurality so as to increase in overall sweep range of the VCSELs 4952. In some instances, this overall sweep range is centered around approximately 850 nm. The laser light from the one or more VCSELs 4952 is propagated through the fiber coupler 5126 to a fiber optic line 5127, where another optical coupler 5118 splits a portion of the optical energy from the one or more VCSELs 4952 along two different paths.

In the first path, approximately 95% of the optical energy is optically transferred to another optical coupler 5119 with approximately 5% of the optical energy being optically transferred to an optical coupler 5120. In the second path, the optical energy is split yet again via an optical coupler 5120. In this regard, approximately 75% of the optical energy from the optical coupler 5120 is transferred to a phase correction detector 5101-1 through an interferometer such as a Fabry Perot interferometer comprising an etalon. The etalon and detector may comprise components of an optical clock 5125. The optical clock 5125 may comprise a single etalon, for example. The etalon may comprise substantially parallel flat surfaces and be tilted with respect to a propagation direction of the laser beam. The surfaces may comprise coated or uncoated surfaces. The material may comprise any suitable light transmissive material with a suitable thickness. For example, the etalon may comprise a thickness within a range from about 0.25 mm to about 5 mm, for example within a range from about 0.5 mm to about 4 mm. The reflectance of the etalon surfaces can be within a range from about 3% to about 10%. The etalon can be tilted with respect to the laser beam propagation direction, for example tilted at an angle within a range from about 5 degrees to about 12 degrees. The finesse of the etalon can be within a range from about 0.5 to about 2.0, for example, for example within a range from about 0.5 to 1.0. The etalon may comprise any suitable material such as an optical glass. The thickness, index of refraction, reflectance and tilt angle of the etalon can be configured to provide a substantially sinusoidal optical signal at the clock box detector. The finesse within the range from about 0.5 to 2.0 can provide substantially sinusoidal detector signals that are well suited for phase compensation as described herein, although embodiments with higher finesse values can be effectively utilized.

In some embodiments, the clockbox may comprise a plurality of etalons. The approach can be helpful in embodiments wherein the one or more VCSELs comprises a plurality of VCSELs, and the plurality of etalons provides additional phase and clock signal information. For example, the clockbox may comprise a first etalon and a second etalon arranged so that light is transmitted sequentially through the first etalon and then the second etalon, e.g. a series configuration, which can provide frequency mixing of the clock box signals and decrease the number of detectors and associated circuitry used to measure phase of the swept source. Alternatively, the plurality of Etalons can be arranged in a parallel configuration with a plurality of etalons coupled to a plurality of detectors.

The phase correction detector 5101-1 may use the light signals from the optical clock 5125 to correct the phase of light reflected from a user's eyes 5109-1 by matching the phases of the one or VCSELs 4952 via phase wrapping of the light from the one or more VCSELs 4952 as described herein. The remaining 25% of the optical energy from the optical coupler 5120 may be optically transferred to a detector 5101-2 for optical safety. For instance, the detector 5101-2 may be used to determine how much optical energy is being transferred to the user's eye 5109-1 or 5109-2, depending on the orientation of the device. If the binocular OCT device 4900 determines that the detector 5101-2 is receiving too much optical energy that may damage the user's eyes, then the binocular OCT device 4900 may operate as a "kill switch" that shuts down the VCSELs 4952. Alternatively or additionally, the binocular OCT device 4900 may monitor the detector 5101-2 to increase or decrease the optical energy from the VCSELs 4952 as deemed necessary for laser safety and/or signal processing. The OCT device may comprise a second safety detector 5101-3 to provide a redundant measurement for improved eye safety.

The optical energy transferred to the optical coupler 5119 (e.g., approximately 95% of the optical energy from the one or more VCSELs 4952) is also split along two paths with approximately 99% of the remaining optical energy being optically transferred along a fiber to an optical coupling element 5122 and with approximately 1% of the remaining optical energy also being optically transferred to a detector 5101-3 for laser safety of the binocular OCT device 4900. The portion of the optical energy transferred to the to the optical coupler 5122 may be split by the optical coupler 5122 between two optical path loops 5110 and 5111 of the Mach-Zender interferometer, approximately 50% each, for example. The optical path loop 5110 may comprise a reference arm of the interferometer provide a reference optical signal for the retinal thickness measurement of the user's eye 5109-1 (e.g., the measurement signal reflected from the user's retina through the optical path loop that you 5111).

The portion of the optical energy transferred through the optical loop 5111 is transferred to the user's left eye 5109-1 along the measurement arm of the Mach-Zender interferometer. For instance, the optical energy being transferred to the user's eye 5109-1 may pass through the OPD correction module 4940 to perform any optical path distance corrections appropriate interferometer of the binocular OCT device 4900. This light may then be scanned across the user's eye 5109-1 via a scanning mirror 5113 of the scanner module 4990 to measure the retinal thickness of the user's eye 5109-1 while the user's eye 5109-1 is fixated on a fixation target 4912-1 (e.g., along a fixation path 5106-1).

The fixation target 4912-1 can be back illuminated with LED 5102-1, and light may be propagated along the optical path 5106-1 through optical elements 5103-1 and 5105-1 and the dichroic mirror 5115, comprising a hot mirror. In some instances, the target of fixation may also include an illumination stop 5104 so as to provide relief to the user's eye 5109-1 while fixating on the target.

The light impinging the user's retina of the eye 5109-1 may be reflected back along the path established by the OPD correction module 4940, the scanning mirror 5113, the focusing element 5114, the dichroic mirror 5115, and the optical element 4916-1, through the optical loop 5111, and back to the optical coupler 5122. In this instance, the optical coupler 5122 may optically transfer the reflected optical energy to an optical coupler 5121 which may couple the reflected optical energy with the optical energy that was split into the optical loop 5110. The optical coupler 5121 may then optically transfer that optical energy to the balanced detector's 5101-4 and 5101-5 such that a retinal thickness measurement can be performed. In doing so, the optical coupler 5121 may split that optical energy to approximately 50% to each of the detectors 5101-1 and 5101-4, such that the interference signals arrive out of phase on the balanced detectors.

The light may be focused through a plurality of optical elements 5112 and 5114, being directed to the user's eye 5109-1 via a dichroic mirror 5115 and focused on the user's retina via the optical element 4916-1. The light from the scanning mirror 5113 and the light reflected from the user's eye 5109 are both shown as reflecting off the dichroic mirror 5115, which may comprise hot mirror 4913 configured to generally reflect infrared light and transmit visible light.

As can be seen in this example, the user's right eye 5109-2 does not receive any optical energy from the one or more VCSELs 4952 with the orientation shown. Rather, the user's right eye 5109-2 is used for binocular fixation with the target 4912-2, which can be back illuminated with another LED 5102-2. The target 4912-2 can be of similar size and shape to target 4912-1 and be presented to the eye with similar optics, so as to provide binuclear fixation. In this regard, the user's right eye 5109-2 may also fixate on the target 4912-2 along an optical path 5106-2 through the optical elements 4916-2, 5105-2, 5103-2, and the illumination stop 5104-2, which comprises similar optical power, separation distances and dimensions to the optics along optical path 5106-1.

The binocular OCT system 4900 can be configured to move optical components to a customized configuration for the user being measured. Lens 4916-1 can be adjusted along optical path 5106-1 in accordance with the refraction, e.g. eyeglass prescription of the eye being measured. Lens 4916-1 can be moved under computer, user or other control to adjust lens 4916-1 to bring the fixation target 4912-1 into focus and to focus the measurement beam of the OCT interferometer on the user's retina. For example, the lens can be translated as shown with arrow 5144. Lens 4916-2 can be moved under computer, user or other control to adjust lens 4916-1 to bring the fixation target 4912-2 into focus on the user's retina. For example, the lens can be translated as shown with arrow 5148. The OPD correction module 4950 can be translated axially toward and away from mirror 5113 as shown with arrows 5146. The OPD correction module 5146 can be moved under computer control to appropriately position the optical path difference between the measurement arm and the reference arm for the user's eye being measured. The interpupillary distance can be adjusted by translating the optical path 5106-2 toward and away from optical path 5106-1.

The free space optics module 4910-2 may comprise one or more components along optical path 5106-2, such as the LED 5101-2, the fixation target 4912-2, lens 5103-2, aperture 5104-2, lens 5105-2, or lens 4916-2. The free space optics module 4910-2 can be translated laterally toward and away from the optical components located along optical path 5106-1 to adjust the inter pupillary distance as shown with arrow 5142. The retinal space retinal thickness optics module 4910-1 may comprise one or more components located along optical path 5106-1, such as the LED 5102-1, the fixation target 5103-1, the aperture 5104-1, the mirror 5116, the lens 5105-1, the mirror 5115, or lens 4916-1. The OPD correction module 5146 may comprise the optical fiber of the measurement arm of the interferometer, and lens 5112 to substantially collimate light from the optical fiber and to focus light from the retina into the optical fiber.

Figure 52:
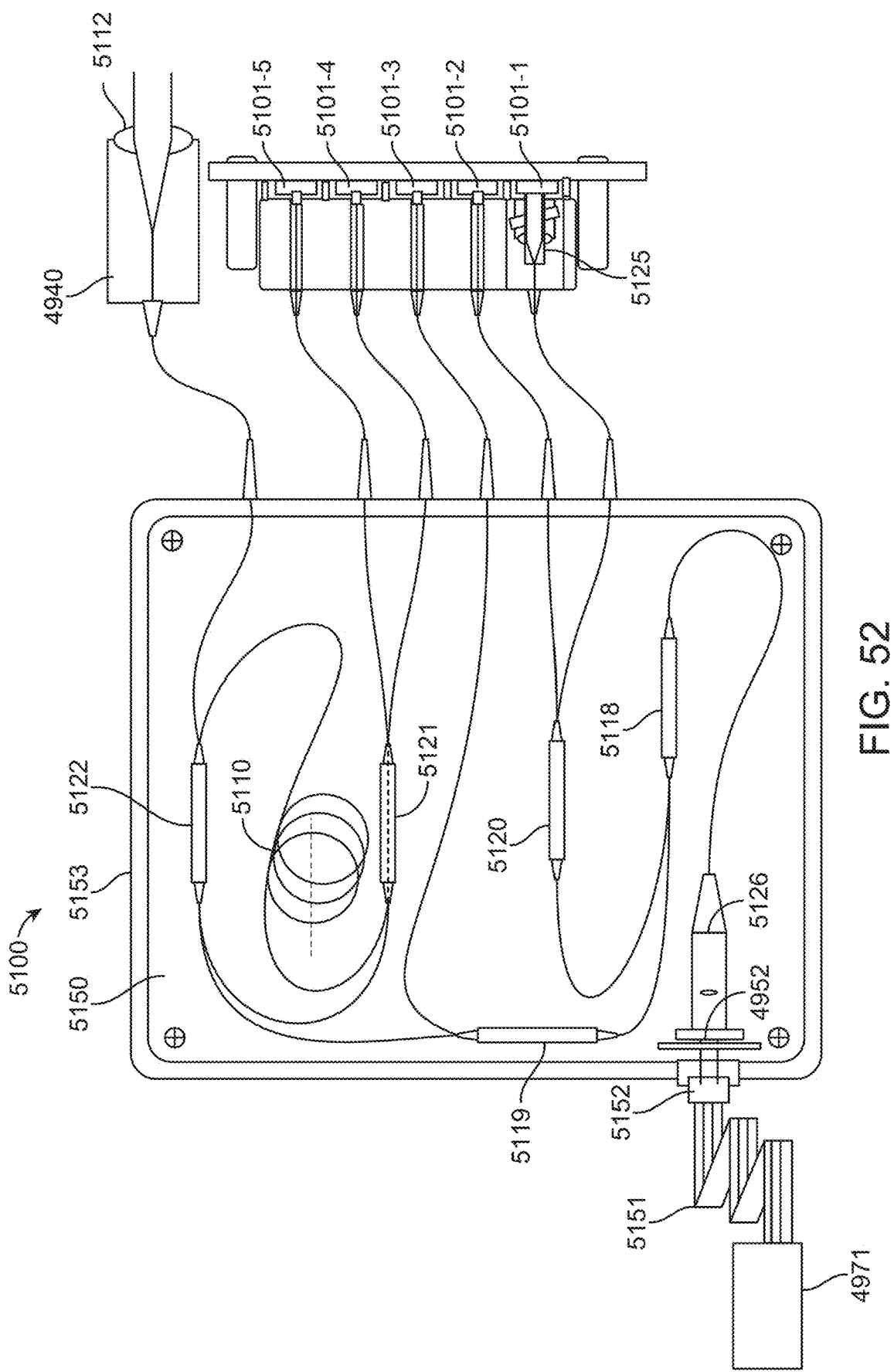
FIG. 52 shows a block diagram of the optical configuration configured on an optical layout board, in accordance with some embodiments.

FIG. 52 shows a block diagram of the optical configuration 5100 configured on an optical layout board 5150, in accordance with some embodiments. For example, the binocular OCT device 4900 may be configured with a plurality of layers extending approximately along planes, each of which layers may be configured to perform a particular function. In this instance, the optical layout board 5150 provides a support for the optical configuration 5100, which can be used to decrease vibrations of the optical components. The optical board 5150 may comprise a plurality of components enclosed within a housing of a fiber optics module as described herein. The plurality of components enclosed within the housing 5153 and supported on the board, may comprise one or more of coupler 5118, coupler 5119, coupler 5120, coupler 5121, coupler 5122, reference arm comprising optical fiber 5110, and any combination thereof. The one or more VCSELs 4952 may be enclosed within the housing. The plurality of optical fibers extending from coupler 5120 can extend through the housing to the appropriate detector, for example to couple to clock box detector 5101-1 and safety detector 5101-2. The optical fiber extending from coupler 5119 can be coupled to a second safety detector 5101-3 and extend though housing 5153. A second optical fiber extending from coupler 5119 can be coupled to the interferometer to measure the sample with optical coupler 5122. The optical fiber portion of the sample measurement arm extending from coupler 5122 and extend to through the housing 5153 to the optical path difference correction module 4940, for example.

The printed circuit board may provide a support layer extending along an electronics plane in which some processing devices (e.g., the main electronic board 4970 including the driving electronics 4971 of FIG. 50) could couple to the optical layout board 5150 through a cable 5151 that connects to a connector 5152 configured with the optical layout board 5150 in order to drive one or more VCSELs 4952.

Figure 53:
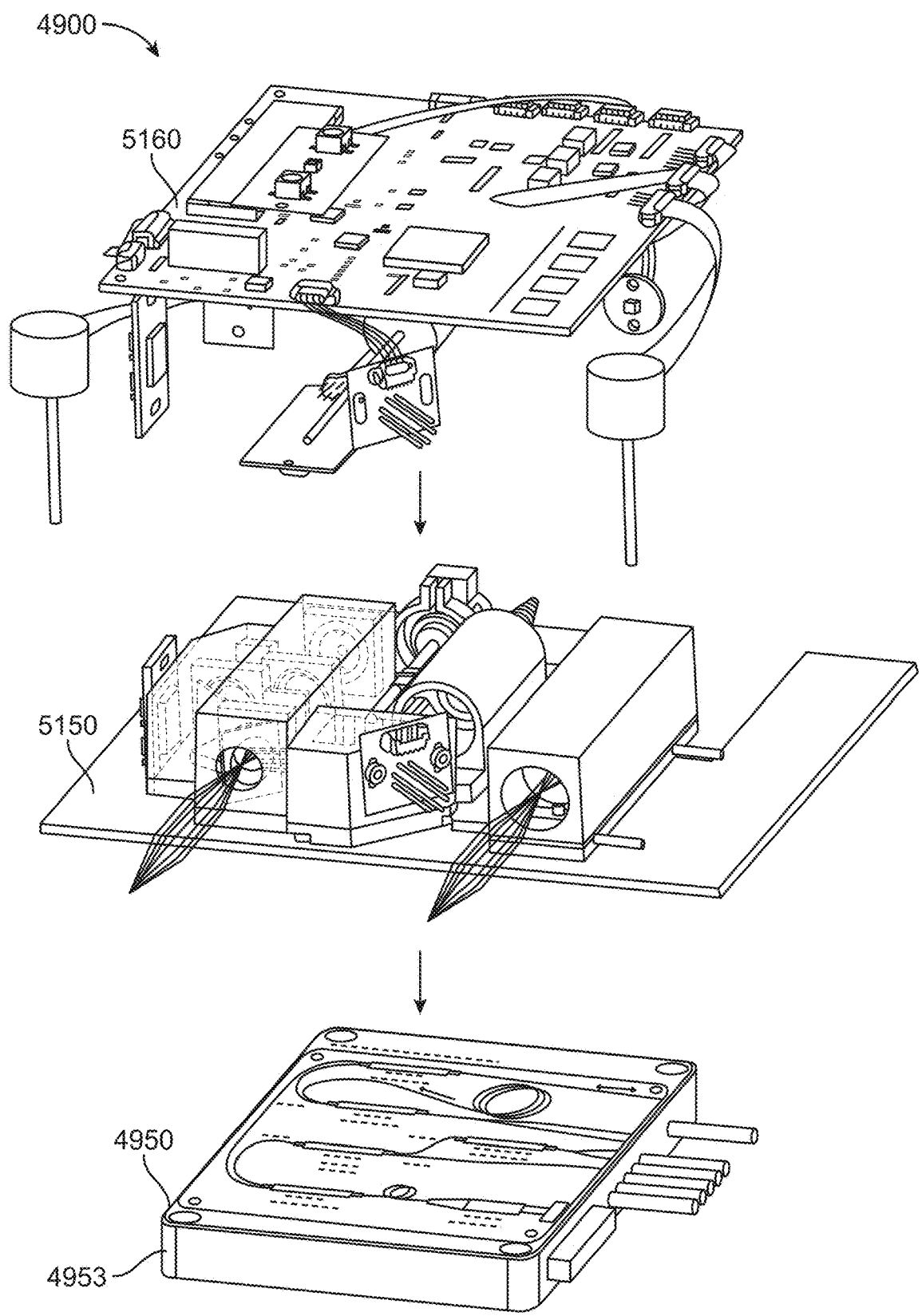
FIG. 53 shows a perspective view of a modular binocular OCT, in accordance with some embodiments.

FIG. 53 shows a perspective view of a modular embodiment of the binocular OCT 4900, in accordance with some embodiments. For instance, the main electronic board 4970 of the binocular OCT 4900 may be implemented as a printed circuit board (PCB) 5160 that is mounted to a housing 4953 enclosing optical components on the optical layout board 5150. The PCB 5160 may provide the power and electronics to control the optical configuration 5100 of the optical layout board 5150. The PCB 5160 may also include or be communicatively coupled to peripheral boards 4932-1, 4932-2, 4943, 4914-1, and 4914-2. The binocular OCT device 4900 may also comprise free space optics modules that are mounted on the optical layout board 5150 and communicatively couple to the main electronic board 4970. The free space optics modules mounted on the optics board may comprise one or more of module 4910-1, module 4910-2, or OPD correction module 4940 as described herein. The free space module 4910-2 can be configured to move in relation to optical layout board 5150 to adjust the inter pupillary distance. The OPD correction module can be configured to move relative to optical layout board 5150.

The interferometer module 4950 may comprise the couplers of the optical fibers as descried herein and the one or more VCSELs 4952. The main electronic board 4970 or one of the peripheral boards may comprise the electronics that drive the VCSELs 4952. The one or more VCSELs 4952 being optically coupled to the optical fibers on the optical layout board 5150, propagate laser light to the optical fibers on the optical layout board 5150. The laser light reflected from the user's eye 4910-1 can be propagated to the PCB 5160 where the photodetector 4972 detects the reflected laser light and converts the light to an electronic analog signal for processing by the analog block 4974.

In some embodiments, the optical layout board 5150 provides damping to the binocular OCT 4900. For instance, if the binocular OCT 4900 were to be dropped, a damping mechanism configured with the optical layout board 5150 may compensate for any oscillatory effects on impact of the binocular OCT 4900 and protect the components thereof (e.g., the optical layout board 5150, the PCB 5160, interferometer module 4950, and the components of each). The mounting plate 5150 may comprise similar damping mechanisms.

Figure 54:
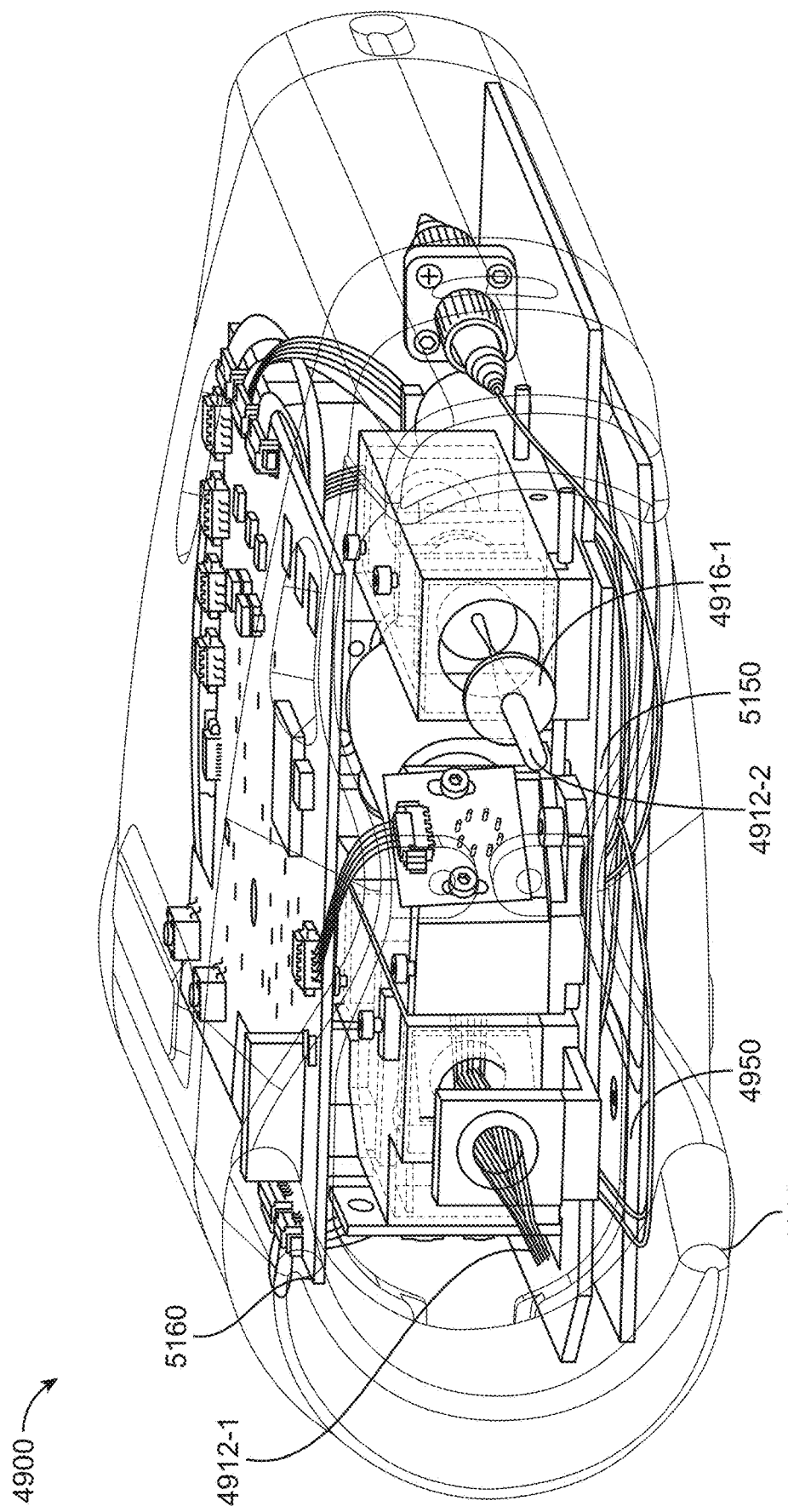
FIG. 54 shows a perspective/cut-away view of the binocular OCT device, in accordance with some embodiments.

FIG. 54 shows a perspective/cut-away view of the binocular OCT 4900, in accordance with some embodiments. In this view, the optical layout board 5150, the PCB 5160, and the interferometer module 4950 are mechanically coupled together in a compact form configured within the housing 4903 of the binocular OCT 4900. As can be seen in this view, the fixation targets 4912-1 and 4912-2 (e.g., LED light) are visible to the user through the lenses 4916-1 and 4916-2, respectively, when the user places the binocular OCT 4900 proximate to the user's eyes. Laser light from the VCSELs 4952 propagate along a portion of the same optical path as the fixation target 4912-1. Thus, when the user gazes on the fixation targets 4912-1 and 4912-2, the laser light from the one or more VCSELs 4952 are operable to propagate through the user's eye and reflect back to the optical layout board 5150 for subsequent processing to determine the user's retinal thickness.

Figure 55:
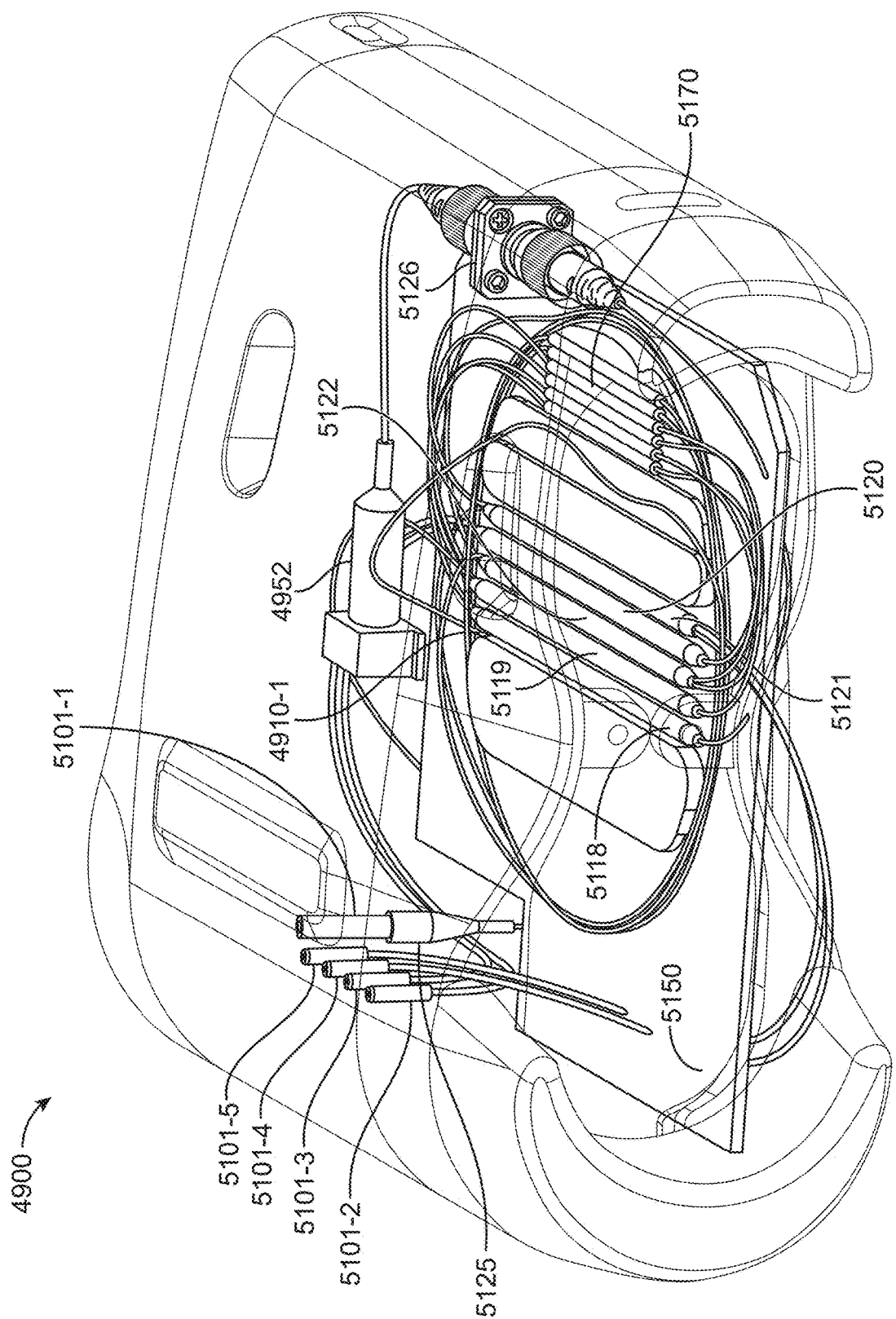
FIG. 55 shows another perspective/cut-away view of the binocular OCT device, in accordance with some embodiments.

FIG. 55 shows another perspective/cut-away view of the binocular OCT 4900, in accordance with some embodiments. In this view, only the optical layout board 5150 is illustrated to show the configuration of the VCSELs 4952, the fiber coupler 5126, the detector's 5105-1-5105-5, the Fabry Perot optical clock 5125, and the optical couplers 5118-5122. The optical layout board 5150 may also comprise splicers 5170.

Figure 56:
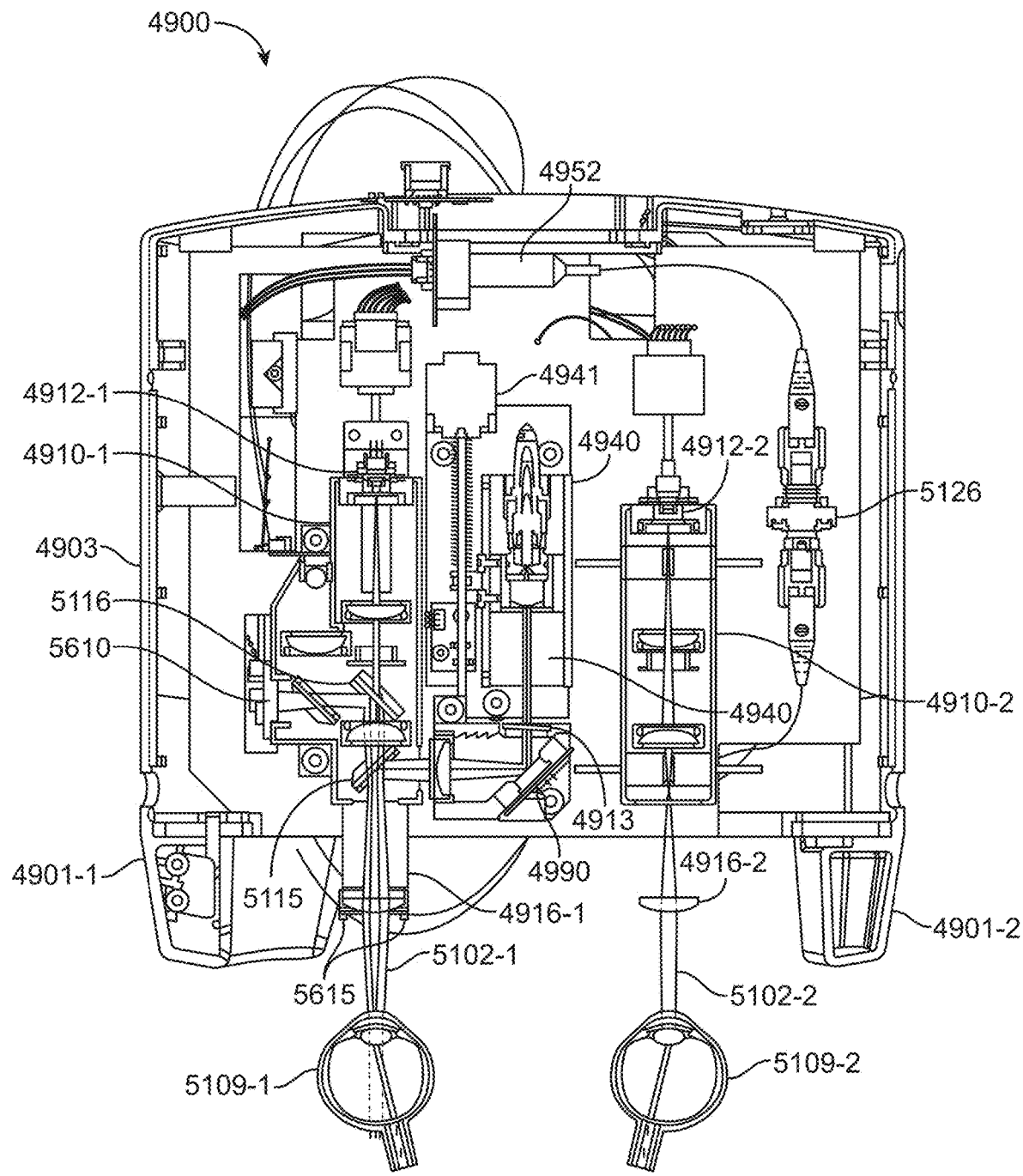
FIG. 56 shows an overhead/cut-away view of the binocular OCT device comprising an eye position sensor, in accordance with some embodiments.
Figure 57:
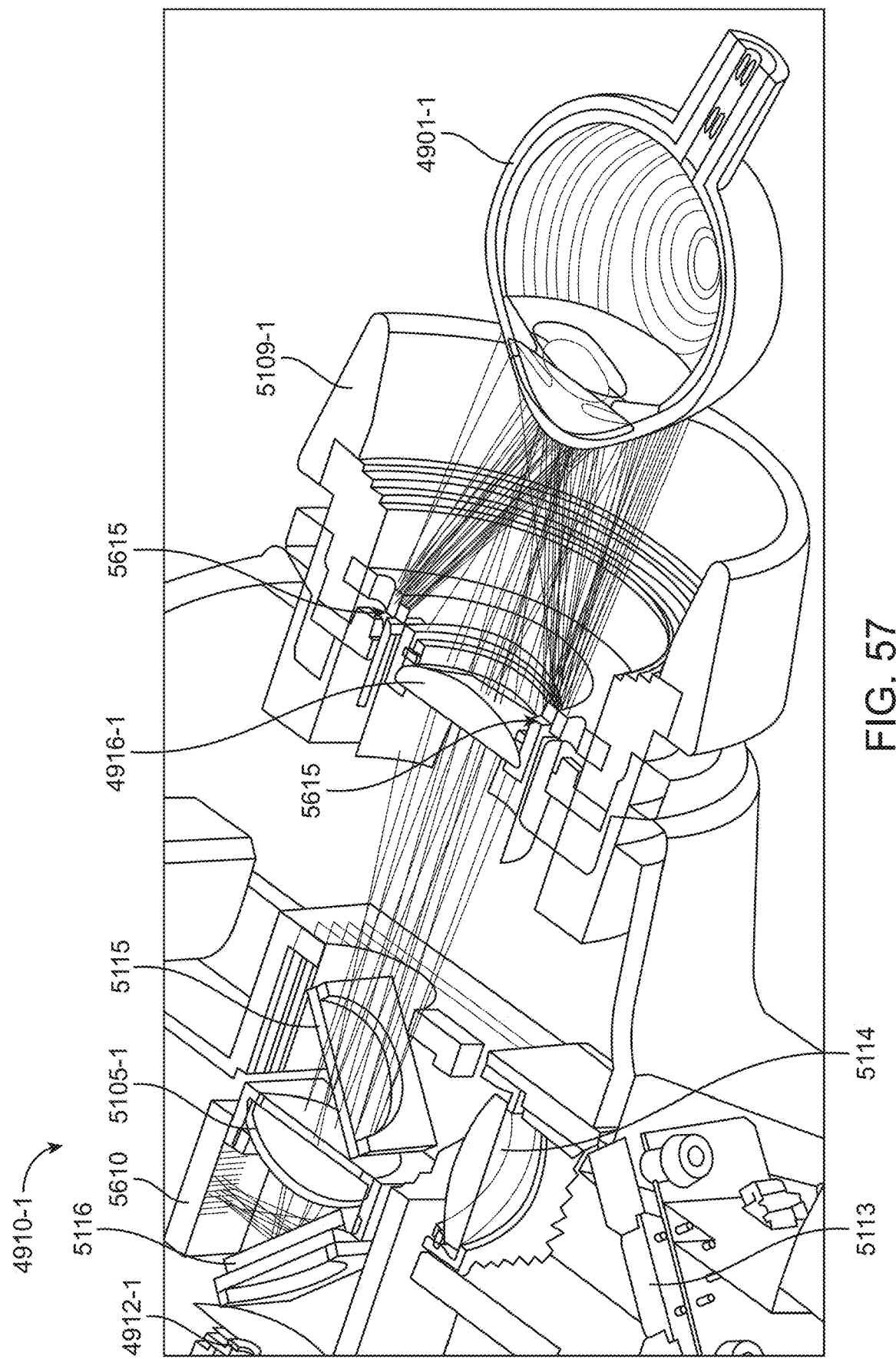
FIG. 57 shows a perspective/cut-away view of the light sources used to generate a Purkinje image of the eye and the positions sensor, in accordance with some embodiments.

FIGS. 56 and 57 show the binocular OCT system 4900 comprising an eye position sensor, in accordance with some embodiments. FIG. 56 shows an overhead/cut-away view of the binocular OCT 4900 comprising an eye position sensor 5610, in accordance with some embodiments. FIG. 57 shows a perspective/cut-away view of the plurality of light sources 5615 used to generate a Purkinje image of the eye and the positions sensor. The eye position sensor 5610 may comprise one or more of an array sensor, a linear array sensor, one dimensional array sensor, a two dimensional array sensor, a complementary metal oxide (CMOS) two dimensional array sensor array sensor, a quadrant detector or a position sensitive detector. The eye position sensor 5610 can be combined with a lens to form an image of the eye on the sensor, such as a Purkinje image from a reflection of light from the cornea of the eye. The eye position sensor can be incorporated into any of the embodiments disclosed herein, such as the binocular OCT system described with reference to FIGS. 49 to 55.

In the view shown, the optical configuration 5100 is mounted on the optical layout board 5150 above the fiber-optic couplings (e.g., the fiber loops 5110 and 5111 of FIG. 51) and the optical couplers 5118-5122, and other fiber components as described herein. Thus, the one or more free space optical components as described herein may be optically coupled to the fiber components thereunder.

As shown, the free space optics modules 4910-1 and 4910-2 are generally aligned with the user's eyes 5109-1 and 5109-2, respectively. The distance between the free space optics modules 4910-1 and 4910-2 may be adjusted according to the user's IPD. In some embodiments, this adjustment is maintained for the user while the binocular OCT 4900 is in the user's possession. For example, the user may be a patient using the binocular OCT 4900 for home use over a certain period of time. So as to ensure that a correct retinal thickness is measured while in the user's possession, the binocular OCT 4900 may prevent the user from adjusting the IPD. Similarly, the binocular OCT 4900 may also prevent the user from adjusting the OPD via the OPD correction module 4940.

As can be seen in this view, the fixation targets 4912-1 and 4912-2 (e.g., LED light targets) pass through various optical elements of their respective free space optics modules 4910-1 and 4910-2. The OPD correction module 4940 receives the laser light from the one or more VCSELs 4952 and directs light toward the scanning mirror 4990 as described herein. Light from the scanning mirror 4990 passes through a lens and is reflected by a dichroic mirror 5115 to the user's eye 5109-1 through the lens 4916-1.

As shown FIG. 57, the plurality of light sources 5615 comprising a first light source and a second light source is used to generate a Purkinje image. Additional light sources may be used to generate the Purkinje image, for example four light sources can be located along approximately orthogonal axes. The plurality of light sources can be configured in many ways, and may comprise one or more of LEDs, waveguides, apertures or optical fibers, and can be arranged in a pattern such as a triangle, rectangle, Placido disk, or the like, so as to form a virtual image of the pattern when reflected from the cornea of the eye. The light from the plurality of light sources is directed toward the eye and reflected from the tear film on the anterior surface of the cornea toward lens 4916-1. The light rays reflected from the cornea are transmitted through beam splitter 5115 and the lens 5105-1 to form an image of the eye on eye position sensor 5610. A mirror 5116 can be located along optical path 5106-1 to reflect light from the plurality of light sources toward the eye position sensor 5610, and the mirror 5116 can be configured to transmit visible light such as green light from the fixation target.

The optical elements coupled to the position sensor 5610 may comprise one or more components of the optical path of the measurement interferometer and the fixation target. Light from the one or more VCSELs can be reflected off scanning mirror 5113, transmitted through lens 5114, reflected from dichroic mirror 5115 toward the lens 4916-1 and directed toward the eye as described herein. The light from the visual fixation target 4912-1 can be directed through lens 5105-1, transmitted through mirror 5115 and lens 4916-1 toward the eye to provide an image on the patient's retina for visual fixation. A beam splitter 5116, such as a dichroic beam splitter, can be located between lens 5105-1 and fixation target 4912-1 in order to reflect light from the plurality of light sources 5615 toward eye position sensor 5610 and transmit visible light from the fixation target.

While the wavelengths of the light sources can be configured in many ways, in some embodiments, the plurality of light sources to generate the Purkinje image comprises a wavelength within a range from about 700 to 800 nm, the fixation target comprises a wavelength within a range from about 500 to 700 nm, and the OCT measurement beam comprises a plurality of wavelengths within a range from about 800 to 900 nm. The mirror 5115 may comprise a hot mirror or dichroic beam splitter configured to reflect light above 800 nm and transmit light below 800 nm. The beam splitter 5116 may comprise a dichroic mirror configured to reflect light above 700 nm and transmit light below 700 nm. In some embodiments, the light from the one or more VCSELs comprises a wavelength within a range from 800 nm to 900 nm, the plurality of light sources 5615 to generate the Purkinje image comprises a wavelength within a range from about 700 nm to 800 nm, and the visual fixation target comprises a wavelength within a range from about 400 nm to about 700 nm, e.g. within a range from about 500 nm to 700 nm.

Figure 58:
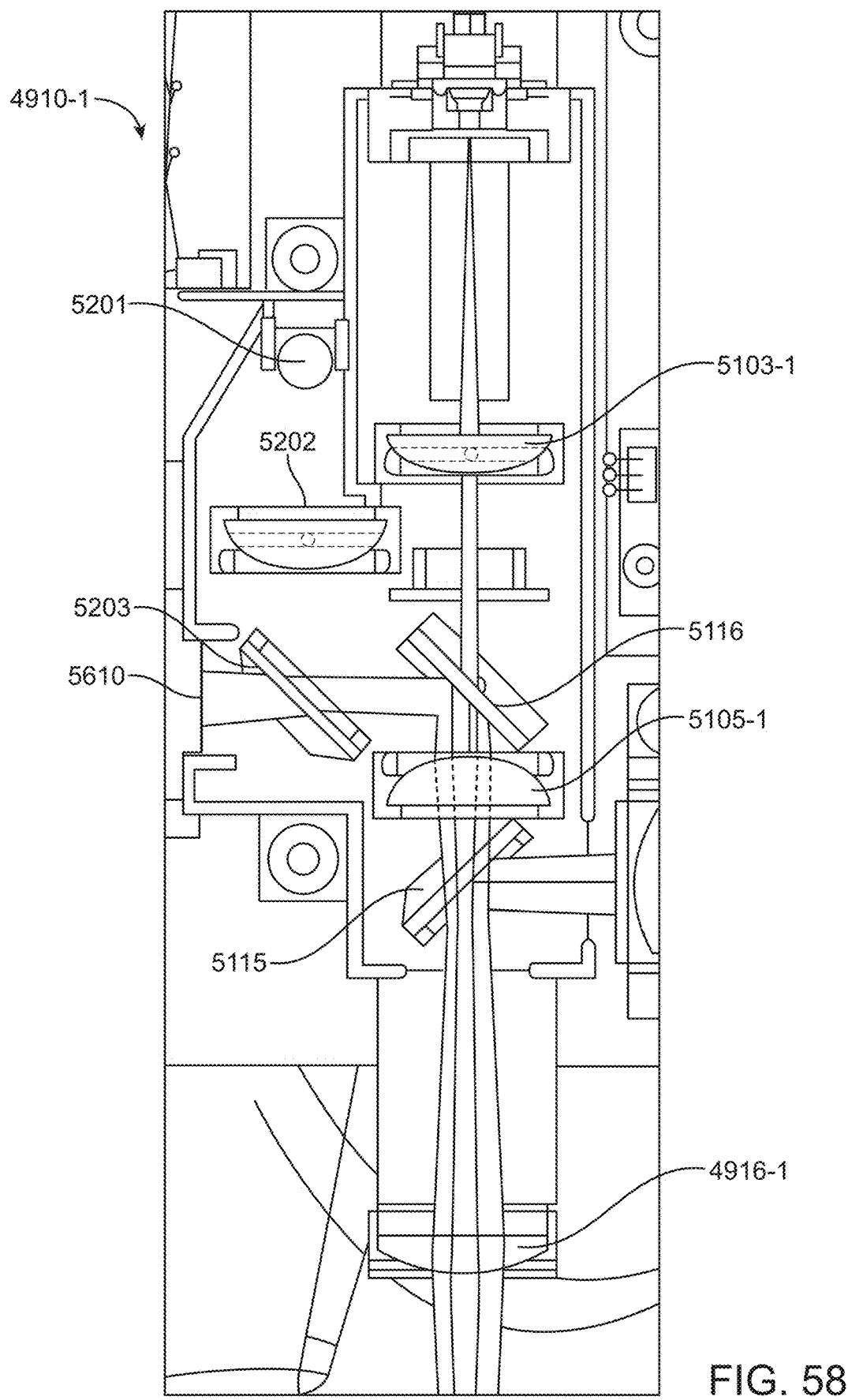
FIG. 58 shows an overhead view of the free space optics comprising a position sensor, in accordance with some embodiments.

FIG. 58 shows an overhead view of the free space optics 4910-1, in accordance with some embodiments. As the laser light enters the free space optics 4910-1, it is reflected off the dichroic mirror 5115 towards the user's eye 5109-1 (not shown) through the optical element 4916-1. The light impinges the user's eye 5109-1 and reflects off the retina thereof back towards the optical element 4916-1. The reflected laser light and is reflected from the dichroic mirror 5115 toward the OPD correction module. The light from the plurality of light sources is reflected from dichroic mirror 5116 toward eye position sensor 4610. The eye position sensor 5610 is operatively coupled to the processor as described herein to positions of the eye as described herein. In alternative embodiments, eye position sensor 5610 can be located at position 5201, and light transmitted through lens 5202 to form the image of the eye on the eye position sensor, such as the Purkinje image as described herein.

The components of binocular OCT device 4900 described with reference to FIGS. 49-58 can be combined to provide a compact OCT device, as will be apparent to one of ordinary skill in the art.

The binocular OCT device 4900 may comprise the handheld OCT device 100 of FIGS. 2, 3A and 3B, and may comprise communication circuitry and be configured to operatively couple to one or more external devices such as mobile patient device 120 as described herein. This connection can be wired, e.g. with a USB connector, or wireless, e.g. with Bluetooth, as described herein. Mobile patient device 120 can be configured to process one or more of the signals from detectors 5101-1 to 5101-5 to generate an A-scan and retinal maps as described herein, for example.

Although FIGS. 49 to 58 make reference to a binocular OCT device 4900, one or more components of binocular OCT device 4900 can be used to construct a mono-ocular OCT device as described herein. For example, free space optics module 4910-2 and the associated translation stage can be removed to adjust interpupillary distance ("IPD") may not be included, and the eyecup configured to cover the eye and block ambient light. In such embodiments, the user can invert the device to measure a second eye as described herein. Alternatively or in combination, an occluder can be provided to cover the non-measured eye with an opaque material to avoid distractions to the non-measured eye. A switch can be coupled to the occluder to provide a signal to the processor to determine which eye is measured, and the data recorded with reference to which eye is being measured as described herein.

Figure 59B:
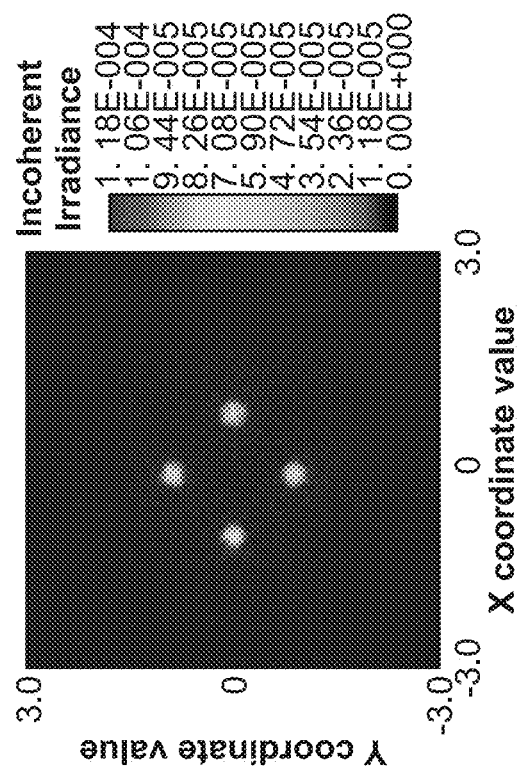
FIG. 59A, FIG. 59B, FIG. 59C, and FIG. 59D show images that can be captured with the eye position sensor to determine a position of the eye in relation to the optical axis, in accordance with some embodiments.
Figure 59A:
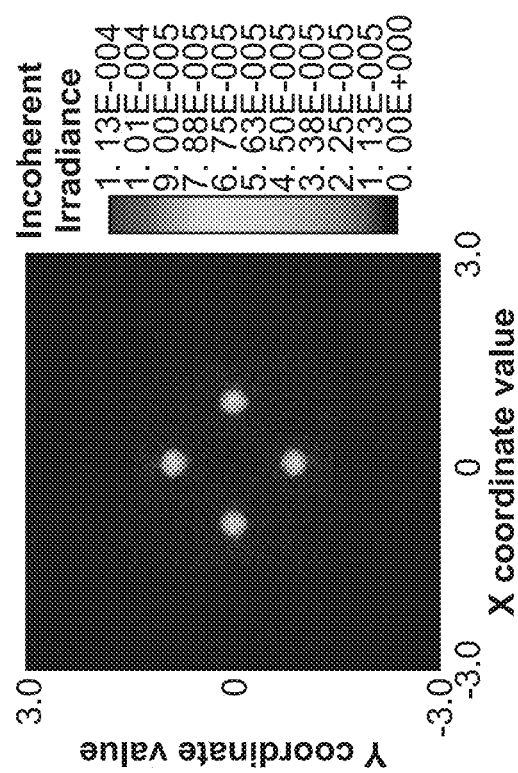
Figure 59D:
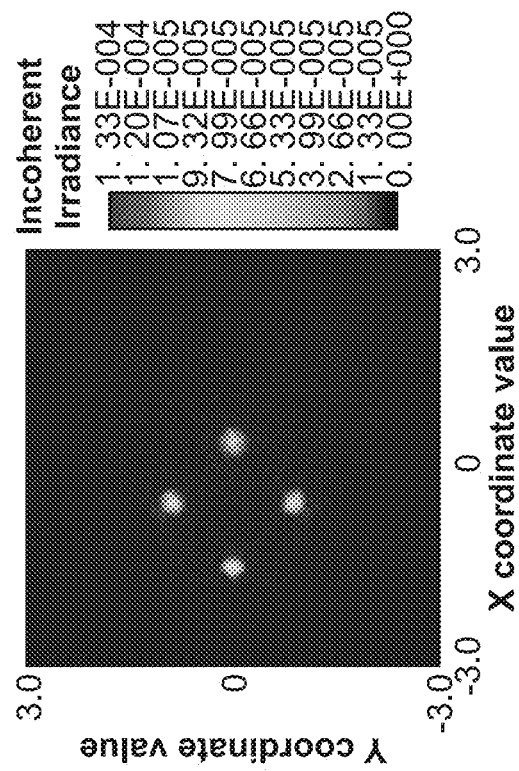
Figure 59C:
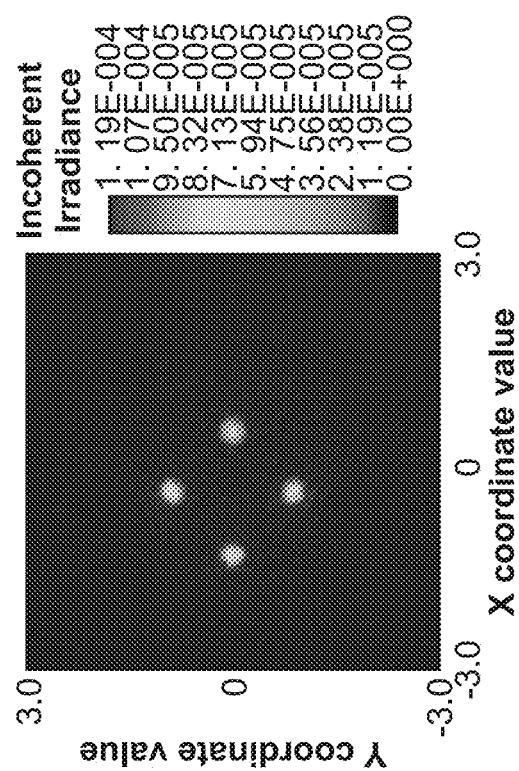

FIGS. 59A-59D show images that can be captured with eye position sensor 5610 to determine a position of the eye in relation to the optical axis 5106-1, in accordance with some embodiments. In each of the images, an image of the plurality of light sources reflected from the cornea is shown. Although an image of the light reflected from the cornea is shown, the eye position sensor may comprise other configurations such as a pupil position imaging configuration, for example. The position of each of four light sources is shown. For instance, FIG. 59A shows an image in which the pupil mismatch is 0 mm and on axis such that the eye is aligned with the free space optics 4910-1 when the user fixates on the fixation target. The position of the eye can be determined in response to the locations of the plurality of light sources imaged onto the eye position detector 5610. In general, an offset of the locations corresponds to translation of the eye in relation to the optical axis of the OCT system. FIGS. 59B, 59C, and 59D illustrate instances where the optical axis of the measurement side of the binocular OCT device 4900 is not perfectly aligned with the eye. More specifically, FIG. 59B shows an alignment error of the cornea of the eye of about 0.5 millimeters along the X-axis. FIG. 59C shows an alignment error of about 1.0 mm along the X-axis, and FIG. 59D shows an alignment error of 1.5 along the X-axis. Similar displacement errors can be calculated along the Y-axis. These displacement errors can be determined with the eye position sensor 5610 along the X-axis and Y-axis, for example the position of the eye with an X, Y coordinate reference in which these axes extend along a plane transverse to the optical axis of the OCT measurement system, such as binocular OCT measurement system.

Figure 60C:
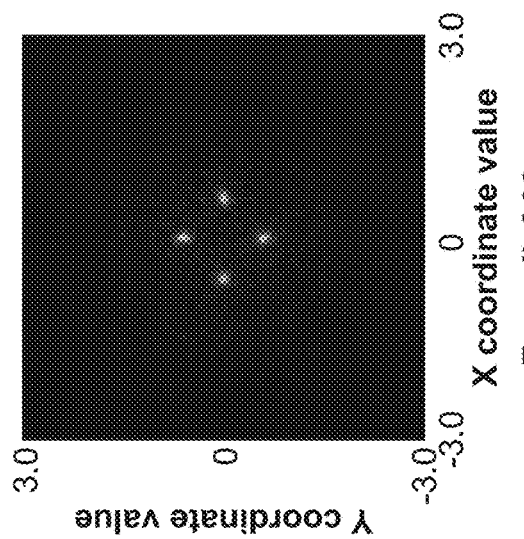
FIG. 60A, FIG. 60B, and FIG. 60C show positions of the plurality of light sources captured with eye position sensor at various eye relief distances between the lens closest to the eye and a user's eye, in accordance with some embodiments.
Figure 60B:
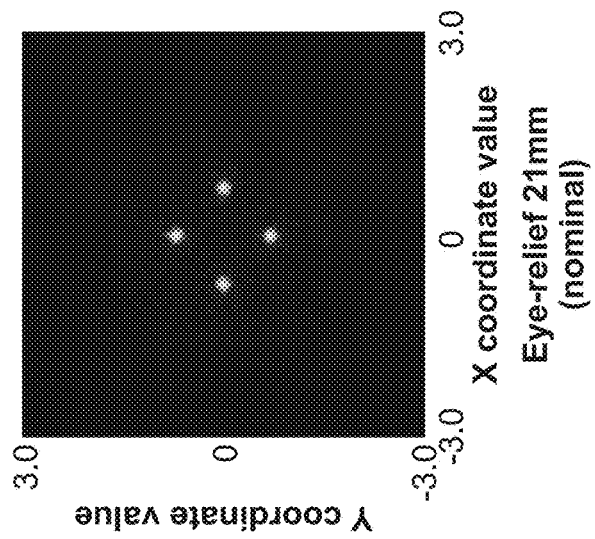
Figure 60A:
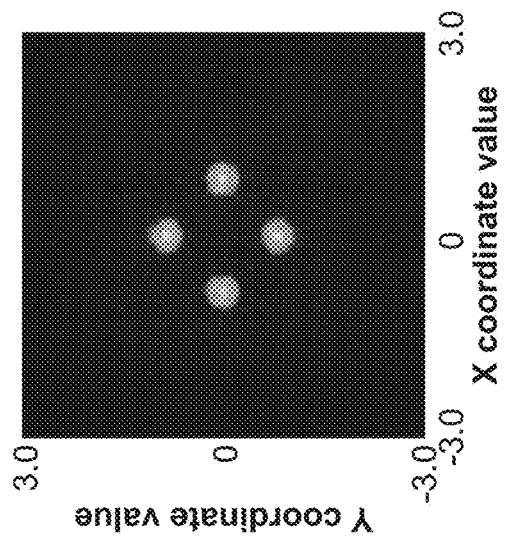

FIGS. 60A-60C show positions of the plurality of light sources captured with eye position sensor 5610 at various eye relief distances between the lens closest to the eye and a user's eye 5109-1, in accordance with some embodiments. In general, the spacing of the image of the plurality of light sources decreases with an increasing relief distance. More specifically, FIG. 60A shows a Purkinje image of light reflected from the plurality of sources at a distance of approximately 16 mm between the user's eye 5109 and the OCT measurement system. FIG. 60B shows an image from position sensor 5610 at a distance of approximately 21 mm. FIG. 60C shows an image of the plurality of light sources from the position sensor at a distance approximately 26 mm between the user's eye 5109 and the OCT measurement system. The spacings between the plurality of light sources decreases with increasing relief distances.

The processor as described herein can be coupled to eye position sensor 5610 to determine the eye relieve distance in X, Y and Z axes. The processor can be coupled to the orientation sensor to determine which eye is measured, and appropriately map the position sensor data to the coordinate reference system of the eye. For example, the X and Y positions of the eye from the sensor 5610 can be inverted when the OCT system comprises an inverted configuration, and the measured positions of the eye appropriately transformed to the user's reference frame. The images captured with the sensor may comprise a combination of X, Y, and Z offsets from an intended position, e.g. 0 alignment error along the X, Y and Z axis.

One or more of the measured eye positions can be used to provide instructions to the user. For example, the user may receive auditory instructions from a mobile device operatively coupled to the OCT measurement system to move the eye left, right, up or down, until the eye is located within a suitable window for OCT retinal thickness measurements as described herein. For example, the system can be configured to acquire OCT measurements once the eye has moved to within about 0.5 of the optical axis of the OCT measurement system. One or more of the fixation targets can be configured to provide a visual cue to the user. For example, one or more of the fixation targets can be configured to change color when the measured eye is brought into sufficient alignment. For example, the fixation target can change color from yellow when not sufficiently aligned to green when sufficiently aligned. In some embodiments, both fixation targets can change color when the OCT system comes into sufficient alignment with the eye. Each of the LEDs that illuminate the fixation target as described herein may comprise two or more emission wavelengths, for example yellow and green wavelengths.

Figures 61A, 61B:
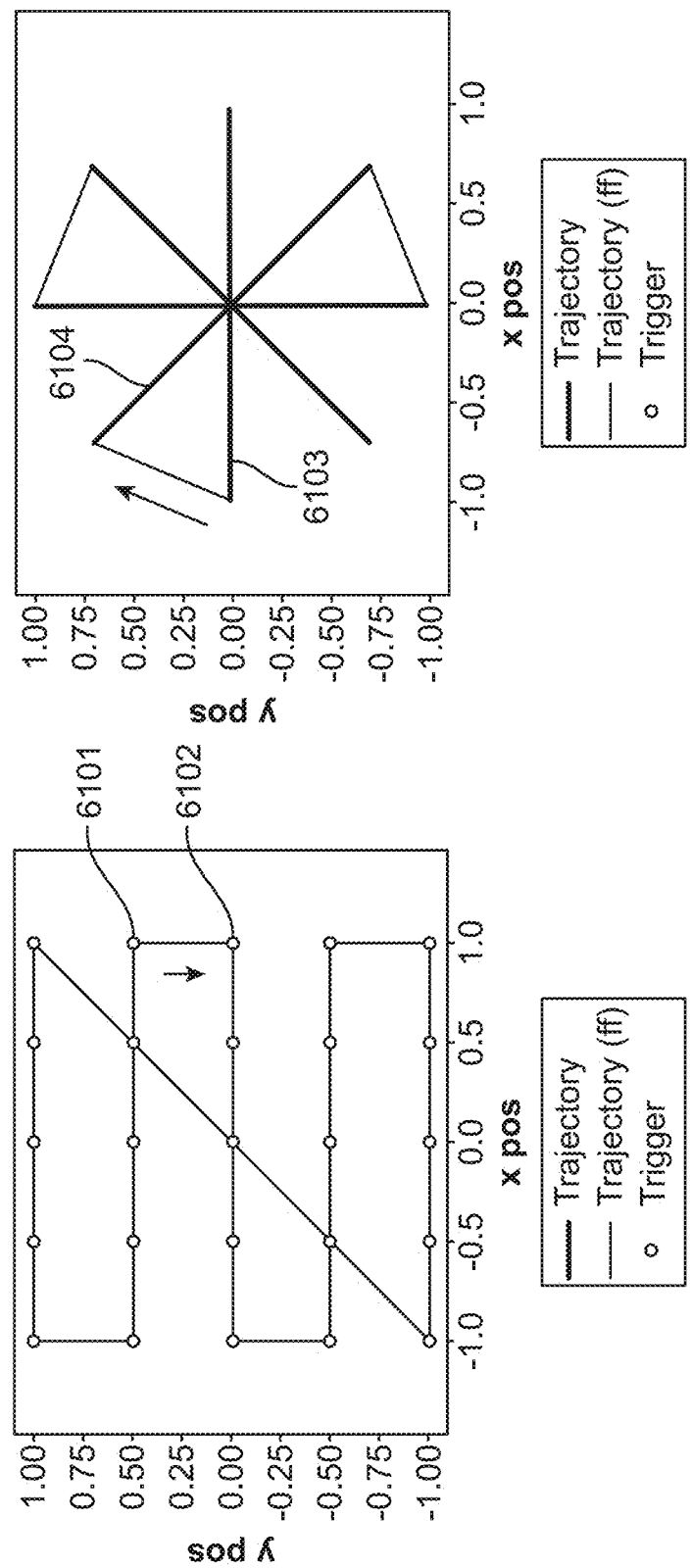
FIG. 61A, FIG. 61B, FIGS. 61C, and 61D show various scan patterns that may be implemented by the scanner module, in accordance with some embodiments.
Figure 61D:
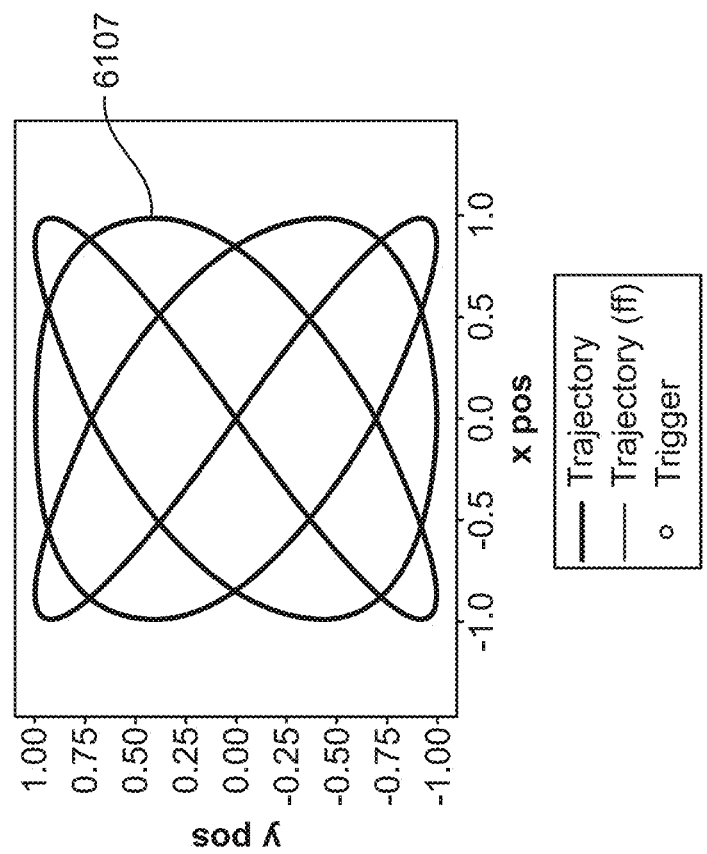
Figure 61C:
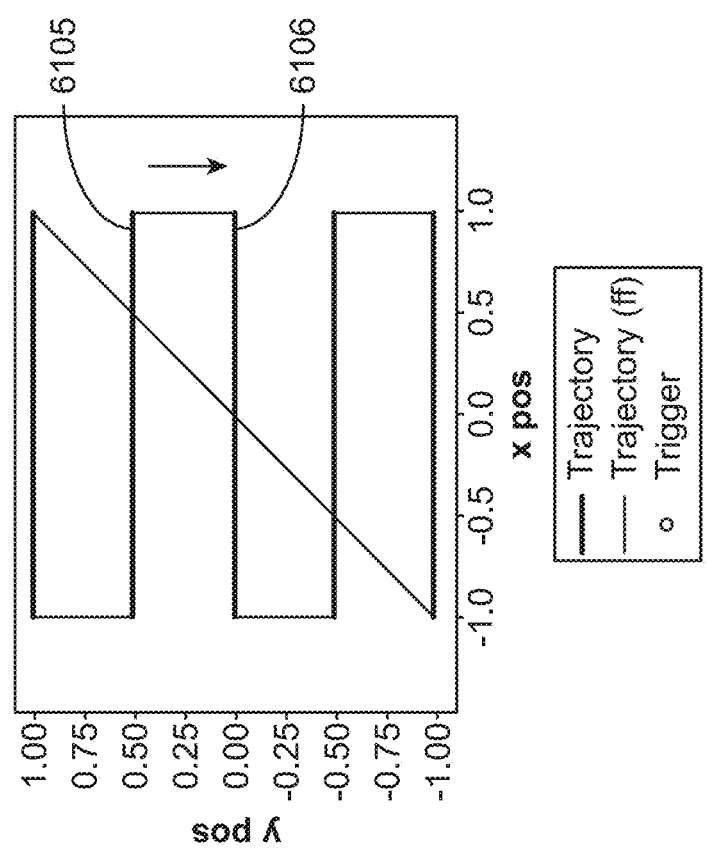

FIGS. 61A-61D show various scan patterns that may be implemented by the scanner module 4990, in accordance with some embodiments. More specifically, FIG. 61A shows a "stop and go" scan trajectory in which the scanner module 4990 dwells the laser light from the VCSELs 4952 on a particular spot on the user's eye 5109 before moving on to a next spot. For instance, the scanner module 4990 may dwell the laser light on a spot 6101 before moving onto the spot 6102 in response to the trigger signal. Alternatively, the scanner module may continuously scan the OCT measurement beam while the one or more VCSEL light sources is swept, such that the measurement beam moves continuously along the eye during an A-scan as described herein. FIG. 61B shows a "star" scan trajectory in which the scanner module 4990 linearly scans the laser light from the VCSELs 4952 on the user's eye 5109. For instance, the scanner module 4990 may scan the laser light measurement beam in a linear manner along the line 6103 before moving along the line 6104. FIG. 61C shows a "continuous" scan trajectory in which the scanner module 4990 linearly scans the laser light from the VCSELs 4952 on the user's eye 5109 before moving on to a next spot. For instance, the scanner module 4990 may scan the laser light in a linear manner along the line 6105 before moving along the line 6106. FIG. 61D shows a Lissajous scan trajectory in which the scanner module 4990 continuously scans the laser light from the VCSELs 4952 on the user's eye 5109 in a Lissajous pattern 6107.

Figure 62:
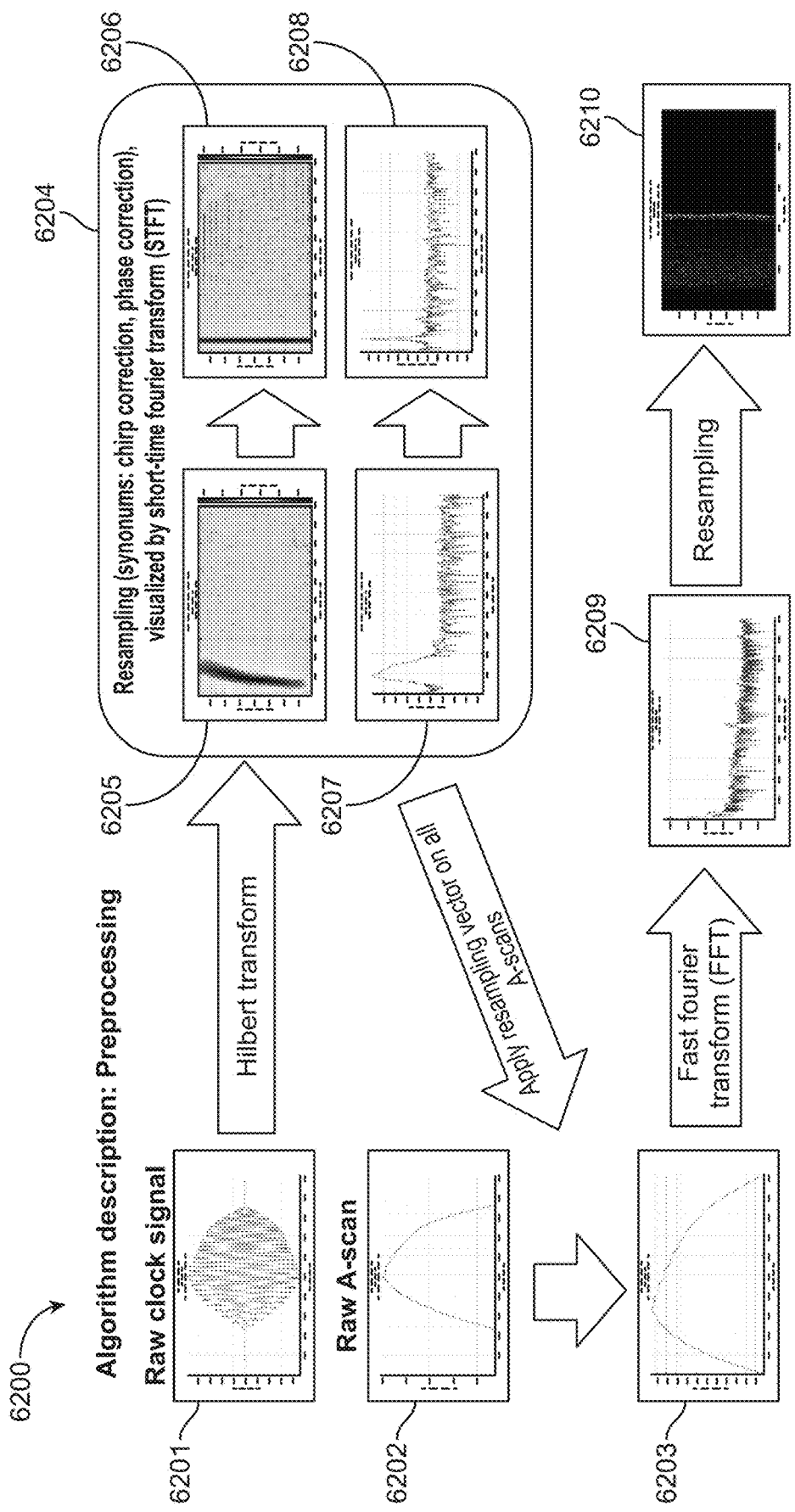
FIG. 62 shows a flow diagram of processing such as preprocessing that may be performed by the OCT system as described herein such as binocular OCT, in accordance with some embodiments.

FIG. 62 shows a flow diagram 6200 of processing such as preprocessing that may be performed by the OCT system as described herein such as binocular OCT 4900, in accordance with some embodiments. A raw clock signal 6201 is received from the detector of the phase compensation module during an A-scan sweep of the swept source as describe herein. The raw clock signal may comprise analog values from the detector after the sampled portion of the swept source light beam is passed through an interferometer such as an etalon as described herein. A raw A-scan sample 6202 is received from the balanced detector of the OCT measurement system as described herein. In some embodiments, the clock signal is synchronously captured with the A-scan signal, in order to accurately resample the A-scan and correct for variations in the rate of wavelength sweeping of the swept source as described herein. The raw clock signal can be transformed with a Hilbert transform, and the resulting phase information can linearized and used to generate a resampling vector 6204. The resampling to generate the resampling vector may comprise one or more of chirp correction, or phase correction.

Short-time Fourier transform (STFT) can be applied to the raw clock signal and visualized in a time-frequency diagram. An image 6205 illustrates non-linear phase of the chirp on the raw clock signal. An image 6206 shows similar information after resampling the raw clock signal with the resampling vector. This operations provided with respect to image 6205 and image 6206 are illustrative to show the effectiveness of chirp correction. Image 6207 shows the result of an FFT applied to the raw clock signal to illustrate peak broadening. Peak broadening can be due to non-linear phase of the chirp signal from the optical clock. Image 6208 shows the result an FFT after resampling the clock signal similar to decrease phase variations of the clock signal, similarly to image 6206, and the peak broadening is significantly reduced. In some embodiments, the resampling is applied to the raw A-scan 6202, and the additional steps described with reference to images 6502, 6206, 6207 and 6208 are not performed, and these images are provided to illustrate the utility of resampling.

The resampling vector is applied to the A-scan data to generate a resampled A-scan 6203. The resampled A-scan is subject to a transform such as a fast Fourier transform to generate intensity values of an individual A-scan 6209. The above process can be repeated to generate a plurality of A-scans. The plurality of A-scans can be resampled to generate a resampled A-scan output 6210 comprising a plurality of A-scans. The resampled output can be used to determine the retinal thickness as described herein.

Figure 63:
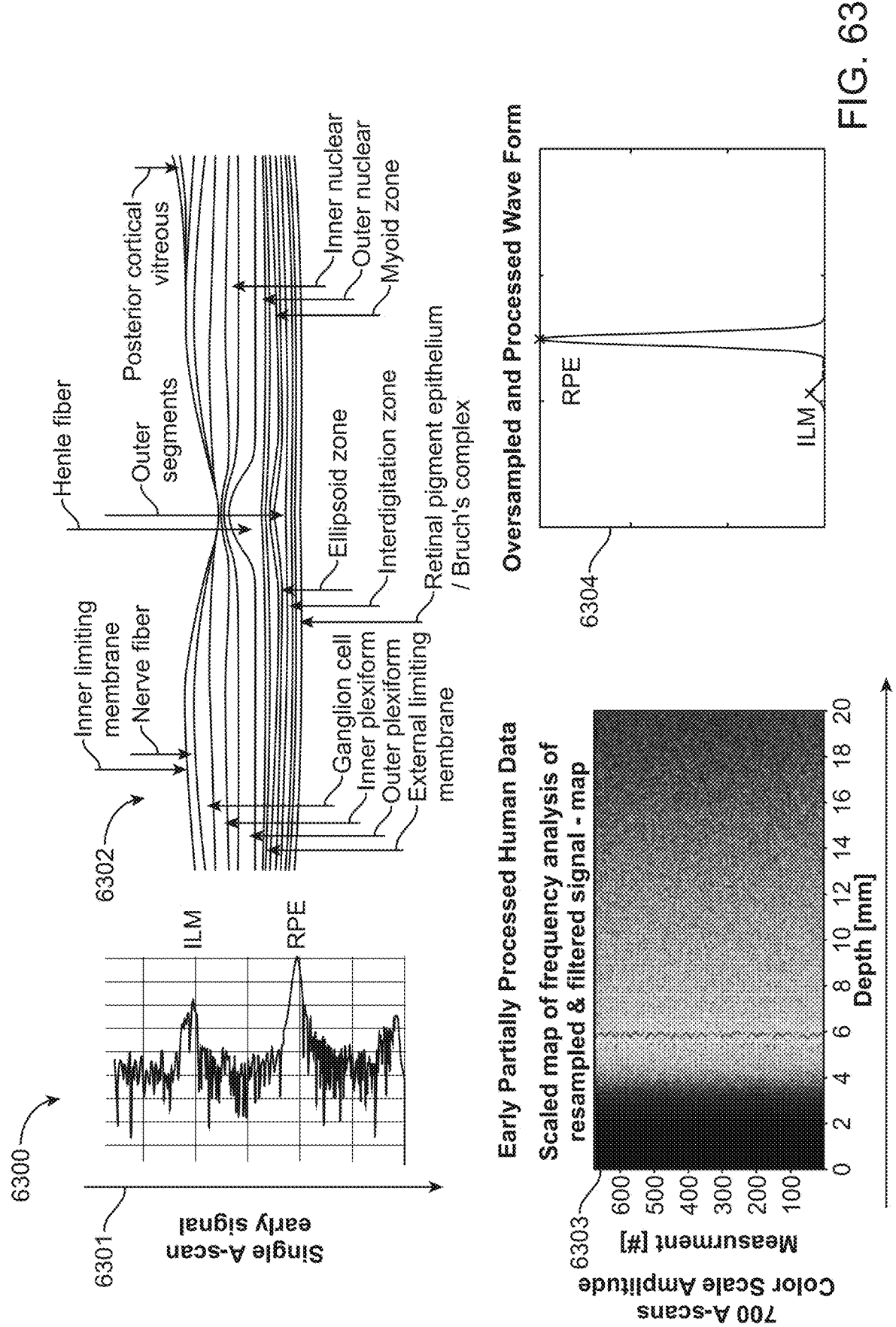
FIG. 63 shows various plots obtained by the preprocessing of flow diagram of FIG. 62, in accordance with some embodiments.

FIG. 63 shows various plots obtained by the preprocessing of flow diagram 6200 of FIG. 62, in accordance with some embodiments. A single A-scan 6301 comprises reflections corresponding to layers of the retina 6302 as indicated by A-scan signal 6301. The retina 6302 comprises several layers and structures including the inner limiting membrane ("ILM"), the nerve fiber layer, the ganglion cell layer, the inner plexiform layer, the outer plexiform layer, the external limiting membrane, the Henle fiber, outer segments, the ellipsoid zone, the interdigitation zone, the retinal pigment epithelium ("RPE"), Bruch's complex, the posterior cortical vitreous, the inner nuclear layer, the outer nuclear layer, and the myoid zone. As can be seen with reference to single A-scan 6301, the reflected signal from the retina comprises a first peak corresponding to the ILM, and a second peak corresponding to the RPE. The retinal thickness can be determined based on the separation distance between the ILM and the RPE. Several A-scans 6303 can be resampled and/or combined to generate combined and/or oversampled waveform data 6304 comprising reflectances of the retina at depths. For example, from 100 to 1000 A-scans can be obtained and resampled and/or oversampled, e.g. 700 samples, to generate the thickness of the retina at a region of the retina corresponding to locations of the measurement beam during the A-scans. The resampled and/or combined data 6304 can be used to determine the location of the RPE and ILM based on the corresponding peaks, and the distance between the two reflectance peaks used to determine the thickness of the retina.

Figure 64:
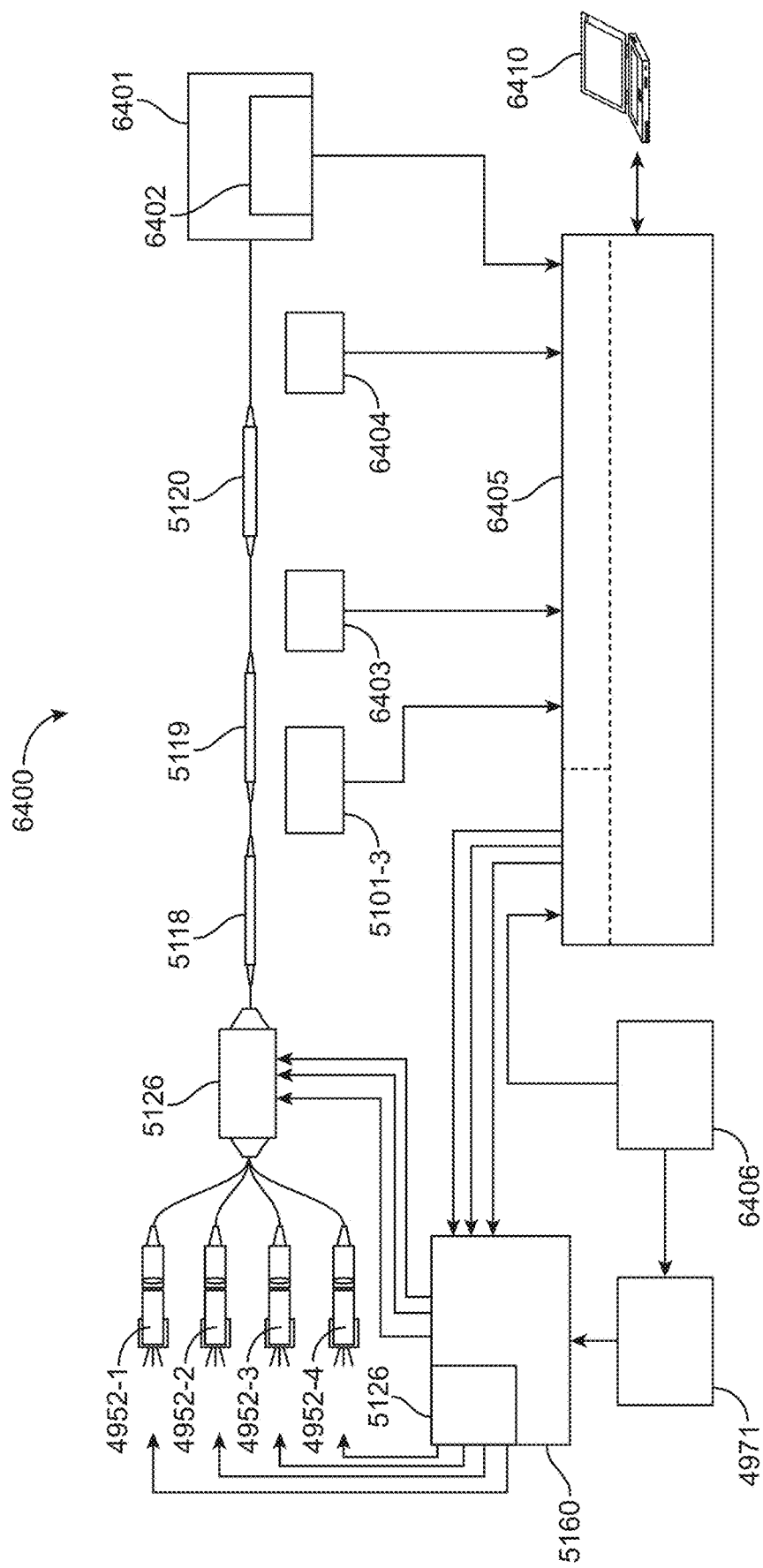
FIG. 64 shows an OCT device in which the one or more VCELs comprises a plurality of VCSELs, in accordance with some embodiments.

FIG. 64 shows an OCT system 6400 comprising in which the one or more VCELs 4952 comprises a plurality of VCSELs, in accordance with some embodiments. The components of OCT system 6400 are well suited for combination with the binocular OCT system 4900 as described herein, and can be used to extend the range of the swept source. The plurality of VCSELs may comprise a first VCSEL 4952-1, a second VCSEL 4952-2, a third VCSEL 4952-3 and a fourth VCSEL 4952-4. Although four VCSELs are shown the plurality of VCSELs may comprise any suitable number of VCSELs to provide a suitable sweep range, such as from two to six VCSELs, for example from three to five VCSELs. The plurality of VCSELs may comprise more than six VCSELs, for example. The plurality of VCSELs is coupled to an optical switch 5126 with a plurality of optical fibers extending from the plurality of VCSELs to the optical switch. The optical switch 5216 can be used to couple the plurality of optical fibers from the VCSELs to a single mode optical fiber. The optical switch 5216 may comprise a solid-state switch, which has a very fast response time and a fast switching repetition rate. The optical switch 5206 may comprise an electro-optical switch, for example without moving mechanical components. The optical switch 5216 may comprise a response time within a range from about 30 nanoseconds ("ns") to about 300 ns. In some embodiments, the speed of the optical switch is related to the electronics of the driver and can be slower, for example within a range from about 250 kHz to about 750 kHz, e.g. about 500 kHz. The optical switch may comprise an N by 1 ("N×1") switch, e.g. a 4×1 switch. In some embodiments, the value of N is within a range from about 2 to 6. The N×1 switch may comprise a plurality of cascaded switches. In some embodiments, 4×1 switch comprises three cascaded 2×1 switches, in which switch 1 selects between VCSEL 1 and VCSEL 2, switch 2 selects between VCSEL 3 and VCSEL 4, and switch 3 selects between switch 1 and switch 2. Although a solid state optical switch is shown, the optical switch may comprise a series of cascaded 2×1 optical fiber splitters, an optical grating, or a series of dichroic beamsplitters, in order to combining light from a plurality of VCSELs into one fiber. For example, the 4×1 optical splitter may comprise a series of cascaded 2×1 fiber splitters.

The optical switch can selectively couple to one of the plurality of optical fibers from the plurality of VCSELs to selectively control which VCSEL is transmitted from the switch to the output optical fiber from the switch. The optical switch is operative coupled to a processor 5160. The processor 5160 may comprise a multiplexer to control illumination of the plurality of VCSELs. The switching of the optical switch and the illumination of the VCSELs can be controlled with the processor to allow sequential scanning of the plurality of VCSELs. The optical switch 5126 is coupled to a first coupler 5118. The first coupler 5118 may comprise a first output fiber directed to a power detector, which may comprise one or more safety detectors as described herein. A second output fiber from coupler 5118 is coupled to a second coupler 5119. The second coupler 5119 can be coupled to a first clockbox 6403 with an optical fiber. The first clockbox 6403 may comprise a first interferometer to generate clock signals as described herein. The second coupler 5119 can be coupled to a third coupler 5120. The third coupler 5120 can be coupled to a second clockbox 6404. The second clockbox may comprise a second interferometer to generate clock signals as described herein. The output of the third coupler 5120 can be coupled to additional components of an OCT measurement system 6401, such as components of binocular OCT measurement system 4900. The OCT system 6400 may comprise one or more components of OCT system 4900, such as a VCSEL driver 4971 and a function generator 6406. The OCT system can be coupled to a mobile device as described herein, such as mobile device 6410 comprising a laptop. The OCT system may comprise a synchronous data acquisition and control system 6405 for synchronously controlling the VCSEL sweeping sequence, the switching of optical switch 5126 and data acquisition of the analog to digital converters coupled to detectors as described herein to record detector signals synchronously.

Figure 66:
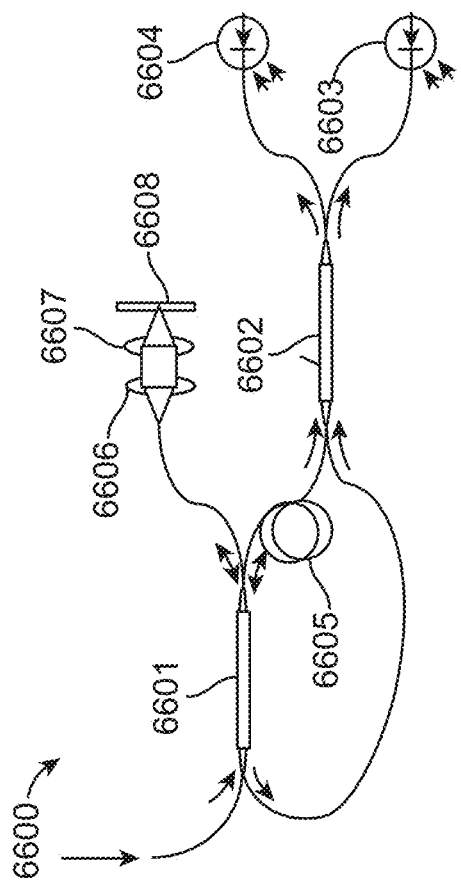
FIG. 66 shows a fiber optic measurement interferometer that may be implemented with an OCT system, such as the binocular OCT device, in accordance with some embodiments.
Figure 65:
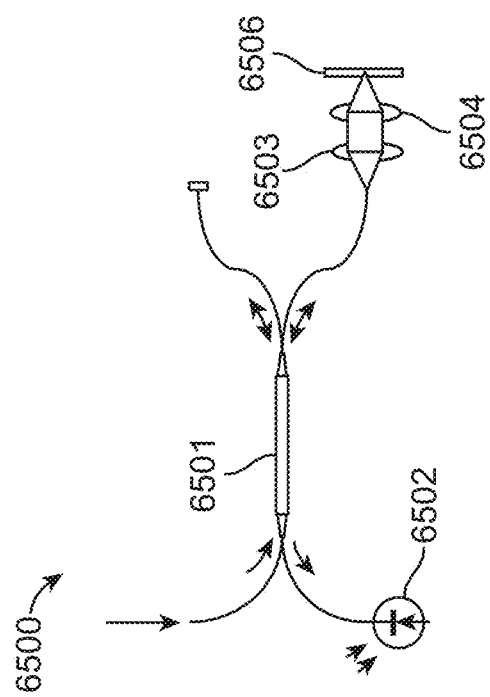
FIG. 65 shows a clock box comprising an interferometer with an adjustable optical path difference, in accordance with some embodiments.

FIG. 65 shows a clock box comprising an interferometer 6500 with an adjustable optical path difference, and FIG. 66 shows a fiber optic measurement interferometer 6600 that may be implemented with an OCT system as described herein, such as the binocular OCT 4900, in accordance with some embodiments. The clock box interferometer 6500 comprises an input optical fiber coupled to a swept light source as described herein. The input optical fiber is coupled to a coupler 6501, which is coupled to an optical fiber coupled to a reference mirror and another optical fiber coupled to a movable mirror 6506. A pair of lenses can be used to focus the light onto movable mirror 6506. The pair of lenses may comprise a first lens 6503 coupled to the optical fiber to collimate light from the optical fiber and a second lens 6506 to focus light into the optical fiber. The second lens 6506 and the mirror 6506 may move together to adjust the optical path difference. A detector 6502 is coupled to the coupler 6501 with an optical fiber and receives the interference signal from the coupler 6501. The frequency of the clock signals can be adjusted by adjusting the optical path length difference with movable mirror 6506. The clock box interferometer 6500 may comprise a Mach-Zender interferometer or a Fabry Perot interferometer as described herein, for example. The OCT system may comprise a plurality of clock boxes, each comprising an adjustable optical path length in order to determine appropriate differences in optical path lengths of the clock boxes to accurately determine the phase of the light from each plurality of VCSELs as described herein.

The fiber optic measurement interferometer 6600 can be coupled to the plurality of VCSEL light sources with optical fibers as described herein, and a plurality of clock box interferometers used to measure the phase of the light from the VCSELs as described herein. A coupler 6601 is coupled to the optical fiber to receive light from the light source, and coupled to a measurement arm of the interferometer and a reference arm of the interferometer. The reference arm may comprise a coiled optical fiber 6605 to adjust the optical path difference, and the measurement arm may comprise a lens 6606 to direct light to the sample 6608. In experimental configurations, the sample 6608 may comprise a mirror 6608 or other test object. A second lens 6607 can be used to focus light to the sample 6608. In binocular OCT measurement systems, the sample comprises a retina of an eye, and the measurement arm may comprise a movable OPD module as described herein. The optical signal from the measurement arm can be coupled to coupler 6601 with an optical fiber. A coupler 6602 can be used to combine the signal from the measurement arm with the signal from the reference arm, and the output directed to balanced detector with a pair of optical fibers as described herein. The balanced detector may comprise a pair of detectors, such as a first detector 6603 and a second detector 6604. The balanced detector can be coupled to the circuitry as described herein, and a processor used to align the phase of a first VCSEL with a second VCSEL as described herein.

Figure 67:
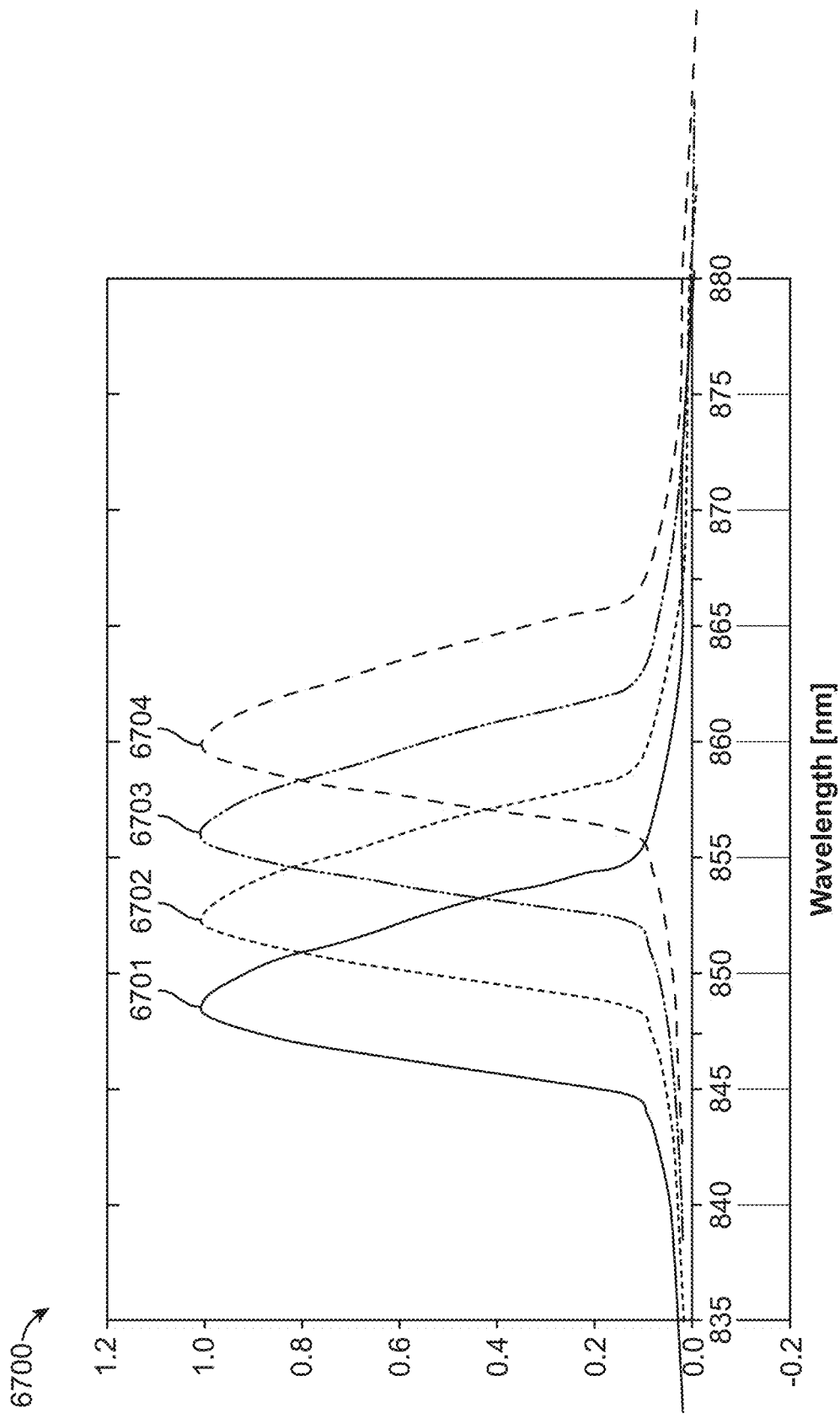
FIG. 67 shows a plot of laser light intensity and wavelength from 4 VCSELs, each of which being swept over a range of wavelengths, in accordance with some embodiments.

FIG. 67 shows a plot 6700 of laser light intensity and wavelength from 4 VCSELs, each of which being swept over a range of wavelengths, in accordance with some embodiments. For instance, when the binocular OCT 4900 is operational and the VCSEL driving electronics 4971 of FIG. 50 begin firing the plurality of VCSELs 4952, the VCSEL driving electronics 4971 may initiate a sequential firing of the VCSELs 4952. Each of the VCSELs 4952 may be swept over approximately 10 nm in wavelength, with approximately 7 nm of wavelength being an "effective sweep range". The effective sweep range can be from about 5 nm to about 10 nm, for example. The overall sweep range is about 22 nm to 23 nm and can centered about approximately 855 nm, for example. The plurality of VCSELs can be used to provide an overall sweep range from about 15 to about 30 nm, for example. The one or more VCSELs may comprise commercially available VCSELs available from many manufactures as described herein, and the plurality of VCSELs may generally emit light at a wavelength from about 800 to 895 nm. The VCSEL output wavelength of the VCSEL can change in response to heating as described herein. The heating can induce one or more of a change in cavity length or a change in refractive index in the gain medium in order to change the wavelength with heating. The temperature change, e.g. caused by current changes of the swept source, can provide a change in refractive index as well as a physical length change of the cavity, e.g. thermal expansion. These two effects can provide a wavelength change of the laser mode of within a range from about 0.04 nm per degree Kelvin ("nm/K") to about 0.1 nm/K, for example about 0.07 nm/K in GaAs. In some embodiments, the gain spectrum shifts in wavelength with temperature changes by an amount within a range from about 0.1 to about 0.5 nm, for example about 0.3 nm/K in GaAs, which may limit the amount of achievable wavelength tuning for one VCSEL.

The one or more VCSELs can be driven with a sweep time from about 1 microsecond to about 100 microseconds for an A-scan, for example at a sweep time can be within a range from about 4 microseconds to about 60 microseconds. In some embodiments, the sweep time is within a range from about 5 microseconds to about 50 microseconds for each VCSEL. In embodiments in which the one or more VCSELs comprises a plurality of VCSELs, the total sweep time for an A-scan may comprise a sweep time comprising a total time to scan each of the plurality of VCSELs, and the sweep time for the A-scan will be correspondingly greater. Each of the plurality of VCSELs may comprise an appropriate range of wavelengths for the sweep.

In this manner, the VCSEL driving electronics 4971 may fire and sweep a first VCSEL so as to produce laser light 6704 over a range of wavelengths that is swept from approximately 856 nm to 866 nm. The VCSEL driving electronics 4971 may then fire and sweep a next VCSEL to produce laser light 6703 over a range of wavelengths that is swept from approximately 852 nm to 862 nm. The VCSEL driving electronics 4971 may then fire and sweep a next VCSEL to produce laser light 6702 over a range of wavelengths that is swept from approximately 848 nm to 858 nm. The VCSEL driving electronics 4971 may then fire and sweep a next VCSEL to produce laser light 6701 over a range of wavelengths that is swept from approximately 845 nm to 855 nm.

Generally, the sweep range of one VCSEL 4952 may overlap a portion of one or more sweep ranges of the other VCSELs. For instance, as can be seen in the plot 6700, the sweep range 6701 of one VCSELs 4952 overlaps portions of the sweep ranges 6702 and 6703 produced by two other VCSELs 4952 in the plurality. Although the wavelengths are shown as overlapping, in some embodiments the VCSEL sweeps do not overlap in time, and can be selectively coupled to the interferometer with an optical switch as described herein.

Figure 68:
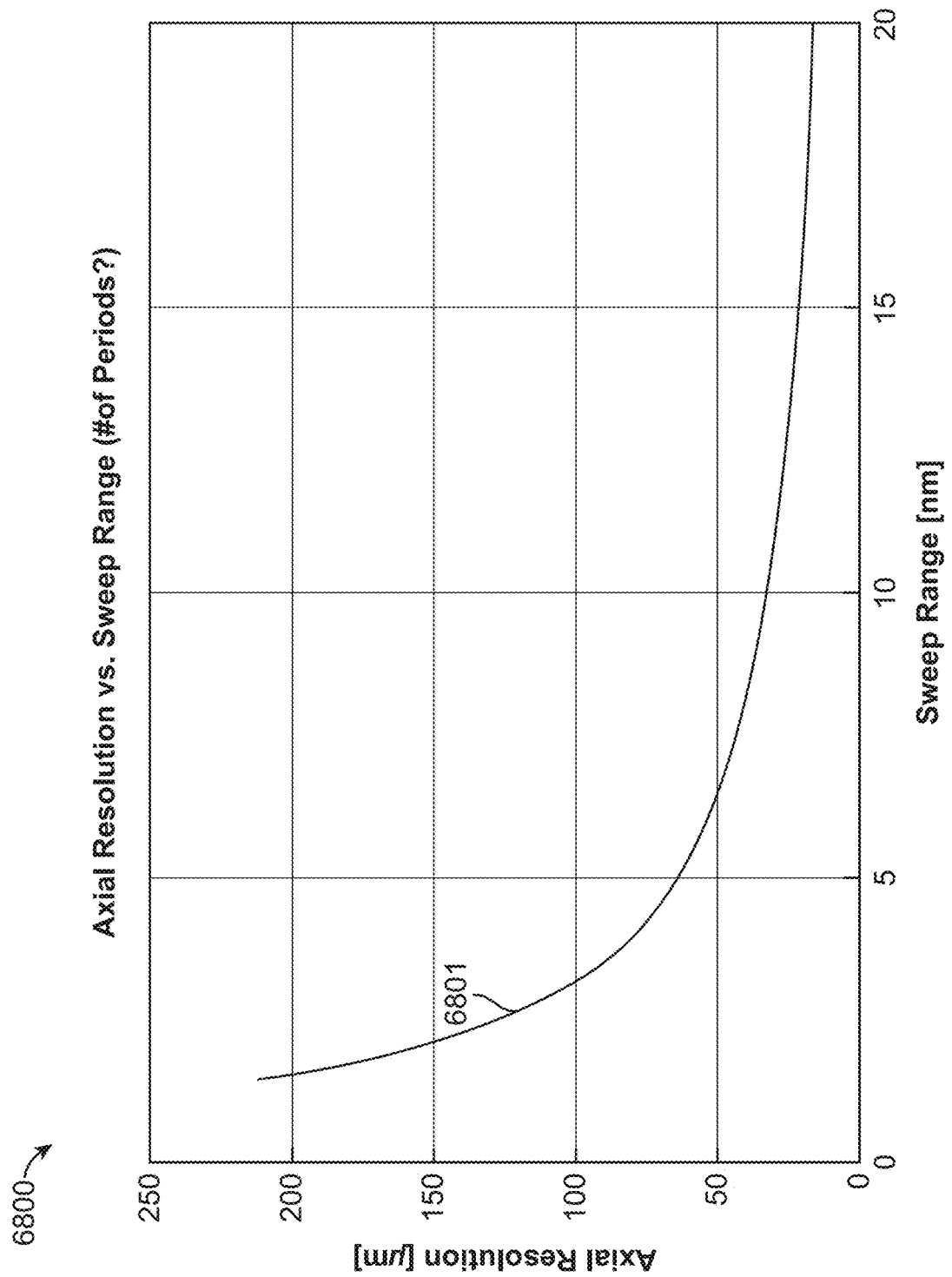
FIG. 68 shows a plot 6800 of the axial resolution 6801 versus the sweep range provided by the VCSELs 4952, in accordance with some embodiments.

FIG. 68 shows a plot 6800 of the axial resolution 6801 versus the sweep range provided by the VCSELs 4952, in accordance with some embodiments. As can be seen in the plot 6800, the value of the axial resolution decreases with respect to the sweep range of the VCSEL. A single VCSEL 4952 may provide about 50 μm resolution when swept over approximately 7 nm of wavelength. However, by using a plurality of VCSELs such as a plurality of VCSELs 4952 (e.g., each of which swept over approximately 5 to 10 nm of wavelength), the binocular OCT 4900 may decrease the resolution value to about 10 μm (micro-meters or microns) and in some instances 7 μm. The axial resolution can be within a range from about 7 μm to about 30 μm, for sample from about 10 μm to about 30 μm.

However, as each of the VCSELs 4952 are swept over a number of different overlapping wavelength ranges, their waveforms are generally different and comprise different phases. In order to combine the information for each of the VCSELs 4952 into a single usable signal, the waveforms of the VCSELs 4952 may be phase matched and stitched together. FIG. 69 shows waveforms of two VCSELs 4952 that are out of phase and suitable for being stitched together into a single signal, in accordance with some embodiments. For instance, the waveform 6901 of a first VCSEL 4952 may be stitched together with the waveform 6902 of an adjacent swept waveform from another VCSEL 4952 in an area where their sweep ranges overlap. To illustrate, when the VCSEL driving electronics 4971 fire and sweep laser light of the first of the plurality of VCSELs 4952, the measurement data may be obtained via the photodetectors 4972. Then, the VCSEL driving electronics 4971 may fire and sweep laser light of the second of the plurality of VCSELs 4952 over range that at least partially overlaps the sweep range of the first VCSEL 4952 as described herein.

Once the clock box phase and OCT measurement arm data is obtained via the photodetectors 4972, processing on each of the sweep ranges of the first and second VCSELs 4952 may be used to identify where phases match. In this example, the laser light of the first VCSEL 4952 has a swept waveform 6901 that is slower than the swept waveform 6902 from the laser light of the second VCSEL 4952, and the two waveforms are also out of phase. The swept waveforms may correspond to the sweep ranges 6704 and 6703 of FIG. 67, for example. The VCSELs can be swept in any order and any suitable sweep rate and ranges as described herein.

Figures 70A, 70B, 70C, 70D:
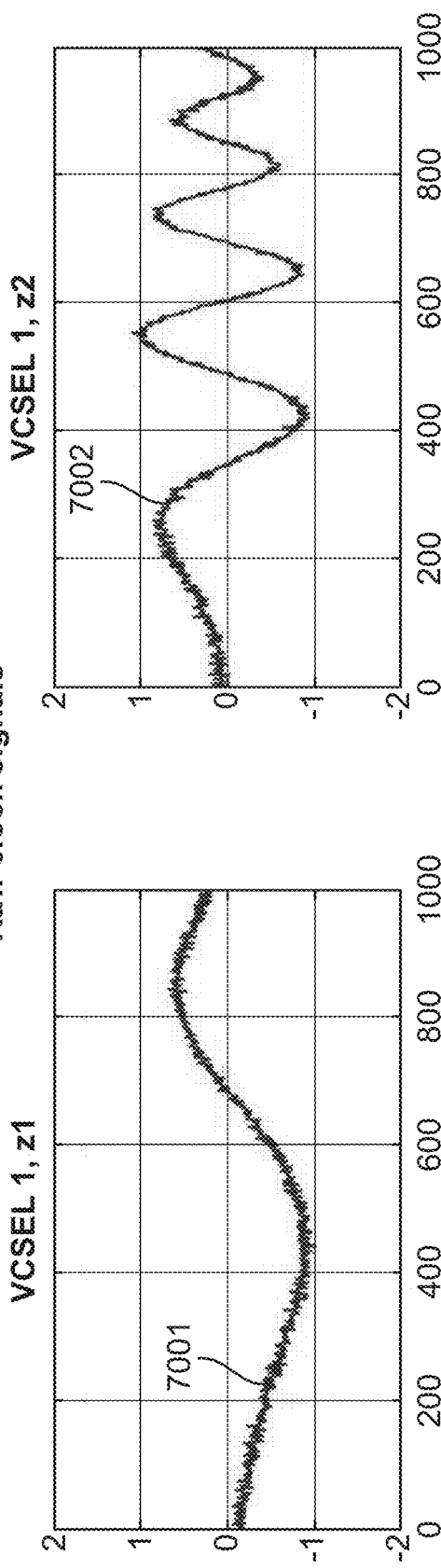
FIG. 70A, FIG. 70B, FIG. 70C, and FIG. 70D show plots of raw clock signals obtained from the first and second VCSELs illustrated in FIG. 69 to illustrate phase extraction of nonlinear clock signals and wavelength sweeps, in accordance with some embodiments.

FIGS. 70A-70D show plots of raw clock signals obtained from the first and second VCSELs 4952 illustrated in FIG. 69 to illustrate phase extraction of nonlinear clock signals and wavelength sweeps, in accordance with some embodiments. For a first VCSEL (VCSEL 1), a first clock box signal 7001 is obtained from a first interferometer (z1) with a first optical path difference and a second clock box signal 7002 is obtained from a second interferometer (z2) with a second optical path difference, as shown in FIGS. 70A and 70B, respectively. For a second VCSEL (VCSEL 2), the first clock box signal 7003 is obtained from the first interferometer (z1) with the first optical path difference and the second clock box signal 7004 is obtained from the second interferometer (z2) with the second optical path difference, as shown in FIGS. 70C and 70D, respectively. In some embodiments, the clock box signals are synchronously recorded with the measurement arm interference signals as described herein.

FIGS. 71A-71D show plots of the phase wrapping of the raw clock signals of FIGS. 70A-70D, in accordance with some embodiments. FIG. 71A shows phase 7101 of the sweep from first VCSEL from the first clock box, and FIG. 71B shows phase 7102 of the sweep from first VCSEL from the second clock box. FIG. 71C shows phase 7103 of the sweep from second VCSEL from the first clock box, and FIG. 71D shows phase 7104 of the sweep from second VCSEL from the second clock box.

Figures 72A, 72B:
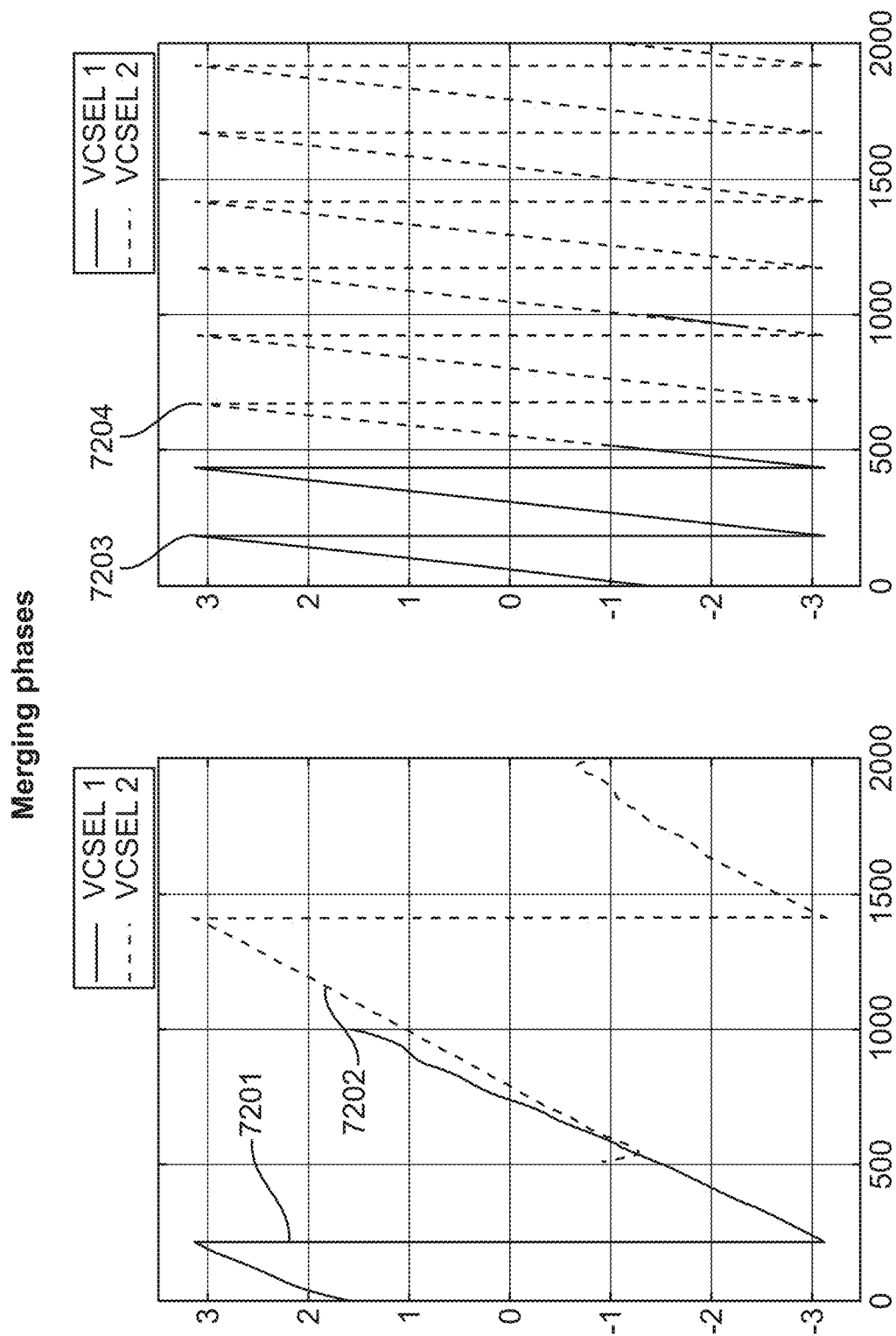
FIG. 72A and FIG. 72B show plots where wrapped phase of two clock signals can be matched (FIG. 72A) generally and then combined into a single phase wrap signal (FIG. 72B), in accordance with some embodiments.

FIGS. 72A and 72B show plots where wrapped phase of two clock signals can be matched (FIG. 72A) generally and then combined into a single phase wrap signal (FIG. 72B), in accordance with some embodiments. The phase wrapped signal 7201 from the first clock box and the first VCSEL can be aligned with the phased wrapped signal 7202 from the first clock box and the second VCSEL. The phase wrapped signal 7203 from the second clock box and the first VCSEL can be aligned with the phased wrapped signal 7204 from the second clock box and the second VCSEL. The first clock signals can be used to provide coarse alignment, and the second clock box signals can be used to provide more precise alignment. For example, the first clock box signals can be used to ensure that the appropriate portions of the second clock box signals are used for alignment. In general, the optical path differences of the interferometers of two clock boxes are sufficiently different to allow alignment of the phases from the swept sources. For example, a first clock box may comprise a first range of frequencies and phases lower than a second range of frequencies and phases provided by second clock box to facilitate alignment. The first range of frequencies can differ from the second range of frequencies by a factor within a range from about 2 to 20, for example differ within a range from about 5 to about 10. The optical path differences can differ by similar amounts. For example, an interferometer of a first clock box may comprise a first optical path difference, and the optical path difference of the second interferometer may comprise a second optical path difference different from the first optical path difference by a ratio within a range from about 2 to 20, for example differ by a ratio within a range from about 5 to about 10.

FIGS. 73A and 73B show plots of clockbox waveform signals generated by first and second VCSELs 4952 being merged without amplitude demodulation, in accordance with some embodiments. A first clockbox signal 7301 from the first VCSEL is shown aligned with the first clockbox signal 7302 from the second VCSEL, in response to aligning the phases as shown in FIGS. 72A and 72B. A second clockbox signal 7303 from the first VCSEL is shown aligned with the second clockbox signal 7304 from the second VCSEL, in response to aligning the phases as shown in FIGS. 72A and 72B. The interferometer signals from the measurement and reference arms of the OCT interferometer can be similarly aligned.

FIGS. 74A and 74B show plots of waveforms generated by first and second VCSELs 4952 being merged with amplitude demodulation, in accordance with some embodiments. A first amplitude demodulated clockbox signal 7401 from the first VCSEL is shown aligned with the first clockbox amplitude demodulated signal 7402 from the second VCSEL. A second amplitude demodulated clockbox signal 7403 from the first VCSEL is shown aligned with the second amplitude demodulated clockbox signal 7404 from the second VCSEL. The interferometer signals from the measurement and reference arms of the OCT interferometer can be similarly demodulated based on the demodulation of the clockbox signals.

Figure 75:
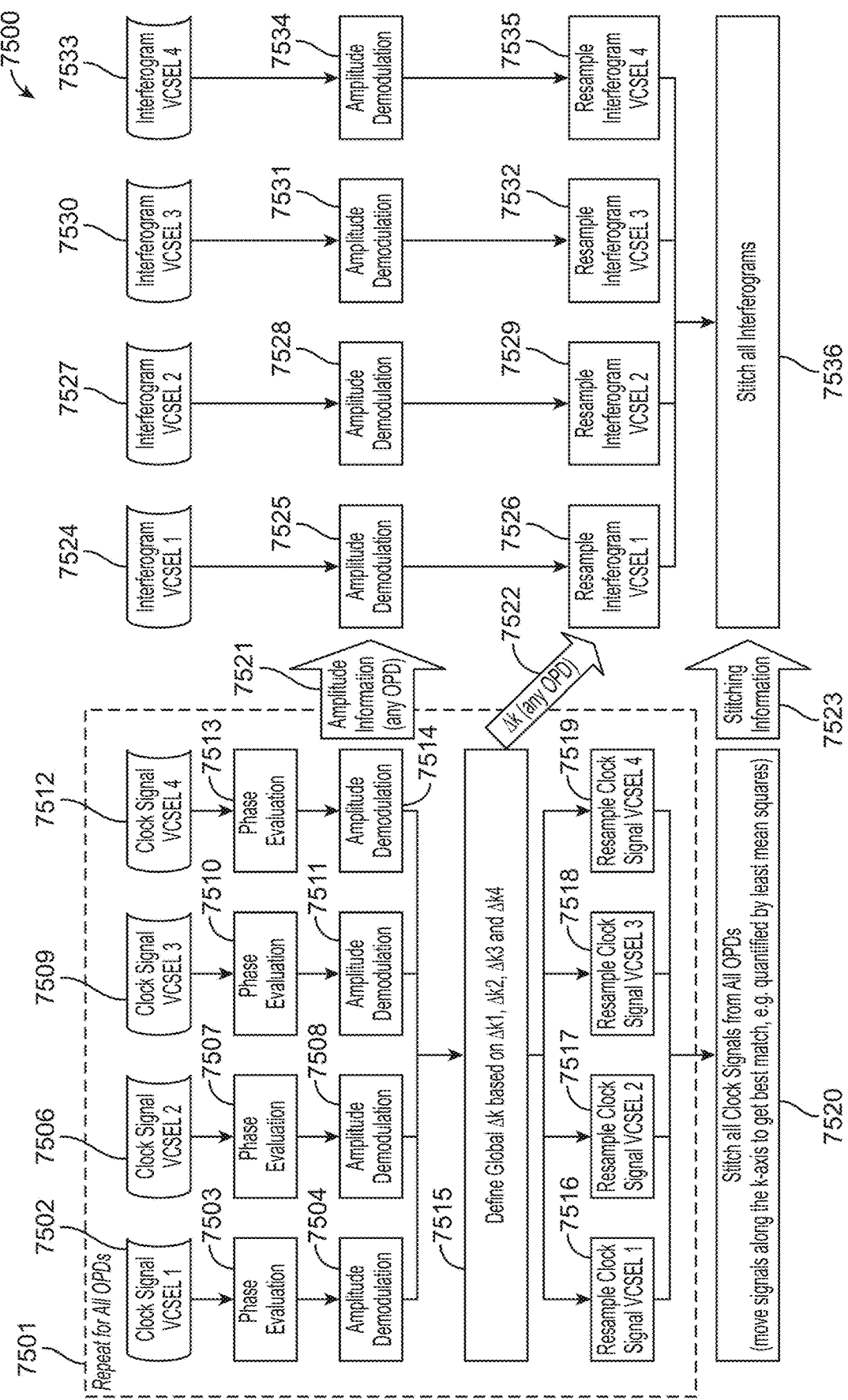
FIG. 75 shows a flow diagram illustrating the process for stitching signals together from a plurality of swept VCSELs, in accordance with some embodiments.

FIG. 75 shows a flow diagram 7500 illustrating the process for stitching signals together from a plurality of swept VCSELs, in accordance with some embodiments.

At a step 7502, a clock signal is generated with VCSEL 1 as described herein. The clock signal may comprise a clock signal from a single interferometer, or a plurality of interferometers as described herein. At a step 7503, the phase of the clock signal for VCSEL 1 is evaluated as described herein. At a step 7504, the clock signal from VCSEL 1 is amplitude demodulated as described herein.

These steps can be repeated for additional VCSELs. For example, at a step 7506, a clock signal is generated with VCSEL 2 as described herein. At a step 7507, the phase of the clock signal for VCSEL 2 is evaluated as described herein. At a step 7508, the clock signal from VCSEL 2 is amplitude demodulated. At a step 7509, a clock signal is generated with VCSEL 3 as described herein. At a step 7510, the phase of the clock signal for VCSEL 3 is evaluated as described herein. At a step 7511, the clock signal from VCSEL 3 is amplitude demodulated. At a step 7512, a clock signal is generated with VCSEL 4 as described herein. At a step 7513, the phase of the clock signal for VCSEL 4 is evaluated as described herein. At a step 7514, the clock signal from VCSEL 4 is amplitude demodulated.

At a step 7515, a global delta ($\Delta$) k is defined based on delta k1 for VCSEL 1, delta k2 for VCSEL 2, delta k3 for VCSEL 3 and delta k4 for VCSEL 4. At a step 7516, the clock signal for VCSEL 1 is resampled based on the global delta k values. At a step 7517, the clock signal for VCSEL 2 is resampled based on the global delta k values. At a step 7518, the clock signal for VCSEL 3 is resampled based on the global delta k values. At a step 7519, the clock signal for VCSEL 4 is resampled based on the global delta k values.

At a step 7501, steps 7502 to 7519 are repeated for additional optical path difference from additional clock boxes as described herein.

At a step 7520, the clock signals are stitched together for each optical path difference. For example, the signals can be moved along the global k-axis to provide a suitable match, for example a best match quantified by a least mean squares fit.

At step 7521, the amplitude demodulation data for each of the clock boxes and optical path lengths can be used to demodulate each of the retinal sample interferograms for each of the VCSELs. At a step 7524, an interferogram comprising interference signals from the OCT measurement and reference arms is generated with VCSEL 1. At a step 7525 the interferogram signal for VCSEL 1 is amplitude demodulated based on the amplitude demodulation from the clock box signal amplitude demodulation at step 7504.

Similar steps can be performed for additional VCSELs. For example, at a step 7527, an interferogram comprising interference signals from the OCT measurement and reference arms is generated with VCSEL 2. At a step 7528 the interferogram signal for VCSEL 2 is amplitude demodulated based on the amplitude demodulation from the clock box signal amplitude demodulation at step 7508. At a step 7530, an interferogram comprising interference signals from the OCT measurement and reference arms is generated with VCSEL 3. At a step 7531 the interferogram signal for VCSEL 3 is amplitude demodulated based on the amplitude demodulation from the clock box signal amplitude demodulation at step 7511. At a step 7533, an interferogram comprising interference signals from the OCT measurement and reference arms is generated with VCSEL 4. At a step 7534 the interferogram signal for VCSEL 4 is amplitude demodulated based on the amplitude demodulation from the clock box signal amplitude demodulation at step 7514.

The retinal sample interferograms for each of the VCSELs can be resampled based on the global delta k values determined with step 7515. At a step 7526, the retinal sample interferogram for VCSEL 1 is resampled in accordance with the global delta k values. At a step 7529, the retinal sample interferogram for VCSEL 2 is resampled in accordance with the global delta k values. At a step 7532, the retinal sample interferogram for VCSEL 3 is resampled in accordance with the global delta k values. At a step 7535, the retinal sample interferogram for VCSEL 4 is resampled in accordance with the global delta k values. At a step 7523, stitching information corresponding to the alignment of the stitched clock values for all OPDs can be used to stitch together the retinal sample interferograms for VCSEL 1 to VCSEL 4. The stitched retinal sample interferograms can then be transformed, e.g. Fourier transformed to generate a profile of intensity reflection along the measurement beam as described herein.

While flow diagram 7500 illustrates a method of generating a swept source OCT A-scan from a plurality of light sources in accordance with some embodiments, several modifications can be made. For example, some of the steps can be removed. Additional steps provided, and the steps can be performed in any order in accordance with the teachings provided herein.

A processor as described herein, can be coupled to the interferometer and configured with instructions to perform one or more steps of the process illustrated with flow diagram 7500.

Figure 76:
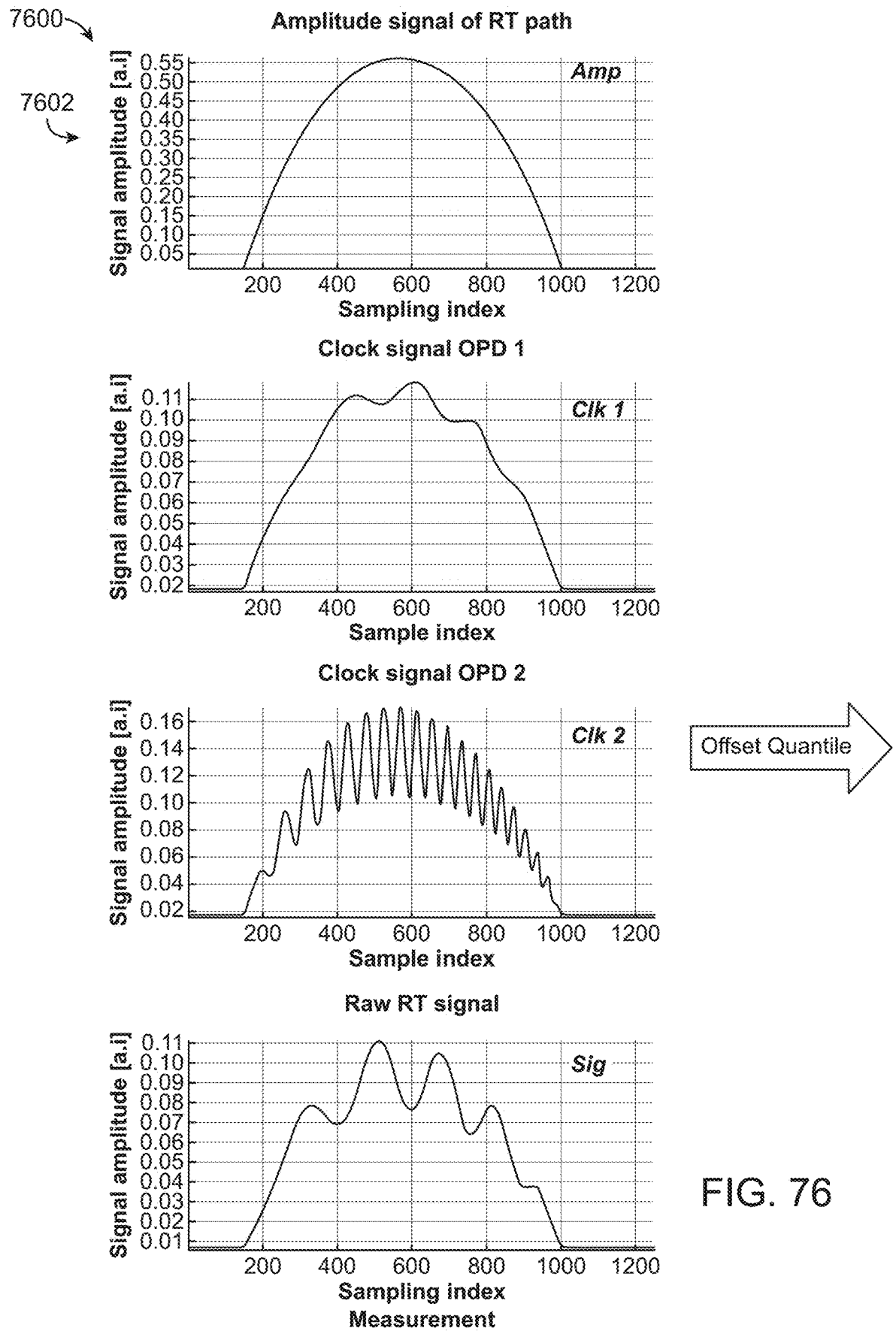
FIG. 76 shows a work flow diagram of a process for combining interference signals to generate an A-scan reflectance signal from a plurality of VCSELs, which can be combined with work flow process, in accordance with some embodiments.

FIG. 76 shows a work flow diagram 7600 of a process for combining interference signals to generate an A-scan reflectance signal from a plurality of VCSELs, which can be combined with work flow process 7500. Sample data 7602 is received from a plurality of detectors. The sample data comprises one or more an amplitude of laser intensity signal from a patient safety detector, a first raw clock signal from a first optical clock, a second raw clock signal from a second optical clock, and an interferometer measurement signal from a retina, as described herein. One more of these detector signals may comprise an offset in which the signal is not zero, even without any light shining on the corresponding detector. At an offset quantile step, the zero offset can be subtracted from one or more of the detector signals, so as to provide a zero offset at the edge of the one or more signals 7604. The offset-subtracted signals can then be amplitude demodulated to provide amplitude demodulated signals 7606. For example, the demodulated clockbox signals and OCT eye measurement signals can then be divided by the amplitude signal so as to normalize these values with respect to the output power of the corresponding VCSEL, resulting in normalized amplitude demodulated signals 7606. The offsets of the normalized signals can then be subtracted so that the signals oscillate around a value of zero, so as to provide zeroed data 7608. At a next step, the section of the signals corresponding to no light emission to the detectors can be set to zero, because the non-zero values of the signal in these sections correspond to noise. At a next step, the phase of the signals is determined from the clockbox signals to provide phase data signals 7612 as described herein. The phase data signals 7612 can be used to resample the data from the detectors to provide resampled data 7614. The phases of the resampled data 7614 can be phase adjusted to provide to provide phase aligned resampled signals 7616. The phase aligned resampled signals can be unified with respect to delta k values to provide unified delta k values 7618. The unified delta k values can be used to stitch together the OCT measurement interferometer signals from each of the plurality of VSCSELs. This data can be Fourier transformed determine the intensity reflectance values of an A-scan signal as described herein. The above steps can be repeated for additional A-scan measurements.

Although the work flow diagram 7600 shows a process in accordance with some embodiments, the process can be modified. For example, some of the steps can be repeated, some of the steps deleted, and the steps can be performed in any suitable order. This process can be combined with steps of other processes and methods as disclosed herein.

A processor as described herein, can be coupled to the interferometer and configured with instructions to perform one or more steps of the process illustrated with flow diagram 7600.

Figure 77:
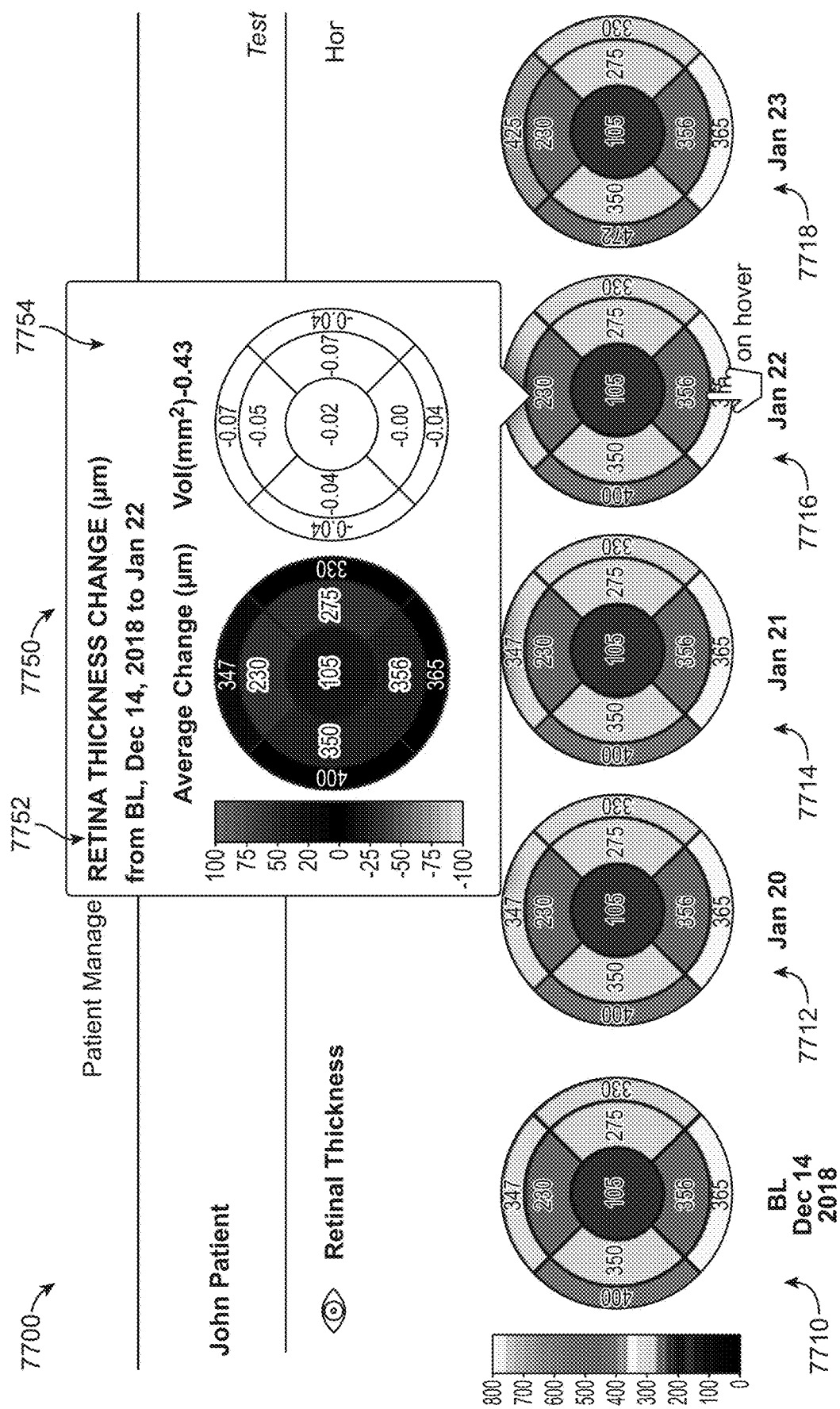
FIG. 77 shows a plurality of output maps of retinal thickness in accordance with some embodiments.

FIG. 77 shows a plurality of output maps 7700 of retinal thickness in accordance with some embodiments. The plurality of images may be shown on a display as described herein. The plurality of output maps may comprise a first output map 7710 from a first OCT measurement on a first day, a second output map 7712 from a second OCT measurement on a second day, a third output map 7714 from a third OCT measurement from a third day, a fourth output map 7716 from a fourth OCT measurement from a fourth day and a fifth output measurement 7718 from a fifth day.

A difference map 7750 shows a difference between an earlier measurement and a selected measurement. The user interface may comprise instructions to receive user input for a user to select a map. In response to the user selection of a map on from specific day, e.g. with a cursor, the processor is configured with instructions to generate a difference map between a baseline map and the selected map.

Each of the plurality of output maps and difference maps comprises a plurality of sectors. The plurality of sectors may comprise a central sector bounded a plurality of annular sectors. The plurality of annular sectors may comprise an inner annular sector and an outer annular sector. Each of the annular sector may comprise for quadrants, such as a left quadrant, a right quadrant, an upper quadrant and a lower quadrant. The thickness of the retina can be displayed in each of the plurality of sectors with a numeric value shown in each sector, and colored in accordance with the retinal thickness for each sector. The color coding can be continuous within each sector, or graded in response to the actual retinal thickness measurements.

The difference maps 7750 can be configured in many ways, and may comprise a map 7752 showing change thickness shown with a numerical value for each of the plurality of segments. The change in thickness can be color coded in accordance with the change in thickness, and the for each sector of the difference map. The difference map may comprise a difference map showing changes in the volume of the retina for a particular sector, which can be calculated based on the cross-sectional area of the sector and the change in thickness.

Additional data can be provided with each of the difference maps, such as a patient identifier. Also, the alignment of the eye relative to the OCT measurement system during the OCT scan of the retina as described herein. For example, the average alignment and one or more of the X, Y and Z coordinate references as described herein is shown with the map, with appropriate transformation to the coordinates of the map shown on the display. Alternatively or in combination, the maps can be adjusted in response the measured position of the eye as described herein, so as to center the map about a location corresponding to zero alignment error, for example.

Figure 78:
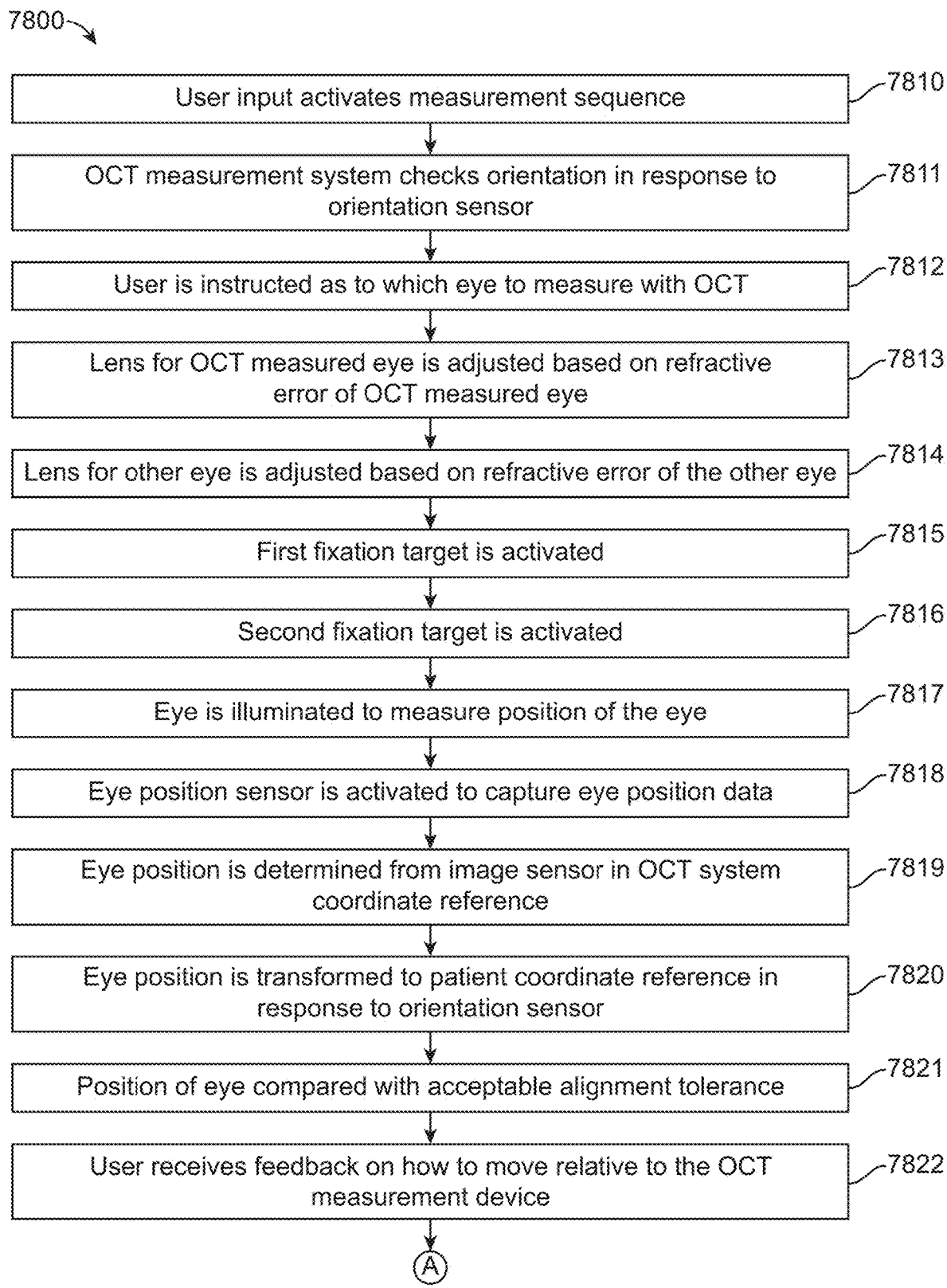
FIG. 78 shows a process for measuring an eye with an OCT device, in accordance with some embodiments.
Figure 78:
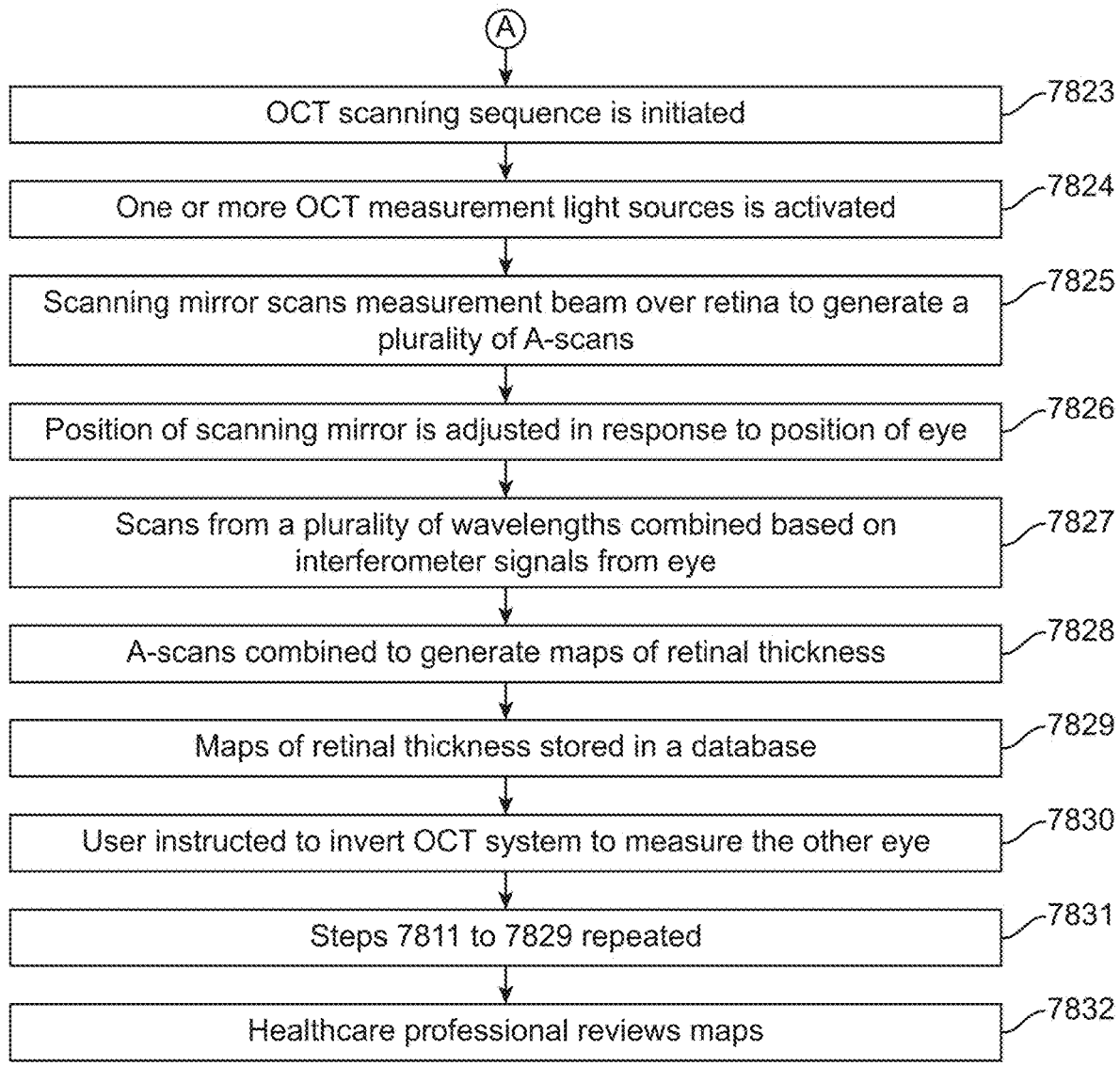

FIG. 78 shows a process 7800 for measuring an eye with an OCT system as described herein, such as a binocular OCT measurement system, in accordance with some embodiments.

At a step 7810, user input activates measurement sequence. The user input may comprise a button, switch, display, or voice command indicating that the user is ready to take a measurement.

At a step 7811, the OCT measurement system checks orientation of the OCT measurement in response to the orientation sensor as described herein.

At a step 7812, the user is instructed as to which eye to measure with OCT system. The instruction may comprise a voice command, an instruction on a display, or an instruction near the fixation target such as a blinking light or color of the fixation target.

At a step 7813, a lens for OCT measured eye is adjusted based on refractive error of OCT measured eye. The refractive error of each eye can be stored in the processor memory and the lens adjusted in response to the orientation of the OCT system. This adjustment can bring the fixation target into focus and focus the OCT measurement beam on the retina.

At a step 7814, a lens for other eye is adjusted based on refractive error of the other eye. This adjustment can bring the fixation target for the other eye into focus.

At a step 7815, a first fixation target is activated. For example, an LED can be turned on to back illuminate the fixation target.

At a step 7816, second fixation target is activated. For example, a second LED can be turned on to back illuminate the fixation target.

At a step 7817, the eye is illuminated to measure position of the eye. The eye can be illuminated as described herein, for example to generate a Purkinje image from the cornea.

At a step 7818, the eye position sensor is activated to capture eye position data. The eye position sensor may comprise any eye position sensor as disclosed herein. For example, the eye position sensor may comprise a CMOS image sensor to generate a Purkinje image.

At a step 7819, the eye position for the measured eye is determined from image sensor in OCT system coordinate reference. The eye position may comprise X, Y positions of the eye and optionally a Z position as described herein.

At a step 7820, the eye position data is transformed to patient coordinate reference in response to orientation sensor. The X and Y values of the eye position can be transformed in response to the orientation of the position sensor as described herein, so that the output position values correspond to the position of the eye from the patient coordinate reference.

At a step 7821, the position of the eye compared with acceptable alignment tolerance.

At a step 7822, the user receives feedback on how to move relative to the OCT measurement device. For example, if the position of the eye is outside the tolerance window, the user is instructed to move the eye relative to the OCT system or to move the OCT system relative to the eye.

At a step 7823, the OCT scanning sequence is initiated. For example, when the eye position is within an acceptable tolerance window, the OCT scanning sequence can be initiated.

At a step 7824, one or more OCT measurement light sources is activated. The light source may comprise a swept source or other light source as disclosed herein.

At a step 7825, a scanning mirror scans measurement beam over retina to generate a plurality of A-scans. The scanning mirror can be scanned in a preprogrammed sequence as described herein.

At a step 7826, the position of the scanning mirror is adjusted in response to position of eye. In some embodiments, the position of the scanning beam and/or scanning pattern is adjusted in response to the measured X and Y positions of the eye, and these positions of the mirror can be adjusted in response to the orientation sensor. This can help to better align the retinal thickness measurement data with repeated scans, for example on different days.

At a step 7827, scans from a plurality of wavelengths are combined based on interferometer signals from eye. Depending on the type of OCT system used, the scans from a plurality of light sources such as a plurality of VCSELs can be combined to generate an A-scan as described herein.

At a step 7828, A-scans are combined to generate maps of retinal thickness. A plurality of A-scans can be generated as the OCT system mirror scans the retina. The above steps can be repeated.

At a step 7829, the maps of retinal thickness are stored in a database. The stored data may comprise additional data such as a patient identifier and a position of the eye when the OCT scan is obtained.

At a step 7830, a user is instructed to invert OCT system. The user can be instructed to invert the OCT system to measure the other eye with the OCT measurement system.

At a step 7831, steps 7811 to 7829 are repeated for the other eye.

At a step 7831, a healthcare professional reviews the maps. The maps can be reviewed to determine changes in retinal thickness with a user interface as described herein. Appropriate steps can be taken such as notifications as described, in response to changes in retinal thickness.

Although process 7800 to measure retinal thickness is described in accordance with an embodiment, the process can be modified in many ways. For example, some of the steps can be repeated, some of the steps omitted, and the steps can be performed in any suitable order. A processor as described herein can be configured to perform one or more steps of process 7800.

EXAMPLES

Example 1: Limit of Detection for RT or RLT Measurements

Figure 14:
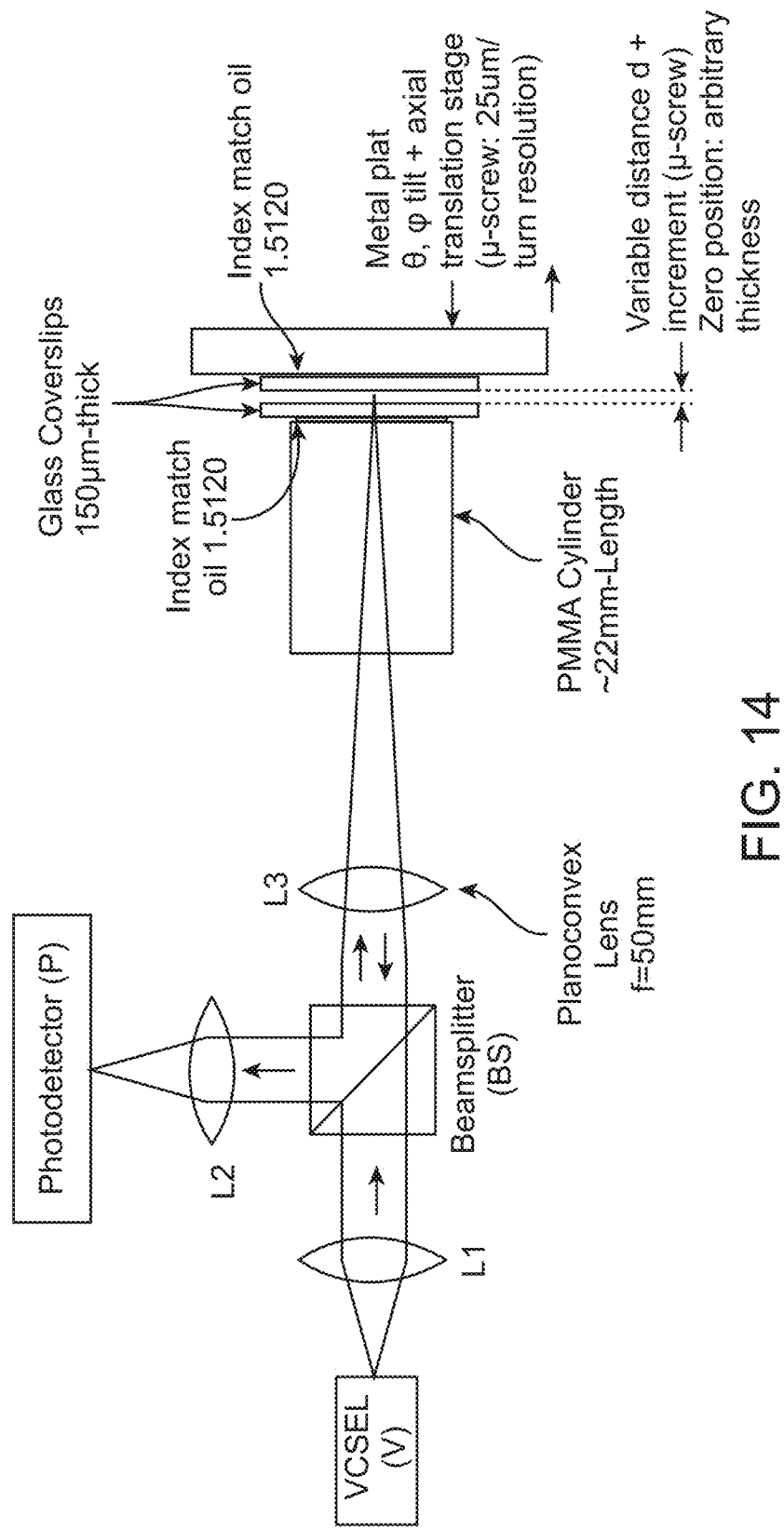
FIG. 14 shows an optical setup for determining the limit of detection of an SS-OCT system utilizing a single VCSEL and no reference arm.

FIG. 14 shows an optical setup for determining the limit of detection for measuring a change in RT or RLT using an SS-OCT system utilizing a single VCSEL and no reference arm. The setup comprises a VCSEL (V), a photodetector (P), a collimating lens (L1), a beamsplitter (BS), a lens (L2) for focusing light onto the photodetector, a lens (L3) for focusing light onto the sample, a 22 mm long cylinder made of polymethylmethacrylate (PMMA), index match oil with a refractive index of 1.5120, two 150 µm thick glass coverslips with an adjustable air gap between them, a second layer of index match oil with a refractive index of 1.5120, and a metal plate connected to a translation stage to produce changes in the distance between the first glass coverslip and the second glass coverslip. The distance between the two coverslips is varied by turning a microscrew with a resolution of 25 µm per turn. The SS-OCT signal is generated by interference between light reflected from the first glass-air interface and the second glass-air interface.

Example 2: Performance of a VCSEL Driven Out of its Rated Operating Range

Figure 15:
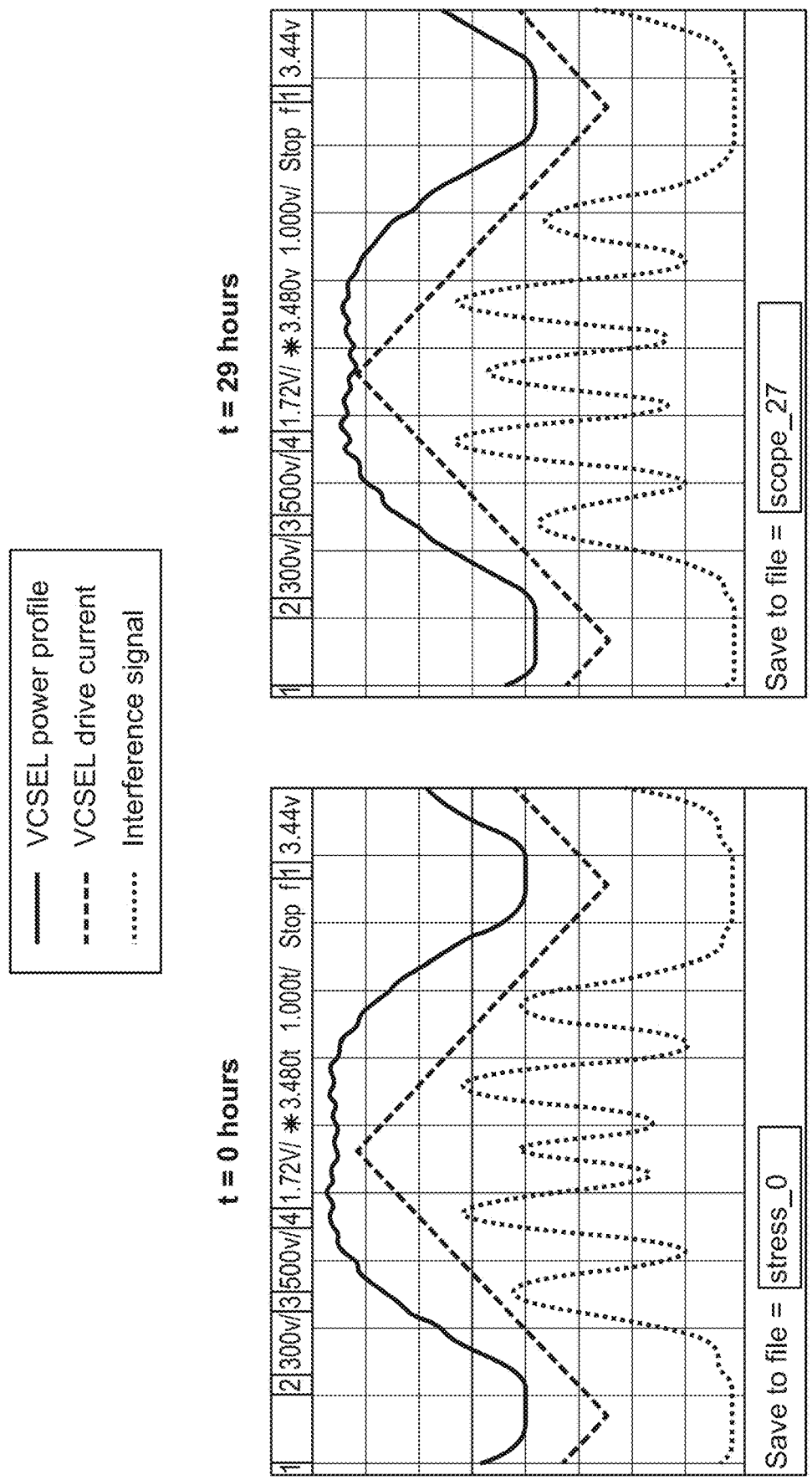
FIG. 15 shows oscilloscope signals at two different points in time for a VCSEL driven out of its rated operating range.

FIG. 15 shows oscilloscope signals at two different points in time for a VCSEL driven out of its rated operating range. The VCSEL had a central wavelength of approximately 850 nm and a rated range of emission wavelengths of approximately 1.8 nm. The VCSEL current was continuously swept in a triangular pattern with a maximum electric current of 15 mA. The current was swept at a frequency of 125 Hz. The experiment consisted of four intervals each of approximately 7.25 hours of continuous sweeping. Between each interval, the VCSEL was shut down for several hours. The VCSEL current (green), VCSEL power (red), and the interference signal (purple) were recorded at least every two hours. The measured values of all three parameters varied little between the first measurement at 0 hours of operation and a subsequent measurement after the VCSEL had been in operation for 29 hours. Thus, it can be concluded that a VCSEL driven out of its rated operating range may continue to produce useful SS-OCT measurements after at least 29 hours of use. This compares favorably with the usage requirements for a VCSEL implemented in a handheld SS-OCT device. Assuming the device is used for 20 seconds per measurement, twice per day, for five years, a VCSEL will accumulate approximately 20 hours of active use. Thus, a handheld SS-OCT device based on a VCSEL driven out of its rated operating range may continue to produce useful results for its entire intended operating life.

Example 3: OCT Signals for Varying Thicknesses

FIG. 16 shows oscilloscope signals for two different configurations of the optical setup of FIG. 14. The VCSEL had a central wavelength of approximately 850 nm and a rated range of emission wavelengths of approximately 1.8 nm. The VCSEL current was continuously swept in a triangular pattern with a maximum electric current of 15 mA. The current was swept at a frequency of 125 Hz. The VCSEL drive current (green) and the interference signal (purple) were recorded using an oscilloscope. Two glass cover slides of 150 µm thickness were placed at an arbitrary distance apart, referred to as the zero position. The zero position was chosen such that 2-3 periods were recorded from the interference signal resulting from light reflecting from the first glass cover slide and light reflecting from the second glass cover slide. Changes in the distance between the two glass coverslips produced changes in the frequency of oscillation of the interference signal. For instance, at the zero position, the interference signal varied with a frequency of approximately 950 Hz. After adding a 25.0 µm displacement from the zero position to the distance between the two coverslips, the interference signal varied with a frequency of approximately 1050 Hz.

Example 4: Extraction of Frequencies from Interference Signals

Figure 17:
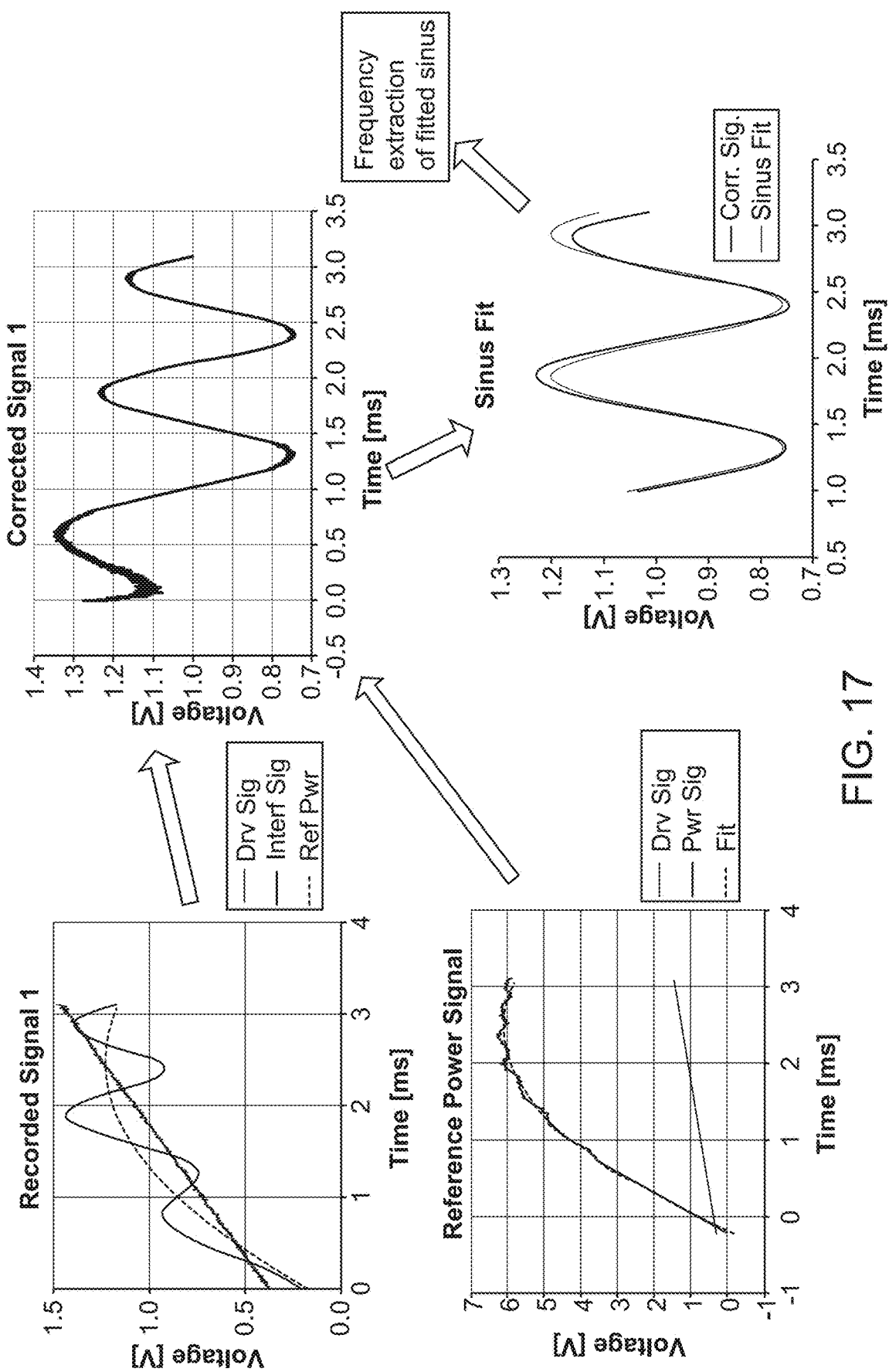
FIG. 17 shows a method of signal processing for extracting the frequency of oscillation of the interference signal generated using an SS-OCT system utilizing a single VCSEL and no reference arm.

FIG. 17 shows a method of signal processing for extracting the frequency of oscillation of the interference signal generated using an SS-OCT system utilizing a single VCSEL and no reference arm. The interference signal recorded on the oscilloscope is corrected by dividing the interference signal by the VCSEL optical power. This produces a slowly decaying sinusoid. The corrected data is then fit to a sinusoid using a non-linear least squares fitting procedure. The frequency of oscillation of the corrected interference signal is extracted from the non-linear least squares fit.

Example 5: Repeatability Measurements

Figure 18:
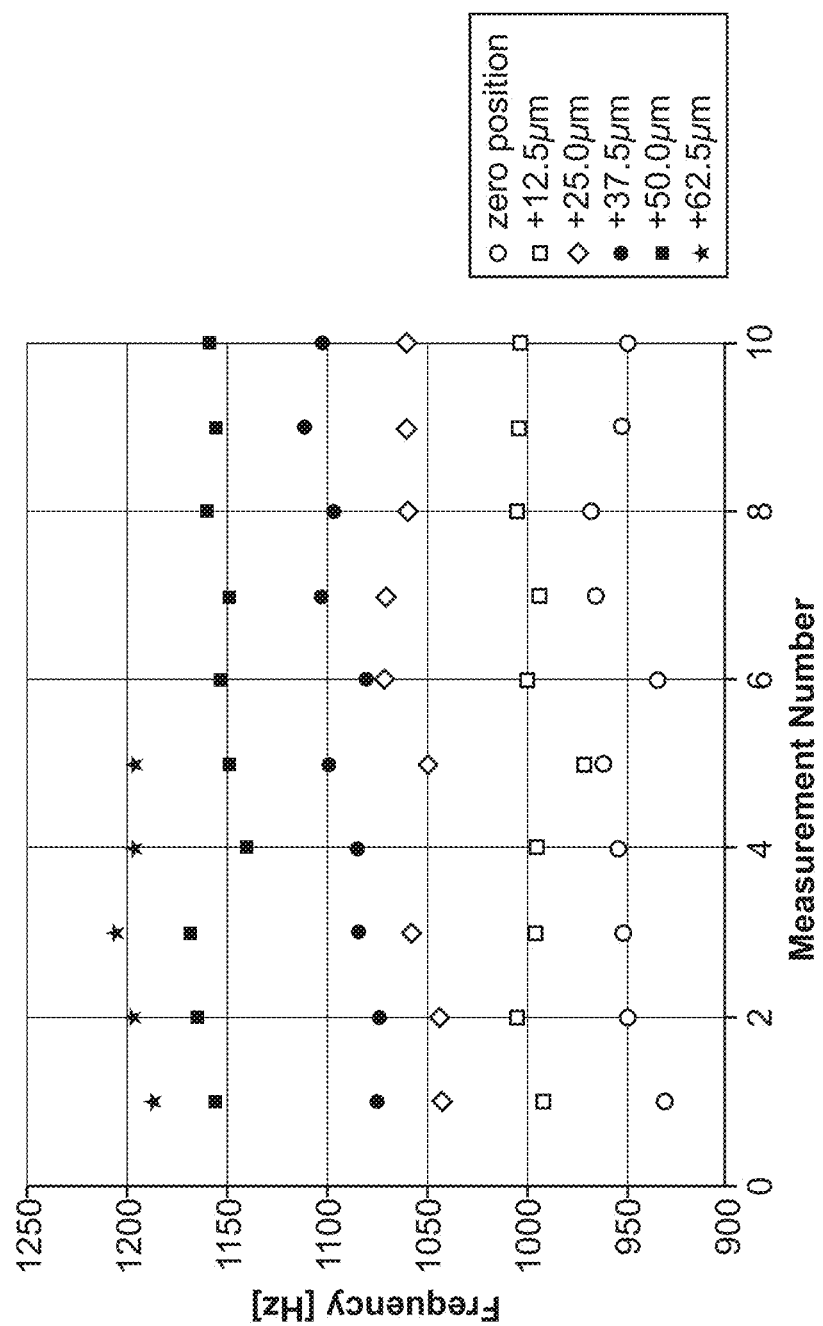
FIG. 18 shows the results of a study to determine the reproducibility of extracting the frequency of oscillation of the interference signal generated using an SS-OCT system utilizing a single VCSEL and no reference arm.

FIG. 18 shows the results of a study to determine the repeatability of extracting the frequency of oscillation of the interference signal generated using an SS-OCT system utilizing a single VCSEL and no reference arm. The distance between the two glass coverslips was varied in increments of 12.5 µm. The frequency of the sinusoidal fit was attained from the interference signal at each value of the distance between the two glass coverslips. The experiment was replicated 5 or 10 times for each value of the distance between the two glass coverslips.

Figure 19:
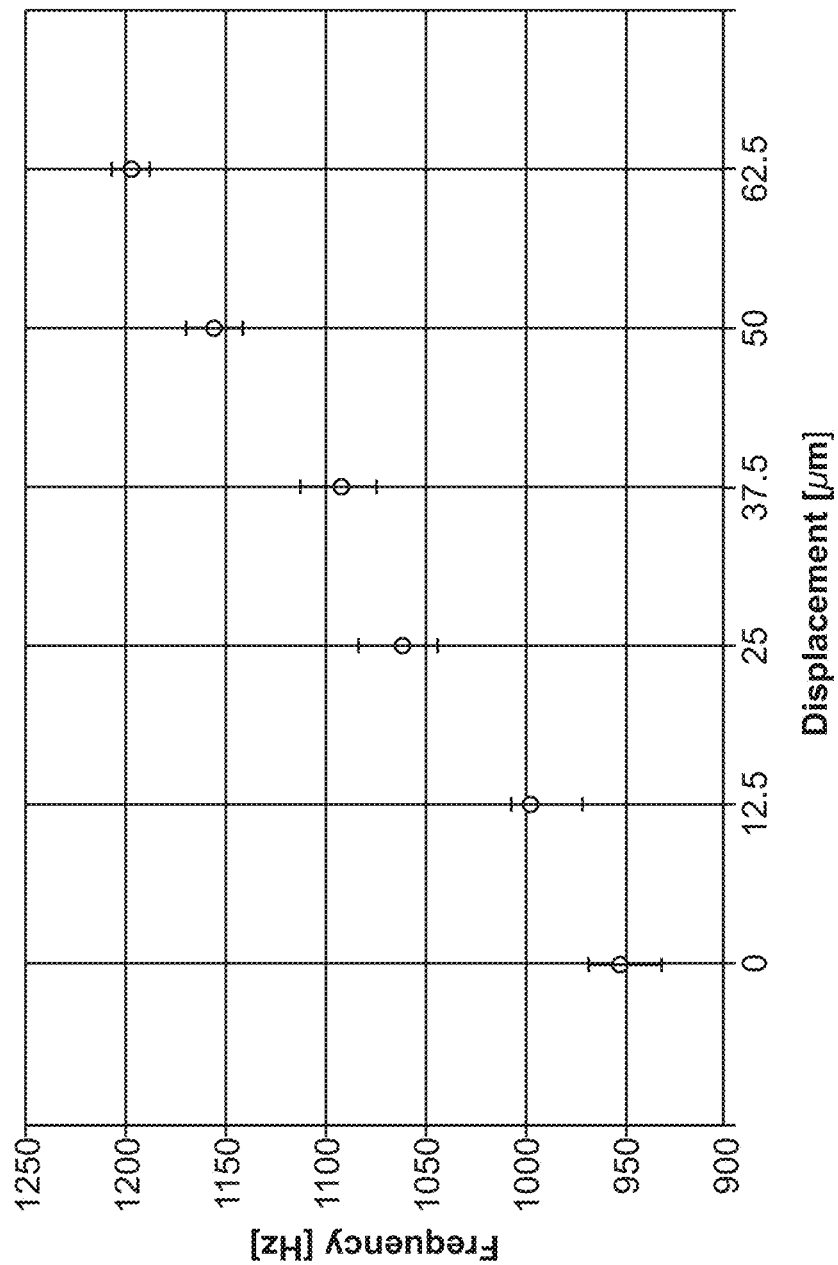
FIG. 19 shows the means and 95% confidence intervals of the frequencies obtained during the study to determine the reproducibility of extracting the frequency of oscillation of the interference signal generated using an SS-OCT system utilizing a single VCSEL and no reference arm.

FIG. 19 shows the means and 95% confidence intervals of the frequencies obtained during the study to determine the reproducibility of extracting the frequency of oscillation of the interference signal generated using an SS-OCT system utilizing a single VCSEL and no reference arm. With the exception of the 25 µm and 37.5 µm data points, each of the tested distances is separated from the other tested distances by more than two standard deviations from the distances 12.5 µm less than itself and 12.5 µm greater than itself. For all data points, each of the tested distances is separated from the other tested distances by more than two standard deviations from the distances 25.0 µm less than itself and 25.0 µm greater than itself. Thus, it can be surmised that this method for determining changes in the thickness of a layer (here, the air gap between two glass coverslips) has a limit of detection for changes in the thickness of a layer which is between 12.5 µm and 25.0 µm. This compares favorably with the operating requirements for a handheld SS-OCT system for measuring changes in the RT.

Example 6: Fundus Imaging

Figure 37A:
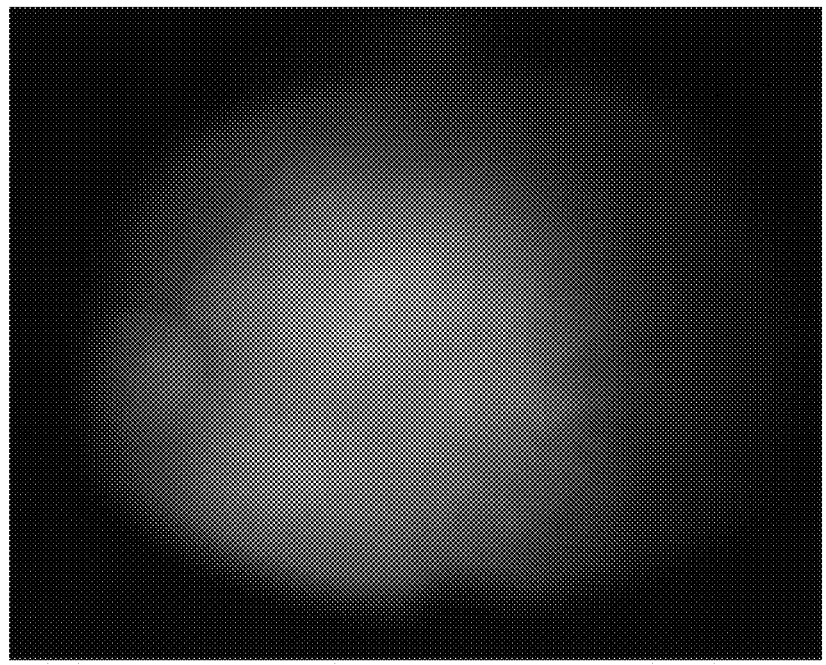
FIG. 37A, FIG. 37B, and FIG. 37C show exemplary fundus images obtained using the systems and methods described herein.
Figure 37B:
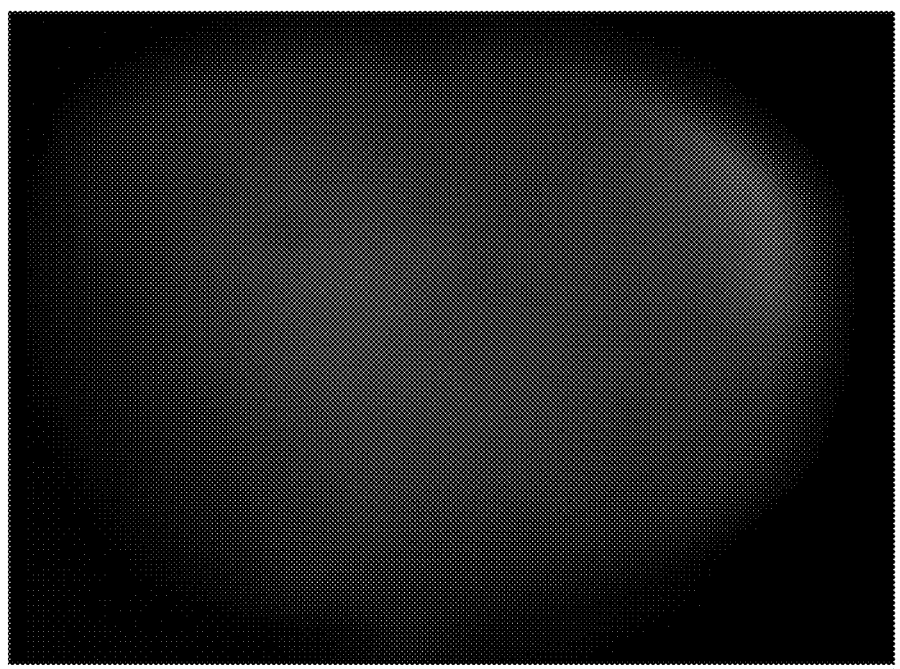
Figure 37C:
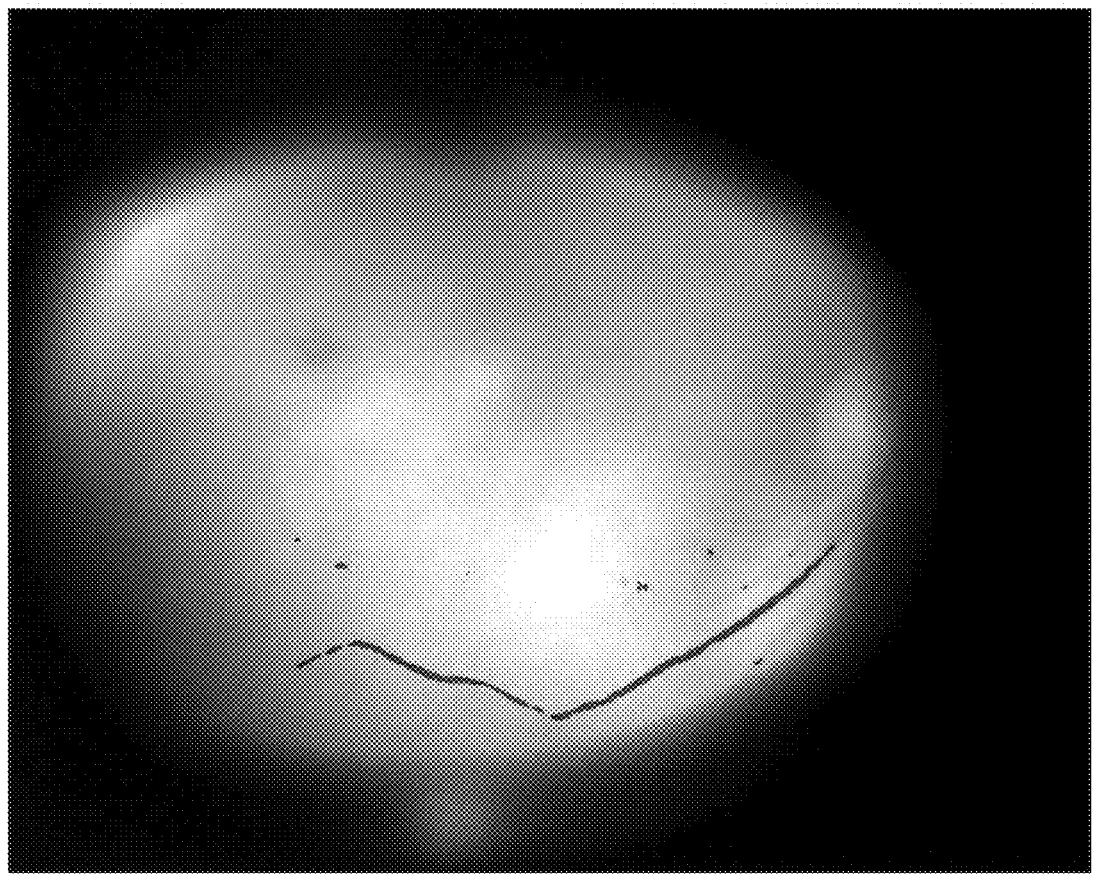

FIGS. 37A-C show exemplary fundus images obtained using the systems and methods described herein. FIG. 37A shows a fundus image with a relatively high contrast and a relatively high amount of observable structure. FIG. 37B shows a fundus image with a relatively low contrast and a relatively low amount of observable structure. FIG. 37C shows an enhanced fundus image subjected to the fundus recognition methods described herein. The fundus image in FIG. 37C was obtained by applying the fundus recognition methods described herein to the image of FIG. 37B (a fundus image with a relatively low contrast and a relatively low amount of observable structure). As shown in FIG. 37C, the vein of the fundus is clearly identified using the fundus recognition methods described herein. Thus, the fundus recognition methods are capable of detecting a location of a substructure of a fundus in a fundus image even when the fundus images are of relatively low quality. The substructure of the fundus may be used for image registration.

Example 7: Re-Sampling for Chirp Correction

Figure 38A:
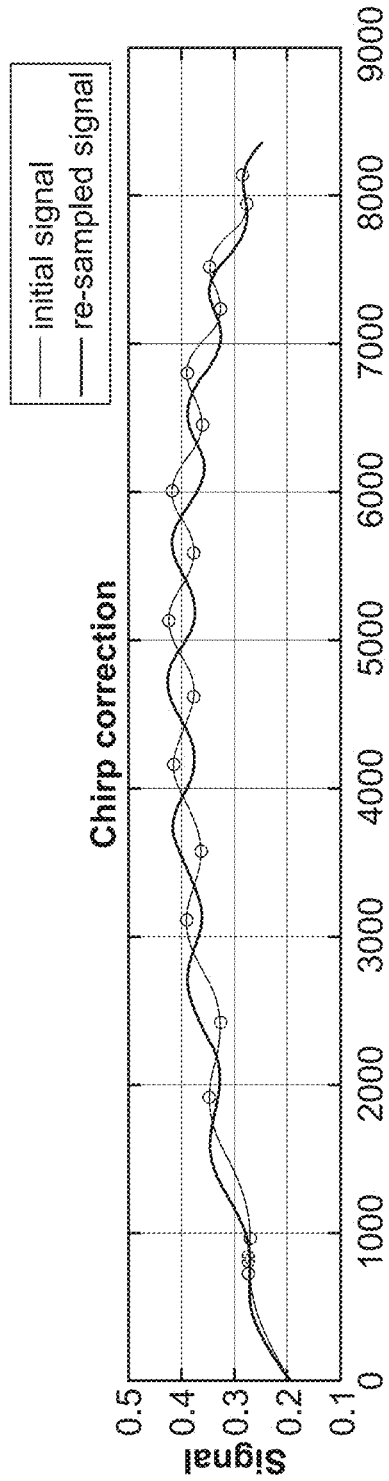
FIG. 38A, and FIG. 38B show the effects of re-sampling for chirp correction of a SS-OCT signal in the time domain.
Figure 38B:
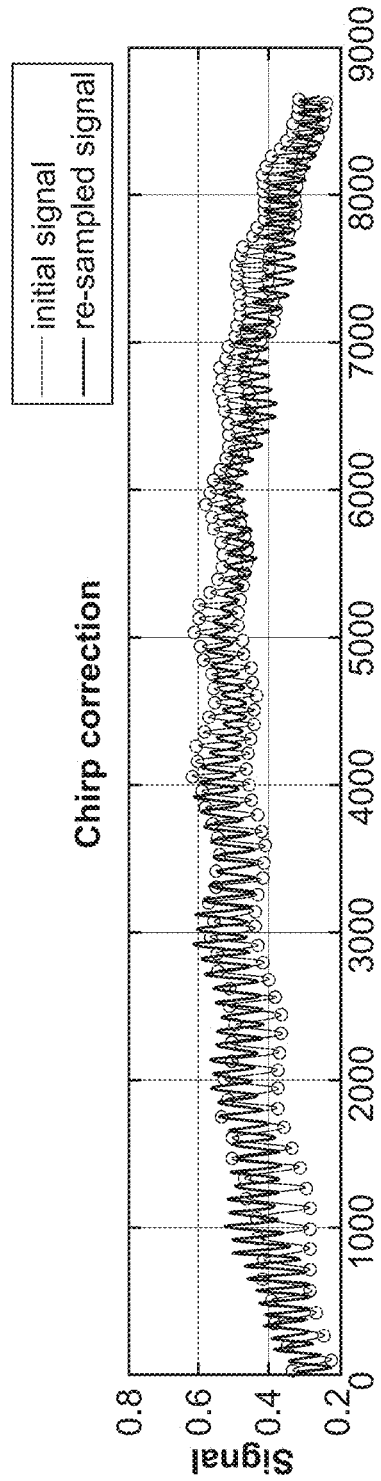

FIGS. 38A-B show the effects of re-sampling for chirp correction of a SS-OCT signal in the time domain. FIG. 38A shows the effects of re-sampling for chirp correction of a SS-OCT signal having a relatively low frequency. FIG. 38B shows the effects of re-sampling for chirp correction of a SS-OCT system having a relatively high frequency. The results of the re-sampling procedure are shown in the frequency domain in FIGS. 39A-C.

Example 8: Frequency Drift of Uncorrected and Chirp Corrected SS-OCT Signals

Figure 39A:
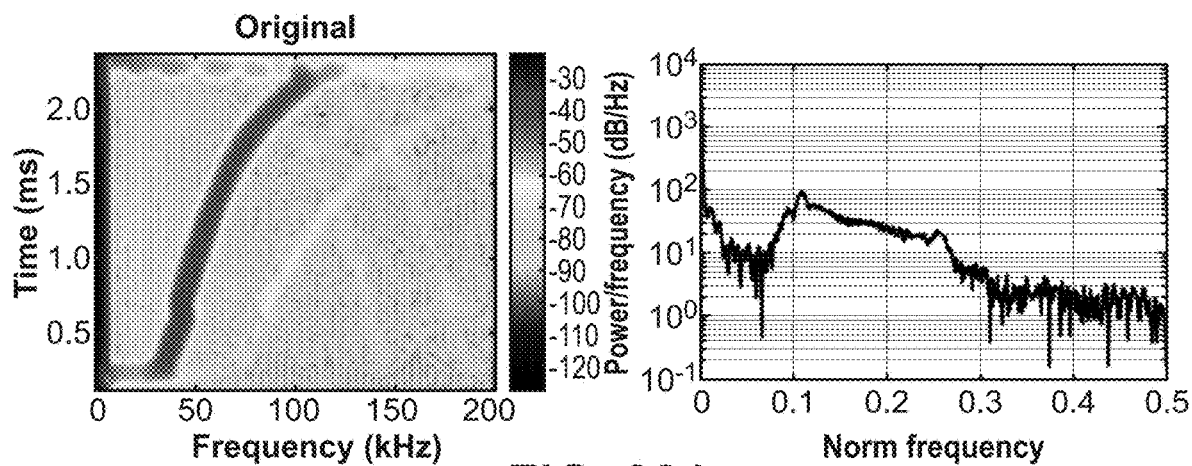
FIG. 39A, FIG. 39B, and FIG. 39C show the frequency drift of uncorrected and chirp corrected SS-OCT signals in the frequency domain.
Figure 39B:
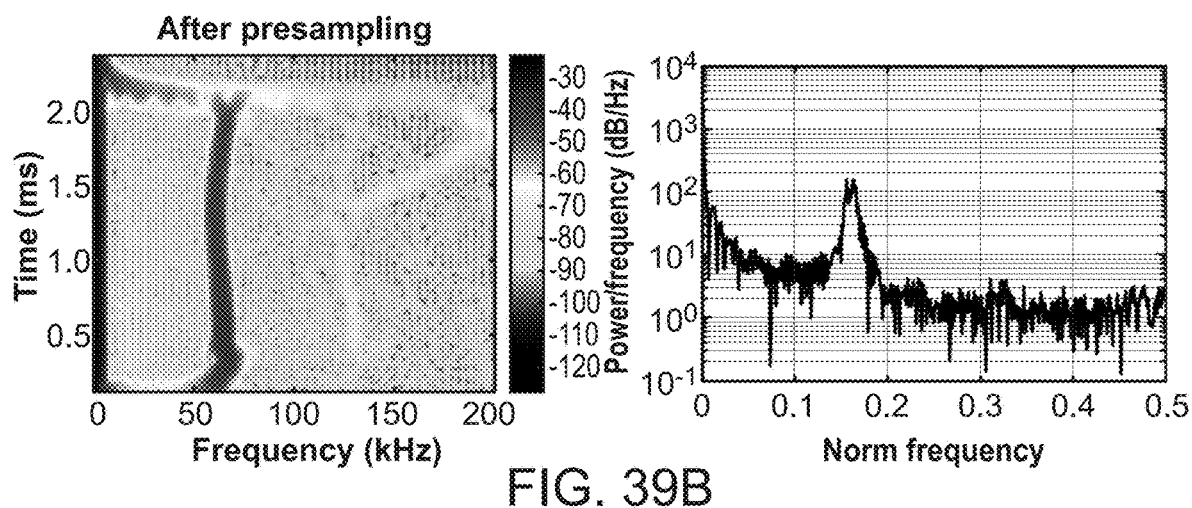
Figure 39C:
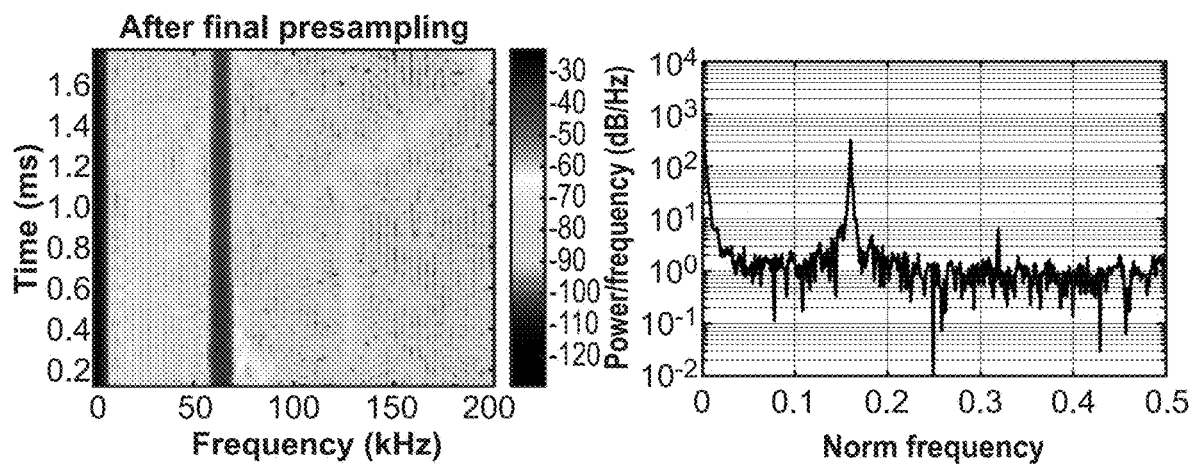

FIGS. 39A-C show the frequency drift of uncorrected and chirp corrected SS-OCT signals in the frequency domain. FIG. 39A shows frequency drift of a SS-OCT signal that has not been corrected by the re-sampling methods for chirp correction described herein. The uncorrected SS-OCT signal is subject to drift over more than 50 kHz over a period of about 2 seconds. FIG. 39B shows frequency drift of a SS-OCT signal that has been subjected to presampling for chirp correction. The signal shows significantly smaller frequency drift, varying by a few Hz over a period of about 2 seconds. FIG. 39C shows frequency drift of a SS-OCT signal that has been subjected to a final resampling for chirp correction. The signal shows still smaller frequency drift, varying by an imperceptible amount over a period of about 1.6 seconds. Thus, frequency drift may be corrected using chirp correction or resampling methods, as described herein. Reduction of the frequency drift using the re-sampling methods described herein results in a narrower measured frequency distribution, yielding more precise RT or RLT measurements with higher signal-to-noise ratios.

Example 9: Phase Drift Due to a Variety of Noise Sources

Figure 40A:
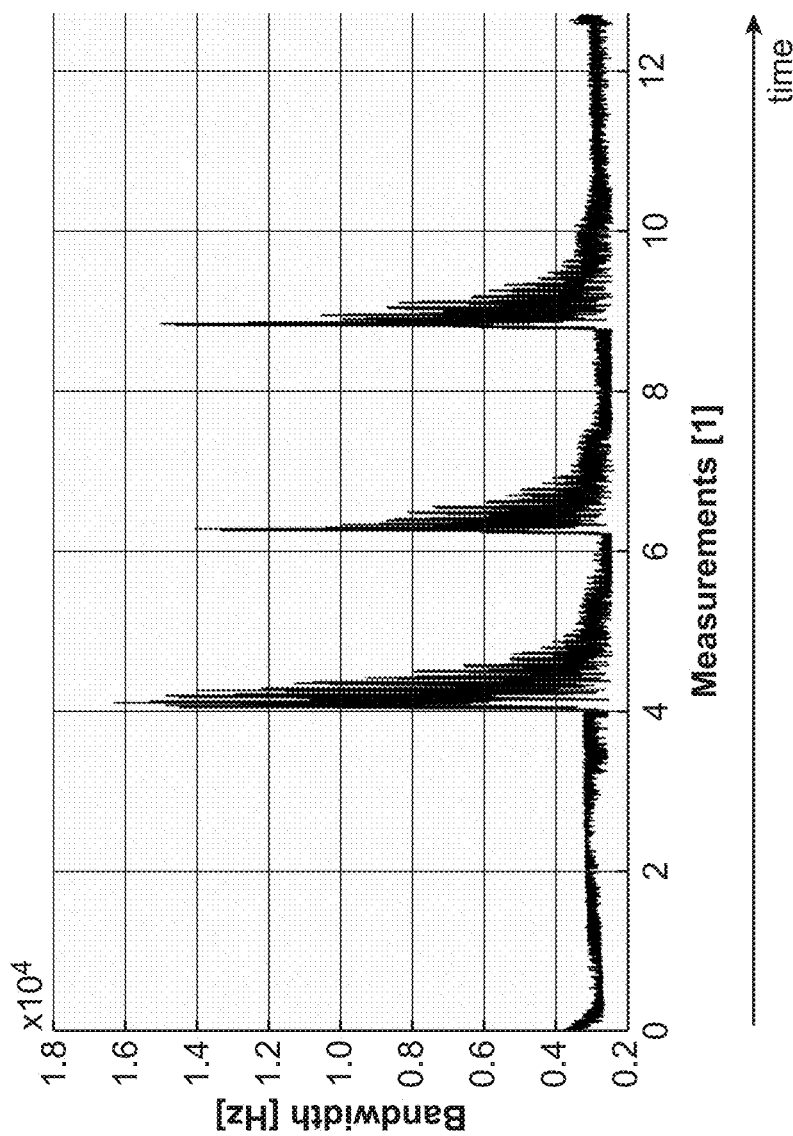
FIG. 40A, FIG. 40B, and FIG. 40C show exemplary phase drifts of uncorrected SS-OCT signals associated with a variety of sources of noise.
Figure 40B:
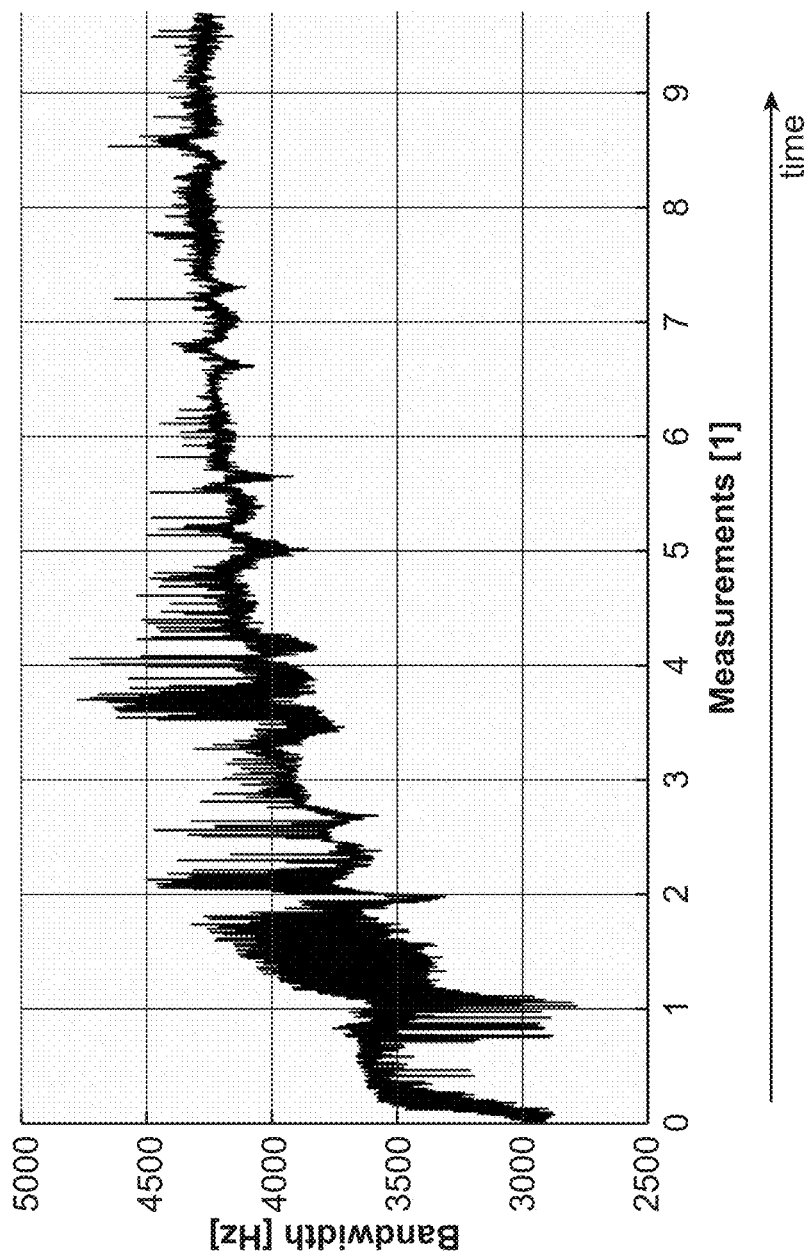
Figure 40C:
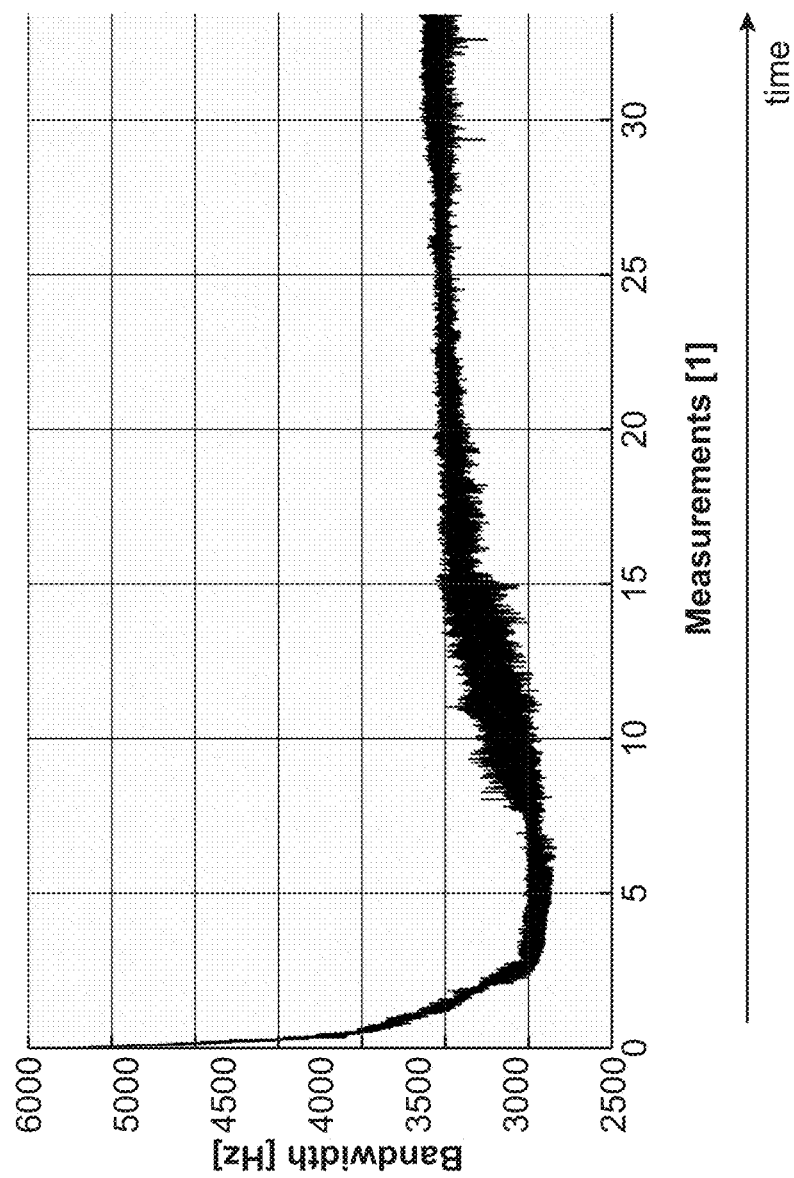

FIGS. 40A-C show exemplary phase drifts of uncorrected SS-OCT signals associated with a variety of sources of noise. FIG. 40A shows phase drift of an SS-OCT signal associated with noise resulting from vibrations. The large spikes in the bandwidth of the SS-OCT signal result from intentionally hitting the floor. FIG. 40B shows phase drift of an SS-OCT signal associated with noise resulting from varying spatial filtering of the light source. The bandwidth of the SS-OCT signal varies by up to 2 kHz over time. FIG. 40C shows phase drift of an SS-OCT signal associated with noise levels resulting from optimal conditions. After transient behavior, the SS-OCT signal settles to a relatively constant bandwidth when operation conditions are kept as constant as possible. Even in this ideal situation, the bandwidth of the SS-OCT signal still varies by up to 500 Hz over time. Thus, it can be seen that uncorrected SS-OCT signals may be subject to significant changes in bandwidth, even when operating at ideal conditions. The SS-OCT signals may be corrected to significantly reduce the variation in bandwidth over time using the resampling methods as described herein.

Example 10: Correction of Phase Shifts Associated with Patient Movement

Figure 41A:
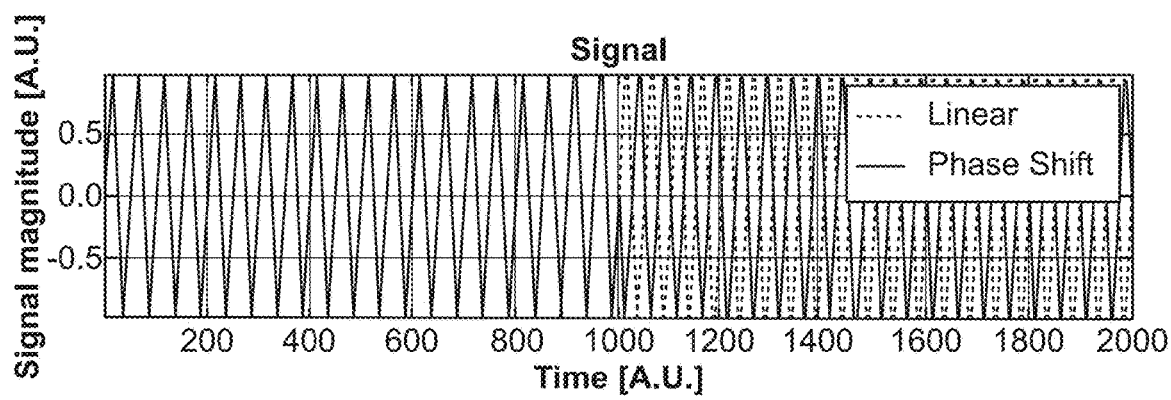
FIG. 41A, FIG. 41B, FIG. 41C, and FIG. 41D show simulations of phase shifts associated with patient movement.
Figure 41B:
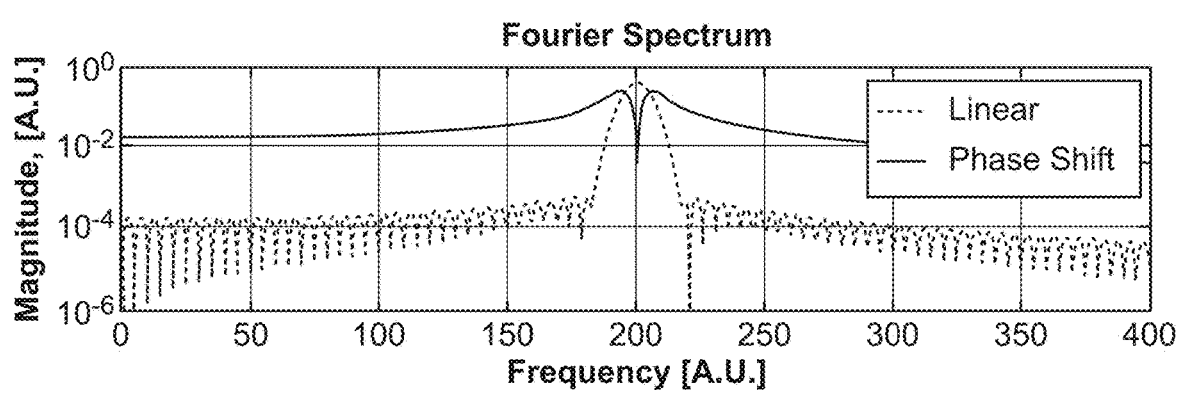
Figure 41C:
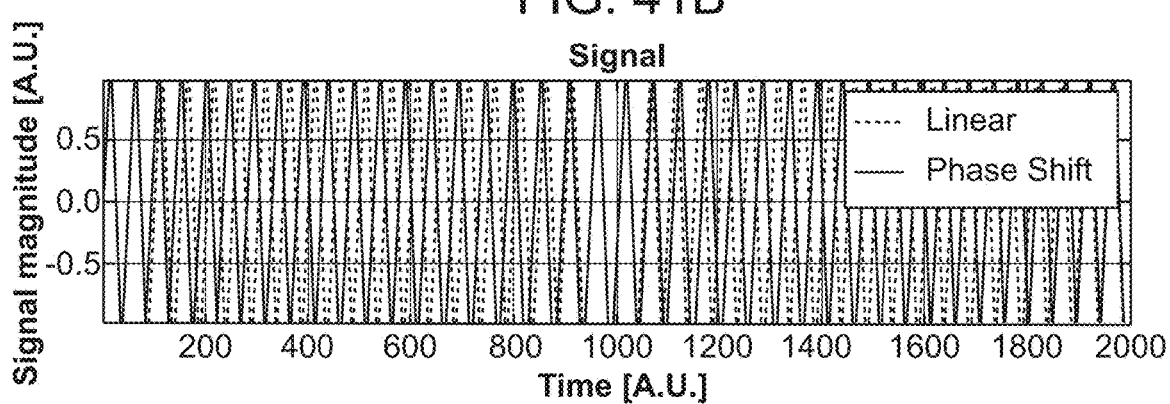
Figure 41D:
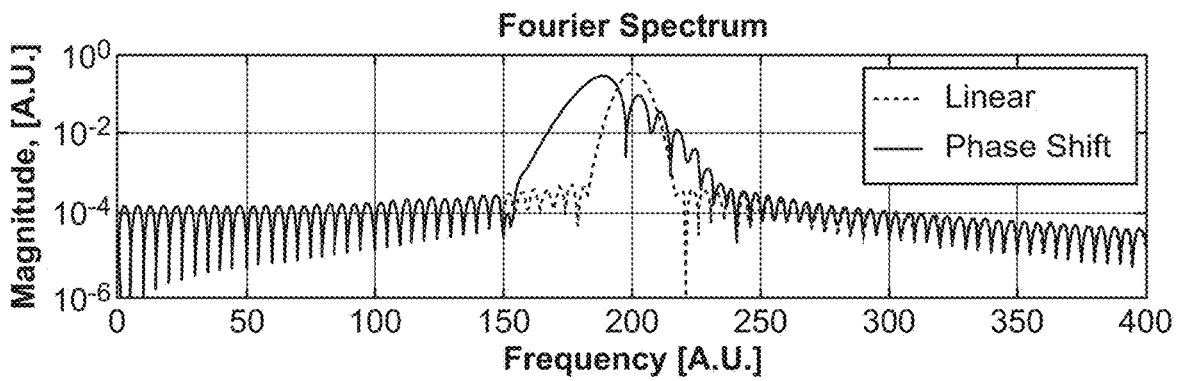

FIGS. 41A-D show simulations of phase shifts associated with patient movement. FIG. 41A shows a simulated signal subjected to a phase shift of $\pi$ radians over a duration of half the signal length. FIG. 41A shows the frequency spectrum of a simulated signal subjected to a phase shift of $\pi$ radians over a duration of half the signal length. A phase shift of $\pi$ radians corresponds to a patient movement of approximately 225 nm for light having a wavelength of 850 nm. The phase shift imparts a significant error in the frequency spectrum. FIG. 41C shows a simulated signal subjected to a phase shift of $\pi$ radians over a duration of a single cycle of the signal. FIG. 41D shows the frequency spectrum of a simulated signal subjected to a phase shift of $\pi$ radians over a duration of a single cycle of the signal. Though present for only a brief amount of time, the phase shift still imparts a significant error in the frequency spectrum. These phase shifts may be corrected by utilizing fast A-scans or chirp correction methods, as described herein.

Figure 42A:
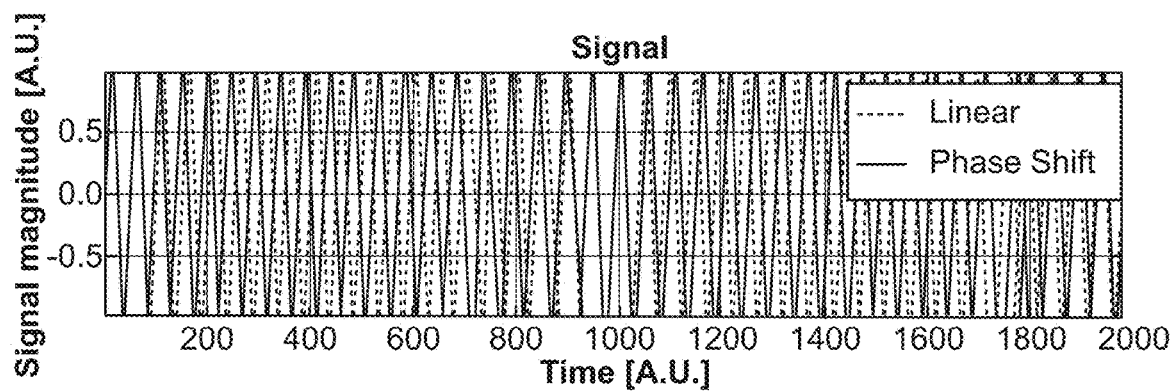
FIG. 42A, FIG. 42B, FIG. 42C, and FIG. 42D show simulations of the effect of A-scan time on the error arising from phase shifts associated with patient movement.
Figure 42B:
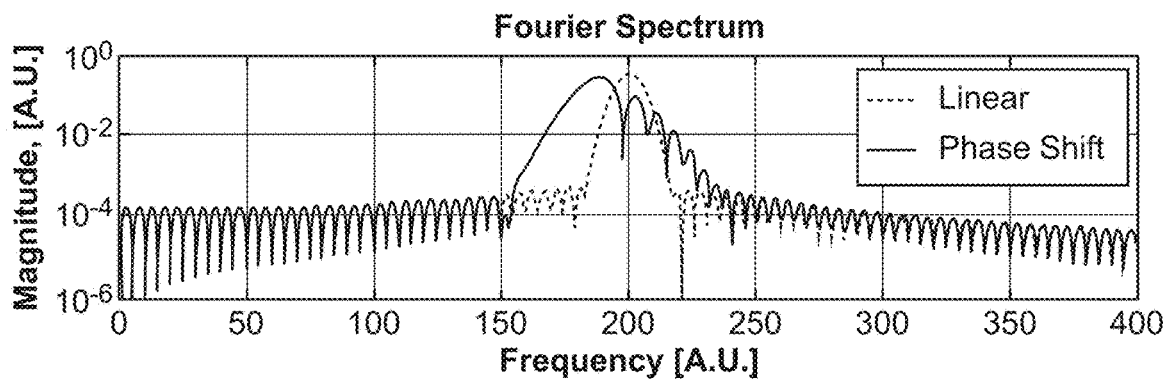
Figure 42C:
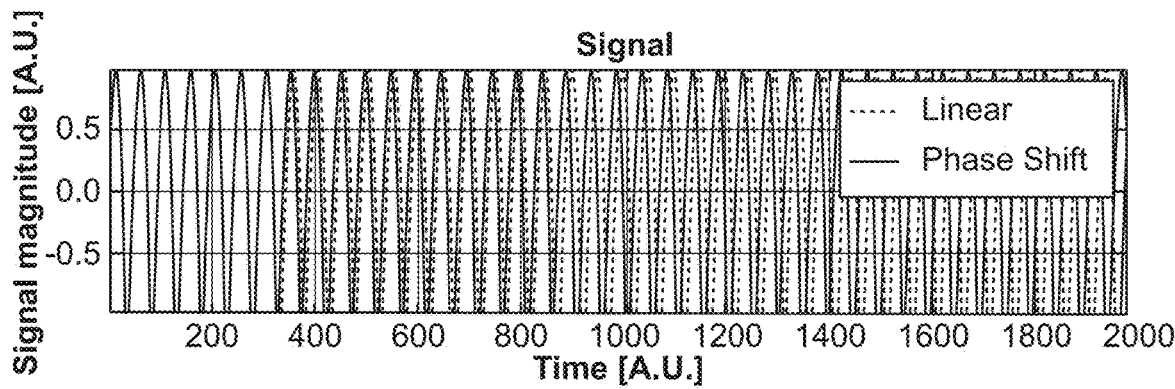
Figure 42D:
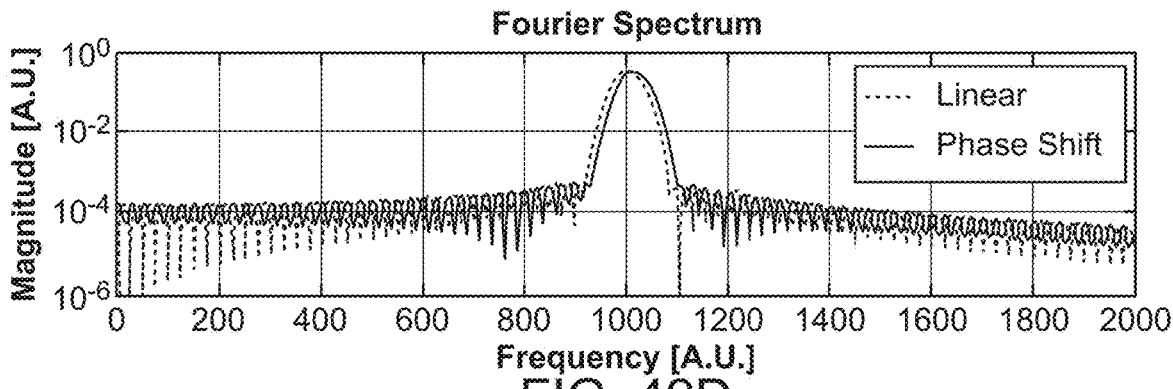

FIGS. 42A-D show simulations of the effect of A-scan time on the error arising from phase shifts associated with patient movement. FIG. 42A shows a simulated signal subjected to a phase shift of $\pi$ radians over a duration of a single cycle of the signal with an A-scan duration of 2 ms. FIG. 42B shows the frequency spectrum of a simulated signal subjected to a phase shift of $\pi$ radians over a duration of a single cycle of the signal with an A-scan duration of 2 ms. The phase shift imparts a significant error in the frequency spectrum for this relatively long A-scan duration. FIG. 42C shows a simulated signal subjected to a phase shift of $\pi$ radians over a duration of a single cycle of the signal with an A-scan duration of 0.4 ms. FIG. 42D shows the frequency spectrum a simulated signal subjected to a phase shift of $\pi$ radians over a duration of a single cycle of the signal with an A-scan duration of 0.4 ms. The phase shift imparts a significantly small error in the frequency spectrum for this relatively short A-scan duration. Thus, noise associated with patient movement may be decreased by utilizing fast A-scans, as described herein.

Example 11: Measurement of Typical Patient Movements

Figure 43A:
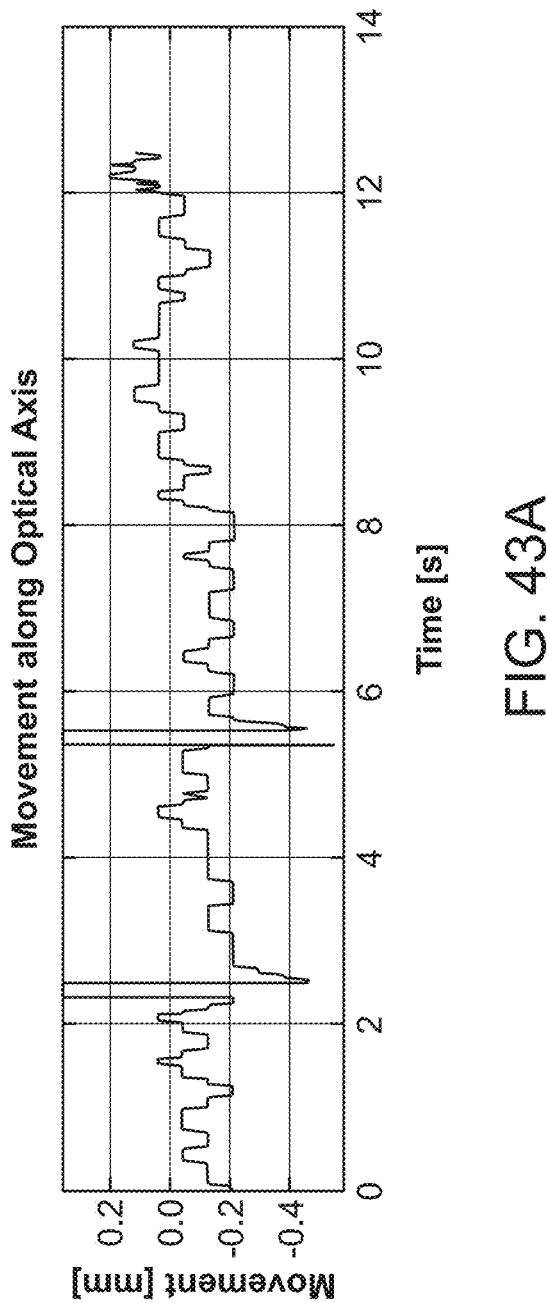
FIG. 43A and FIG. 43B show the amplitude of typical patient movements.
Figure 43B:
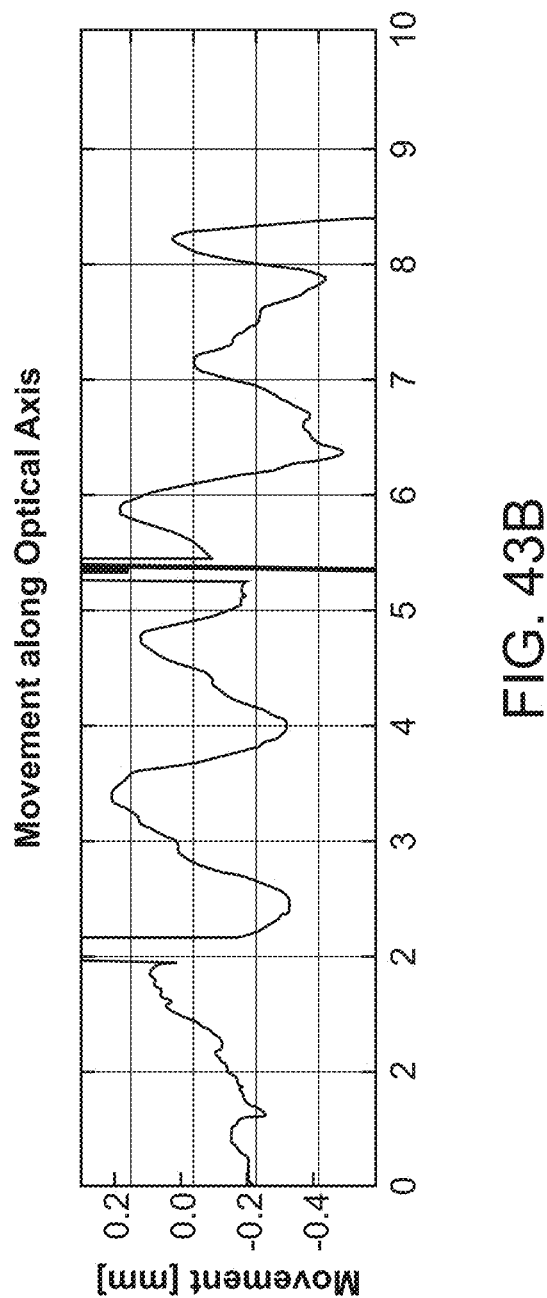

FIGS. 43A-B show the amplitude of typical patient movements. FIG. 43A shows movement along the optical axis for a patient maintaining himself as steady as possible. The large jumps between positions arise due to patient blinking. Ignoring blinking, a typical patient movement has an amplitude of about 0.25 mm and a duration of about 1.2 s, for a typical movement rate of 210 nm/ms. Such movement rates can be corrected for by using the fast A-scan methods described herein. A maximum patient movement has an amplitude of about 0.25 mm and a duration of about 0.16 s, for a maximum movement rate of 1,560 nm/ms. FIG. 43B shows movement along the optical axis for a patient who is intentionally moving. Ignoring blinking, a typical intentional patient movement has an amplitude of about 2.19 mm and a duration of about 0.76 s, for a typical intentional movement rate of 2,900 nm/ms.

Clause 1. A compact optical coherence tomography (OCT) system to measure a thickness of a retina of an eye, the compact OCT system comprising:

a detector;

a light source comprising a plurality of light sources configured to generate a plurality of light beams, each of the plurality of light beams comprising a range of wavelengths different from other light beams of the plurality in order to extend a spectral range of the light source;

a plurality of optical elements coupled to the light source to direct the plurality of light beams into the retina and generate a plurality of interference signals at the detector; and circuitry coupled to the detector and the plurality of light sources to determine the thickness in response to the plurality of interference signals.

Clause 2. The compact OCT system of clause 1, wherein the range of wavelengths of each of the plurality of light beams partially overlaps with at least one of the other light beams of the plurality.

Clause 3. The compact OCT system of clause 1, wherein the plurality of light sources comprises a plurality of VCSELs and wherein the circuitry is configured to sequentially activate each of the plurality of VCSELs in order to extend the spectral range.

Clause 4. The compact OCT system of clause 1, wherein the light source comprises a first VCSEL and a second VCSEL and the light beam comprises light from the first VSCEL and the second VSCEL.

Clause 5. The compact OCT system of clause 4, wherein the circuitry is configured to drive the first VCSEL and the second VCSEL in sequence with similar sweep frequencies in order to sweep first wavelengths of light from the first VSCEL and second wavelengths of light the second VSCEL with similar rates and optionally wherein the similar sweep frequencies and the similar rates of the first VSCEL and the second VSCEL are within 5% of each other and optionally within 1% of each other.

Clause 6. The compact OCT system of clause 4, wherein the circuitry is configured to have the first VSCEL on when the second VSCEL is off and have the second VSCEL on when the first VSCEL is off and to inhibit temporal overlap of light from the first VSCEL and the second VSCEL and wherein the second VSCEL is configured to turn on and emit light having wavelengths within about 0.1 nm of light from the first VSCEL when the first VSCEL is turned off.

Clause 7. The compact OCT system of clause 4, further comprising one or more of a beamsplitter or an optical fiber to couple light from the first VSCEL.

Clause 8. The compact OCT system of clause 1, further comprising a plurality phase compensation modules optically coupled to the light source and electrically coupled to the circuitry to characterize phases of the plurality of light beams, wherein the circuitry is configured to combine the plurality of interference signals to determine the thickness of the retina in response to the phases of the plurality of light beams.

Clause 9. The compact OCT system of clause 8, wherein each of the plurality of phase compensation modules comprises an interferometer configured to transmit the plurality of light beams to a detector with a change in intensity in response to wavelength and optionally wherein the interferometer comprises a Fabry Perot interferometer or a Michelson interferometer and optionally wherein the interferometer comprises a reference optical path length different from other interferometers of the plurality of phase compensation modules.

Clause 10. The compact OCT system of clause 9, wherein the interferometer comprises a Fabry Perot etalon and the reference optical path corresponds to a distance between opposing reflecting surfaces of the Fabry Perot etalon and an index of refraction of a material disposed in between.

Clause 11. The compact OCT system of clause 9, wherein the interferometer comprises the Michelson interferometer and the reference optical path comprises an optical path along a leg of the Michelson interferometer.

Clause 12. The compact OCT system of clause 8, wherein the plurality of phase compensation modules comprises a first module and a second module, the first module configured to generate a first compensation signal comprising a first frequency in response to a change in wavelength of the light source, the second module configured to generate a second compensation signal comprising a second frequency in response to the change in wavelength of the light source, the first frequency less than the second frequency and optionally wherein the first and second compensation signals are generated simultaneously.

Clause 13. The compact OCT system of clause 12, wherein the circuitry is configured with instructions to combine a first signal of the plurality of signals and a second signal of the plurality of signals from the retina in response to the first compensation signal and the second compensation signal in order to determine the thickness of the retina.

Clause 14. The compact OCT system of clause 13, wherein the first compensation signal and the second compensation signal comprise signals generated in response to the first signal of the plurality of signals from the retina and wherein a third compensation signal and a fourth compensation signal are generated from the first and second compensation modules, respectively, when the second signal of the plurality of signals is generated from the retina, and wherein the first and second signals of the plurality of signals from the retina are combined in response to the first compensation signal, the second compensation signal, the third compensation signal, and the fourth compensation signal.

Clause 15. The compact OCT system of clause 8, wherein each of the plurality of phase compensation signals and the plurality of signals from the retina are generated with a common clock signal and indexed in response to said clock signal in order to combine the plurality of signals from the sample structure in response to the plurality of compensation signals.

Clause 16. The compact OCT system of clause 1, further comprising:

an orientation sensor to determine which eye of a subject is being measured, wherein the OCT measurement system is configured to measure a first eye of the subject with a first orientation and to be inverted to measure a second eye of the subject with a second orientation.

Clause 17. The compact OCT system of clause 1, wherein the compact OCT system measures a change in retinal thickness at a precision (or repeatability) less than an axial resolution of the compact OCT system, the change in retinal thickness comprising a first thickness at a first time and a second thickness at a second time.

Clause 18. The compact OCT system of clause 1, wherein a change in retinal thickness measured with the compact OCT system is less than an axial resolution of the compact OCT system.

Clause 19. The compact OCT system of clause 1, wherein the light beam comprises a variable wavelength and wherein the circuitry is configured to vary the wavelength with a drive current from the circuitry.

Clause 20. The compact OCT system of clause 1, wherein the thickness is measured faster than characteristic frequencies of movement of the compact OCT system in relation to the eye, and wherein the movement is selected from the group consisting of movement related to the patient holding the OCT system in his hand, eye movement, and tremor.

Clause 21. The compact OCT system of clause 1, wherein the light source, the plurality of optical elements, the detector, and the circuitry are configured to be held in front of the eye with the detector no more than about 200 mm from the eye.

Clause 22. The compact OCT system of clause 1, further comprising a viewing target for the patient to align the light beam with a fovea of the eye and wherein the viewing target comprises one or more of the light beam or light from a light emitting diode.

Clause 23. The compact OCT system of clause 1, wherein the light source comprises a vertical cavity surface emitting laser (VCSEL) configured to vary an emission wavelength of the light beam over a range from about 5 to 10 nm.

Clause 24. The compact OCT system of clause 23, wherein the VCSEL has a specified maximum rated range of wavelength variation.

Clause 25. The compact OCT system of clause 24, wherein the circuitry is configured to drive the VCSEL beyond the specified maximum range of wavelength variation by at least about 1 nm and optionally within a range from about 1 nm to 5 nm beyond the specified maximum range of wavelength variation.

Clause 26. The compact OCT system of clause 24, wherein the circuitry is configured to drive the VSCEL above the maximum of the rated wavelength range for each of a plurality of measurements and to delay a first measurement from a second measurement by an amount within a range from about 1 milliseconds ("ms") to about 100 milliseconds in order to inhibit overheating of the VSCEL and optionally within a range from about 5 ms to about 20 ms.

Clause 27. The compact OCT system of clause 26, wherein the circuitry is configured to drive the VSCEL above the maximum of the rated wavelength range with a drive current having a waveform, the waveform having a first portion above a maximum rated current of the VSCEL and a second portion below the maximum rated current of the VSCEL and wherein the first portion comprises no more than about 50 percent of a duration of the waveform in order to inhibit overheating of the VSCEL.

Clause 28. The compact OCT system of clause 1, wherein the circuitry is configured to cause an emitted wavelength to sweep over a range of wavelengths with a sweeping frequency and the circuitry is configured to determine the thickness in response to frequencies of the interference signal.

Clause 29. The compact OCT system of clause 28, wherein the sweeping frequency is within a range from about 50 Hz to about 10 kHz, and optionally within a range from about 100 Hz to about 5 kHz, or from about 1 kHz to about 5 kHz.

Clause 30. The compact OCT system of clause 28, wherein the sweeping frequency is faster than an ocular tremor of a user, or a hand tremor of the user and optionally wherein the sweeping frequency is faster than a frequency of the ocular tremor of the user or a frequency of the hand tremor of the user.

Clause 31. The compact OCT system of clause 1, wherein the circuitry is configured to heat the light source to change the wavelength.

Clause 32. The compact OCT system of clause 1, wherein the plurality of optical elements is arranged to provide a reference optical path and a measurement optical path and the interference signal results from interference of light along the reference optical path and the measurement optical path.

Clause 33. The compact OCT system of clause 1, wherein the plurality of optical elements is arranged to provide a reference optical path and a measurement optical path and the interference signal results from interference of light from the reference optical path and light from the measurement optical path.

Clause 34. The compact OCT system of clause 1, wherein the plurality of optical elements is arranged to provide a measurement optical path and the interference signal results from interference of light from layers of the retina along the measurement optical path and optionally without a reference optical path.

Clause 35. The compact OCT system of clause 1, wherein the circuitry comprises a processor configured to transform the interference signal into an intensity profile of light reflected along an optical path of the beam directed into the eye and to determine the thickness of the retina in response to the intensity profile.

Clause 36. The compact OCT system of clause 35, wherein the intensity profile comprises a plurality of reflected peaks and the processor is configured with instructions to determine the thickness in response to the plurality of reflected peaks.

Clause 37. The compact OCT system of clause 35, wherein the processor is configured with instructions to determine the intensity profile in response to frequencies of the interference signal and optionally wherein the intensity profile is determined with a fast Fourier transform of the interference signal measured with the detector.

Clause 38. The compact OCT system of clause 35, wherein frequencies of the interference signal correspond to separation distances of layers of the retina and a rate of change of the wavelength of the light source.

Clause 39. The compact OCT system of clause 35, wherein frequencies of the interference signal correspond to separation distances of layers of the retina and a rate of change of a wavelength of the beam emitted from the light source.

Clause 40. The compact OCT system of clause 1, further comprising a viewing target to align the tomography system with a fovea of the eye and wherein the viewing target comprises one or more of the light beams, a target defined with a light emitting diode, or a VCSEL.

Clause 41. The compact OCT system of clause 1, further comprising housing to support the light source, the optical elements, the detector, and the circuitry, and wherein the housing is configured to be held in a hand of a user in front of the eye in order to direct the light beam into the eye.

Clause 42. The compact OCT system of clause 41, wherein the housing has a cylindrical shape with a plurality of indentations on a curved surface for ease of gripping.

Clause 43. The compact OCT system of clause 41, further comprising a sensor to measure which eye is measured in response to an orientation of the housing.

Clause 44. The compact OCT system of clause 41, further comprising an occlusion structure to occlude one eye while the other eye is measured, the occlusion structure coupled to the housing and the sensor to determine which eye is measured.

Clause 45. The compact OCT system of clause 41, wherein the housing comprises a body and a lid rotatably attached to the body, wherein when in an open position, the lid is configured to rotate around the body.

Clause 46. The compact OCT system of clause 41, further comprising a battery, wherein the battery is located further away from the detector than the light source.

Clause 47. The compact OCT system of clause 46, further comprising a docking station to receive the housing and charge the battery contained within the housing to power the light source and the circuitry, the docking station comprising wireless communication circuitry to transmit the thickness to a remote server and optionally wherein the wireless communication circuitry comprises a Global System for Mobile Communications (GSM), third generation (3G), or fourth generation (4G) module.

Clause 48. The compact OCT system of clause 1, wherein the circuity is configured to receive or transmit data through a communication network.

Clause 49. The compact OCT system of clause 1, wherein the communication network includes the Internet, a cellular network, or a short-range communication network.

Clause 50. The compact OCT system of any one of the preceding clauses, wherein the compact OCT system has a mass within a range from about 50 grams to about 500 grams and optionally within a range from about 100 grams to about 400 grams.

Clause 51. The compact OCT system of any one of the preceding clauses, wherein the compact OCT system has a maximum distance across within a range from about 10 mm to about 100 mm and optionally within a range from about 25 mm to about 70 mm.

Clause 52. The compact OCT system of any one of the preceding clauses, further comprising:

a housing, wherein the light source, the detector, the circuitry, and the optical elements are contained within the housing;

an optical fiber coupled to the light source and the detector, the optical fiber extending from the compact OCT system; and an alignment structure coupled to a distal end of the optical fiber to align the light beam with the eye and direct the light beam to the eye.

Clause 53. A binocular OCT system for measuring a left eye and a right eye of a user, the system comprising:

a first adjustable lens optically coupled to an OCT measurement system and a first fixation target, the first adjustable lens configured to compensate for a refractive error of the left eye or the right eye; and a second lens optically coupled to a second fixation target, the second lens configured to compensate for a refractive error of the left eye or the right eye;

wherein the OCT measurement system is configured to be inverted to measure the left eye or the right eye.

Clause 54. The binocular OCT system of clause 53, further comprising:

an orientation sensor to determine whether a left eye or a right of eye of user is being measured with the OCT measurement system; and a processor operatively coupled to the first lens, the second lens and the orientation sensor, the processor configured with instructions to adjust the first lens to the refractive error of the right eye and the second lens to the refractive error of left eye when the OCT system comprises an orientation to measure the right eye, and to adjust the first lens to the refractive error of the left eye and the second lens to the refractive error of the right eye when the OCT system comprises an orientation to measure the left eye.

Clause 55. The binocular OCT system of clause 53, wherein the OCT measurement system comprises a first orientation to measure a first eye of the user, and a second orientation to measure a second eye of the user, the second orientation inverted relative to the first orientation.

Clause 56. The binocular OCT system of clause 53, wherein the first lens movable relative to the fixation target and the OCT measurement system to compensate for the refractive error of the left eye or the right eye and wherein the second lens movable to compensate for the refractive error of the left eye or the right eye Clause 57. The binocular OCT system of clause 53, wherein the processor comprises a non-transitory computer readable medium configured with instructions to store the refractive error of the right eye and the refractive error of the left eye and to adjust the first lens and the second lens in response to the stored refractive error of the right and the stored refractive error of the left eye and the orientation sensor.

Clause 58. The binocular OCT system of clause 53, wherein the first lens, the OCT system and the first fixation target share a first optical path and the second lens and the second fixation target share a second optical path, and wherein a separation distance between the first optical path and the second optical path is adjustable to an interpupillary distance between the right eye and the left eye of the user and optionally manually adjustable Clause 59. The binocular OCT system of clause 58, wherein the first lens and the second lens are configured to translate on the first optical path and the second optical path respectively, and wherein the processor is configured with instructions to translate the first lens to a right eye position to correct for the refractive error of the right eye and to a left eye position to correct for the refractive error of the second eye and to translate the second lens to a right eye position to correct for the refractive error of the right eye and to a left eye position to correct for the refractive error of the left eye.

Clause 60. The binocular OCT system of clause 53, wherein the OCT system comprises a reference arm and a measurement arm, the measurement arm comprising an optical fiber comprising an end oriented toward a lens along an optical path the measurement arm, wherein the end and the lens are configured to translate along the optical path to decrease an optical path difference between the reference arm.

Clause 61. The binocular OCT system of clause 60, wherein the end and the lens are operatively coupled to the processor to move the end and the lens in response to the optical path difference and optionally wherein the optical path difference remains substantially fixed between measurements of the first eye and the second eye.

Clause 62. The binocular OCT system of clause 60, wherein the end and the lens are configured to translate along an optical path difference compensation axis, the first lens is configured to translate along a first axis and the second lens is configured to translate along a second axis, and wherein the optical path difference compensation axis, the first axis and the second axis are substantially parallel to each other to within about five degrees.

Clause 63. The binocular OCT system of clause 62, wherein the optical path difference compensation axis is located between the first axis and the second axis.

Clause 64. The binocular OCT system of clause 53, further comprising a camera to image an anterior portion of the eye and determine a position of the eye in relation to an axis extending between the first adjustable lens and the first fixation target, and wherein the processor is operably coupled to the camera to determine the position of the eye in response to a signal from the orientation sensor and the image and optionally wherein the image comprises one or more of an image of a pupil of the eye or a Purkinje image of light reflected from a cornea of the eye.

Clause 65. The binocular OCT system of clause 64, wherein the processor is configured with instructions to adjust a measurement region on a retina of the eye in response to the signal from the orientation sensor.

Clause 66. The binocular OCT system of clause 64, wherein the processor is configured to adjust an output map of retinal thickness in response to the orientation sensor.

Clause 67. The binocular OCT system of clause 64, wherein the orientation sensor comprises an accelerometer or a gyroscope.

Clause 68. The binocular OCT system of clause 53, wherein the OCT measurement system comprises one or more of a time domain OCT measurement system, a swept source OCT measurement system, spectral domain OCT measurement system or a multiple reflectance OCT measurement system.

Clause 69. A binocular OCT system comprising:
a printed circuit board comprising a processor and a plurality of electrical components coupled to the processor;
a support comprising a plurality of optics modules mounted on the support, the plurality of optics modules comprising a scanner, a first fixation target, a second fixation target and a plurality of lenses coupled to the scanner, the first fixation target and the second fixation target;
an interferometer module comprising a plurality of optical fibers, a plurality of optical fiber couplers, an optical fiber reference arm and an optical fiber portion of a measurement arm; and
an external housing enclosing the printed circuit board, the support and the interferometer module and wherein the printed circuit board, the support and the interferometer module are arranged in a stacked configuration within the external housing.

Clause 70. The binocular OCT system of clause 69, wherein the stacked configuration comprises a first orientation when a first eye is measured and a second orientation when a second eye is measured, the second orientation inverted relative to the first orientation.

Clause 71. The binocular OCT system of clause 69, wherein the support is located between the printed circuit board and the interferometer module.

Clause 72. The binocular OCT system of clause 69, wherein the support comprises a plate with the plurality of optics modules mounted thereon.

Clause 73. The binocular OCT system of clause 69, wherein the interferometer module comprises a housing enclosing the plurality and optical fibers and the plurality of optical fiber couplers, the reference arm and the portion of a measurement arm.

Clause 74. The binocular OCT system of clause 73, wherein the plurality of optical fibers comprises a source optical fiber coupled to a swept source laser and optionally wherein the swept source laser is located inside the housing.

Clause 75. The binocular OCT system of clause 73, wherein the plurality of optical fibers comprises a pair of optical fibers extending from a first and second arm coupler located within the housing to a pair of balanced detectors located outside the housing and wherein the first and second arm coupler couples the reference arm to the optical fiber portion of the measurement arm and optionally wherein the pair of balanced detectors is operatively coupled to the processor on the printed circuit board.

Clause 76. The binocular OCT system of clause 73, wherein the optical fiber portion of the measurement arm extends from an optical coupler coupled to the optical fiber reference arm within the housing to an end outside the housing, the end coupled to a lens to direct a measurement light beam toward an eye of the user.

Clause 77. The binocular OCT system of clause 73, wherein the plurality of optical fibers comprises a phase monitor optical fiber coupled to a swept source laser, the phase monitor optical fiber extending from a coupler located within the housing to an end located outside the housing, the end optically coupled to an etalon and a phase detector to measure a phase of light emitted from the swept source laser and optionally wherein the phase detector is operatively coupled to the processor on the printed circuit board.

Clause 78. The binocular OCT system of clause 73, wherein the plurality of optical fibers comprises a pair of optical power monitor fibers, the pair of optical monitor fibers extending from a coupler located within the housing to a pair of optical monitor detectors, the pair of optical monitor detectors configured to independently measure power of the swept source laser and optionally wherein the pair of optical monitor detectors is operatively coupled to the processor on the printed circuit board.

Clause 79. An OCT system to measure an eye of a user, the OCT system comprising:
a fixation target visible to the eye;
an OCT interferometer configured to measure thickness of a retina of the eye;
a plurality of light sources arranged to reflect from a cornea of the eye and generate a Purkinje image comprising reflections of the plurality of light sources from the cornea.
a sensor to measure a position of the Purkinje image reflected from the cornea; and
a processor operatively coupled to the sensor to determine a position of the eye in response to the Purkinje image.

Clause 80. The OCT system of clause 79, wherein the processor is configured with instructions to provide auditory or visual cues to the user to move the eye into alignment with the OCT interferometer.

Clause 81. The OCT system of clause 80, further comprising an orientation sensor coupled to a housing of the OCT system and wherein the user is instructed to move the eye in a first direction or a second direction opposite the first direction in response to the orientation sensor.

Clause 82. The OCT system of clause 80, wherein the auditory cues comprise instructions to the user to move the eye one or more of left, right, up or down.

Clause 83. The OCT system of clause 80, wherein the visual cues comprise one or more of a flashing fixation target, a change in frequency of a flashing fixation target, or a change in a color of a fixation target.

Clause 84. The OCT system of clause 79, wherein sensor comprises a camera comprising a sensor array to capture the Purkinje image and the processor is configured with instructions to determine the position of the eye in response to the reflections of the plurality of light sources and optionally wherein the camera comprises a CMOS sensor array.

Clause 85. The OCT system of clause 79, wherein sensor comprises one or more of a quadrant detector or a position sensitive detector to determine the position of the eye in response to the reflections of the plurality of light sources.

Clause 86. The OCT system of clause 79, further comprising a scanner coupled to the processor to scan a measurement beam the OCT interferometer over an area of a retina of the eye to generate a map of retinal thickness and record a position of the eye in response to the Purkinje image.

Clause 87. The OCT system of clause 86, wherein the processor is configured to output the map of retinal thickness and the position of the eye.

Clause 88. The OCT system of clause 86, wherein the processor is configured to adjust a position of the map of retinal thickness in response to the position of the eye.

Clause 89. The OCT system of clause 88, further comprising an orientation sensor, and wherein the processor is configured to adjust the position of the map of retinal thickness in response to the orientation sensor.

Clause 90. The OCT system of clause 89, wherein the processor is configured to adjust the position of the map along the retina in a first direction in response to the orientation sensor in a first orientation and to adjust the map in a second direction opposite the first direction in response to the orientation sensor in a second orientation opposite the first direction.

Clause 91. The OCT system of clause 86, wherein the processor is configured to adjust a position of a scan pattern on the retina in response to the position of the eye.

Clause 92. The OCT system of clause 91, further comprising an orientation sensor, and wherein the processor is configured to adjust the position of the scan pattern on the retina in response to the orientation sensor.

Clause 93. The OCT system of clause 92, wherein the processor is configured to adjust the position of scan pattern on the retina in a first direction in response to the orientation sensor in a first orientation and to adjust the scan pattern in a second direction opposite the first direction in response to the orientation sensor in a second orientation opposite the first direction.

Clause 94. The OCT system of clause 79, further comprising a user input operatively coupled to the processor to trigger a plurality of processor instructions, the plurality of instructions comprising instructions to illuminate the fixation target, illuminate the plurality of light sources, acquire positions of the eye in response to the sensor, provide instructions to the user to align the eye with the OCT interferometer, scan the retina with the OCT measurement beam, and implement a safety pause of a laser from the OCT interferometer.

Clause 95. The OCT system of clause 94, wherein the processor is configured with instructions to determine XY positions of the eye in relation to the OCT measurement beam in response to locations of the reflections in the Purkinje image, the XY positions of the eye corresponding to locations transverse to the OCT measurement beam and optionally wherein each of the XY positions corresponds to a central location between reflections of the plurality of light sources of the Purkinje image and optionally wherein the central location corresponds to a midpoint between a first pair of reflections and a midpoint between a second pair of reflections of the Purkinje image.

Clause 96. The OCT system of clause 95, wherein the processor is configured with instructions to determine a Z position of the eye corresponding to a distance along the OCT measurement beam in response to distances between the reflections in the Purkinje image.

Clause 97. The OCT system of clause 94, wherein the processor is configured with instructions to automatically scan the retina in response to a position of the eye with an amount of error, the amount of error within a range from 0.2 mm to about 0.75 mm.

Clause 98. The OCT system of clause 94, wherein illumination of the fixation target overlaps and illumination of the plurality of light sources overlap with scanning of the retina with the OCT measurement beam.

Clause 99. The OCT system of clause 94, wherein a scanned region of the retina comprises dimensions across within a range from about 1 mm to about 3 mm and wherein a number of A-scans comprises from about 5000 A-scans to about 40,000 A-scans over a time within a range from about 0.5 seconds to about 3 seconds and wherein the safety pause is within a range from about 2 to 10 seconds.

Clause 100. The OCT system of clause 94, wherein the user input comprises one or more of a button, a proximity sensor, a switch, a capacitive sensor, a touch screen, or a voice command.

Clause 101. The OCT system of clause 86, wherein an optical path extends between the fixation target and the eye and the OCT interferometer measurement beam overlaps with the optical path and the plurality of light sources is distributed around the optical path.

Clause 102. The OCT system of clause 94, further comprising a first beam splitter configured to reflect the measurement beam from a scanning mirror and transmit light from the Purkinje image and the fixation target, a second beam splitter configured to reflect light from the Purkinje image to the sensor and transmit light from the fixation target.

Clause 103. The OCT system of clause 102, wherein the plurality of light sources to generate the Purkinje image comprises a wavelength within a range from about 700 to 800 nm, the fixation target comprises a wavelength within a range from about 500 to 700 nm, and the OCT measurement beam comprises a plurality of wavelengths within a range from about 800 to 900 nm.

Clause 104. The OCT system of clause 102, wherein the plurality of light sources to generate the Purkinje image comprises from 3 to 8 light sources and optionally wherein the plurality of light sources comprises from 3 to 8 light emitting diodes.

Clause 105. A compact optical coherence tomography (OCT) system to measure a thickness of a retina of an eye, the compact OCT system comprising:

a detector;

a light source comprising a one or more VCSELs to sweep one or more light beams over a range of wavelengths;

a plurality of optical elements coupled to the light source to direct the light beam into the retina and generate a plurality of interference signals at the detector; and circuitry coupled to the detector and the plurality of light sources to determine the thickness in response to the plurality of interference signals.

Clause 106. The compact OCT system of clause 105, further comprising a plurality phase compensation modules optically coupled to the one or more VCSELs and electrically coupled to the circuitry to characterize phases of the one or more light beams, wherein the circuitry is configured to combine the plurality of interference signals to determine the thickness of the retina in response to the phases of the one or more of light beams.

Clause 107. The compact OCT system of clause 106, wherein each of the plurality of phase compensation modules comprises an interferometer configured to transmit the one or more of light beams to a detector with a change in intensity in response to wavelength and optionally wherein the interferometer comprises a Fabry Perot interferometer or a Michelson interferometer and optionally wherein the interferometer comprises a reference optical path length different from other interferometers of the plurality of phase compensation modules.

Clause 108. The compact OCT system of clause 107, wherein the interferometer comprises a Fabry Perot etalon and the reference optical path corresponds to a distance between opposing reflecting surfaces of the Fabry Perot etalon and an index of refraction of a material disposed in between.

Clause 109. The compact OCT system of clause 107, wherein the interferometer comprises the Michelson interferometer and the reference optical path comprises an optical path along a leg of the Michelson interferometer.

Clause 110. The compact OCT system of clause 106, wherein the plurality of phase compensation modules comprises a first module and a second module, the first module configured to generate a first compensation signal comprising a first frequency in response to a change in wavelength of the one or more light sources, the second module configured to generate a second compensation signal comprising a second frequency in response to the change in wavelength of the one or more light sources, the first frequency less than the second frequency and optionally wherein the first and second compensation signals are generated simultaneously.

Clause 111. The compact OCT system of clause 110, wherein the circuitry is configured with instructions to combine a first signal of the one or more of signals and a second signal of the one or more signals from the retina in response to the first compensation signal and the second compensation signal in order to determine the thickness of the retina.

Clause 112. The compact OCT system of any one of clauses 105 to 111 wherein the one or more VCSELs comprises a single VCSEL.

Clause 113. The OCT system of any one of the preceding clauses, wherein a scanner is configured to scan a measurement beam along the retina with a trajectory and optionally wherein the trajectory comprises one or more of a stop and go trajectory, a continuous trajectory, a star trajectory of a Lissajous trajectory.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An OCT system to measure an eye of a user, the OCT system comprising:
   a fixation target visible to the eye;
   an OCT interferometer configured to measure thickness of a retina of the eye;
   a plurality of light sources arranged to reflect from a cornea of the eye and generate a Purkinje image comprising reflections of the plurality of light sources from the cornea;
   a sensor to measure a position of the Purkinje image reflected from the cornea;
   a processor operatively coupled to the sensor to determine a position of the eye and record a position of the eye in response to the Purkinje image; and
   a user input operatively coupled to the processor to trigger a plurality of processor instructions, the plurality of processor instructions comprising instructions to illuminate the fixation target, illuminate the plurality of light sources, acquire positions of the eye in response to the sensor, provide instructions to the user to align the eye with the OCT interferometer, scan the retina with an OCT measurement beam, and implement a safety pause of a laser from the OCT interferometer.

2. The OCT system of claim 1, wherein the processor is configured with instructions to provide auditory or visual cues to the user to move the eye into alignment with the OCT interferometer.

3. The OCT system of claim 2, further comprising an orientation sensor coupled to a housing of the OCT system and wherein the user is instructed to move the eye in a first direction or a second direction opposite the first direction in response to the orientation sensor.

4. The OCT system of claim 2, wherein the auditory cues comprise instructions to the user to move the eye one or more of left, right, up or down.

5. The OCT system of claim 2, wherein the visual cues comprise one or more of a flashing fixation target, a change in frequency of the flashing fixation target, or a change in a color of the flashing fixation target.

6. The OCT system of claim 1, wherein the sensor comprises a camera comprising a sensor array to capture the Purkinje image and the processor is configured with instructions to determine the position of the eye in response to the reflections of the plurality of light sources.

7. The OCT system of claim 1, wherein sensor comprises one or more of a quadrant detector or a position sensitive detector to determine the position of the eye in response to the reflections of the plurality of light sources.

8. The OCT system of claim 1, further comprising a scanner coupled to the processor to scan the OCT measurement beam over an area of the retina of the eye to generate a map of retinal thickness and record a position of the eye in response to the Purkinje image.

9. The OCT system of claim 8, wherein the processor is configured to output the map of retinal thickness and the position of the eye.

10. The OCT system of claim 8, wherein the processor is configured to adjust a position of the map of retinal thickness in response to the position of the eye.

11. The OCT system of claim 10, further comprising an orientation sensor, and wherein the processor is configured to adjust the position of the map of retinal thickness in response to the orientation sensor.

12. The OCT system of claim 11, wherein the processor is configured to adjust the position of the map along the retina in a first direction in response to the orientation sensor in a first orientation and to adjust the map in a second direction opposite the first direction in response to the orientation sensor in a second orientation opposite the first direction.

13. The OCT system of claim 8, wherein the processor is configured to adjust a position of a scan pattern on the retina in response to the position of the eye.

14. The OCT system of claim 13, further comprising an orientation sensor, and wherein the processor is configured to adjust the position of the scan pattern on the retina in response to the orientation sensor.

15. The OCT system of claim 14, wherein the processor is configured to adjust the position of the scan pattern on the retina in a first direction in response to the orientation sensor in a first orientation and to adjust the scan pattern in a second direction opposite the first direction in response to the orientation sensor in a second orientation opposite the first direction.

16. The OCT system of claim 8, wherein an optical path extends between the fixation target and the eye and the OCT measurement beam overlaps with the optical path and the plurality of light sources is distributed around the optical path.

17. The OCT system of claim 1, wherein the processor is configured with instructions to determine XY positions of the eye in relation to the OCT measurement beam in response to locations of the reflections in the Purkinje image, the XY positions of the eye corresponding to locations transverse to the OCT measurement beam.

18. The OCT system of claim 17, wherein the processor is configured with instructions to determine a Z position of the eye corresponding to a distance along the OCT measurement beam in response to distances between the reflections in the Purkinje image.

19. The OCT system of claim 1, wherein the processor is configured with instructions to automatically scan the retina in response to a position of the eye with an amount of error, the amount of error within a range from 0.2 mm to about 0.75 mm.

20. The OCT system of claim 1, wherein illumination of the fixation target and illumination of the plurality of light sources overlap with scanning of the retina with the OCT measurement beam.

21. The OCT system of claim 1, wherein a scanned region of the retina comprises dimensions across within a range from about 1 mm to about 3 mm and wherein a number of A-scans comprises from about 5000 A-scans to about 40,000 A-scans over a time within a range from about 0.5 seconds to about 3 seconds and wherein the safety pause is within a range from about 2 to 10 seconds.

22. The OCT system of claim 1, wherein the user input comprises one or more of a button, a proximity sensor, a switch, a capacitive sensor, a touch screen, or a voice command.

23. The OCT system of claim 1, further comprising a first beam splitter configured to reflect the OCT measurement beam from a scanning mirror and transmit light from the Purkinje image and the fixation target, a second beam splitter configured to reflect light from the Purkinje image to the sensor and transmit light from the fixation target.

24. The OCT system of claim 23, wherein the plurality of light sources to generate the Purkinje image comprises a wavelength within a range from about 700 to 800 nm, the fixation target comprises a wavelength within a range from about 500 to 700 nm, and the OCT measurement beam comprises a plurality of wavelengths within a range from about 800 to 900 nm.

25. The OCT system of claim 23, wherein the plurality of light sources to generate the Purkinje image comprises from 3 to 8 light sources.

* * * * *